United States Patent
Quattropani et al.

(10) Patent No.: US 11,046,712 B2
(45) Date of Patent: *Jun. 29, 2021

(54) GLYCOSIDASE INHIBITORS

(71) Applicant: Asceneuron SA, Lausanne (CH)

(72) Inventors: Anna Quattropani, Rolle (CH);
Santosh S. Kulkarni, Bangalore (IN);
Awadut Gajendra Giri, Bangalore (IN)

(73) Assignee: Asceneuron SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,689

(22) Filed: May 15, 2019

(65) Prior Publication Data

US 2019/0367533 A1 Dec. 5, 2019

Related U.S. Application Data

(63) Continuation of application No. 15/507,375, filed as application No. PCT/EP2015/069598 on Aug. 27, 2015, now Pat. No. 10,336,775.

(30) Foreign Application Priority Data

Aug. 28, 2014 (IN) .......................... 2766/MUM/2014

(51) Int. Cl.
| | | |
|---|---|---|
| *C07D 513/04* | (2006.01) | |
| *C07D 403/12* | (2006.01) | |
| *C07D 405/14* | (2006.01) | |
| *C07D 413/14* | (2006.01) | |
| *A61K 31/454* | (2006.01) | |
| *A61K 31/496* | (2006.01) | |
| *A61K 31/497* | (2006.01) | |
| *A61K 31/498* | (2006.01) | |
| *A61K 31/501* | (2006.01) | |
| *A61K 31/506* | (2006.01) | |
| *A61K 31/5377* | (2006.01) | |
| *C07D 401/12* | (2006.01) | |
| *C07D 405/12* | (2006.01) | |
| *C07D 413/12* | (2006.01) | |
| *C07D 417/12* | (2006.01) | |
| *C07D 417/14* | (2006.01) | |
| *C07D 487/04* | (2006.01) | |
| *C07D 285/135* | (2006.01) | |
| *A61K 45/06* | (2006.01) | |
| *A61K 31/517* | (2006.01) | |
| *A61K 31/519* | (2006.01) | |
| *C07D 277/46* | (2006.01) | |

(52) U.S. Cl.
CPC .......... *C07D 513/04* (2013.01); *A61K 31/454* (2013.01); *A61K 31/496* (2013.01); *A61K 31/497* (2013.01); *A61K 31/498* (2013.01); *A61K 31/501* (2013.01); *A61K 31/506* (2013.01); *A61K 31/517* (2013.01); *A61K 31/519* (2013.01); *A61K 31/5377* (2013.01); *A61K 45/06* (2013.01); *C07D 277/46* (2013.01); *C07D 285/135* (2013.01); *C07D 401/12* (2013.01); *C07D 403/12* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 3,299,067 A | | 1/1967 | Gilbert et al. |
| 3,457,263 A | * | 7/1969 | Laubie ................. C07D 473/32 544/277 |
| 3,485,757 A | | 12/1969 | Shapiro |
| 3,489,757 A | * | 1/1970 | Koppe ................. C07D 417/04 544/369 |
| 4,600,025 A | | 7/1986 | Grigg et al. |
| 5,935,974 A | | 8/1999 | Rae et al. |
| 7,582,769 B2 | | 9/2009 | Murray et al. |

(Continued)

FOREIGN PATENT DOCUMENTS

| | | |
|---|---|---|
| CN | 1791594 A | 6/2006 |
| CN | 103435606 | 12/2013 |

(Continued)

OTHER PUBLICATIONS

Abdel-Magid, A. F. et al. "Reductive Amination of Aldehydes and Ketones with Sodium Triacetoxyborohydride. Studies on Direct and Indirect Reductive Amination Procedures" J. Org. Chem., (1996), 61, pp. 3849-3862.

(Continued)

*Primary Examiner* — Heidi Reese
(74) *Attorney, Agent, or Firm* — Cooley LLP

(57) ABSTRACT

The disclosure relates to compounds of formula (I) useful in the treatment of tauopathies and Alzheimer's disease (I)

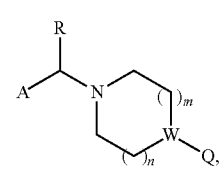

wherein A, R, W, Q, n, and m are described herein.

20 Claims, No Drawings

(56) References Cited

U.S. PATENT DOCUMENTS

| | | |
|---|---|---|
| 8,008,326 B2 | 8/2011 | Borza et al. |
| 9,120,781 B2 | 9/2015 | Li et al. |
| 10,336,775 B2 | 7/2019 | Quattropani et al. |
| 10,344,021 B2 | 7/2019 | Quattropani et al. |
| 10,696,668 B2 | 6/2020 | Quattropani et al. |
| 2004/0106645 A1 | 6/2004 | Blackburn et al. |
| 2006/0287340 A1 | 12/2006 | Moriya et al. |
| 2008/0300276 A1 | 12/2008 | Borza et al. |
| 2009/0012078 A1 | 1/2009 | Andrews et al. |
| 2009/0163545 A1 | 6/2009 | Goldfarb |
| 2010/0022517 A1 | 1/2010 | Richards et al. |
| 2011/0053982 A1 | 3/2011 | Fay et al. |
| 2011/0060012 A1 | 3/2011 | Meyers et al. |
| 2011/0060019 A1 | 3/2011 | Murray et al. |
| 2012/0208808 A1 | 8/2012 | Buchstaller et al. |
| 2016/0031871 A1 | 2/2016 | Yu et al. |

FOREIGN PATENT DOCUMENTS

| | | |
|---|---|---|
| EP | 2301936 | 3/2011 |
| EP | 2687507 | 1/2014 |
| FR | 1311316 | 12/1962 |
| JP | 2010/270034 | 12/2010 |
| WO | WO1993/021181 | 10/1993 |
| WO | WO1997/043279 | 11/1997 |
| WO | WO1998/046590 | 10/1998 |
| WO | WO99/21850 | 5/1999 |
| WO | WO02/094799 | 11/2002 |
| WO | WO2003/092678 | 11/2003 |
| WO | WO2004/002481 | 1/2004 |
| WO | WO2004/005293 | 1/2004 |
| WO | WO2004/022558 | 3/2004 |
| WO | WO2004/094380 | 11/2004 |
| WO | WO2005/110982 | 11/2005 |
| WO | WO2006/092049 | 9/2006 |
| WO | WO2007/115077 | 10/2007 |
| WO | WO2007/135398 | 11/2007 |
| WO | WO2007/146122 | 12/2007 |
| WO | WO2008/012623 | 1/2008 |
| WO | WO2008/025170 | 3/2008 |
| WO | WO2009/011904 | 1/2009 |
| WO | WO2009/053373 | 4/2009 |
| WO | WO2009/131926 | 10/2009 |
| WO | WO2010/018868 | 2/2010 |
| WO | WO2010/021381 | 2/2010 |
| WO | WO2010/022517 | 3/2010 |
| WO | WO2010/026989 | 3/2010 |
| WO | WO2010/089127 | 8/2010 |
| WO | WO2010/101949 | 9/2010 |
| WO | WO2010/108115 | 9/2010 |
| WO | WO2010/108268 | 9/2010 |
| WO | WO2010/151318 | 12/2010 |
| WO | WO2011/140640 | 11/2011 |
| WO | WO2012/037298 | 3/2012 |
| WO | WO2012/061927 | 5/2012 |
| WO | WO2012/062157 | 5/2012 |
| WO | WO2012/062759 | 5/2012 |
| WO | WO2012/083435 | 6/2012 |
| WO | WO2012/117219 | 9/2012 |
| WO | WO2013/028715 | 2/2013 |
| WO | WO2013/066729 | 5/2013 |
| WO | WO2014/023723 | 2/2014 |
| WO | WO2014/032187 | 3/2014 |
| WO | WO2014/159234 | 10/2014 |
| WO | WO2015/083028 | 6/2015 |
| WO | WO2015/128333 | 9/2015 |
| WO | WO2015/164508 | 10/2015 |
| WO | WO2017/001660 | 1/2017 |
| WO | WO2017/076900 | 5/2017 |
| WO | WO2017/087858 | 5/2017 |
| WO | WO2017/087863 | 5/2017 |
| WO | WO2017/091818 | 6/2017 |
| WO | WO2017/106254 | 6/2017 |
| WO | WO2017/144633 | 8/2017 |
| WO | WO2017/144635 | 8/2017 |
| WO | WO2017/144637 | 8/2017 |
| WO | WO2017/144639 | 8/2017 |
| WO | WO2018/026371 | 2/2018 |
| WO | WO2018/109198 | 6/2018 |
| WO | WO2018/109202 | 6/2018 |
| WO | WO2018/140299 | 8/2018 |
| WO | WO2018/141984 | 8/2018 |
| WO | WO2018/153507 | 8/2018 |
| WO | WO2018/153508 | 8/2018 |
| WO | WO2018/154133 | 8/2018 |
| WO | WO2018/217558 | 11/2018 |

OTHER PUBLICATIONS

Albertson, N. F. "Alkylation with Non-ketonic Mannich Bases. Aminothiazoles and Pyrrole" J. Am. Chem. Soc., 1948, 70(2), 669-670.

Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging" J. Med. Chem., (2012), 55, pp. 8685-8699.

Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles" Tetrahedron, (2009), 65, pp. 9989-9996.

Bastin, R. J. et al. "Salt Selection and Optimisation Procedures for Pharmaceutical New Chemical Entities", Organic Process Research & Development, 2000, 4, 427-435.

Berge, S. M. et al. "Pharmaceutical Salts", Journal of Pharmaceutical Sciences, 1977, 66(1), 1-19.

Biscoe, M. R. et al. "A New Class of Easily Activated Palladium Precatalysts for Facile C—N Cross-Coupling Reactions and Low Temperature Oxidative Addition of Aryl Chlorides", J. Am. Chem. Soc., 2008, 130, 6686-6687.

Bohnert, T. et al. "Plasma Protein Binding: From Discovery to Development", J. Pharmaceutical Sciences, 2013, 102, 2953-2994.

Bras, N. F. et al. "Glycosidase inhibitors: a patent review (2008-2013)" Expert Opinion on Therapeutic Patents, vol. 24, No. 8, 2014, pp. 857-874.

Bundgaard, H. "Design and Application of Prodrugs", from A Textbook of Drug Design and Development Chapter 5, Harwood Academic Publishers, 1991, 113-191.

Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.

CAS Registry (Online) Nos. 948053-91-6; 540512-02-5; 697229-62-2; 346662-52-0; 345992-64-5 (STN database summary sheets) Sep. 26, 2007.

"Chemical Encyclopedia", vol. 4, pp. 990-993, 1988. (Machine translation attached).

Chen, Y. et al. "Discovery of new acetylcholinesterase and butyrylcholinesterase inhibitors through structurebased virtual screening", RSC Advances, 2017, 7(6), 3429-3438.

Collet, A. "Resolution of Racemates: Did you say 'Classical?'", Angewandte Chemie International Edition, 1998, 37(23), 3239-3241.

Dassanayaka, S. and Jones, S. "O-GlcNAc and the cardiovascular system", Pharmacology & Therapeutics, 2014, 142, 62-71.

Database registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4.

Database Pubchem Compound (Online) NCBI; Jan. 24, 2012, XP002768130, Database accession No. CID 54914491.

Database PubChem Compound (Online) NCBI; May 28, 2009; XP002768131, Database accession No. CID 28798635.

Database PubChem Compound, NCBI; Apr. 9, 2016; XP002768133, Database accession No. CID 118902929.

Database Registry Chemical Abstracts Service, 2016, CID120907609, 10 pages.

Database Registry, Chemical Abstracts Service, Jan. 11, 2017, XP002768132, Database accession No. 2055841-81-9.

(56) References Cited

OTHER PUBLICATIONS

Dorfmueller, H. C. et al. "Cell-Penetrant, Nanomolar O-GlcNAcase Inhibitors Selective against Lysosomal Hexosaminidases", Chem. Biol., 2010, 17, 1250-1255.
Dubois, B. et al. "Preclinical Alzheimer's disease: Definition, natural history, and diagnostic criteria", Alzheimers Dement., 2016, 12, 292-323.
Dubois B, et al. "Advancing research diagnostic criteria for Alzheimer's disease: the IWG-2 criteria", Lancet Neurol., 2014, 13, 614-629.
Dyatkin, A.B. et al. "Determination of the Absolute Configuration of a Key Tricyclic Component of a Novel Vasopressin Receptor Antagonist by Use of Vibrational Circular Dichroism", Chirality, 2002, 14, 215-219.
Ellman, J. A et al. "N-tert-Butanesulfinyl mines: Versatile Intermediates for the Asymmetric Synthesis of Amines" Acc. Chem. Res. (2002), 35, pp. 984-995.
Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.
Frings, M. et al. "Sulfoximines from a Medicinal Chemist's Perspective: Physicochemical and in vitro Parameters Relevant for Drug Discovery", European Journal of Medicinal Chemistry, 2017, 126, 225-245.
Goho, A. "Tricky Business", Science News, 2004, 166(8), 122-124.
Golub, T. R. et al. "Molecular Classification of Cancer: Class Discovery and Class Prediction by Gene Expression Monitoring", Science, 1999, 286, 531-537.
Gould, P. L. "Salt selection for basic drugs", International Journal of Pharmaceutics, 1986, 33, 201-217.
Graham, D. L. et al. "Increased O-GlcNAcylation reduces pathological tau without affecting its normal phosphorylation in a mouse model of tauopathy", Neuropharmacology, 2014, 79, 307-313.
Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54 (11), 3935-3949.
Haleblian, J.; McCrone, W. "Pharmaceutical Applications of Polymorphism", J. Pharm. Sci., 1969, 58(8), 911-929.
Haleblian, J. "Characterization of Habits and Crystalline Modification of Solids and Their Pharmaceutical Applications", J. Pharm. Sci., 1975, 64(8), 1269-1288.
Hemming, K. "Product Class 6: 1,2,4-Oxadizoles" Science of Synthesis, (2004), 13(6), pp. 127-184.
Jakopin Z. et al. "Recent Advances in the Synthesis of 1,2,4- and 1,3,4-Oxadiazoles" Current Organic Chemistry, (2008), 12(10), pp. 850-898.
Kempson, J. "Name Reactions in Heterocyclic Chemistry II" John Wiley & Sons. Eds. Jie Jack Li and E. J. Corey, (2011), pp. 299-308.
Kim, E. J. et al. "Enzymatic characterization of O-GlcNAcase isoforms using a fluorogenic GlcNAc substrate", Carbohydrate Research, 2006, 341(8), 971-982.
Kim, E. J. "Chemical Arsenal for the Study of O-GlcNAc", Molecules, 2011, 16, 1987-2022.
Knapp, S. et al. "An Allosamizoline/ Glucosamine Hybrid NAGase Inhibitor", Synlett, 1997, 5, 435-436.
Lefebvre, T. "Recall sugars, forget Alzheimer's", Nature Chemical Biology, 2012, 8(4), 325-326.
Legros, J. et al. "Applications of Catalytic Asymmetric Sulfide Oxidations to the Syntheses of Biologically Active Sulfoxides", Adv. Synth. Catal., 2005, 347, 19-31.
Liu, X. et al. "Rational Use of Plasma Protein and Tissue Binding Data in Drug Design", J. Med. Chem. 2014, 57, 8238-8248.
Marwaha, A. et al. "Bioisosteric Transformations and Permutations in the Triazolopyrimidine Scaffold to Identify the Minimum Pharmacophore Required for Inhibitory Activity against Plasmodium falciparum Dihydroorotate Dehydrogenase", J. Med. Chem., 2012, 55(17), 7425-7436.

Mariappa, D. et al. "A mutant O-GlcNAcase as a probe to reveal global dynamics of the *Drosophila* O-GlcNAc developmental proteome", Biochem J., 2015, 470(2), 255-262.
Marotta, N. P. et al. "O-GlcNAc modification blocks the aggregation and toxicity of the Parkinson's disease associated protein α-synuclein", Nat. Chem, 2015, 7(11), 913-920.
Masuda, N. et al. "Studies of nonnucleoside HIV-1 reverse transcriptase inhibitors. Part 1: Design and synthesis of thiazolidenebenzenesulfonamides", Bioorg. Med. Chem., 2004, 12, 6171-6182.
Mittur A. "Piribedil: Antiparkinsonian Properties and Potential Clinical Utility in Dopaminergic Disorders" Current Drug Therapy (2011), 6, pp. 17-34.
Moradi-Afrapoli, F. et al. "In vitro α-glucosidase inhibitory activity of phenolicconstituents from aerial parts of Polygonum hyrcanicum", DARU Journal of Pharmaceutical Sciences, 2012, 20(1), 37, 6 pages.
Nandi, A. et al. "Global Identification of O-GlcNAc-Modified Proteins", Anal. Chem., 2006, 78, 452-458.
Nelson, P. T. et al. "Correlation of Alzheimer Disease Neuropathologic Changes With Cognitive Status: A Review of the Literature", J. Neuropathol. Exp. Neurol., 2012, 71(5), 362-381.
Nettekoven, M. et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis, 2003, 1649-1652.
Obach, R. S. "Prediction of human clearance of twenty-nine drugs from hepatic microsomal intrinsic clearance data: and examination of in vitro half-life approach and nonspecific binding to microsomes", Drug. Metab. Dispos., 1999, 27(11), 1350-1359.
Okamura, H. et al. "Rhodium-Catalyzed Imination of Sulfoxides and Sulfides: Efficient Preparation of N-Unsubstituted Sulfoximines and Sulfilimines", Organic Letters, 2004, 6, 1305-1307.
O'Mahony, G. E. et al. "Synthesis of enantioenriched sulfoxides" Arkivoc, 2011, 1-110.
Orain, D. et al. "Synthesis of Orthogonally Protected 2,6-Diazaspiro[3.5]nonane and 2,6-Diazaspiro[3.4]octane Analogues as Versatile Building Blocks in Medicinal Chemistry", Synlett, 2015, 26(13), 1815-1818.
Papillon, J. P. N. et al. "Discovery of N-[5-(6-Chloro-3-cyano-l-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58(23), 9382-9394.
Park, M.-J. et al. "High Glucose-induced O-GlcNAcylated Carbohydrate Response Element-binding Protein (ChREBP) Mediates Mesangial Cell Lipogenesis and Fibrosis", J. Biol. Chem., 2014, 289, 13519-13530.
Rouhi, A. M. et al. "The Right Stuff: From Research and Development to the Clinic, Getting Drug Crystals Right is Full of Pitfalls." Chem. Eng. News. (2003):32-35.
SantaCruz, K. et al. "Tau Suppression in a Neurodegenerative Mouse Model Improves Memory Function", Science, 2005, 309, 476-481.
Serajuddin, A. T. M. "Salt formation to improve drug solubility", Advanced Drug Delivery Reviews, 2007, 59(7), 603-616.
Shan, X. et al. "Reduced protein O-glycosylation in the nervous system of the mutant SOD1 transgenic mouse model of amyotrophic lateral sclerosis", Neuroscience Letters, 2012, 516, 296-301.
Shen, Q. et al. "Hydroxycoumarin Derivatives: Novel and Potent α-Glucosidase Inhibitors", J. Med. Chem., 2010, 53(23), 8252-8259.
Shirude, P. et al. "Lead Optimization of 1,4-Azaindoles as Antimycobacterial Agents", J. Med. Chem., 2014, 57(13), 5728-5737.
Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.
Skedelj, V. et al. "Discovery of the first inhibitors of bacterial enzyme D-aspartate ligase from Enterococcus faecium (Asl$_{fm}$)", Eur. J. Med. Chem., 2013, 67, 208-220.

(56) References Cited

OTHER PUBLICATIONS

Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.
Sperling, R. A. et al. "Toward defining the preclinical stages of Alzheimer's disease: Recommendations from the National Institute on Aging-Alzheimer's Association workgroups on diagnostic guidelines for Alzheimer's disease", Alzheimers Dement., 2011, 7, 280-292.
Spillantini, M. G.; Goedert, M. "Tau pathology and neurodegeneration", Lancet Neurol., 2013, 12, 609-622.
Tamura, B. K. et al. "Weight Loss in Patients with Alzheimer's Disease" J. Nutrition for the Elderly (2008), 26(3-4), pp. 21-38.
Tan, H. et al. "Rational Screening Approach for Classical Chiral Resolution under Thermodynamic Equilibrium: A Case Study of Diphenyl-Substituted N-Methyl-Piperazine", Organic Process Research and Development, 2011, 15(1), 53-63.
Tanuwidjaja, J. et al. "One-Pot Asymmetric Synthesis of Either Diastereomer of tert-Butanesulfinyl-protected Amines from Ketones", J. Org. Chem. 2007, 72, 626-629.
The U. S. Pharmacopeia 38—National Formulary 35 Chapter 941, Characterization of crystalline and partially crystalline solids by X-ray powder diffraction (XRPD) Official May 1, 2015, 427-431.
Thiel, O. R. et al. "Practical Synthesis of a Vanilloid Receptor-1 Antagonist" J. Org. Chem., (2008), 73(9), pp. 3508-3515.
Trapannone, R. et al. "O-GlcNAc transferase inhibitors: current tools and future challenges", Biochemical Society Transactions, 2016, 44(1), 88-93.
Vasudevan, A. et al. "Identification of aminopiperidine benzamides as MCHr1 antagonists", Bioorganic & Medicinal Chemistry Letters, 2005, 15(14), 3412-3416.
Volpe, D. A. "Application of Method Suitability for Drug Permeability Classification", The AAPS Journal, 2010, 12(4), 670-678.
Wall, G. M. "Pharmaceutical Applications of Drug Crystal Studies", Pharm. Manuf., 1986, 3, 32-42.
Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.
Waterman, K. C. "Improved Protocol and Data Analysis for Accelerated Shelf-Life Estimation of Solid Dosage Forms", Pharm. Res., 2007, 24(4), 780-790.
Weinberg, K. et al. "Synthesis and differential functionalisation of pyrrolidine and piperidine based spirodiamine scaffolds", Tetrahedron, 2013, 69(23), 4694-4707.
Wermuth, C. G. et al. "Designing Prodrugs and Bioprecursors I: Carrier Prodrugs", The Practice of Medicinal Chemistry: Chapter 31, Academic Press, 1996, 671-696.
Wiessner et al. "A novel non-carbohydrate o-linked beta-n-acetylglucosaminidase inhibitor increases tau o-glcnacylation In vivo", Abstracts of the Annual Meeting of the Society for Neuroscience, Society for Neuroscience, 2013, 43, 2 pages.
Williams, D. R. et al. "Pathological tau burden and distribution distinguishes progressive supranuclear palsy-parkinsonism from Richardson's syndrome", Brain, 2007, 130, 1566-1576.
Yoshida, M. et al. "Study of biodegradable copoly(L-lactic acid/glycolic acid) formulations with controlled release of Z-100 for application in radiation therapy", Int. J. Pharm., 1995, 115, 61-67.
Yuzwa, S. A. et al. "Mapping O-GlcNAc modification sites on tau and generation of a site-specific O-GlcNAc tau antibody", Amino Acids, 2011, 40, 857-868.
Yuzwa, S. A. et al. "A potent mechanism-inspired O-GlcNAcase inhibitor that blocks phosphorylation of tau in vivo", Nat. Chem. Biol., 2008, 4(8), 483-490.
Yuzwa, S. A. et al. "Increasing O-GlcNAc slows neurodegeneration and stabilizes tau against aggregation", Nat. Chem. Biol., 2012, 8(4), 393-399.
Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.
Hiroshi Yamanaka, Hiroshi Miyazaki and Naomi chi Murakami, Chemical Abstract, "Separation of optical isomers", Japan, Gakkai Shopping Santa, 1989, No. 6, pp. 8, 9, 124, 212, and 213 (21 pages).

* cited by examiner

GLYCOSIDASE INHIBITORS

RELATED APPLICATIONS

This application is a continuation of U.S. application Ser. No. 15/507,375, filed Feb. 28, 2017, now U.S. Pat. No. 10,336,775, which is a U.S. National Phase application, filed under 35 U.S.C. § 371(c), of International Application No. PCT/EP2015/069598, filed Aug. 27, 2015, which claims the benefit of, and priority to, Indian Patent Application No. 2766/MUM/2014, filed Aug. 28, 2014, the entire contents of each of which are incorporated herein by reference in their entireties.

The present invention relates to a medicament comprising a compound of formula (I)

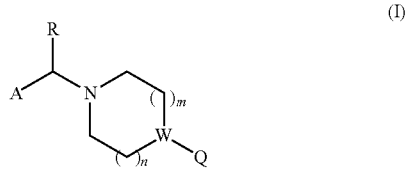

(I)

wherein A, R, W, Q, n and m have the meaning according to the claims, and/or physiologically acceptable salts, tautomers, solvates, stereoisomers and derivatives thereof. The compounds of formula (I) can be used as glycosidase inhibitors. Objects of the invention are also pharmaceutical compositions comprising the compounds of formula (I), and the use of the compounds of formula (I) for the treatment of one or more tauopathies and Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including tauopathies, Alzheimer's disease (AD), Parkinson's disease, and cancer.

For example, it is well established that AD and a number of related tauopathies including Progressive Supranuclear Palsy (PSP), Down's syndrome, Pick's disease, Niemann-Pick Type C disease and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of tauopathies and Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. Moreover, it has been described that the O-GlcNAc modification of tau directly inhibits its aggregation without perturbing the conformational properties of tau monomers. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal 1-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from studies showing that when transgenic mice harboring human tau are treated with kinase inhibitors, they do not develop typical motor defects and, in another case, show a decreased level of insoluble tau. These studies provide a clear link between lowering tau phosphorylation levels and alleviating AD-like behavioral symptoms in a murine model of this disease.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and related Synucleinopathies, and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type ii diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

Low molecular weight OGA inhibitors are e.g. disclosed in the international applications WO 2008/025170 and WO 2014/032187. However, no OGA inhibitor has reached the market yet. Thus, there is still a need for low molecular weight molecules that selectively inhibit OGA.

U.S. Pat. No. 3,489,757, mentions i.a. the following compounds:

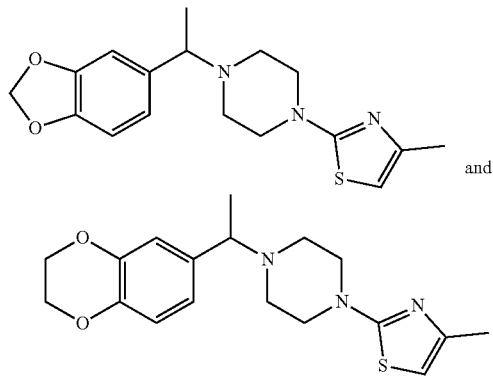

(1-[1-(1,3-benzodioxol-5-yl)ethyl]-4-(4-methyl-2-thiazolyl)-piperazine (example 144) and 2-(4-(1-(2,3-dihydrobenzo[b][1,4]dioxin-6-yl)ethyl)piperazin-1-yl)-4-methylthiazole).

U.S. Pat. No. 3,485,757 teaches the respective compounds for the treatment of hypertension and does not relate to the use in the treatment of neurodegenerative diseases, stress, cancer or diabetes or to OGA inhibitor activity.

U.S. Pat. No. 3,299,067 discloses compounds as medicaments, in particular as peripheral vasodilators, analgesics and anti-inflammatory agents. U.S. Pat. No. 3,299,067 does not disclose any OGA inhibitor activity. The compounds of U.S. Pat. No. 3,299,067 bear a methylene group in the bridging position. U.S. Pat. No. 3,299,067 does not refer to any OGA inhibitor activity.

WO 99/21850 discloses compounds that bind to the dopamine D4 receptor subtype and are said to be useful in treatment of various neuropsychological disorders. However, the compounds are not active as OGA inhibitors. For example, compound 5 of WO 99/21850 shows the following data, when measured according to Example B01 of the present application (Human O-GlcNAcase enzyme inhibition assay):

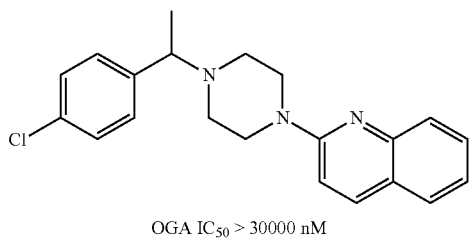 [SMILES: CC(c1ccc(Cl)cc1)N1CCN(c2ccc3ccccc3n2)CC1]

OGA IC$_{50}$ > 30000 nM

Compounds that modulate MCH binding to MCH receptors are presented in WO 2005/110982. The compounds are said to be useful in the treatment of eating disorders, sexual disorders, diabetes, heart disease, and stroke, which are unrelated to the indications of the present invention. The compounds are not active as OGA inhibitors. For instance, the compound of example 72 of WO 2005/110982 provides the following data, when measured according to Example B01 of the present application:

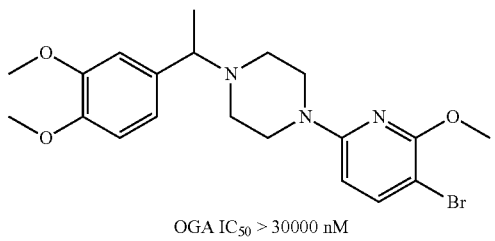

OGA IC$_{50}$ > 30000 nM

WO 2009/053373 discloses molecules for the treatment of PARP-mediated disorders, such as neurodegenerative diseases. The molecules of WO 2009/053373 are not useful as OGA inhibitors. For instance, the compound of example 56 of WO 99/21850 shows the following data, when measured according to Example B01 of the present application:

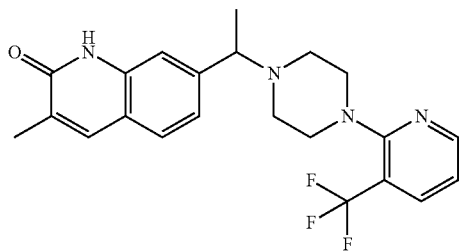

OGA IC$_{50}$ > 30000 nM

The present invention has the object of finding novel compounds having valuable properties, in particular those which can be used for the preparation of medicaments.

It has been surprisingly found that the compounds according to the invention and salts thereof have very valuable pharmacological properties. In particular, they act as glycosidase inhibitors. The invention relates to compounds of formula (I)

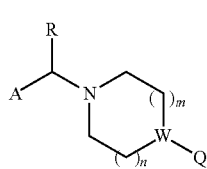

(I)

wherein
R is straight chain or branched alkyl having 1 to 6 carbon atoms, wherein 1 to 5 hydrogen atoms may be replaced by Hal or OH. Preferably R is methyl, CH$_2$OH, CF$_3$, CHF$_2$, CH$_2$F;
W is CH or N, preferably N;
A denotes one of the following groups:

X is N or CR'''. Preferably all or or one or two of X in a group are CH;
X$^1$, X$^2$ is N or CR''';
X$^3$ is N or CR'''';
Y is O, S, SO or SO$_2$. Preferably Y is O or S;
R', R'' denote each independently H, Hal or straight chain or branched alkyl having 1 to 12 carbon atoms. Preferably both are either H, F or methyl;
R''', R'''' independently denote H, Hal, NR$^3$R$^4$, CHR$^3$R$^4$, OR$^3$, CN, straight chain or branched alkyl having 1 to 12 carbon atoms, wherein 1 to 3 CH$_2$-groups may be replaced by a group selected from O, NR$^3$, S, SO, SO$_2$, CO, COO, OCO, CONR$^3$, NR$^3$CO and wherein 1 to 5 hydrogen atoms may be replaced by Hal, NR$^3$R$^4$ or NO$_2$. Preferably both R''' and/or R'''' are H, Hal, NR$^3$R$^4$, CHR$^3$R$^4$, OR$^3$, CN or alkyl;
R'''' denotes H, Hal, NR$^3$R$^4$, CHR$^3$R$^4$, CN, straight chain or branched alkyl having 1 to 12 carbon atoms, wherein 1 to 3 CH$_2$-groups may be replaced by a group selected from O, NR$^3$, S, SO, SO$_2$, CO, COO, OCO, CONR$^3$, NR$^3$CO and wherein 1 to 5 hydrogen atoms may be replaced by Hal, NR$^3$R$^4$ or NO$_2$. Preferably, R'''' is H, Hal or alkyl;

R³, R⁴ denote each independently H or a straight chain or branched alkyl group having 1 to 12 carbon atoms, preferably H, methyl or ethyl;

Q denotes one of the following groups:

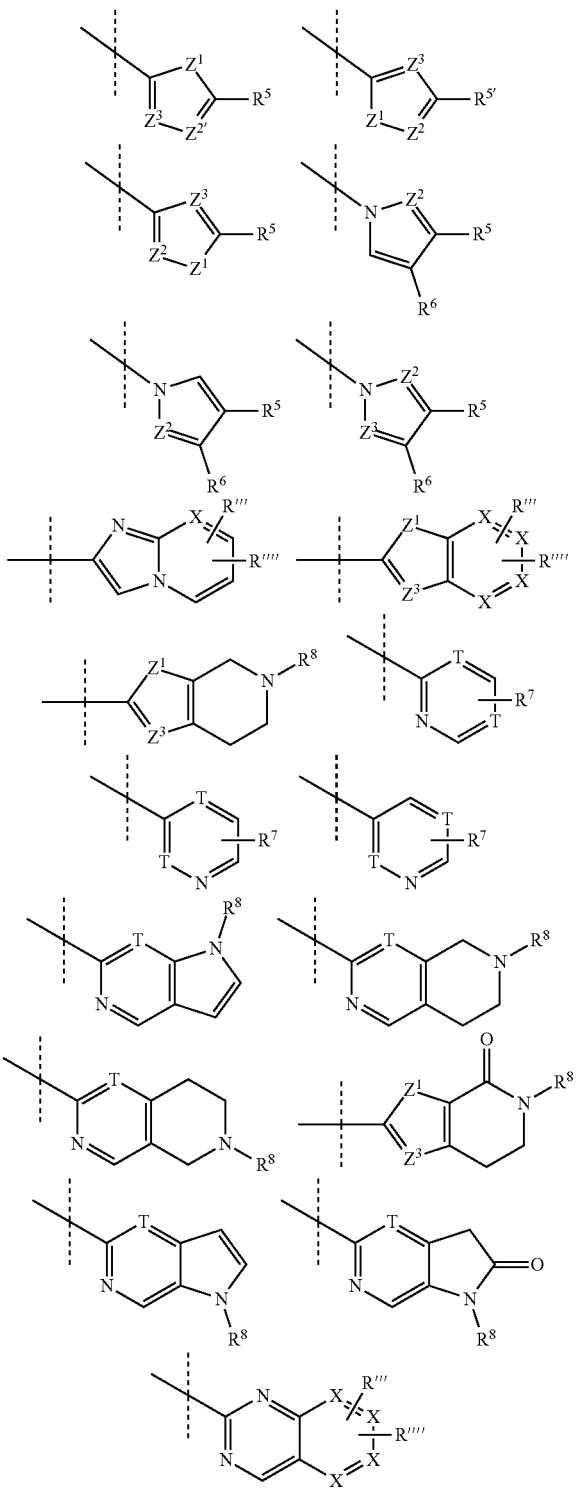

$Z^1$ is S, O, NR³;
$Z^2$, $Z^3$ independently denote CR⁵ or N;
$Z^{2'}$ is CR⁵' or N;
T is N, CH or CR⁷;

R⁵, R⁶, R⁷ independently denote H, Hal, NR³R⁴, NO₂, straight chain or branched alkyl having 1 to 12 carbon atoms, wherein 1 to 3 CH₂-groups may be replaced by a group selected from O, NR³, S, SO, SO₂, CO, COO, OCO, CONR³, NR³CO and wherein 1 to 5 hydrogen atoms may be replaced by Hal, NR³R⁴, NO₂, OR³, Het, Ar, Cyc, or denote Ar, Het or Cyc;

R⁵' denotes H, Hal, NR³R⁴, NO₂, a straight chain or branched alkyl having 2 to 12 carbon atoms, or a straight chain or branched alkyl having 1 to 12 carbon atoms, wherein 1 to 3 CH₂-groups are replaced by a group selected from O, NR³, S, SO, SO₂, CO, COO, OCO, CONR³, NR³CO and/or wherein 1 to 5 hydrogen atoms are replaced by Hal, NR³R⁴, NO₂, OR³, Het, Ar Cyc, or R⁵, denotes Ar, Het or Cyc; R⁵' may also denote methyl, in cases where R is other than methyl and/or W is CH and/or A is other than

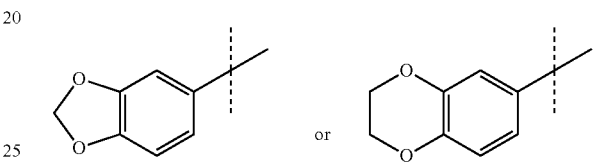

and/or n or m are 0, 2 or 3 and/or Z¹ is O or NR³ and/or Z² is N and/or Z³ is CR⁵ and/or R⁵ is other than H and/or the compound of formula I is not a racemate;

R⁸ denotes H, methyl or straight chain or branched alkyl having 2 to 12 carbon atoms, wherein 1 to 3 CH₂-groups may be replaced by a group selected from O, NR³, S, SO, SO₂, CO, COO, OCO, CONR³, NR³CO and wherein 1 to 5 hydrogen atoms may be replaced by Hal, NR³R⁴ or NO₂;

Hal denotes F, Cl, Br or I, preferably F, Cl or Br;

Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from R⁵, Hal and OR³:

Ar denotes a 6-membered carbocyclic aromatic ring or a fused or non-fused bicylic aromatic ring system, which is optionally substituted by 1 to 3 substituents independently selected from R⁵, OR³ and Hal;

Cyc denotes a saturated carbocyclic ring having from 3 to 8 carbon atoms which is optionally substituted by 1 to 3 substituents independently selected from R⁵ or Hal or OH;

m and n denote independently from one another 0, 1, 2 or 3
and pharmaceutically usable derivatives, solvates, salts, prodrugs, tautomers, enantiomers, racemates and stereoisomers thereof, including mixtures thereof in all ratios and compounds of formula I, wherein one or more H atoms are replaced by D (deuterium).

Specifically, formula (I) includes the following two enantiomers of formula Ia and Ib:

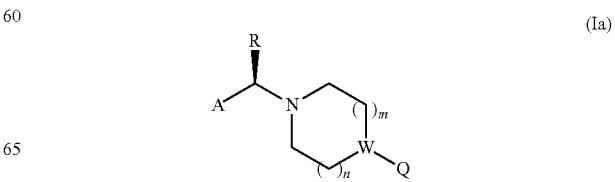
(Ia)

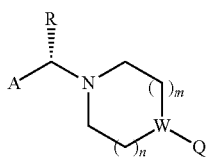

(Ib)

wherein A, R, W, Q, n and m have the meaning given above.

Throughout the specification, R in formula I, Ia and Ib is preferably methyl. The indices m and n in formula I, Ia and Ib are preferably simultaneously 1.

Most preferably, compounds of formula I are the compounds of formula A and B:

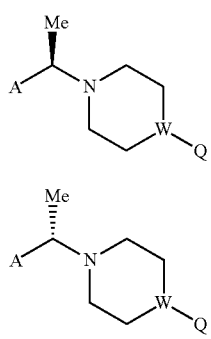

(A)

(B)

If individual groups, such as T, occurs more than once in a compound of formula I, it can have the same or different meanings according to the respective definition of that group.

Preferred compounds of the present invention are preferably used in their non-racemic form, i.e. as enantiomerically pure compounds or their enantiomerically enriched mixtures of the enantiomers. If R is an unsubstituted straight chain or branched alkyl having 1 to 6 carbon atoms, such as methyl, ethyl, n-propyl or iso-butyl, the S-enantiomers of compounds of formula I are preferred. Very preferred are formulae Ib and B.

In general, compounds of formula I are preferred that contain one ore more preferred groups such as R' to R'''' or $R^3$ to $R^7$ or indices such as m or n. Compounds of formula I are the more preferred, the more preferred groups or indices they contain.

If substituents, such as the group $R^8$, are connected to the remainder of the molecule through a heteroatom, the connecting atom in the respective group is preferably a carbon atom or the respective group is H.

The invention also relates to the use of compounds of formula (I) as a medicament.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention. It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

An enantiomerically enriched mixture denotes a compound of Formula (I) or related formula having an enantiomeric excess, as measured by methods well known by one skilled in the art, of 10% or more, preferably 50% or more, and more preferably more than 95%. Most preferably an enantiomerically enriched mixture denotes a compound of Formula (I) or related Formulae having an enantiomeric excess of more than 98%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01. The determination of the stereochemistry (S) or (R) is performed using standard rules of the nomenclature well known by one skilled in the art. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, iso-propyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In an embodiment of the invention, A denotes unbranched or branched alkyl having 1-10 C atoms, in which 1-7 H atoms may be replaced independently from one another by Hal. A preferred embodiment of A denotes unbranched or branched alkyl having 1-6 C atoms, in which 1-4 atoms may be replaced independently from one another by Hal. In a more preferred embodiment of the invention, A denotes unbranched or branched alkyl having 1-4 C atoms, in which 1-3 H atoms can be replaced independently from one another by Hal, particularly by F and/or Cl. It is most preferred that A denotes unbranched or branched alkyl having 1-6 C atoms. Highly preferred is C^-alkyl. A C^-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "cycloalkyi" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyi radical may also be part of a bi- or polycyclic system, where, for example, the cycloalkyi radical is fused to an aryl, heteroaryl or heterocyclyl radical as defined herein by any possible and desired ring member(s). The bonding to the compounds of the general formula (I) can be effected via any possible ring member of the cycloalkyi radical. Examples of suitable cycloalkyi radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Ar and aryl are preferably selected from the following group: phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluoro-phenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2.5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazoM-, -4- or -5-yl, 1,2,4-triazo-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5indolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl.

The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes piperidinyl, 4-hydroxypiperidinyl, piperazinyl, 4-methylpiperazinyl. pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyi) or alkoxy group (e.g. $CF_3$ and $CF_3O$). It shall be understood that the respective denotation of Hal is independently of one another in any radical of the invention.

R is preferably straight chain alkyl having 1 to 4 carbon atoms, wherein 1 to 5 hydrogen atoms may be replaced by Hal or OH. More preferably R is methyl or ethyl, and most preferably methyl.

W is preferably N.

A preferably denotes one of the following groups:

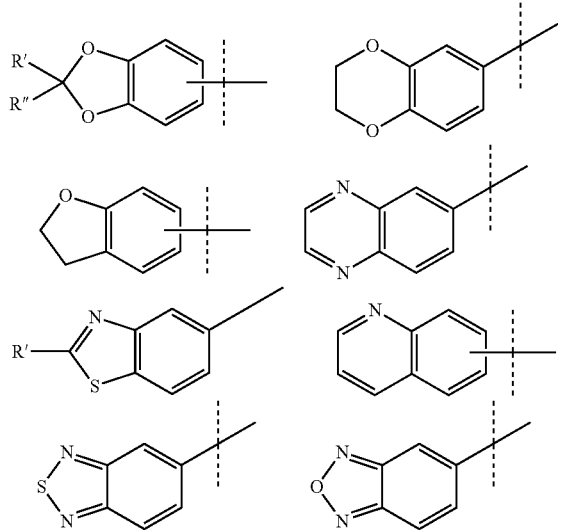

A is especially preferred one of the following groups:

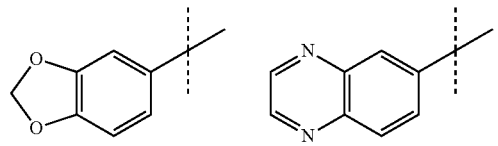

Q is preferably

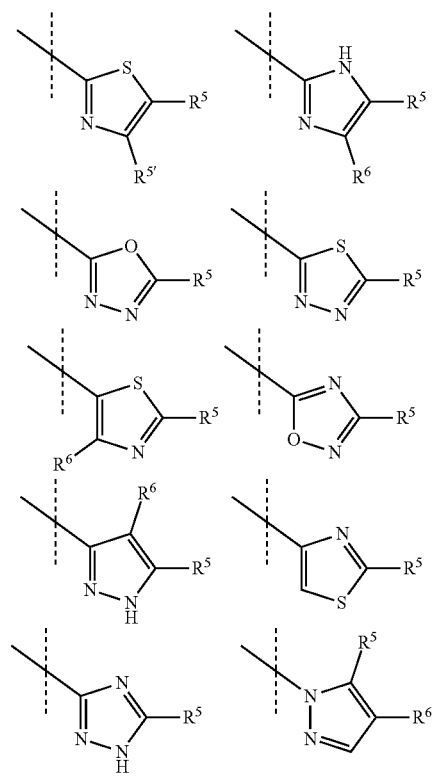

-continued

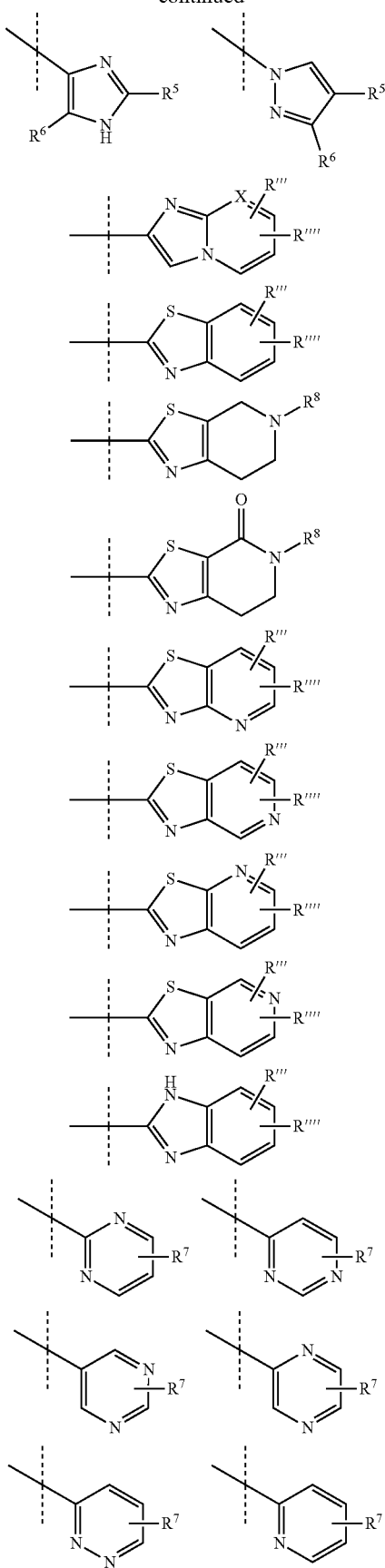

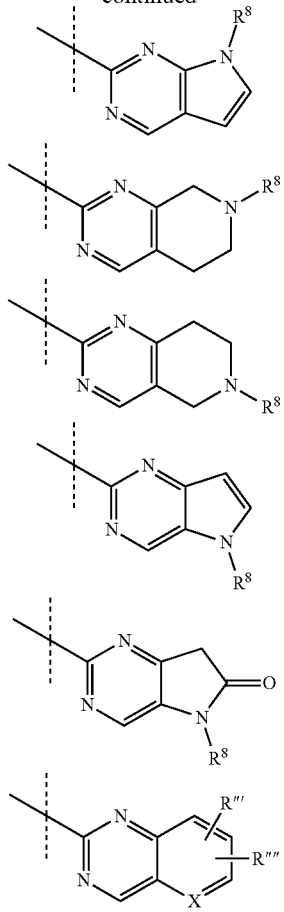

R⁵, R⁵', R⁶ are preferably independently H, Hal, NR³R⁴, NO₂, phenyl, 2-, 3- or 4-hydroxy or methoxyphenyl, alkyl, preferably methyl, ethyl, isopropyl, isobutyl, tert-butyl, CF₃, alkoxy (Oalkyl), preferably methoxy or ethoxy, hydroxyalkylen, preferably CH₂OH, alkoxyalkylen preferably CH₂OCH₃, COOH, COOalkyl, preferably COOCH₃, COOCH₂CH₃, CONHalkyl, preferably CONHCH₃, CONHCH₂CH₃, CONHisopropyl, CONHcyclohexyl, CONH₂, CON(CH₃)₂, NHCOalkyl, preferably NHCOCH₃, NHCOCH₂OH₃, NHCOPropyl, NHCOisopropyl, NHCO-cyclopropyl, NHCO-4-Chloro-phenyl, NHCH₂CH₃, NHCH₂CH₂CH₃, NHCOCH₂CH₂OH, CO—N-morpholinyl, CON(CH₃)CH₂CH₂N(CH₃)₂, CO-1-piperidinyl, CO-4-hydroxy-1-piperidinyl, CO-1-piperazinyl, CO-4-methyl-1-piperazinyl, CH₂—N-morpholinyl, CH₂N(H)COCH₃, CH₂N(CH₃)COCH₃, CH₂N H₂, NH₂, CH(OH)CH₃, CH(OR³)CH₃

Most preferably, one of R⁵, R⁶ is H.

R⁷ has preferably the meaning of R⁵ and R⁶. More preferably, R⁷ is H, OCH₃, CH₃, CH₂CH₃, CF₃, Hal, preferably Cl, I, F, NH₂, NO₂, CONHalkyl, preferably CONHCH₃, CON(CH₃)₂, NHCOalkyl such as NHCOCH₃, NHalkyl, such as NHCH₂CH₂CH₃, COOalkyl, preferably COOCH₂CH₃, hydroxyalkylen, preferably CH₂OH, CH(CH₃)OH, C(CH₃)₂OH, cyclohexyl, cyclopentyl, morpholinyl, tetrahydrofuranyl. Preferably cyclohexyl, cyclopentyl, morpholinyl, tetrahydrofuranyl are substituted by OH. Most preferred are:

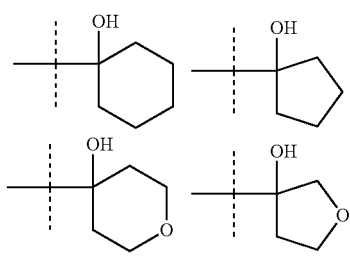

$R^8$ is preferably H, COalkyl or alkyl. More preferably, $R^8$ is H, COmethyl or methyl.

Most preferably, m and n simultaneously denote 1.

Accordingly, the subject-matter of the invention relates to compounds of formula (I) as medicament, in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

Particularly highly preferred embodiments are those compounds of formula (I) listed in Table 1 and/or physiologically acceptable salts thereof.

TABLE 1

Compounds of formulae (I). OGA enzyme inhibition assay:

| No | Structure | Configuration specification | OGA IC50 (M) |
|---|---|---|---|
| 1 | 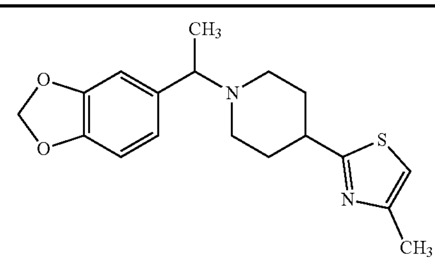 | Racemic | ++ |
| 2 | 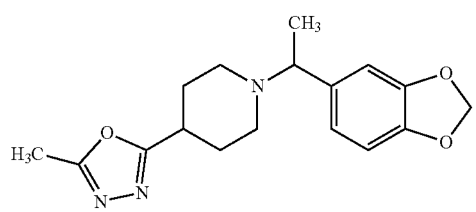 [SMILES: Cc1nnc(C2CCN(C(C)c3ccc4c(c3)OCO4)CC2)o1] | Racemic | ++ |
| 3 | 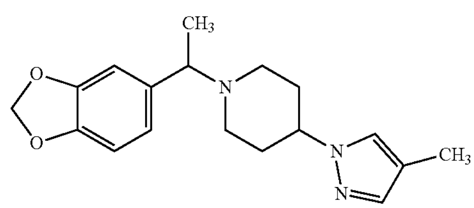 [SMILES: Cc1cnn(C2CCN(C(C)c3ccc4c(c3)OCO4)CC2)c1] | Racemic | + |
| 4 | 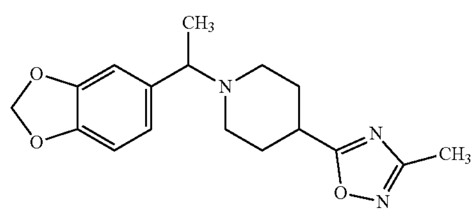 [SMILES: Cc1noc(C2CCN(C(C)c3ccc4c(c3)OCO4)CC2)n1] | Racemic | ++ |
| 5 | 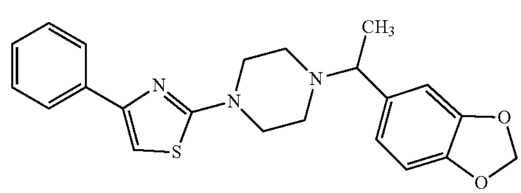 [SMILES: CC(c1ccc2c(c1)OCO2)N1CCN(c2nc(-c3ccccc3)cs2)CC1] | Racemic | ++ |

TABLE 1-continued

Compounds of formulae (I). OGA enzyme inhibition assay:

| No | Structure | Configuration specification | OGA IC50 (M) |
|----|-----------|----------------------------|--------------|
| 6  | 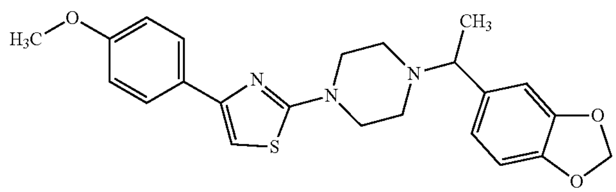 [SMILES: COc1ccc(-c2csc(N3CCN(C(C)c4ccc5c(c4)OCO5)CC3)n2)cc1]          | Racemic | + |
| 7  | 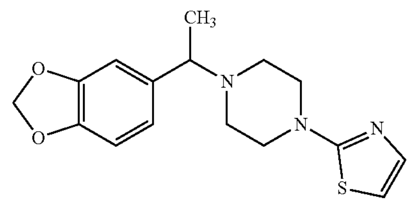 [SMILES: CC(c1ccc2c(c1)OCO2)N1CCN(c2nccs2)CC1]          | Racemic | ++ |
| 8  | 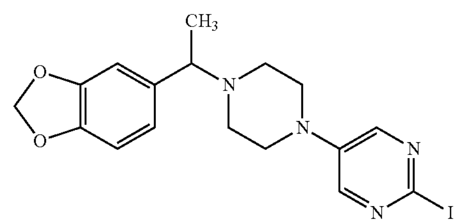 [SMILES: CC(c1ccc2c(c1)OCO2)N1CCN(c2cnc(I)nc2)CC1]          | Racemic | +++ |
| 9  | 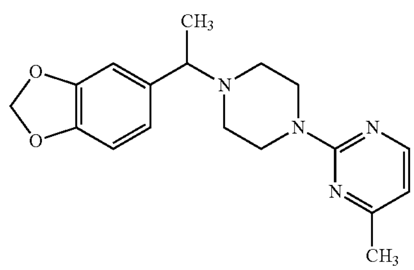 [SMILES: Cc1ccnc(N2CCN(C(C)c3ccc4c(c3)OCO4)CC2)n1]          | Racemic | ++ |
| 10 | 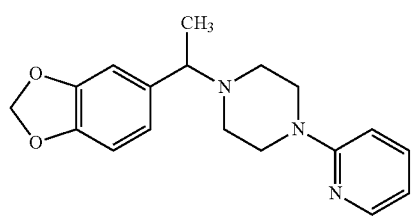 [SMILES: CC(c1ccc2c(c1)OCO2)N1CCN(c2ccccn2)CC1]          | Racemic | ++ |
| 11 | 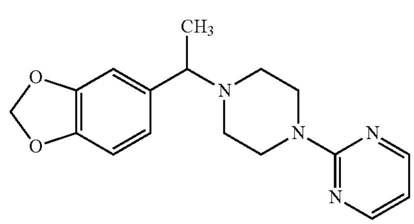 [SMILES: CC(c1ccc2c(c1)OCO2)N1CCN(c2ncccn2)CC1]          | Racemic | +++ |
| 12 | 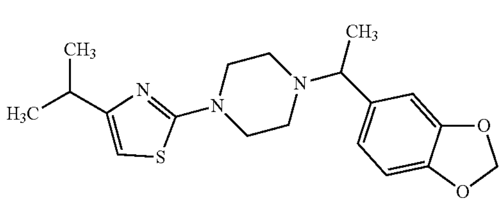 [SMILES: CC(C)c1csc(N2CCN(C(C)c3ccc4c(c3)OCO4)CC2)n1]          | Racemic | ++ |

TABLE 1-continued

Compounds of formulae (I). OGA enzyme inhibition assay:

| No | Structure | Configuration specification | OGA IC50 (M) |
|---|---|---|---|
| 13 | 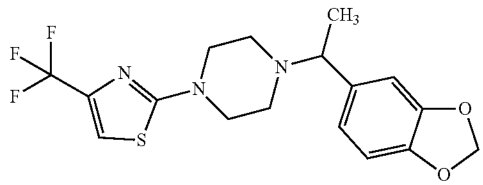 [SMILES: CC(c1ccc2c(c1)OCO2)N1CCN(c2nc(C(F)(F)F)cs2)CC1] | Racemic | ++ |
| 14 | 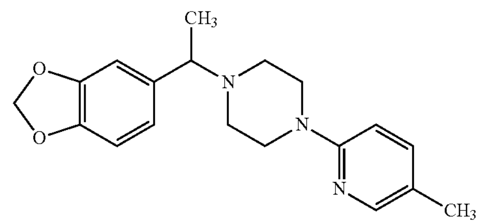 [SMILES: Cc1ccc(N2CCN(C(C)c3ccc4c(c3)OCO4)CC2)nc1] | Racemic | ++ |
| 15 | 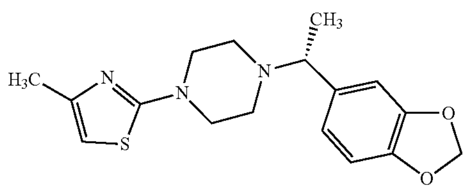 [SMILES: Cc1csc(N2CCN([C@H](C)c3ccc4c(c3)OCO4)CC2)n1] | Chiral HPLC Method C: 2nd eluting compound | +++ |
| 16 | 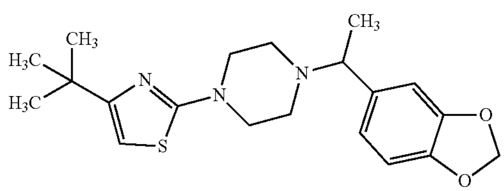 [SMILES: CC(c1ccc2c(c1)OCO2)N1CCN(c2nc(C(C)(C)C)cs2)CC1] | Racemic | + |
| 17 | 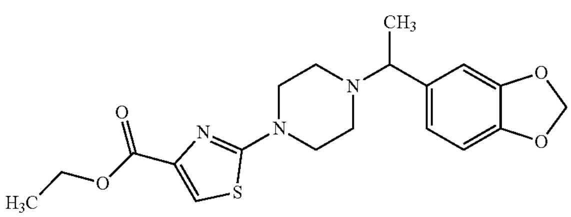 [SMILES: CCOC(=O)c1csc(N2CCN(C(C)c3ccc4c(c3)OCO4)CC2)n1] | Racemic | ++ |
| 18 | 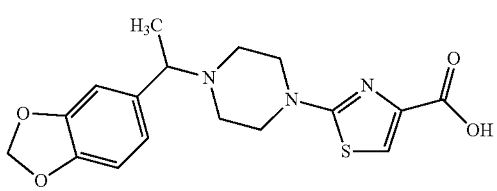 [SMILES: CC(c1ccc2c(c1)OCO2)N1CCN(c2nc(C(=O)O)cs2)CC1] | Racemic | +++ |
| 19 | 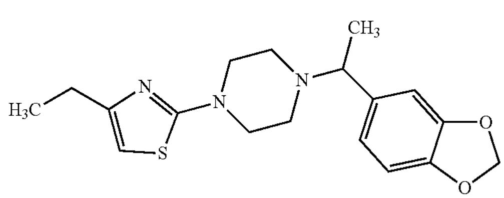 [SMILES: CCc1csc(N2CCN(C(C)c3ccc4c(c3)OCO4)CC2)n1] | Racemic | ++ |

TABLE 1-continued

Compounds of formulae (I). OGA enzyme inhibition assay:

| No | Structure | Configuration specification | OGA IC50 (M) |
|---|---|---|---|
| 20 | 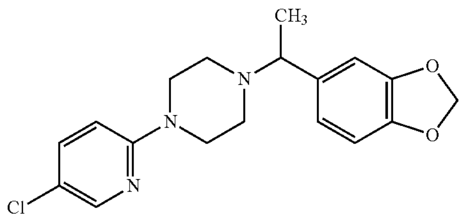 [SMILES: CC(c1ccc2c(c1)OCO2)N1CCN(c2ccc(Cl)cn2)CC1] | Racemic | ++ |
| 21 | 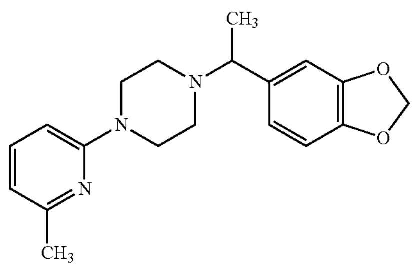 [SMILES: Cc1cccc(N2CCN(C(C)c3ccc4c(c3)OCO4)CC2)n1] | Racemic | ++ |
| 22 | 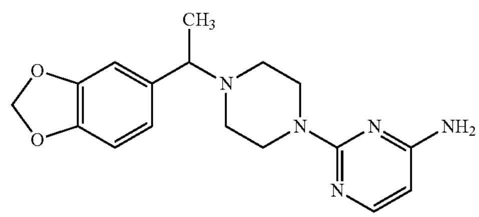 [SMILES: CC(c1ccc2c(c1)OCO2)N1CCN(c2nccc(N)n2)CC1] | Racemic | +++ |
| 23 | 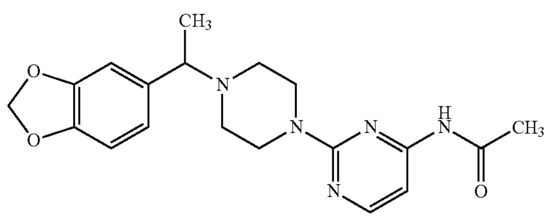 [SMILES: CC(=O)Nc1ccnc(N2CCN(C(C)c3ccc4c(c3)OCO4)CC2)n1] | Racemic | +++ |
| 24 | 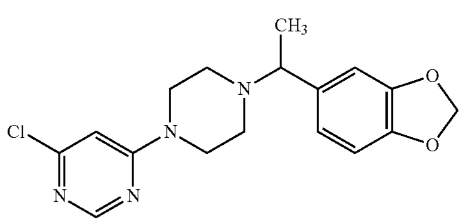 [SMILES: CC(c1ccc2c(c1)OCO2)N1CCN(c2cc(Cl)ncn2)CC1] | Racemic | +++ |
| 25 | 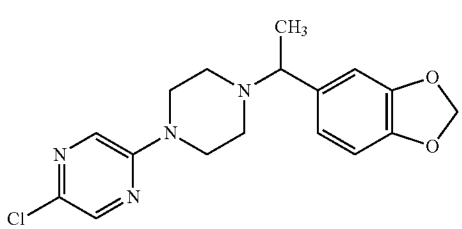 [SMILES: CC(c1ccc2c(c1)OCO2)N1CCN(c2cnc(Cl)cn2)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 26 | 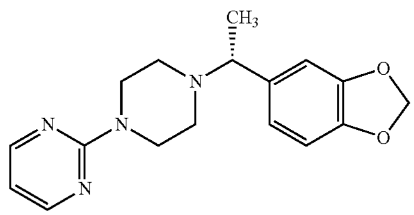 [SMILES: C[C@H](c1ccc2c(c1)OCO2)N1CCN(c2ncccn2)CC1] | Chiral HPLC Method D: 2nd eluting compound | +++ |
| 27 | 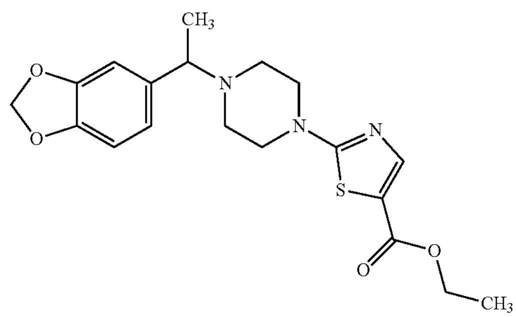 [SMILES: CCOC(=O)c1cnc(N2CCN(C(C)c3ccc4c(c3)OCO4)CC2)s1] | Racemic | ++ |
| 28 | 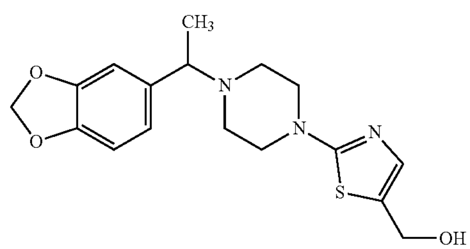 [SMILES: CC(c1ccc2c(c1)OCO2)N1CCN(c2ncc(CO)s2)CC1] | Racemic | +++ |
| 29 | 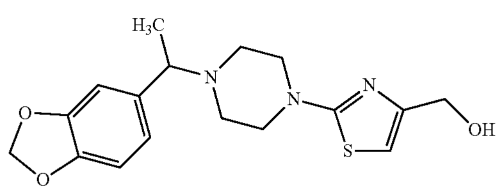 [SMILES: CC(c1ccc2c(c1)OCO2)N1CCN(c2nc(CO)cs2)CC1] | Racemic | +++ |
| 30 | 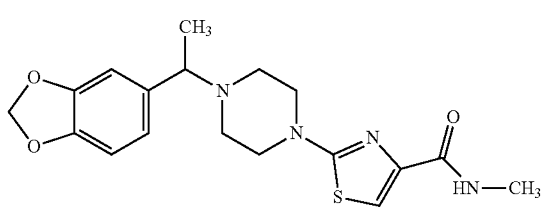 [SMILES: CNC(=O)c1csc(N2CCN(C(C)c3ccc4c(c3)OCO4)CC2)n1] | Racemic | +++ |
| 31 | 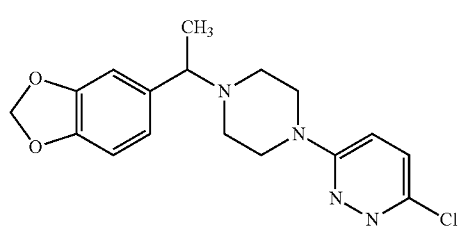 [SMILES: CC(c1ccc2c(c1)OCO2)N1CCN(C2=CC=C(Cl)NN2)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 32 | (1-(benzo[d][1,3]dioxol-5-yl)ethyl)piperazinyl-thiazole-4-carboxamide N-isopropyl | Racemic | ++ |
| 33 | (1-(benzo[d][1,3]dioxol-5-yl)ethyl)piperazinyl-thiazole-4-carboxamide N-cyclohexyl | Racemic | ++ |
| 34 | (S)-1-(2,3-dihydrobenzo[b][1,4]dioxin-6-yl)ethyl piperazinyl pyrimidine | Chiral HPLC Method D: 2nd eluting compound | ++++ |
| 35 | 1-(benzo[d][1,3]dioxol-5-yl)ethyl piperazinyl-thiazole-4-carboxamide | Racemic | +++ |
| 36 | 1-(benzo[d][1,3]dioxol-5-yl)ethyl piperazinyl-4-methylthiazole | Racemic | +++ |
| 37 | 1-(benzo[d][1,3]dioxol-5-yl)ethyl piperazinyl-2-methylthiazole | Racemic | ++++ |
| 38 | 1-(benzo[d][1,3]dioxol-5-yl)ethyl piperazinyl-5-chloropyrimidine | Racemic | +++ |

TABLE 1-continued

Compounds of formulae (I). OGA enzyme inhibition assay:

| No | Structure | Configuration specification | OGA IC50 (M) |
|----|-----------|----------------------------|--------------|
| 39 | 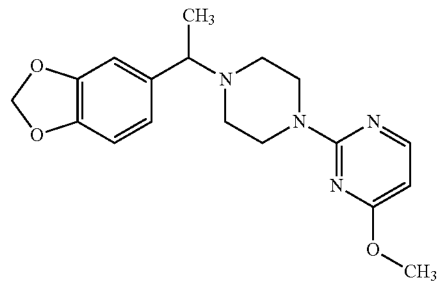 [SMILES: COc1ccnc(N2CCN(C(C)c3ccc4c(c3)OCO4)CC2)n1] | Racemic | +++ |
| 40 | 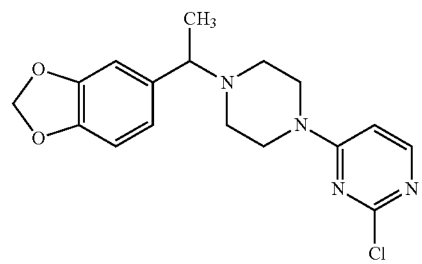 [SMILES: CC(c1ccc2c(c1)OCO2)N1CCN(c2ccnc(Cl)n2)CC1] | Racemic | +++ |
| 41 | 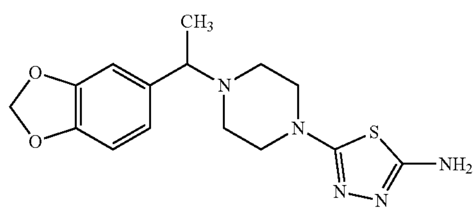 | Racemic | +++ |
| 42 | 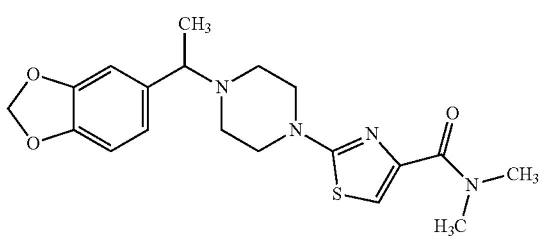 [SMILES: CC(c1ccc2c(c1)OCO2)N1CCN(c2nc(C(=O)N(C)C)cs2)CC1] | Racemic | ++ |
| 43 | 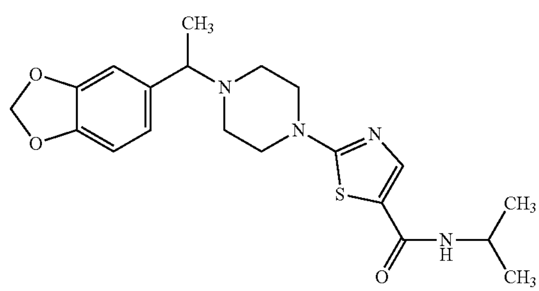 [SMILES: CC(C)NC(=O)c1cnc(N2CCN(C(C)c3ccc4c(c3)OCO4)CC2)s1] | Racemic | +++ |
| 44 | 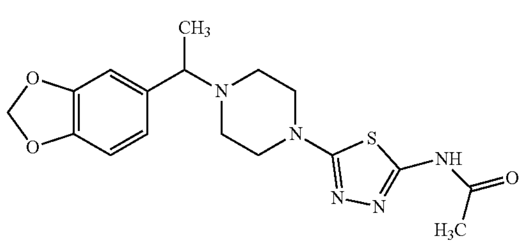 [SMILES: CC(=O)Nc1nnc(N2CCN(C(C)c3ccc4c(c3)OCO4)CC2)s1] | Racemic | ++++ |

TABLE 1-continued
Compounds of formulae (I). OGA enzyme inhibition assay:
| No | Structure | Configuration specification | OGA IC50 (M) |
|---|---|---|---|
| 45 | 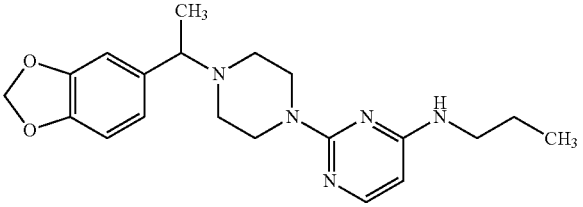 [SMILES: CCCNc1ccnc(N2CCN(C(C)c3ccc4c(c3)OCO4)CC2)n1] | Racemic | ++ |
| 46 | 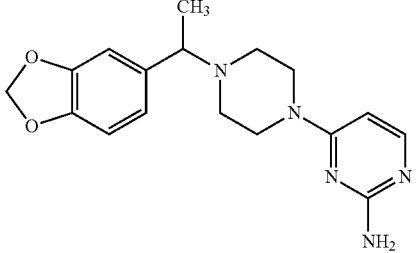 [SMILES: CC(c1ccc2c(c1)OCO2)N1CCN(c2ccnc(N)n2)CC1] | Racemic | +++ |
| 47 | 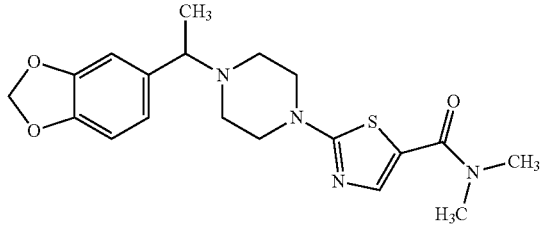 [SMILES: CC(c1ccc2c(c1)OCO2)N1CCN(c2ncc(C(=O)N(C)C)s2)CC1] | Racemic | +++ |
| 48 | 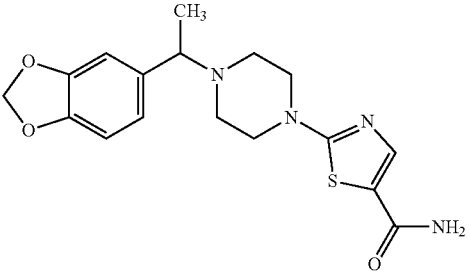 [SMILES: CC(c1ccc2c(c1)OCO2)N1CCN(c2ncc(C(N)=O)s2)CC1] | Racemic | ++++ |
| 49 | 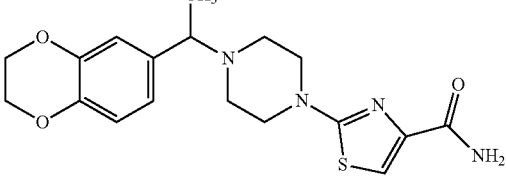 | Racemic | ++ |
| 50 | 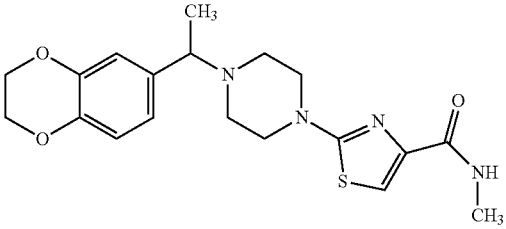 [SMILES: CNC(=O)c1csc(N2CCN(C(C)c3ccc4c(c3)OCCO4)CC2)n1] | Racemic | +++ |

TABLE 1-continued
Compounds of formulae (I). OGA enzyme inhibition assay:
| No | Structure | Configuration specification | OGA IC50 (M) |
|---|---|---|---|
| 51 | 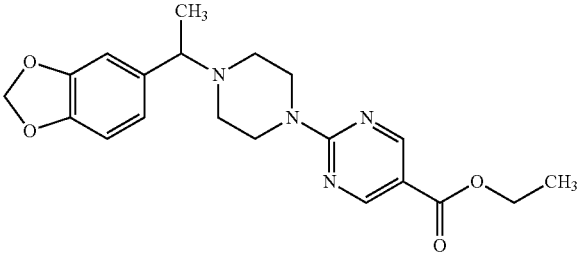 [SMILES: CCOC(=O)c1cnc(N2CCN(C(C)c3ccc4c(c3)OCO4)CC2)nc1] | Racemic | +++ |
| 52 | 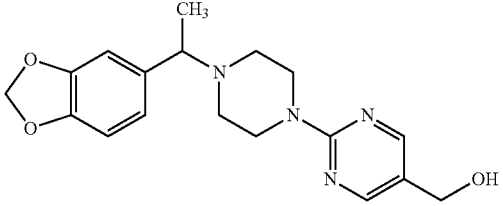 [SMILES: CC(c1ccc2c(c1)OCO2)N1CCN(c2ncc(CO)cn2)CC1] | Racemic | ++++ |
| 53 | 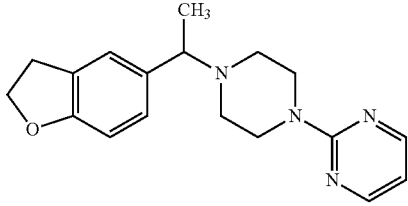 | Racemic | ++ |
| 54 | 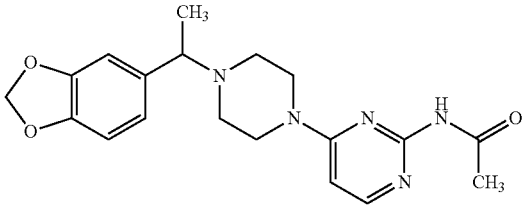 [SMILES: CC(=O)Nc1nccc(N2CCN(C(C)c3ccc4c(c3)OCO4)CC2)n1] | Racemic | +++ |
| 55 | 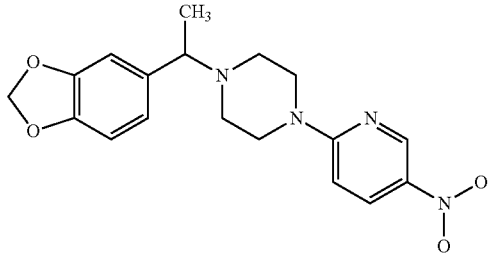 [SMILES: CC(c1ccc2c(c1)OCO2)N1CCN(c2ccc(N(O)O)cn2)CC1] | Racemic | +++ |
| 56 | 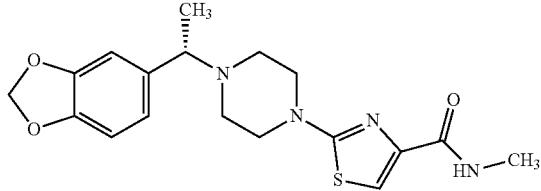 [SMILES: CNC(=O)c1csc(N2CCN([C@@H](C)c3ccc4c(c3)OCO4)CC2)n1] | Chiral HPLC Method E: 2nd eluting compound | ++++ |

TABLE 1-continued

Compounds of formulae (I). OGA enzyme inhibition assay:

| No | Structure | Configuration specification | OGA IC50 (M) |
|---|---|---|---|
| 57 | 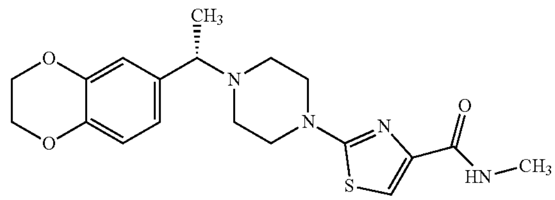 [SMILES: CNC(=O)c1csc(N2CCN([C@@H](C)c3ccc4c(c3)OCCO4)CC2)n1] | Chiral HPLC Method E: 2nd eluting compound | ++++ |
| 58 | 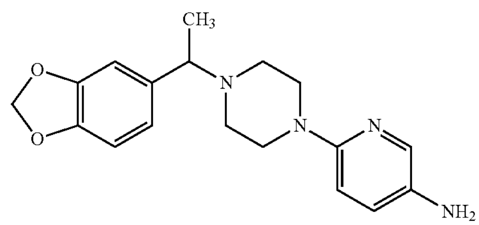 | Racemic | +++ |
| 59 | 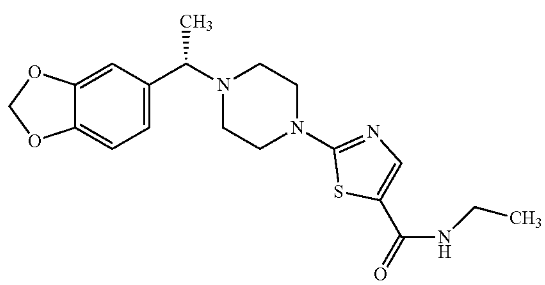 [SMILES: CCNC(=O)c1cnc(N2CCN([C@@H](C)c3ccc4c(c3)OCO4)CC2)s1] | Chiral HPLC Method D: 1st eluting compound | + |
| 60 | 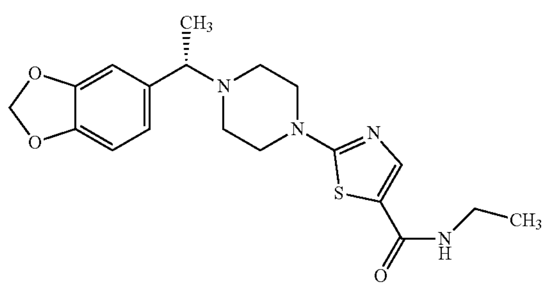 [SMILES: CCNC(=O)c1cnc(N2CCN([C@@H](C)c3ccc4c(c3)OCO4)CC2)s1] | Chiral HPLC Method D: 2nd eluting compound | +++ |
| 61 | 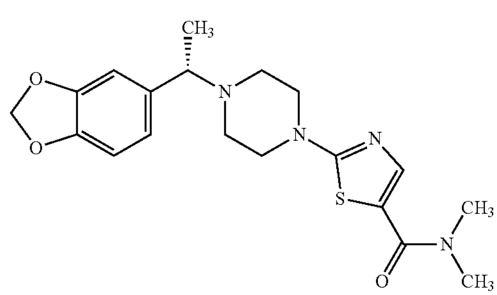 [SMILES: C[C@@H](c1ccc2c(c1)OCO2)N1CCN(c2ncc(C(=O)N(C)C)s2)CC1] | Chiral HPLC Method D: 2nd eluting compound | +++ |

TABLE 1-continued

Compounds of formulae (I). OGA enzyme inhibition assay:

| No | Structure | Configuration specification | OGA IC50 (M) |
|---|---|---|---|
| 62 | 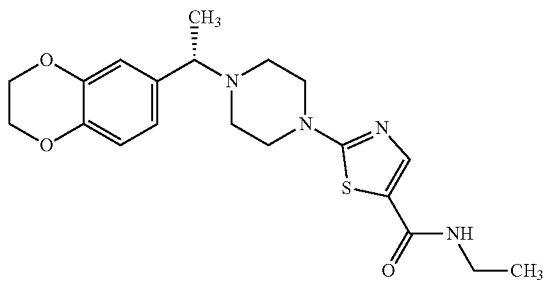 [SMILES: CCNC(=O)c1cnc(N2CCN([C@@H](C)c3ccc4c(c3)OCCO4)CC2)s1] | Chiral HPLC Method A: 1st eluting compound | +++ |
| 63 | 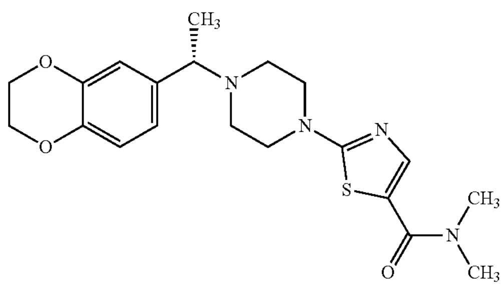 [SMILES: C[C@@H](c1ccc2c(c1)OCCO2)N1CCN(c2ncc(C(=O)N(C)C)s2)CC1] | Chiral HPLC Method D: 1st eluting compound | + |
| 64 | 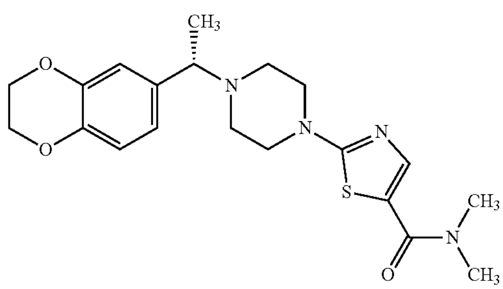 [SMILES: C[C@@H](c1ccc2c(c1)OCCO2)N1CCN(c2ncc(C(=O)N(C)C)s2)CC1] | Chiral HPLC Method D: 2nd eluting compound | ++++ |
| 65 | 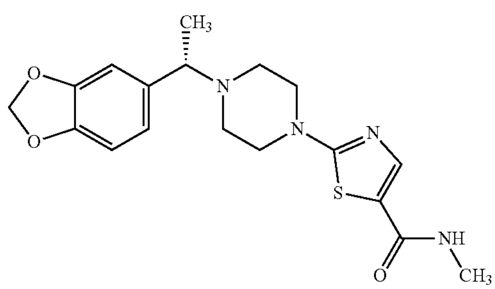 [SMILES: CNC(=O)c1cnc(N2CCN([C@@H](C)c3ccc4c(c3)OCO4)CC2)s1] | Chiral HPLC Method D: 1st eluting compound | + |
| 66 | 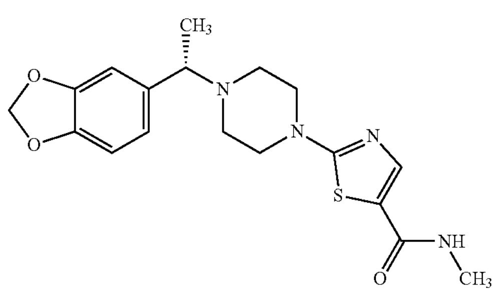 [SMILES: CNC(=O)c1cnc(N2CCN([C@@H](C)c3ccc4c(c3)OCO4)CC2)s1] | Chiral HPLC Method D: 2nd eluting compound | ++++ |

TABLE 1-continued
Compounds of formulae (I). OGA enzyme inhibition assay:
| No | Structure | Configuration specification | OGA IC50 (M) |
|---|---|---|---|
| 67 | 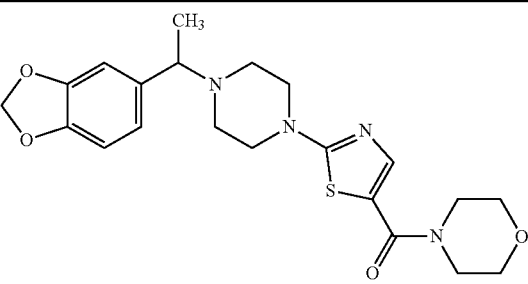 | Racemic | +++ |
| 68 | 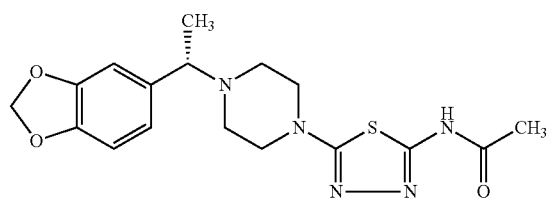 [SMILES: CC(=O)Nc1nnc(N2CCN([C@@H](C)c3ccc4c(c3)OCO4)CC2)s1] | Chiral HPLC Method D: 1st eluting compound | + |
| 69 | 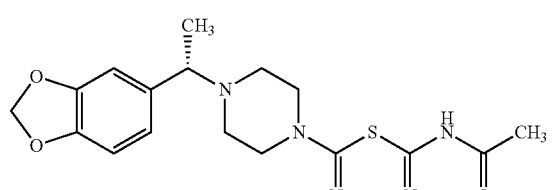 | Chiral HPLC Method D: 2nd eluting compound | ++++ |
| 70 | 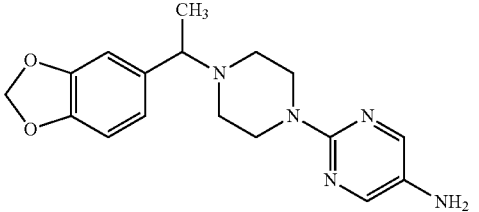 | Racemic | ++ |
| 71 | 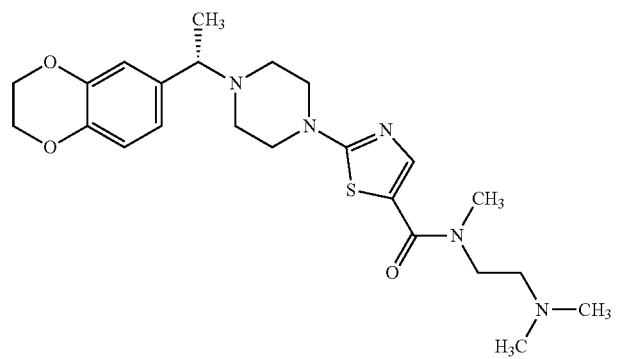 [SMILES: C[C@@H](c1ccc2c(c1)OCCO2)N1CCN(c2ncc(C(=O)N(C)CCN(C)C)s2)CC1] | Chiral HPLC Method D: 2nd eluting compound | ++++ |
| 72 | 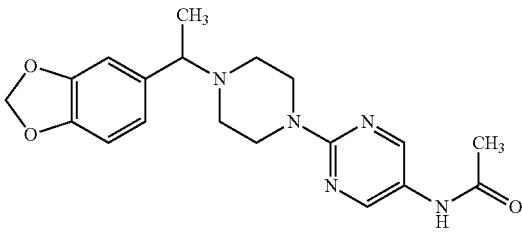 | Racemic | ++++ |

TABLE 1-continued

Compounds of formulae (I). OGA enzyme inhibition assay:

| No | Structure | Configuration specification | OGA IC50 (M) |
|----|-----------|----------------------------|--------------|
| 73 | 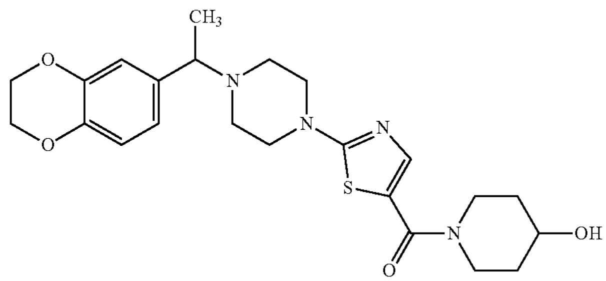 [SMILES: CC(c1ccc2c(c1)OCCO2)N1CCN(c2ncc(C(=O)N3CCC(O)CC3)s2)CC1] | Racemic | +++ |
| 74 | 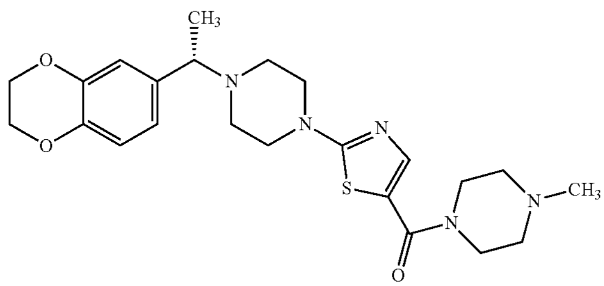 [SMILES: C[C@@H](c1ccc2c(c1)OCCO2)N1CCN(c2ncc(C(=O)N3CCN(C)CC3)s2)CC1] | Chiral HPLC Method D: 1st eluting compound | + |
| 75 | 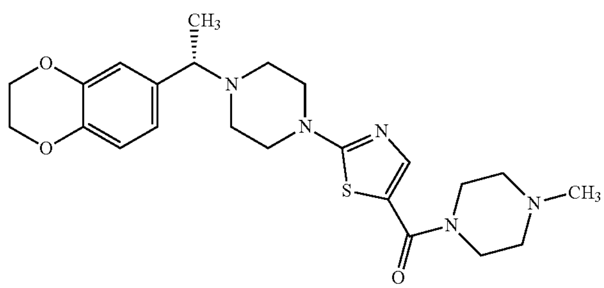 [SMILES: C[C@@H](c1ccc2c(c1)OCCO2)N1CCN(c2ncc(C(=O)N3CCN(C)CC3)s2)CC1] | Chiral HPLC Method D: 2nd eluting compound | ++++ |
| 76 | 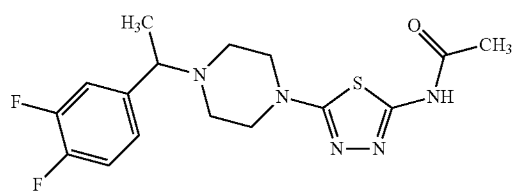 [SMILES: CC(=O)Nc1nnc(N2CCN(C(C)c3ccc(F)c(F)c3)CC2)s1] | Racemic | + |
| 77 | 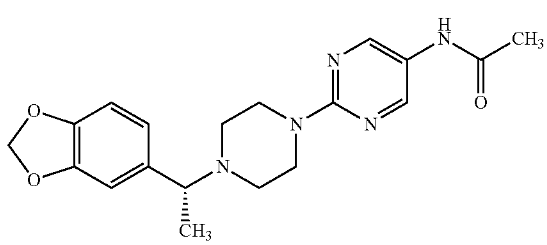 | Chiral HPLC Method L: 1st eluting compound | + |
| 78 | 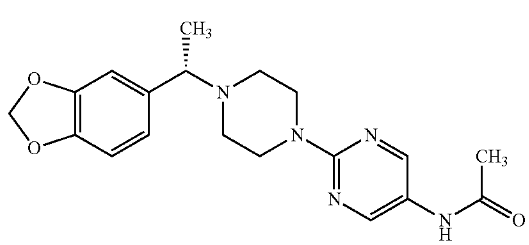 | Chiral HPLC Method L: 2nd eluting compound | ++++ |

TABLE 1-continued
Compounds of formulae (I). OGA enzyme inhibition assay:
| No | Structure | Configuration specification | OGA IC50 (M) |
|---|---|---|---|
| 79 | 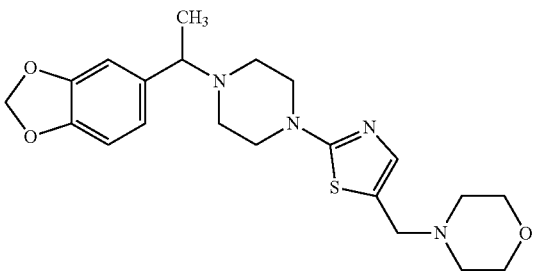 [SMILES: CC(c1ccc2c(c1)OCO2)N1CCN(c2ncc(CN3CCOCC3)s2)CC1] | Racemic | +++ |
| 80 | 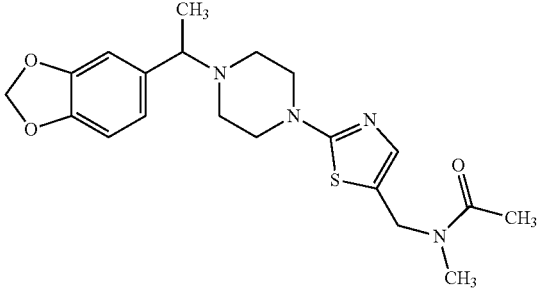 [SMILES: CC(=O)N(C)Cc1cnc(N2CCN(C(C)c3ccc4c(c3)OCO4)CC2)s1] | Racemic | ++++ |
| 81 | 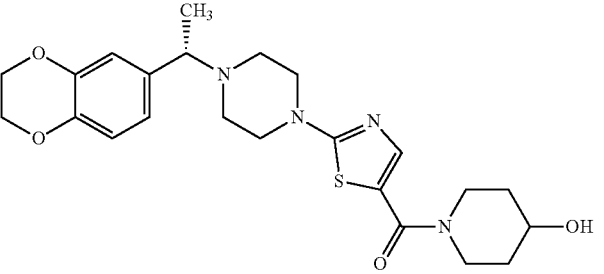 [SMILES: C[C@@H](c1ccc2c(c1)OCCO2)N1CCN(c2ncc(C(=O)N3CCC(O)CC3)s2)CC1] | Chiral HPLC Method B: 2nd eluting compound | ++++ |
| 82 | 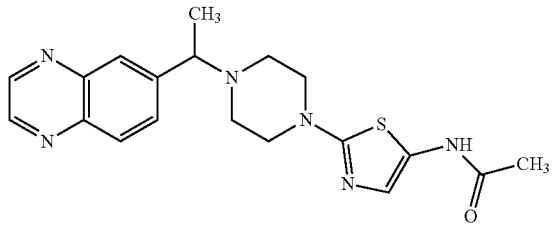 [SMILES: CC(=O)Nc1cnc(N2CCN(C(C)c3ccc4nccnc4c3)CC2)s1] | Racemic | +++ |
| 83 | 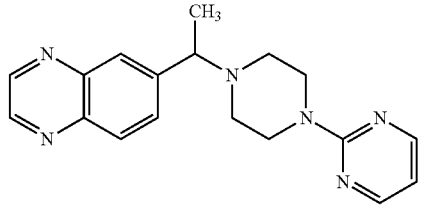 [SMILES: CC(c1ccc2nccnc2c1)N1CCN(c2ncccn2)CC1] | Racemic | +++ |
| 84 | 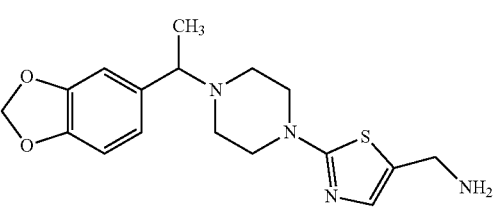 [SMILES: CC(c1ccc2c(c1)OCO2)N1CCN(c2ncc(CN)s2)CC1] | Racemic | +++ |

TABLE 1-continued

Compounds of formulae (I). OGA enzyme inhibition assay:

| No | Structure | Configuration specification | OGA IC50 (M) |
|----|-----------|-----------------------------|--------------|
| 85 | 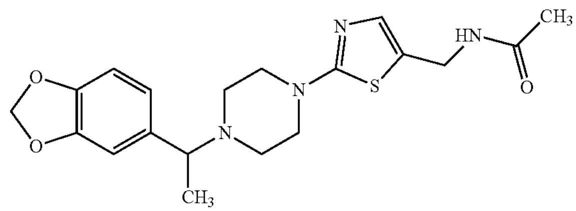 [SMILES: CC(=O)NCc1cnc(N2CCN(C(C)c3ccc4c(c3)OCO4)CC2)s1] | Racemic | ++++ |
| 86 | 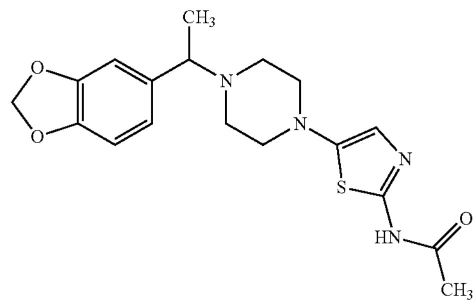 [SMILES: CC(=O)Nc1ncc(N2CCN(C(C)c3ccc4c(c3)OCO4)CC2)s1] | Racemic | ++++ |
| 87 | 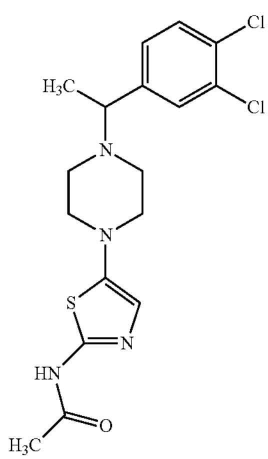 [SMILES: CC(=O)Nc1ncc(N2CCN(C(C)c3ccc(Cl)c(Cl)c3)CC2)s1] | Racemic | + |
| 88 | 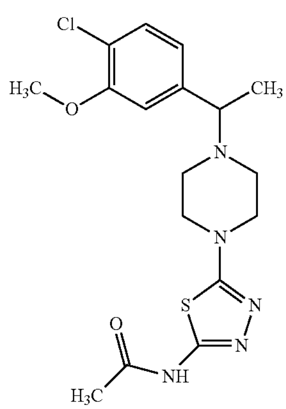 [SMILES: COc1cc(C(C)N2CCN(c3nnc(NC(C)=O)s3)CC2)ccc1Cl] | Racemic | + |

TABLE 1-continued

Compounds of formulae (I). OGA enzyme inhibition assay:

| No | Structure | Configuration specification | OGA IC50 (M) |
|---|---|---|---|
| 89 | 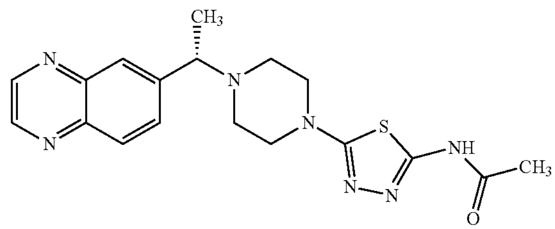 [SMILES: CC(=O)Nc1nnc(N2CCN([C@@H](C)c3ccc4nccnc4c3)CC2)s1] | Chiral HPLC Method D: 2nd eluting compound | ++++ |
| 90 | 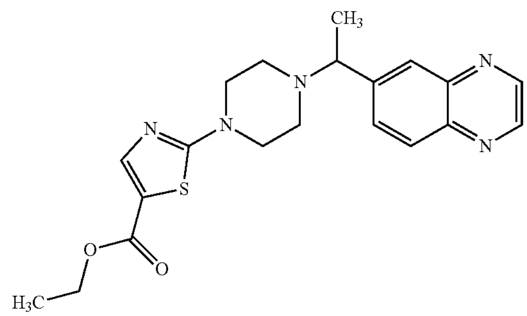 [SMILES: CCOC(=O)c1cnc(N2CCN(C(C)c3ccc4nccnc4c3)CC2)s1] | Racemic | ++ |
| 91 | 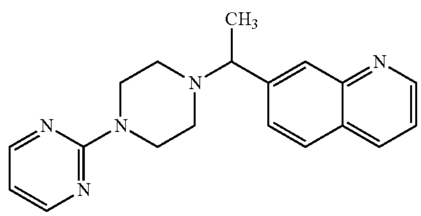 | Racemic | +++ |
| 92 | 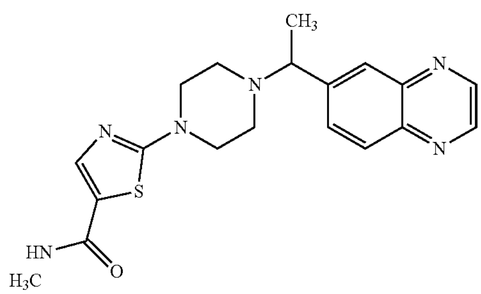 | Racemic | +++ |
| 93 | 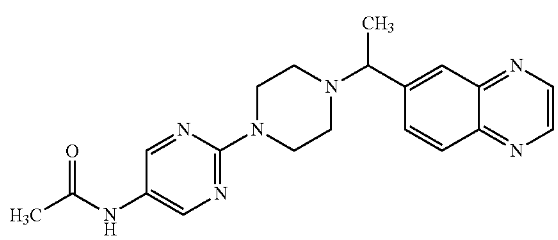 [SMILES: CC(=O)Nc1cnc(N2CCN(C(C)c3ccc4nccnc4c3)CC2)nc1] | Racemic | ++++ |
| 94 | 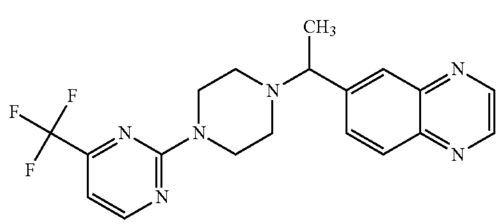 [SMILES: CC(c1ccc2nccnc2c1)N1CCN(c2nccc(C(F)(F)F)n2)CC1] | Racemic | ++ |

TABLE 1-continued

Compounds of formulae (I). OGA enzyme inhibition assay:

| No | Structure | Configuration specification | OGA IC50 (M) |
|---|---|---|---|
| 95 | 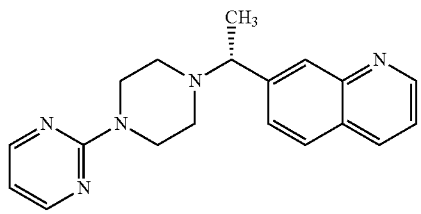 [SMILES: C[C@H](c1ccc2cccnc2c1)N1CCN(c2ncccn2)CC1] | Chiral HPLC Method D: 2nd eluting compound | +++ |
| 96 | 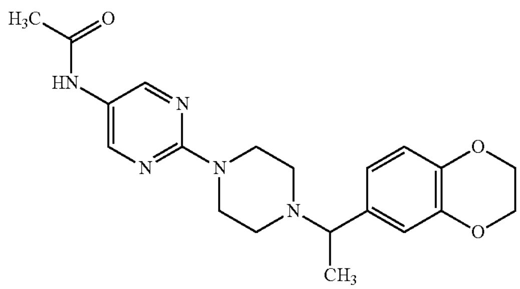 [SMILES: CC(=O)Nc1cnc(N2CCN(C(C)c3ccc4c(c3)OCCO4)CC2)nc1] | Racemic | ++++ |
| 97 | 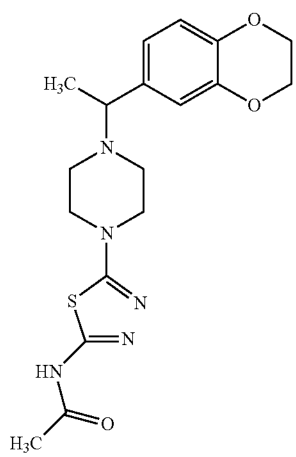 [SMILES: CC(=O)NC(=N)SC(=N)N1CCN(C(C)c2ccc3c(c2)OCCO3)CC1] | Racemic | ++++ |
| 98 | 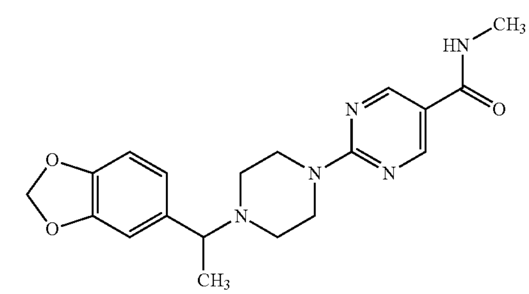 [SMILES: CNC(=O)c1cnc(N2CCN(C(C)c3ccc4c(c3)OCO4)CC2)nc1] | Racemic | ++++ |
| 99 | 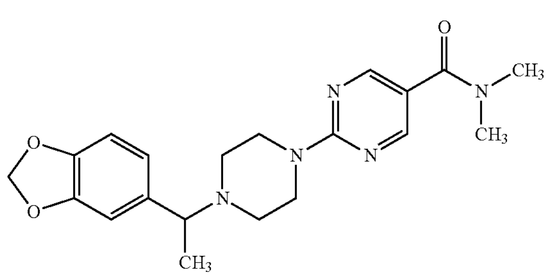 [SMILES: CC(c1ccc2c(c1)OCO2)N1CCN(c2ncc(C(=O)N(C)C)cn2)CC1] | Racemic | ++++ |

TABLE 1-continued

Compounds of formulae (I). OGA enzyme inhibition assay:

| No | Structure | Configuration specification | OGA IC50 (M) |
|---|---|---|---|
| 100 | 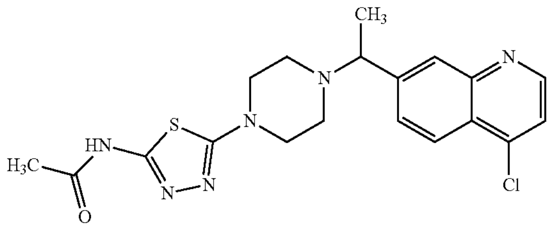 [SMILES: CC(=O)Nc1nnc(N2CCN(C(C)c3ccc4c(Cl)ccnc4c3)CC2)s1] | Racemic | ++ |
| 101 | 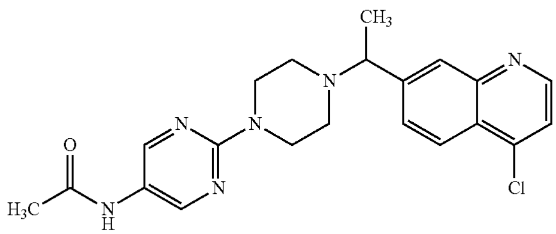 [SMILES: CC(=O)Nc1cnc(N2CCN(C(C)c3ccc4c(Cl)ccnc4c3)CC2)nc1] | Racemic | ++ |
| 102 | 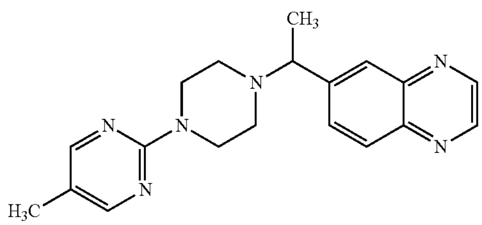 [SMILES: Cc1cnc(N2CCN(C(C)c3ccc4nccnc4c3)CC2)nc1] | Racemic | +++ |
| 103 | 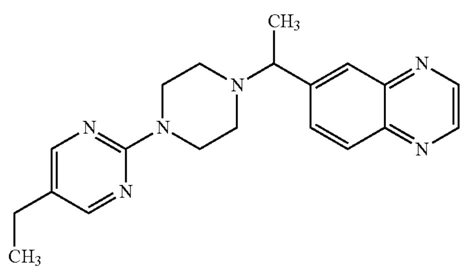 [SMILES: CCc1cnc(N2CCN(C(C)c3ccc4nccnc4c3)CC2)nc1] | Racemic | +++ |
| 104 | 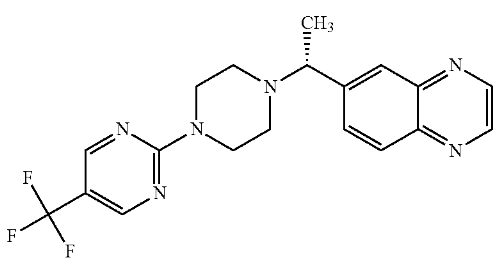 [SMILES: C[C@H](c1ccc2nccnc2c1)N1CCN(c2ncc(C(F)(F)F)cn2)CC1] | Chiral HPLC Method L: 2nd eluting compound | +++ |
| 105 | 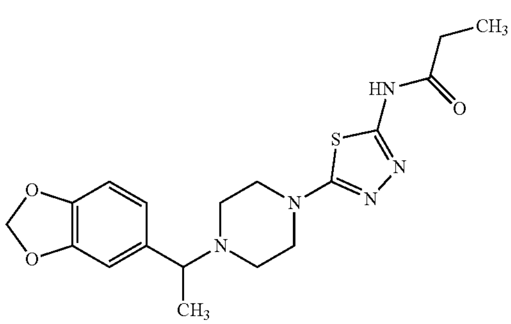 [SMILES: CCC(=O)Nc1nnc(N2CCN(C(C)c3ccc4c(c3)OCO4)CC2)s1] | Racemic | ++++ |

TABLE 1-continued
Compounds of formulae (I). OGA enzyme inhibition assay:
| No | Structure | Configuration specification | OGA IC50 (M) |
|---|---|---|---|
| 106 | 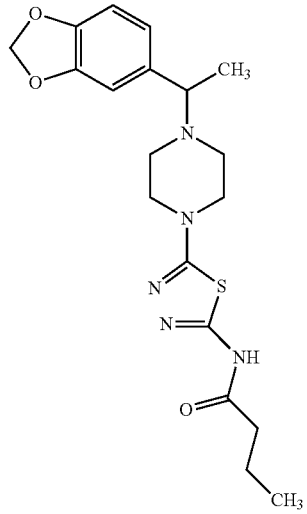 [SMILES: CCCC(=O)NC(=N)SC(=N)N1CCN(C(C)c2ccc3c(c2)OCO3)CC1] | Racemic | ++++ |
| 107 | 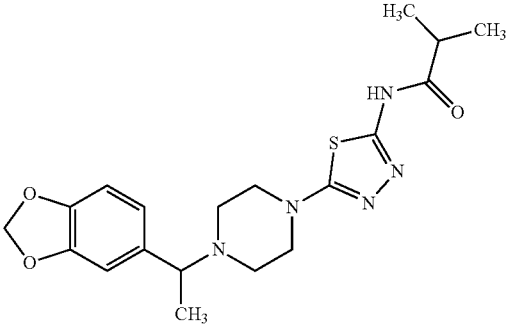 [SMILES: CC(C)C(=O)Nc1nnc(N2CCN(C(C)c3ccc4c(c3)OCO4)CC2)s1] | Racemic | ++++ |
| 108 | 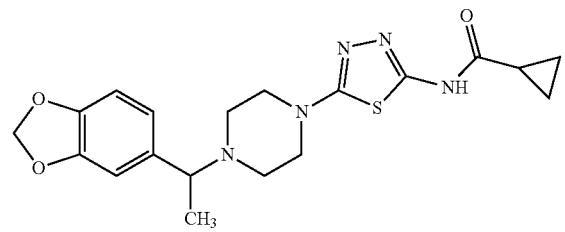 [SMILES: CC(c1ccc2c(c1)OCO2)N1CCN(c2nnc(NC(=O)C3CC3)s2)CC1] | Racemic | ++++ |

TABLE 1-continued

Compounds of formulae (I). OGA enzyme inhibition assay:

| No | Structure | Configuration specification | OGA IC50 (M) |
|---|---|---|---|
| 109 | 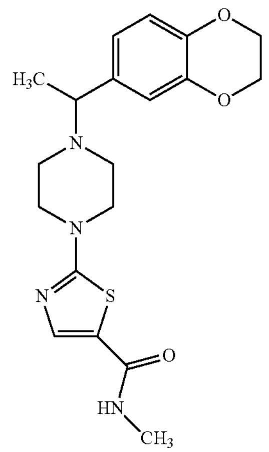 [SMILES: CNC(=O)c1cnc(N2CCN(C(C)c3ccc4c(c3)OCCO4)CC2)s1] | Racemic | ++++ |
| 110 | 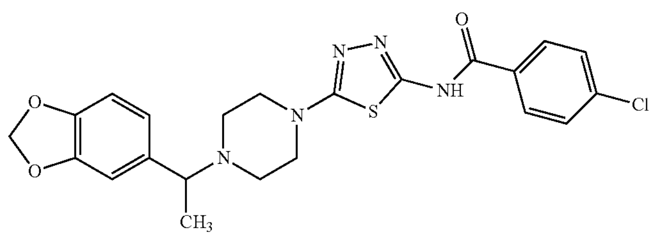 [SMILES: CC(c1ccc2c(c1)OCO2)N1CCN(c2nnc(NC(=O)c3ccc(Cl)cc3)s2)CC1] | Racemic | +++ |
| 111 | 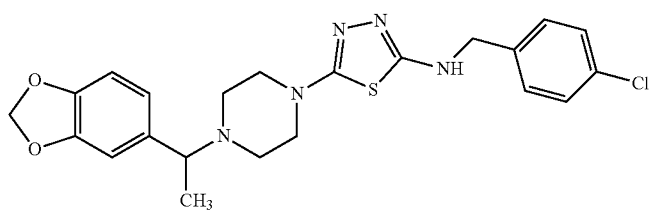 [SMILES: CC(c1ccc2c(c1)OCO2)N1CCN(c2nnc(NCc3ccc(Cl)cc3)s2)CC1] | Racemic | +++ |
| 112 | 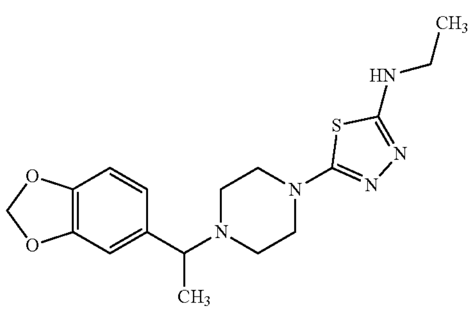 [SMILES: CCNc1nnc(N2CCN(C(C)c3ccc4c(c3)OCO4)CC2)s1] | Racemic | +++ |
| 113 | 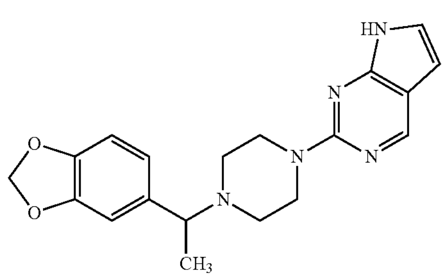 [SMILES: CC(c1ccc2c(c1)OCO2)N1CCN(c2ncc3cc[nH]c3n2)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 114 | 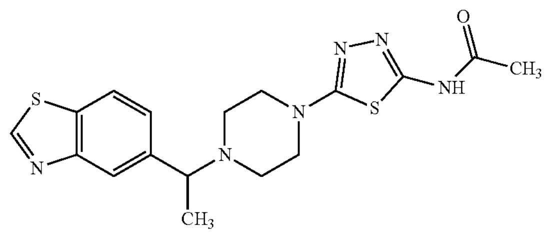 [SMILES: CC(=O)Nc1nnc(N2CCN(C(C)c3ccc4scnc4c3)CC2)s1] | Racemic | ++++ |
| 115 | 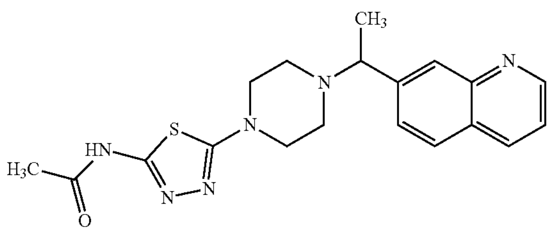 [SMILES: CC(=O)Nc1nnc(N2CCN(C(C)c3ccc4cccnc4c3)CC2)s1] | Racemic | +++ |
| 116 | 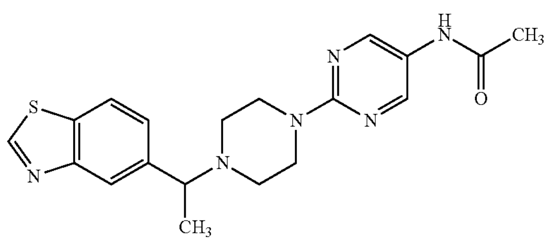 | Racemic | ++++ |
| 117 | 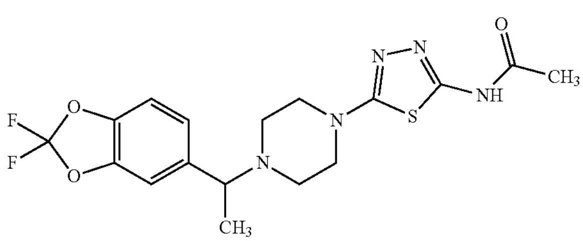 [SMILES: CC(=O)Nc1nnc(N2CCN(C(C)c3ccc4c(c3)OC(F)(F)O4)CC2)s1] | Racemic | ++ |
| 118 | 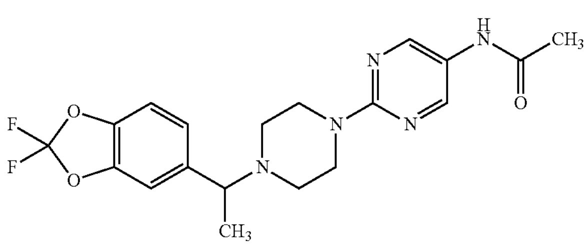 [SMILES: CC(=O)Nc1cnc(N2CCN(C(C)c3ccc4c(c3)OC(F)(F)O4)CC2)nc1] | Racemic | ++ |
| 119 | 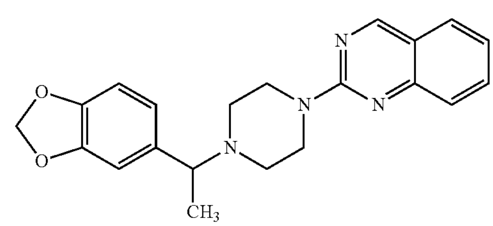 [SMILES: CC(c1ccc2c(c1)OCO2)N1CCN(c2ncc3ccccc3n2)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 120 | 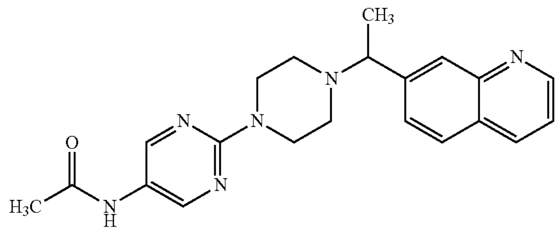 [SMILES: CC(=O)Nc1cnc(N2CCN(C(C)c3ccc4cccnc4c3)CC2)nc1] | Racemic | ++ |
| 121 | 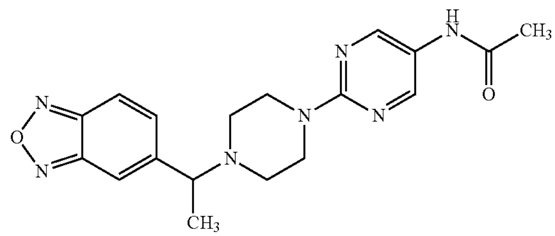 [SMILES: CC(=O)Nc1cnc(N2CCN(C(C)c3ccc4nonc4c3)CC2)nc1] | Racemic | + |
| 122 | 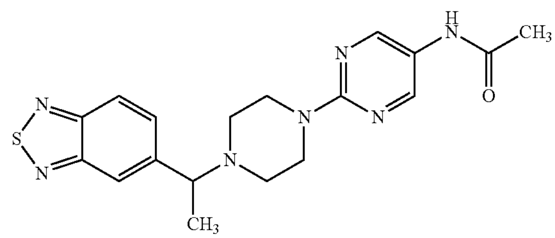 [SMILES: CC(=O)Nc1cnc(N2CCN(C(C)c3ccc4nsnc4c3)CC2)nc1] | Racemic | ++++ |
| 123 | 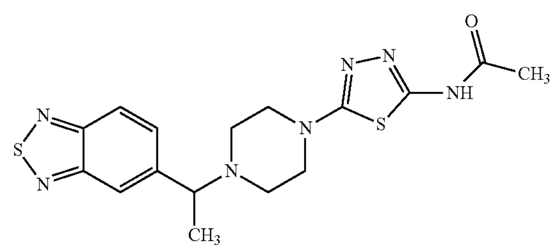 [SMILES: CC(=O)Nc1nnc(N2CCN(C(C)c3ccc4nsnc4c3)CC2)s1] | Racemic | ++++ |
| 124 | 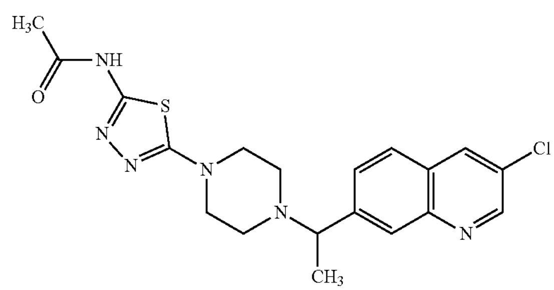 [SMILES: CC(=O)Nc1nnc(N2CCN(C(C)c3ccc4cc(Cl)cnc4c3)CC2)s1] | Racemic | + |
| 125 | 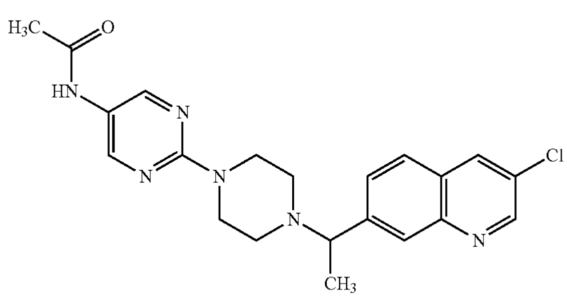 [SMILES: CC(=O)Nc1cnc(N2CCN(C(C)c3ccc4cc(Cl)cnc4c3)CC2)nc1] | Racemic | + |

TABLE 1-continued

Compounds of formulae (I). OGA enzyme inhibition assay:

| No | Structure | Configuration specification | OGA IC50 (M) |
|---|---|---|---|
| 126 | 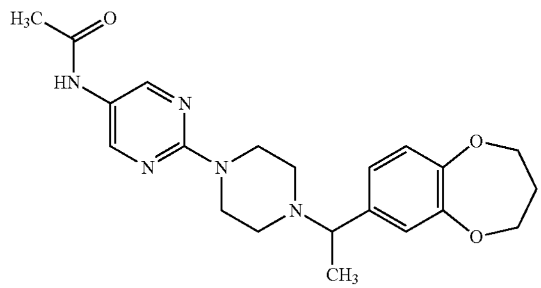 [SMILES: CC(=O)Nc1cnc(N2CCN(C(C)c3ccc4c(c3)OCCCO4)CC2)nc1] | Racemic | ++ |
| 127 | 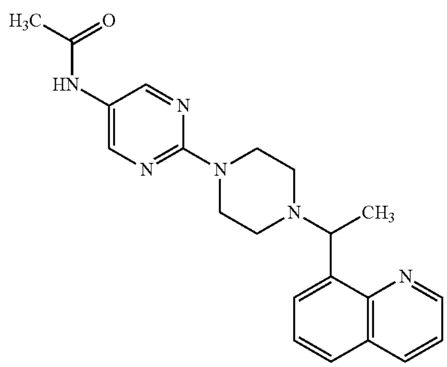 [SMILES: CC(=O)Nc1cnc(N2CCN(C(C)c3cccc4cccnc34)CC2)nc1] | Racemic | + |
| 128 | 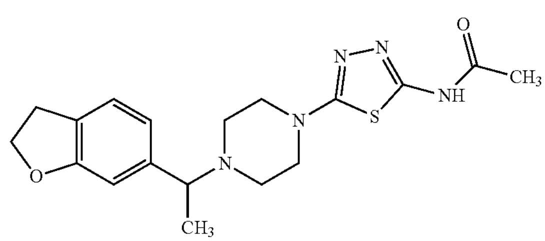 [SMILES: CC(=O)Nc1nnc(N2CCN(C(C)c3ccc4c(c3)OCC4)CC2)s1] | Racemic | ++++ |
| 129 | 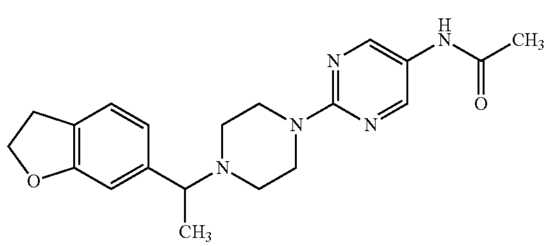 [SMILES: CC(=O)Nc1cnc(N2CCN(C(C)c3ccc4c(c3)OCC4)CC2)nc1] | Racemic | ++++ |
| 130 | 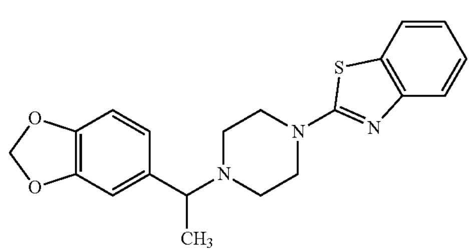 [SMILES: CC(c1ccc2c(c1)OCO2)N1CCN(c2nc3ccccc3s2)CC1] | Racemic | ++ |

TABLE 1-continued

Compounds of formulae (I). OGA enzyme inhibition assay:

| No | Structure | Configuration specification | OGA IC50 (M) |
|---|---|---|---|
| 131 | 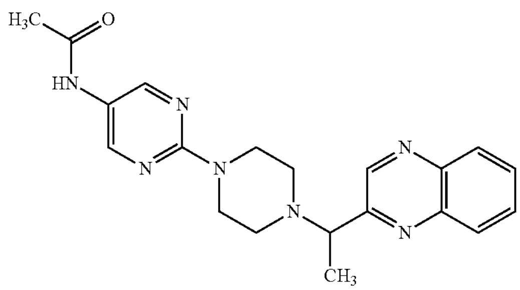 [SMILES: CC(=O)Nc1cnc(N2CCN(C(C)c3cnc4ccccc4n3)CC2)nc1] | Racemic | + |
| 132 | 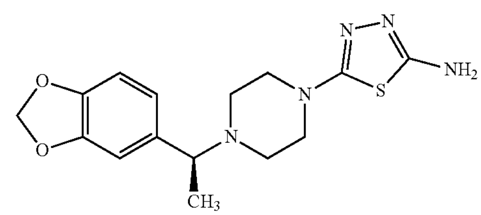 [SMILES: C[C@@H](c1ccc2c(c1)OCO2)N1CCN(c2nnc(N)s2)CC1] | S configuration; synthesized from Intermediate 16 | ++++ |
| 133 | 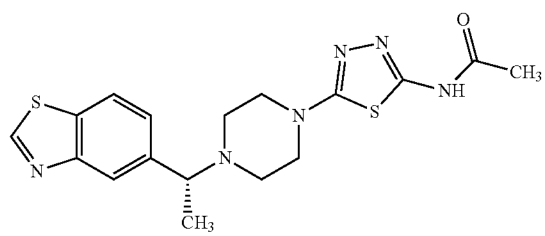 | Chiral HPLC Method D: 2nd eluting compound | ++++ |
| 134 | 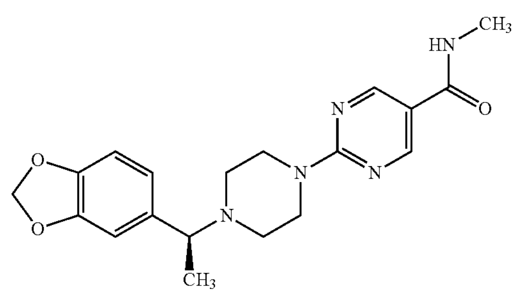 | S configuration; synthesized from Intermediate 16 | ++++ |
| 135 | 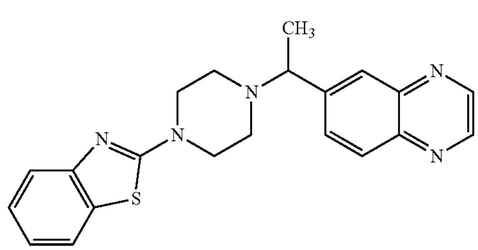 [SMILES: CC(c1ccc2nccnc2c1)N1CCN(c2nc3ccccc3s2)CC1] | Racemic | + |
| 136 | 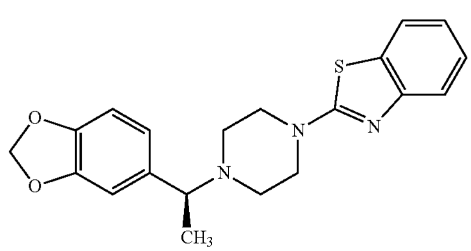 [SMILES: C[C@@H](c1ccc2c(c1)OCO2)N1CCN(c2nc3ccccc3s2)CC1] | S configuration; synthesized from Intermediate 16 | ++ |

TABLE 1-continued

Compounds of formulae (I). OGA enzyme inhibition assay:

| No | Structure | Configuration specification | OGA IC50 (M) |
|---|---|---|---|
| 137 | 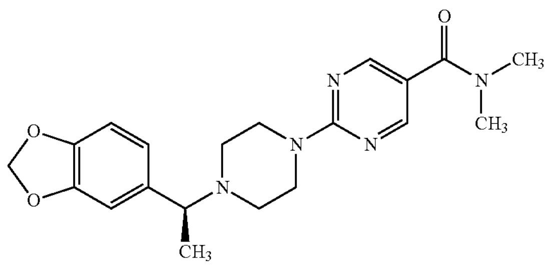 | S configuration; synthesized from Intermediate 16 | ++++ |
| 138 | 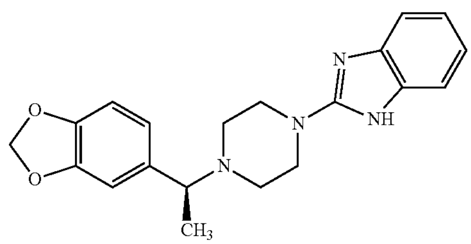 [SMILES: C[C@@H](c1ccc2c(c1)OCO2)N1CCN(c2nc3ccccc3[nH]2)CC1] | S configuration; synthesized from Intermediate 16 | + |
| 139 | 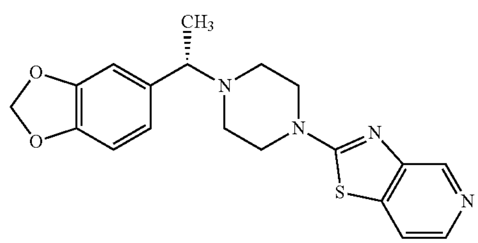 [SMILES: C[C@@H](c1ccc2c(c1)OCO2)N1CCN(c2nc3cnccc3s2)CC1] | S configuration; synthesized from Intermediate 16 | +++ |
| 140 | 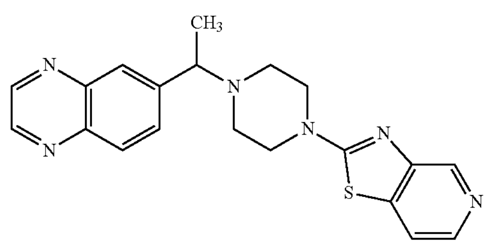 [SMILES: CC(c1ccc2nccnc2c1)N1CCN(c2nc3cnccc3s2)CC1] | Racemic | ++ |
| 141 | 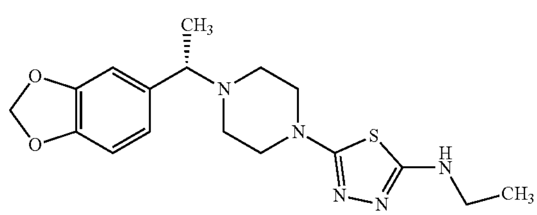 [SMILES: CCNc1nnc(N2CCN([C@@H](C)c3ccc4c(c3)OCO4)CC2)s1] | S configuration; synthesized from Intermediate 16 | +++ |
| 142 | 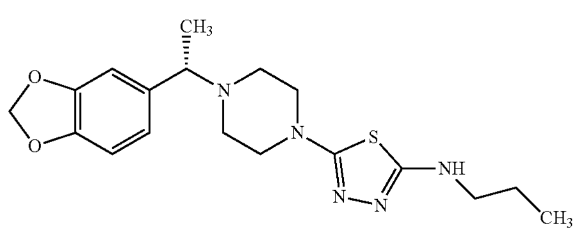 [SMILES: CCCNc1nnc(N2CCN([C@@H](C)c3ccc4c(c3)OCO4)CC2)s1] | S configuration; synthesized from Intermediate 16 | +++ |

TABLE 1-continued

Compounds of formulae (I). OGA enzyme inhibition assay:

| No | Structure | Configuration specification | OGA IC50 (M) |
|---|---|---|---|
| 143 | 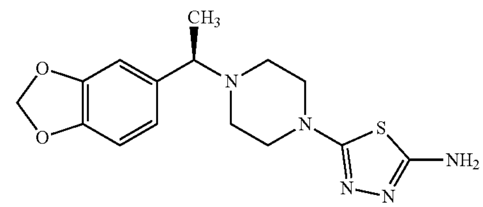 [SMILES: C[C@H](c1ccc2c(c1)OCO2)N1CCN(c2nnc(N)s2)CC1] | R configuration; synthesized from Intermediate 24 | |
| 144 | 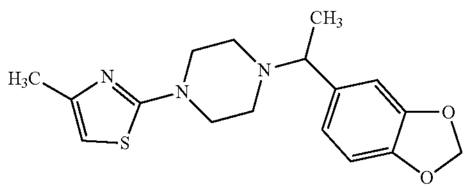 [SMILES: Cc1csc(N2CCN(C(C)c3ccc4c(c3)OCO4)CC2)n1] | Racemic | ++ |
| 145 | 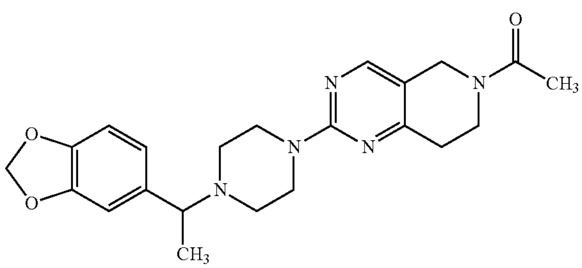 [SMILES: CC(=O)N1CCc2nc(N3CCN(C(C)c4ccc5c(c4)OCO5)CC3)ncc2C1] | | |
| 146 | 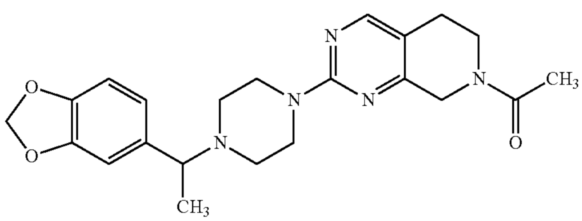 [SMILES: CC(=O)N1CCc2cnc(N3CCN(C(C)c4ccc5c(c4)OCO5)CC3)nc2C1] | | |
| 147 | 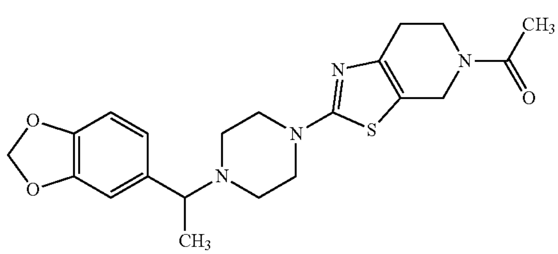 [SMILES: CC(=O)N1CCc2nc(N3CCN(C(C)c4ccc5c(c4)OCO5)CC3)sc2C1] | | |
| 148 | 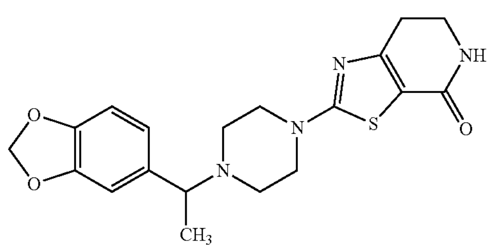 [SMILES: CC(c1ccc2c(c1)OCO2)N1CCN(c2nc3c(s2)C(=O)NCC3)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 149 | 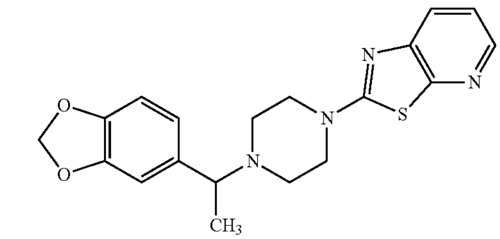 | | |
| 150 | 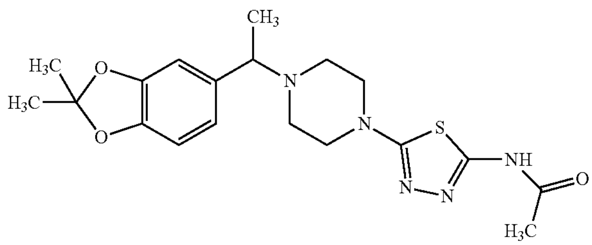 [SMILES: CC(=O)Nc1nnc(N2CCN(C(C)c3ccc4c(c3)OC(C)(C)O4)CC2)s1] | | |
| 151 | 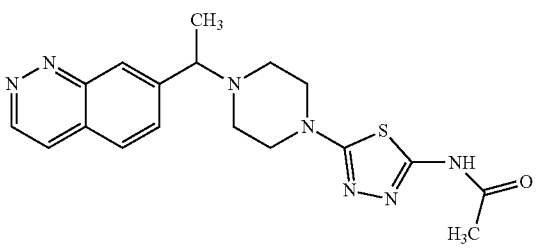 [SMILES: CC(=O)Nc1nnc(N2CCN(C(C)c3ccc4ccnnc4c3)CC2)s1] | | |
| 152 | 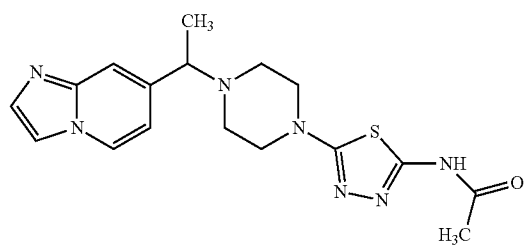 [SMILES: CC(=O)Nc1nnc(N2CCN(C(C)c3ccn4ccnc4c3)CC2)s1] | | |
| 153 | 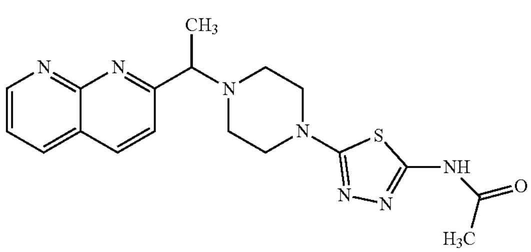 [SMILES: CC(=O)Nc1nnc(N2CCN(C(C)c3ccc4cccnc4n3)CC2)s1] | | |
| 154 | 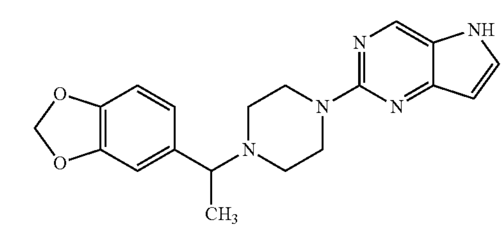 [SMILES: CC(c1ccc2c(c1)OCO2)N1CCN(c2ncc3[nH]ccc3n2)CC1] | | |

TABLE 1-continued

Compounds of formulae (I). OGA enzyme inhibition assay:

| No | Structure | Configuration specification | OGA IC50 (M) |
|---|---|---|---|
| 155 | 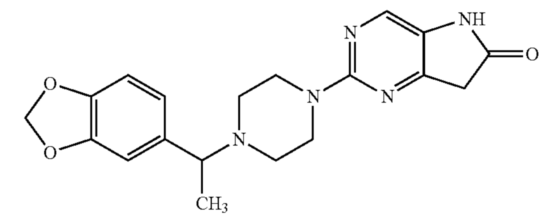 [SMILES: CC(c1ccc2c(c1)OCO2)N1CCN(c2ncc3c(n2)CC(=O)N3)CC1] | | |
| 156 | 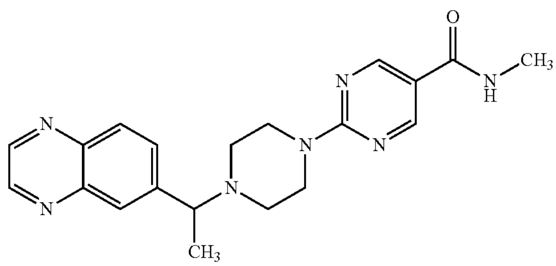 [SMILES: CNC(=O)c1cnc(N2CCN(C(C)c3ccc4nccnc4c3)CC2)nc1] | | |
| 157 | 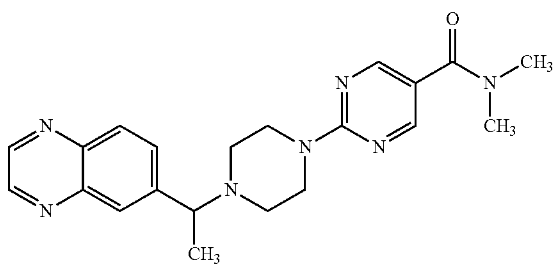 [SMILES: CC(c1ccc2nccnc2c1)N1CCN(c2ncc(C(=O)N(C)C)cn2)CC1] | | |
| 158 | 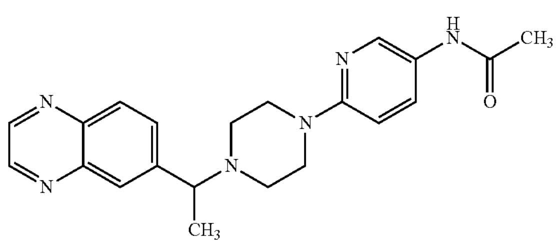 [SMILES: CC(=O)Nc1ccc(N2CCN(C(C)c3ccc4nccnc4c3)CC2)nc1] | | |
| 159 | 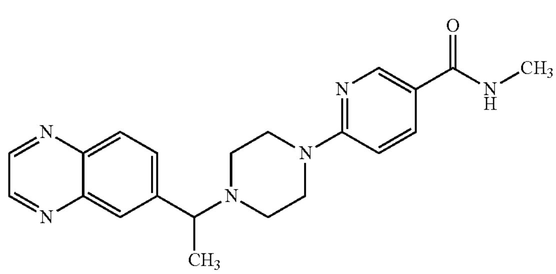 [SMILES: CNC(=O)c1ccc(N2CCN(C(C)c3ccc4nccnc4c3)CC2)nc1] | | |
| 160 | 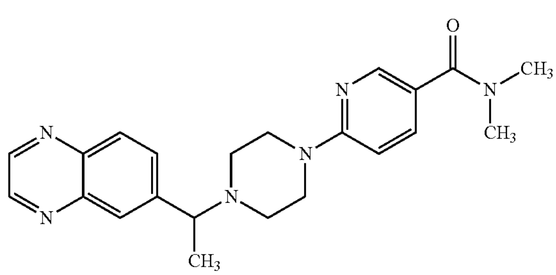 | | |

TABLE 1-continued
Compounds of formulae (I). OGA enzyme inhibition assay:
| No | Structure | Configuration specification | OGA IC50 (M) |
|---|---|---|---|
| 161 | 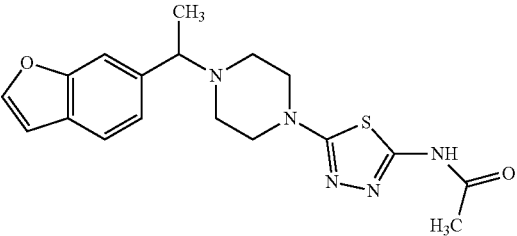 [SMILES: CC(=O)Nc1nnc(N2CCN(C(C)c3ccc4ccoc4c3)CC2)s1] | | |
| 162 | 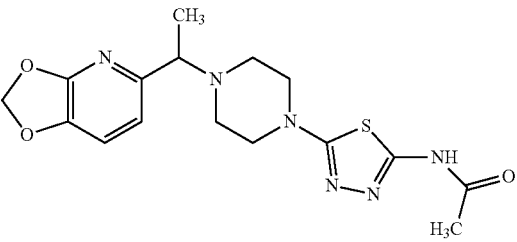 [SMILES: CC(=O)Nc1nnc(N2CCN(C(C)c3ccc4c(n3)OCO4)CC2)s1] | | |
| 163 | 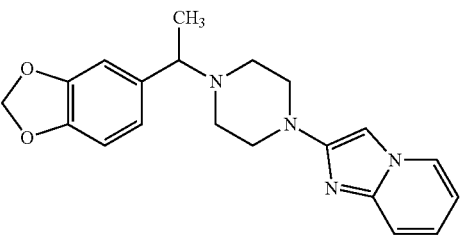 [SMILES: CC(c1ccc2c(c1)OCO2)N1CCN(c2cn3ccccc3n2)CC1] | | |
| 164 | 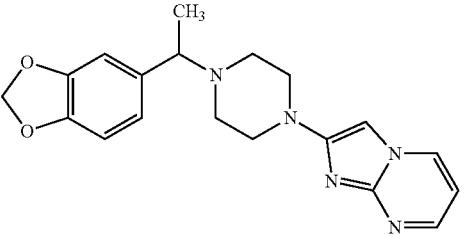 [SMILES: CC(c1ccc2c(c1)OCO2)N1CCN(c2cn3cccnc3n2)CC1] | | |
| 165 | 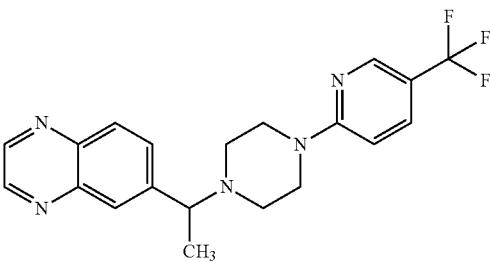 [SMILES: CC(c1ccc2nccnc2c1)N1CCN(c2ccc(C(F)(F)F)cn2)CC1] | Racemic | ++ |
| 166 | 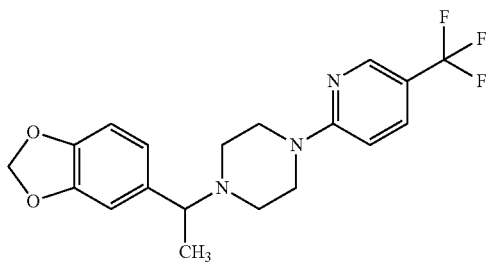 [SMILES: CC(c1ccc2c(c1)OCO2)N1CCN(c2ccc(C(F)(F)F)cn2)CC1] | Racemic | +++ |

TABLE 1-continued

Compounds of formulae (I). OGA enzyme inhibition assay:

| No | Structure | Configuration specification | OGA IC50 (M) |
|---|---|---|---|
| 167 | 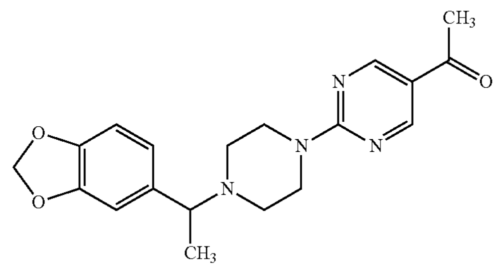 [SMILES: CC(=O)c1cnc(N2CCN(C(C)c3ccc4c(c3)OCO4)CC2)nc1] | Racemic | ++++ |
| 168 | 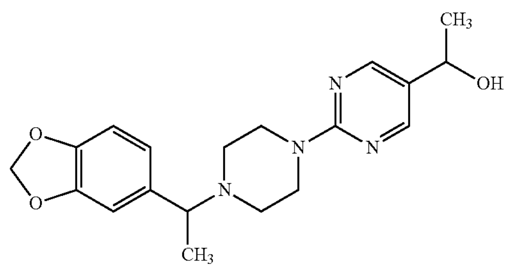 [SMILES: CC(O)c1cnc(N2CCN(C(C)c3ccc4c(c3)OCO4)CC2)nc1] | Racemic | ++++ |
| 169 | 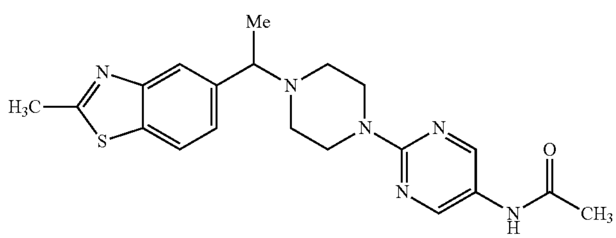 [SMILES: CC(=O)Nc1cnc(N2CCN(C(C)c3ccc4sc(C)nc4c3)CC2)nc1] | Racemic | ++++ |
| 170 | 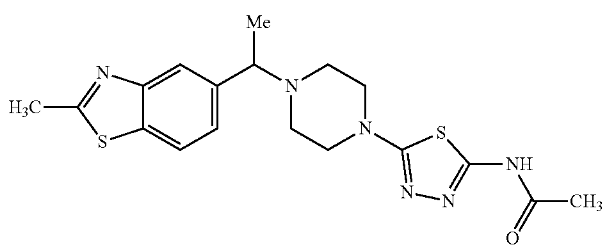 [SMILES: CC(=O)Nc1nnc(N2CCN(C(C)c3ccc4sc(C)nc4c3)CC2)s1] | Racemic | ++++ |
| 171 | 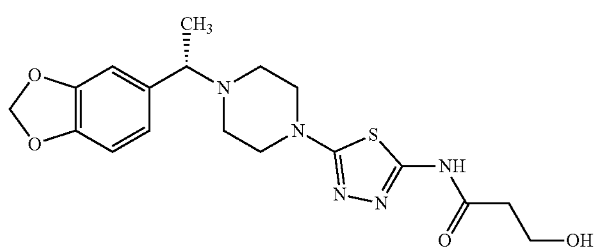 [SMILES: C[C@@H](c1ccc2c(c1)OCO2)N1CCN(c2nnc(NC(=O)CCO)s2)CC1] | S configuration; synthesized from Intermediate 16 | ++++ |
| 172 | 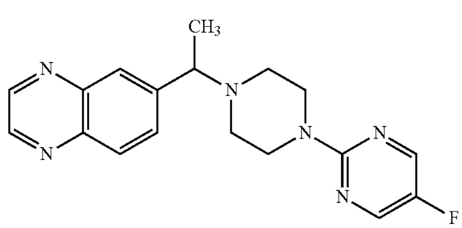 [SMILES: CC(c1ccc2nccnc2c1)N1CCN(c2ncc(F)cn2)CC1] | Racemic | +++ |

TABLE 1-continued

Compounds of formulae (I). OGA enzyme inhibition assay:

| No | Structure | Configuration specification | OGA IC50 (M) |
|----|-----------|----------------------------|--------------|
| 173 | 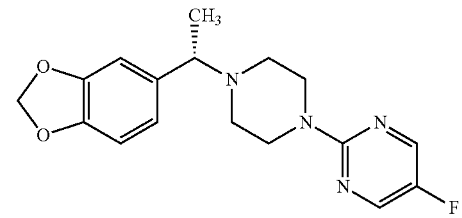 [SMILES: C[C@@H](c1ccc2c(c1)OCO2)N1CCN(c2ncc(F)cn2)CC1] | S configuration; synthesized from Intermediate 16 | ++++ |
| 174 | 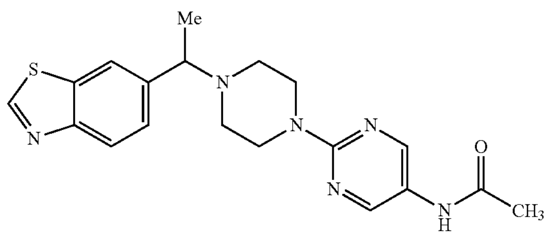 [SMILES: CC(=O)Nc1cnc(N2CCN(C(C)c3ccc4ncsc4c3)CC2)nc1] | Racemic | + |
| 175 | 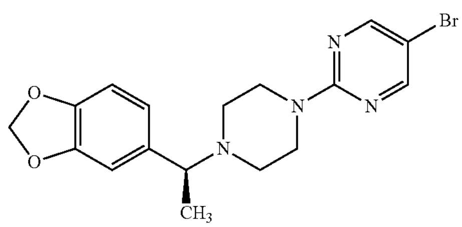 [SMILES: C[C@@H](c1ccc2c(c1)OCO2)N1CCN(c2ncc(Br)cn2)CC1] | S configuration; synthesized from Intermediate 16 | ++++ |
| 176 | 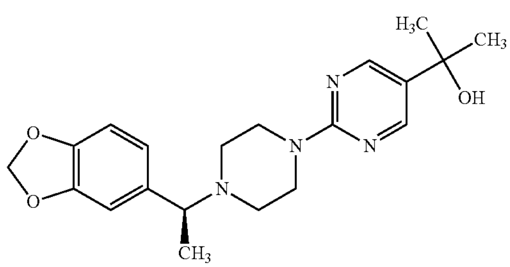 | S configuration; synthesized from Intermediate 16 | ++++ |
| 177 | 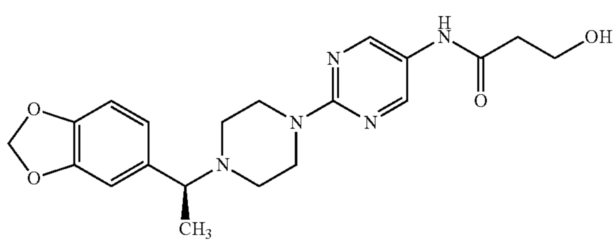 [SMILES: C[C@@H](c1ccc2c(c1)OCO2)N1CCN(c2ncc(NC(=O)CCO)cn2)CC1] | S configuration; synthesized from Intermediate 16 | ++++ |
| 178 | 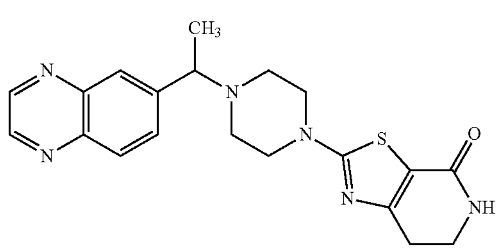 [SMILES: CC(c1ccc2nccnc2c1)N1CCN(c2nc3c(s2)C(=O)NCC3)CC1] | Racemic | ++ |

TABLE 1-continued

Compounds of formulae (I). OGA enzyme inhibition assay:

| No | Structure | Configuration specification | OGA IC50 (M) |
|---|---|---|---|
| 179 | 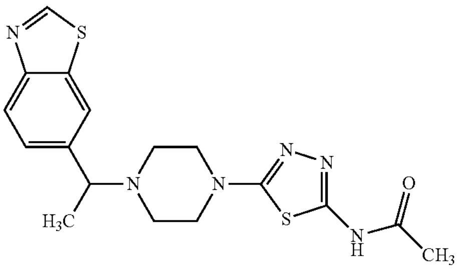 [SMILES: CC(=O)Nc1nnc(N2CCN(C(C)c3ccc4ncsc4c3)CC2)s1] | Racemic | + |
| 180 | 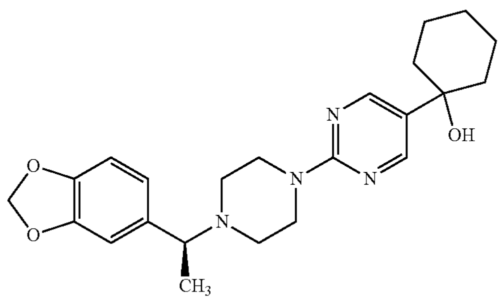 | S configuration; synthesized from Intermediate 16 | ++++ |
| 181 | 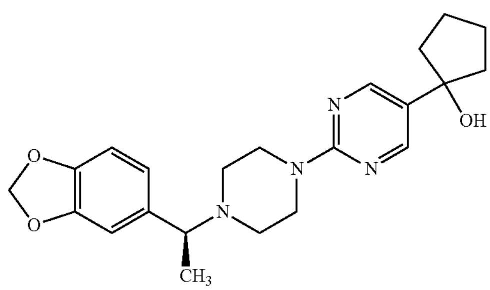 [SMILES: C[C@@H](c1ccc2c(c1)OCO2)N1CCN(c2ncc(C3(O)CCCC3)cn2)CC1] | S configuration; synthesized from Intermediate 16 | ++++ |
| 182 | 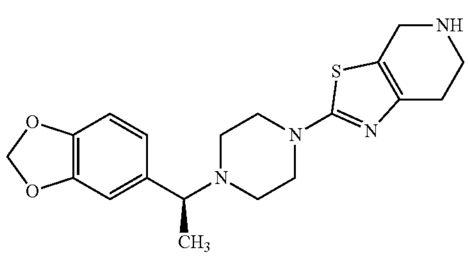 [SMILES: C[C@@H](c1ccc2c(c1)OCO2)N1CCN(c2nc3c(s2)CNCC3)CC1] | S configuration; synthesized from Intermediate 16 | ++++ |
| 183 | 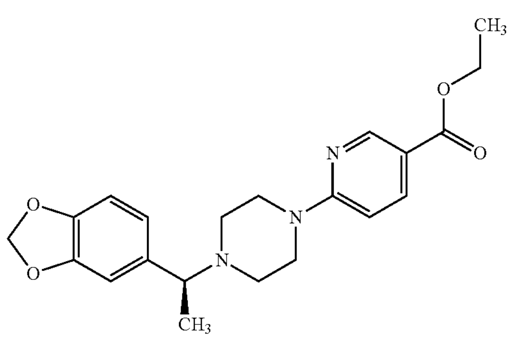 | S configuration; synthesized from Intermediate 16 | +++ |

TABLE 1-continued

Compounds of formulae (I). OGA enzyme inhibition assay:

| No | Structure | Configuration specification | OGA IC50 (M) |
|---|---|---|---|
| 184 | 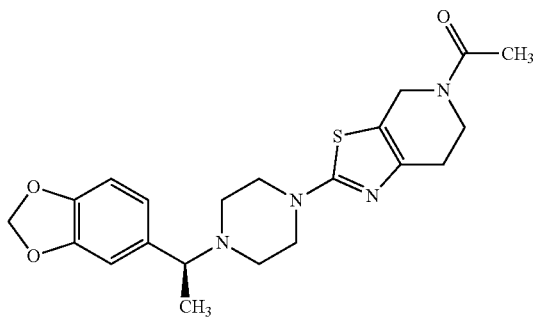 [SMILES: CC(=O)N1CCc2nc(N3CCN([C@@H](C)c4ccc5c(c4)OCO5)CC3)sc2C1] | S configuration; synthesized from Intermediate 16 | ++++ |
| 185 | 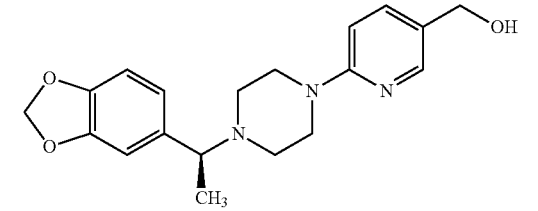 [SMILES: C[C@@H](c1ccc2c(c1)OCO2)N1CCN(c2ccc(CO)cn2)CC1] | S configuration; synthesized from Intermediate 16 | ++++ |
| 186 | 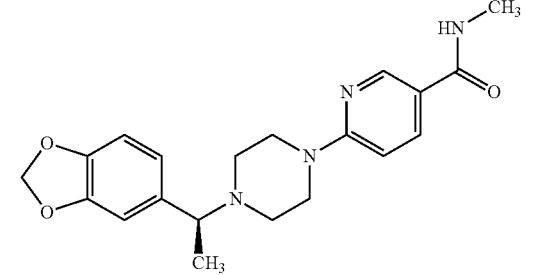 [SMILES: CNC(=O)c1ccc(N2CCN([C@@H](C)c3ccc4c(c3)OCO4)CC2)nc1] | S configuration; synthesized from Intermediate 16 | ++++ |
| 187 | 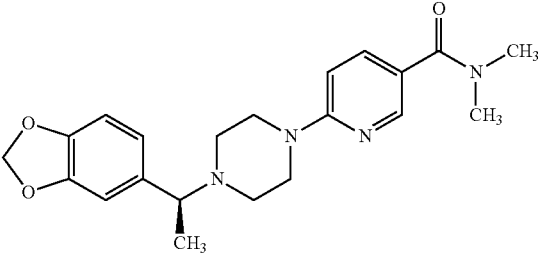 | S configuration; synthesized from Intermediate 16 | ++++ |
| 188 | 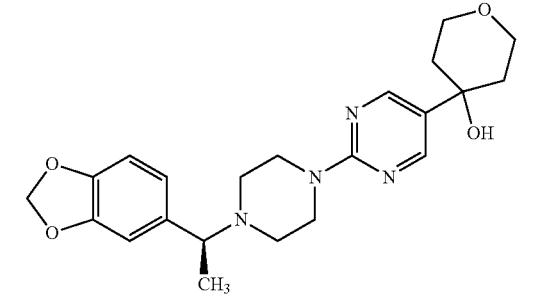 [SMILES: C[C@@H](c1ccc2c(c1)OCO2)N1CCN(c2ncc(C3(O)CCOCC3)cn2)CC1] | S configuration; synthesized from Intermediate 16 | ++++ |

TABLE 1-continued

Compounds of formulae (I). OGA enzyme inhibition assay:

| No | Structure | Configuration specification | OGA IC50 (M) |
|---|---|---|---|
| 189 | 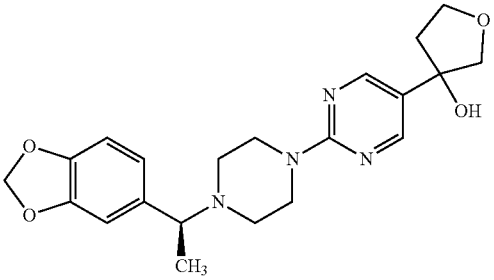 [SMILES: C[C@@H](c1ccc2c(c1)OCO2)N1CCN(c2ncc(C3(O)CCOC3)cn2)CC1] | S configuration; synthesized from Intermediate 16 | ++++ |
| 190 | 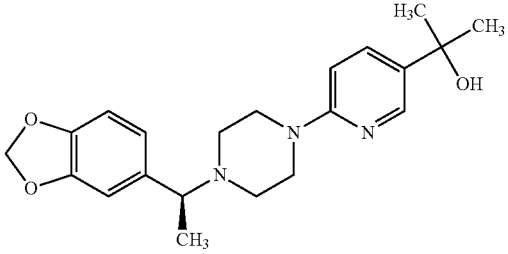 [SMILES: C[C@@H](c1ccc2c(c1)OCO2)N1CCN(c2ccc(C(C)(C)O)cn2)CC1] | S configuration; synthesized from Intermediate 16 | ++++ |
| 191 | 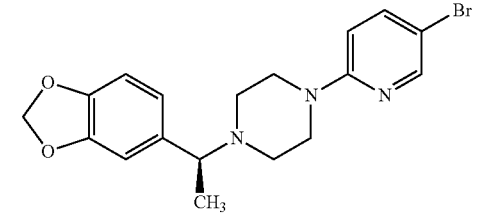 | S configuration; synthesized from Intermediate 16 | +++ |
| 192 | 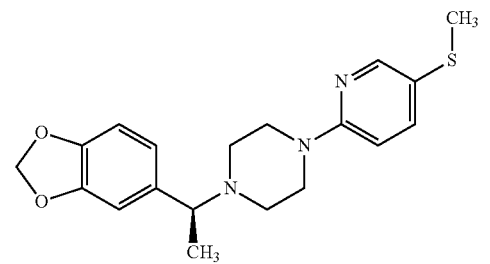 | S configuration; synthesized from Intermediate 16 | ++++ |
| 193 | 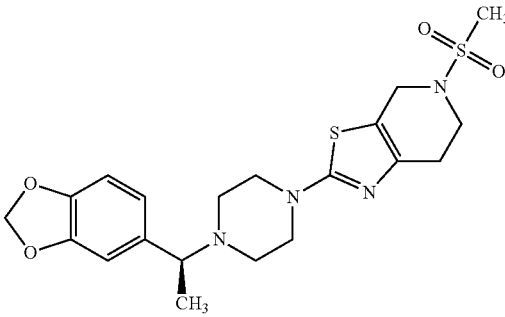 | S configuration; synthesized from Intermediate 16 | ++++ |

TABLE 1-continued
Compounds of formulae (I). OGA enzyme inhibition assay:
| No | Structure | Configuration specification | OGA IC50 (M) |
|---|---|---|---|
| 194 | 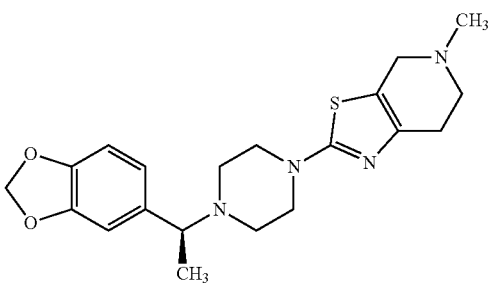 [SMILES: C[C@@H](c1ccc2c(c1)OCO2)N1CCN(c2nc3c(s2)CN(C)CC3)CC1] | S configuration; synthesized from Intermediate 16 | ++++ |
| 195 | 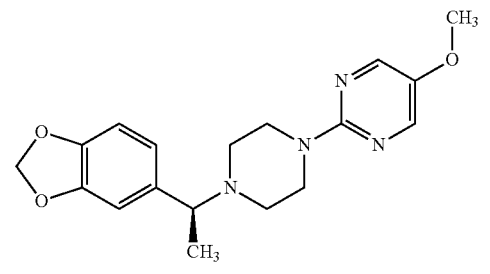 [SMILES: COc1cnc(N2CCN([C@@H](C)c3ccc4c(c3)OCO4)CC2)nc1] | S configuration; synthesized from Intermediate 16 | ++++ |
| 196 | 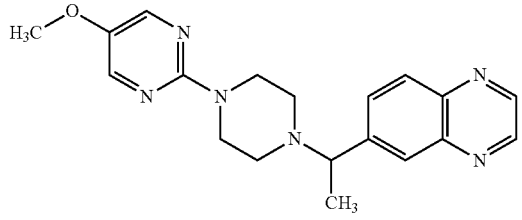 [SMILES: COc1cnc(N2CCN(C(C)c3ccc4nccnc4c3)CC2)nc1] | Racemic | +++ |
| 197 | 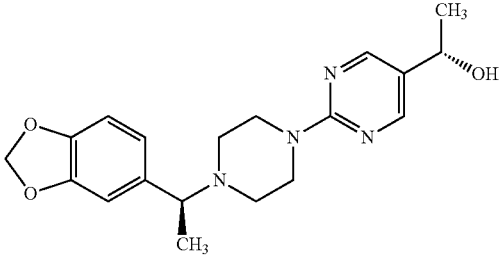 [SMILES: C[C@H](O)c1cnc(N2CCN([C@@H](C)c3ccc4c(c3)OCO4)CC2)nc1] | Chiral HPLC Method J: 2nd eluting compound | ++++ |
| 198 | 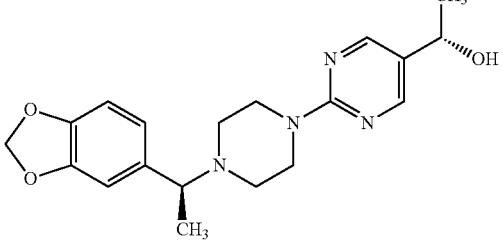 | Chiral HPLC Method J: 1st eluting compound | ++++ |

TABLE 1-continued

Compounds of formulae (I). OGA enzyme inhibition assay:

| No | Structure | Configuration specification | OGA IC50 (M) |
|---|---|---|---|
| 199 | 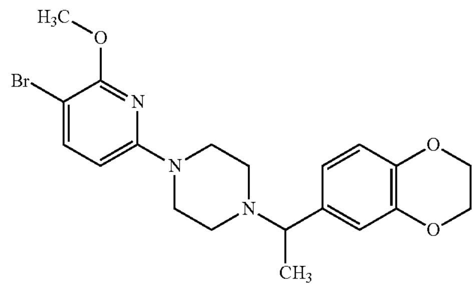 [SMILES: COc1nc(N2CCN(C(C)c3ccc4c(c3)OCCO4)CC2)ccc1Br] | Racemic | +++ |
| 200 | 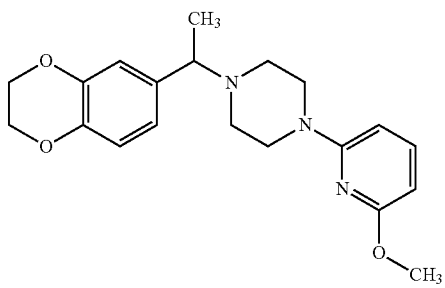 [SMILES: COc1cccc(N2CCN(C(C)c3ccc4c(c3)OCCO4)CC2)n1] | Racemic | +++ |
| 201 | 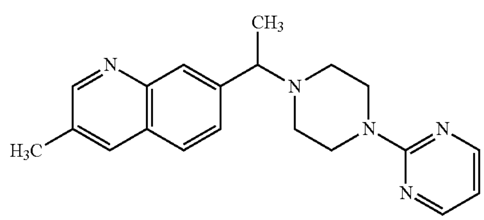 [SMILES: Cc1cnc2cc(C(C)N3CCN(c4ncccn4)CC3)ccc2c1] | Racemic | + |
| 202 | 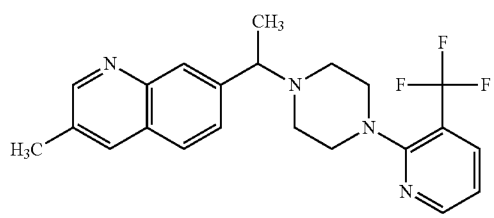 [SMILES: Cc1cnc2cc(C(C)N3CCN(c4ncccc4C(F)(F)F)CC3)ccc2c1] | Racemic | |

Activity range of the compounds of Formula (I) is the following:
+ 1 to 10 µM
++ 0.2 to 1 µM
+++ 0.2 to 0.05 µM
++++ below 0.05 µM As can be seen above, a number of compounds according to formula I are very potent OGA inhibitors, for example compounds of example 34 (in particular the second eluting compound (S)-2-(4-(1-(2,3-Dihydrobenzo[b][1,4]dioxin-6-yl)ethyl)piperazin-1-yl)pyrimidine), 37, 44, 48, 52, 56 (the second eluting compound (S)-2-(4-(1-(benzo[d][1,3]dioxol-5-yl)ethyl)piperazin-1-yl)-N-methylthiazole-4-carboxamide), 69 (the second eluting compound (S)—N-(5-(4-(1-(benzo[d][1,3]dioxol-5-yl)ethyl)piperazin-1-yl)-1,3,4-thiadiazol-2-yl)acetamide), 72 and 75 (the second eluting compound (S)-(2-(4-(1-(2,3-dihydrobenzo[b][1,4]dioxin-6-yl)ethyl)piperazin-1-yl)thiazol-5-yl)(4-methylpiperazin-1-yl)methanone), 114, 116, 128, 129, 132, 134, 137, 168, 173, 176, 180, 181, 182.

Preferred compounds of the present invention demonstrate adequate properties for use as a drug. In particular such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) *Pharm Res* 24(4); 780-790), stability in the presence of liver microsome (Obach R. S. (1999) *Drug Metab Dispos* 27(11); 1350-135) and the permeability (e.g. Caco-2 permeability assay, Calcagno A. M. (2006) *Mol Pharm* 3(1); 87-93); alternatively, they are described in Examples below, such as Example B02 describing the determination of O-GlcNAcylation level of total proteins measured in brain extracts. Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below:

Ac (acetyl), aq (aqueous), h (hour), g (gram), L (liter), mg (milligram), MHz (Megahertz), M (micromolar), min (minute), mm (millimeter), mmol (millimole), mM (millimolar), m.p. (melting point), equiv (equivalent), mL (milliliter), L (microliter), ACN (acetonitrile), AcOH (acetic acid), BINAP (2,2'-bis(disphenylphosphino)-1,1'-binaphthalene), BOC (tert-butoxy-carbonyl), CBZ (carbobenzoxy), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethylamine), DMF (dimethylformamide), DMSO (dimethylsulfoxide), DMSO-d$_6$ (deuterated dimethylsulfoxide), EDC (1-(3-dimethyl-amino-propyl)-3-ethyl-carbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), 1-PrOH (2-propanol), K$_2$CO$_3$ (potassium carbonate), LC (Liquid Chromatography), MD Autoprep (Mass directed Autoprep), MeOH (methanol), MgSO$_4$ (magnesium sulfate), MS (mass spectrometry), MTBE (Methyl tert-butyl ether), Mtr. (4-Methoxy-2,3,6-trimethylbenzensulfonyl), MW (microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), POA (phenoxy-acetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition SO$_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Depending on the nature of A, R, W, Q, m and n, different synthetic strategies may be selected for the synthesis of compounds of Formula (I). In the process illustrated in the following schemes, A, R, W, Q, m and n are as above-defined in the description unless otherwise mentioned.

Compounds of Formula (I), wherein A, R, W, Q, m and n are defined as above, can be prepared from alternative compounds of Formula (I), using suitable interconversion procedures such as those described hereinafter in the examples, or conventional interconversion procedures well known by one skilled in the art.

Compound of formula (I) can be separated into compounds of formula (Ia) and (Ib) by chiral chromatography or by chiral resolution, re-crystallization with use of an optically active acid, using methods known by one skilled in the art and as described below in the examples (Scheme 1).

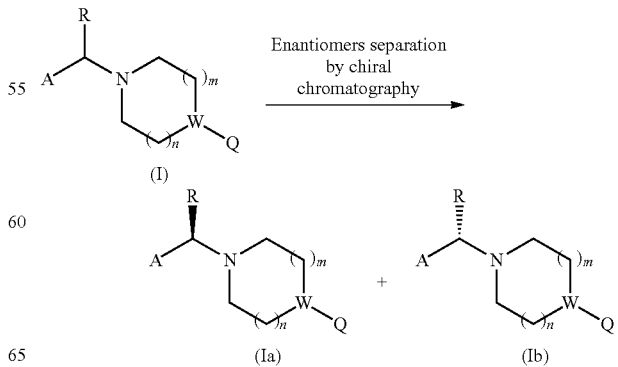

Compounds of formula (Ic), wherein A, R, Q, m and n are defined as above and W=N, can be prepared by the addition of an amine of formula (II) to a heterocycle of formula (III), where LG is a leaving group as defined above. This addition can be performed under thermic conditions, heating both compounds at a temperature between 50° C. and 200° C., using regular heating or microwave irradiation, in the presence of a base, such as but not limited to TEA, DIEA, $K_2CO_3$ or $Cs_2CO_3$, in a polar solvent, e.g. DMF, DMA or NMP. Alternatively, this addition can be catalysed by a metal complex, such as but not limited to $PdCl_2$, $Pd(OAc)_2$, $Pd_2(dba)_3$ in the presence of a ligand, e.g. BINAP, o-Tol$_3$P, X-Phos, and a base, e.g. NaOfBu, $Cs_2CO_3$ or $K_2CO_3$, in a suitable solvent or solvent mixture, for example dioxane, Toluene/MeOH, at a temperature between RT to 150° C., preferably at RT, for a few hours, e.g. one hour to 24 h (Scheme 2). Amine of formula (II) is obtained after deprotection of compound (IVa). PG is a suitable protecting group, which is compatible with the chemistry described below, such as but not limited to BOC. It can be removed under acidic conditions, such as but not limited to HCl in MeOH or dioxane or TFA in DCM, yielding isolation of amine (II).

can be prepared from ester functionality, such as but not limited to oxadiazole, thiadiazole and thiazole, (Jakopin, Z. et al. *Curr. Org. Chem.* 2008, 12, 850-898. Hemming, K. *Science of Synthesis*, 2004, 13, 127-184. Augustine, J. K. et al. *Tetrahedron*, 2009, 65, 9989-9996. 37. Kempson, J. *Name Reactions in Heterocyclic Chemistry II* (2011), 299-308). Depending on the nature of Q, compound of formula (Id) can be obtained from compound (IVc) by displacement of the leaving group LG, as defined above, in the presence of a base such as but not limited to $Cs_2CO_3$ in a polar solvent, e.g. DMF, DMSO or NMP (Scheme 3). Alternatively compound of formula (Id) can be prepared by metal catalysed cross coupling reaction with a suitable boronic acid (Va) or ester (Vb) and an heterocycle of formula (III), using conditions known by a person skilled in the art, such as but not limited to $Pd(PPh_3)_4$ as catalyst, $K_2CO_3$ as base, dioxane as solvent at temperature ranging from RT to 180° C. (Scheme 3). Hydrogenation of the resulting coupling product in the presence of a catalyst such as $Pd(OH)_2$, would yield compound of formula (Id) (e.g. Andres, J.-I. et al. *J. Med. Chem.* 2012, 55, 8685-8699) (Scheme 3).

Scheme 3

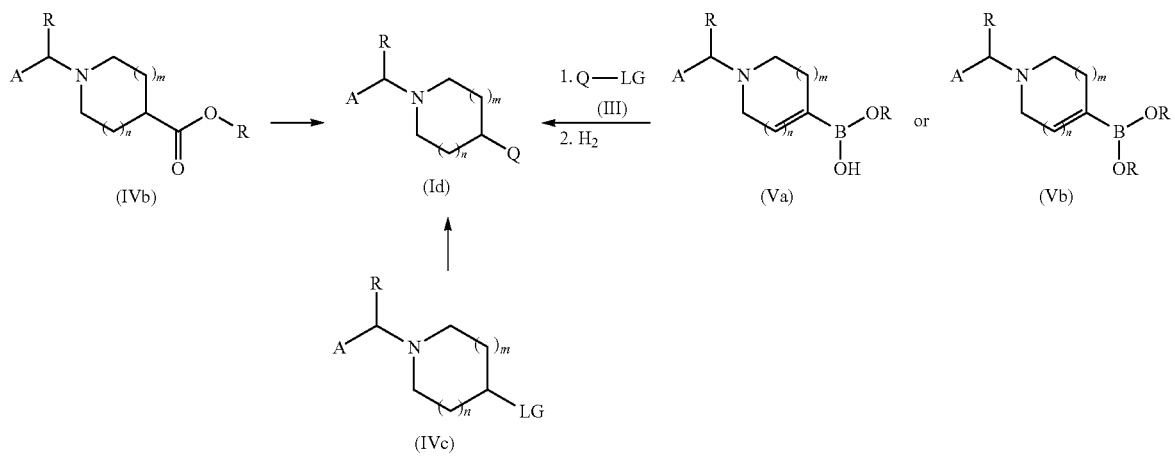

Scheme 2

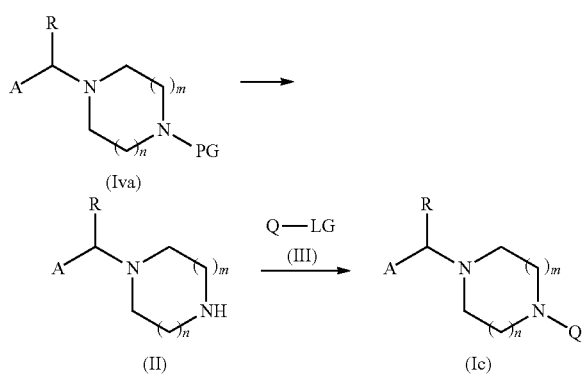

Compounds of formula (Id), wherein A, R, Q, m and n are defined as above and W=CH, can be prepared from an ester (IVb) using method known by a person killed in the art and as described in the examples below. Different heterocycles Q Compound of formula (IV), wherein A, R, W, Q, m and n are defined as above and $Y^1$ is a protecting group PG when W=N or an ester when W=CH, can be prepared from the corresponding ketone (IX) by reductive amination with amine (VI), using conditions known to the one skilled in the art, such as but not limited to the use of $NaBH(OAc)_3$ as reducing agent, in the presence of one equivalent of AcOH in DCE. Alternatively, reductive amination can be performed in two steps, with first imine formation, that can be catalysed by $Ti(OiPr)_4$, followed by reduction with suitable reducing agent, such as but not limited to $NaBH_4$ in MeOH (Abdel-Magid, A. F. at al. *J. Org. Chem.* 1996, 61, 3849-3862). Alternatively, ketone (IX) can be reduced into the corresponding alcohol (VIII) using usual reductive agents such as $NaBH_4$ in an alcoholic solvent, such as MeOH. Alcohol functionality can be then transformed into a suitable leaving group, such as but not limited to Cl or OMs, using conditions known to a person skilled in the art. The addition of amine (VI) to intermediate (VII) would yield the formation of compound (IV).

Scheme 4

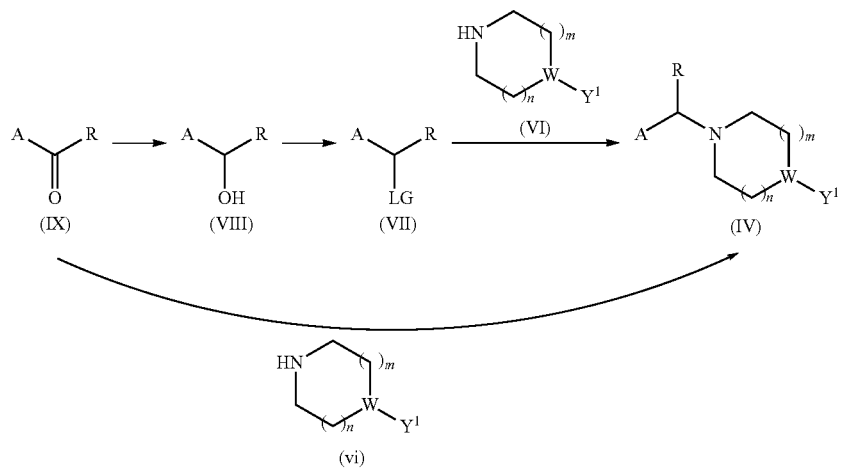

Alternatively, compound of formula (X), wherein W, Q, m and n are defined as above and PG is a suitable protecting group, such as but not limited to BOC, can be prepared from amine (XI), from compounds (XII), wherein m, n and PG are defined as above and $Y^2$ is an ester or a leaving group, or from compounds (XIIIa) or (XIIIb) (Scheme 5).

When W is N, compound of formula (X) can be prepared by the addition of an amine of formula (XI) to a heterocycle of formula (III), where LG is a leaving group as defined above. This addition can be performed under thermic conditions or can be catalysed by a metal complex, using conditions known by a person skilled in the art and as described below in the examples.

When W is CH, compound of formula (X) can be prepared from an ester (XII), wherein $Y^2$=COOR and W=CH, using method known by a person skilled in the art and as described in the examples below. Different heterocycles Q can be prepared from ester functionality, such as but not limited to oxadiazole, thiadiazole and thiazole, (Jakopin, Z. et al. *Curr. Org. Chem.* 2008, 12, 850-898. Hemming, K. *Science of Synthesis*, 2004, 13, 127-184. Augustine, J. K. et al. *Tetrahedron*, 2009, 65, 9989-9996. 37. Kempson, J. *Name Reactions in Heterocyclic Chemistry II* (2011), 299-308). Depending on the nature of Q, compound of formula (X) can be obtained from compound (XII), wherein W is CH and $Y^2$=LG as defined above, by displacement of the leaving group LG in the presence of a base such as but not limited to $Cs_2CO_3$ in a polar solvent, e.g. DMF, DMSO or NMP.

Compound of formula (X), wherein Q is a thiazole, can be obtained from compound (XII), wherein $Y^2$ is an aminomethanecarbothioyl group, and a suitable alpha-bromo ketone, using conditions know by a person skilled in the art.

Alternatively, compound of formula (X) can be prepared by metal catalysed cross coupling reaction with a suitable boronic acid (XIIIa) or ester (XIIIb), and a heterocycle of formula (III), using conditions known by a person skilled in the art, such as but not limited to $Pd(PPh_3)_4$ as catalyst, $K_2CO_3$ as base, dioxane as solvent at temperature ranging from RT to 180° C. (Scheme 5). Hydrogenation of the resulting coupling product in the presence of a catalyst such as $Pd(OH)_2$, would yield compound of formula (X) (e.g. Andres, J.-I. et al. *J. Med. Chem.* 2012, 55, 8685-8699) (Scheme 5).

PG is a suitable protecting group, which is compatible with the chemistry described above, such as but not limited to BOC. It can be removed under acidic conditions, such as but not limited to HCl in MeOH or dioxane or TFA in DCM, yielding isolation of amine (XIV). It can be further transformed into compound of formula (I) by reductive alkylation with ketone of formula (IX), following conditions well known by a person skilled in the art, as described in the examples (Abdel-Magid, A. F. at al. *J. Org. Chem.* 1996, 61, 3849-3862). Alternatively, amine (XIV) addition to compound (VII), prepared as described above and in the examples, would yield the formation of compound of formula (I).

Scheme 5

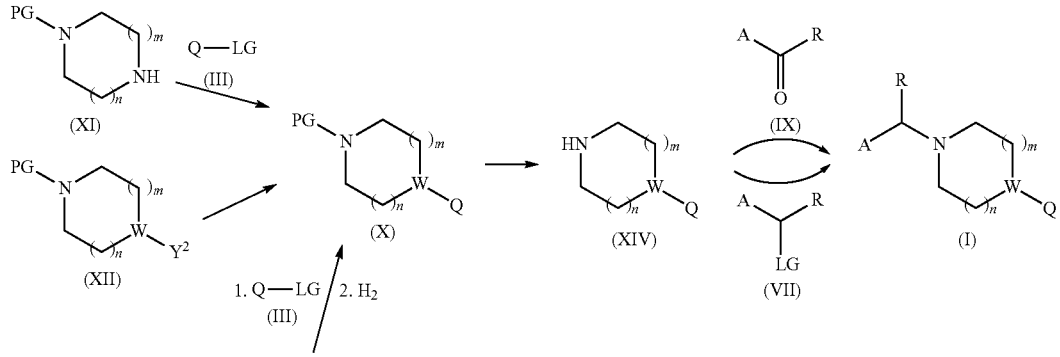

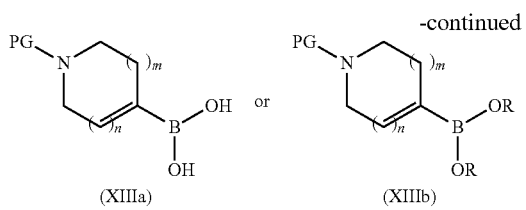

Amine of formula (II) can be separated into amines of formula (IIa) and (IIb) by chiral chromatography or chiral resolution by re-crystallization with an optically active acid, using methods known by one skilled in the art and as described below in the examples (Scheme 6).

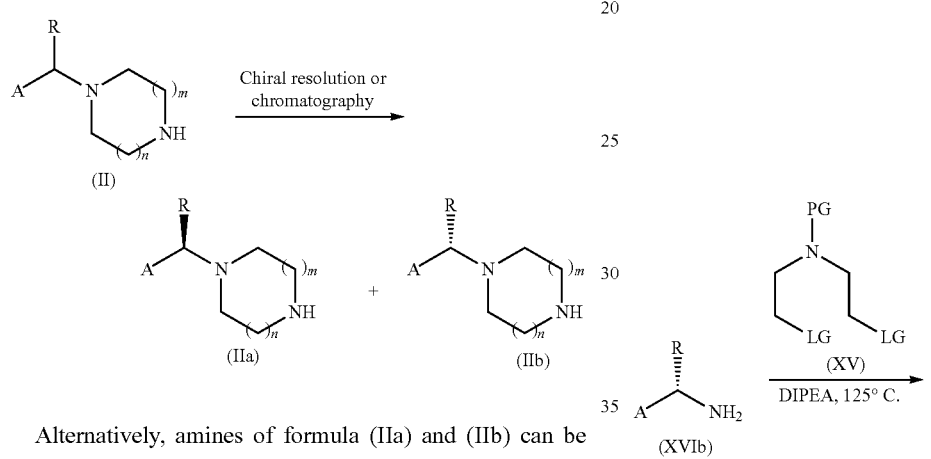

Alternatively, amines of formula (IIa) and (IIb) can be synthesized from chiral amines (XVIa) and (XVIb) respectively. Addition of amines (XVIa) and (XVIb) to reagent (XV), wherein PG is a protecting group, e.g. BOC or SO₂Tol and LG is a leaving group, e.g. Cl, would yield the formation of protected amines (IVe) and (IVf) respectively (Thiel, O. R. et al. *J. Org. Chem.* 2008, 73, 3508-3515). Deprotection conditions need to be selected based on the nature of the PG, such as HCl in dioxane or MeOH or TFA in DCM for BOC protecting group. Alternatively a mixture of HBr, AcOH and 4-hydroxybenzoic acid or a mixture of H₂SO₄ and trifluoroacetic acid at temperatures ranging from RT to 100° C. would be used to cleave a sulfonamide protecting group, such as para-toluene sulfonamide.

Scheme 7

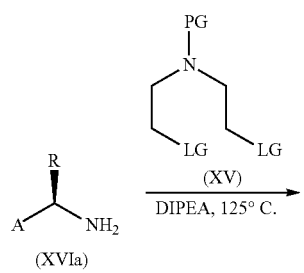

For the preparation of amines of formula (XVIa) and (XVIb), ketone of formula (IX) can be transformed into chiral imine (XVIII), reacting with a chiral auxiliary, such as but not limited to tert-butanesulfinamide group in the presence of titanium ethoxide (Ellman J. A. et al. *Acc. Chem. Res.* 2002, 35, 984-995). It can be further transformed into sulfinamide (XVIIa) or (XVIIIb), depending on the conditions used for the reduction step, as described in the reference from Ellman J. A. et al. *J. Org. Chem.* 2007, 72, 626-629.

Scheme 8

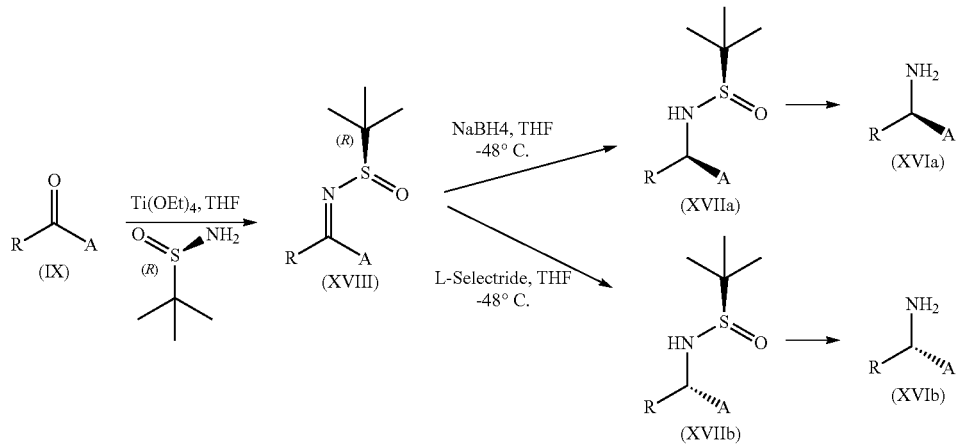

Alternatively aldehyde of formula (XIX) can be transformed into alcohol of formula (VIII) with addition of a suitable nucleophile, such as but not limited to a Grignard reagent (Scheme 9). In another process, ketone of formula (IXa) can be obtained by Stille cross coupling reaction between aryl halide (XX) and tributyl(1-ethoxyvinyl)tin in the presence of a catalyst, such as but not limited to Pd(PPh$_3$)$_2$Cl$_2$ in toluene at temperatures ranging from RT to 110° C. (Scheme 10).

Scheme 9

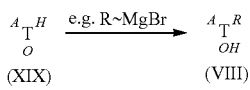

Scheme 10

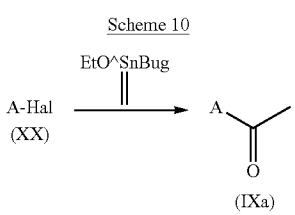

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., /V, /v-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, H$_2$O, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

The present invention also relates to a process for manufacturing compounds of formula (I) comprising the steps of:

The compounds of formula (I) and sub-formulae thereof are accessible via the routes above. The starting materials, are usually known to the skilled artisan, or they can be easily prepared by known methods.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization.

General chemical modifications are known to the one skilled in the art. Halogenation of aryls or hydroxy substitution by halogens of acids, alcohols, phenols, and their tautomeric structures can be preferably carried out by use of POCl$_3$, or SOCl$_2$, PCl$_5$, SO$_2$Cl$_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even overnight. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like Et$_3$N, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd (PPh$_3$)$_4$, or Pd(OAc)$_2$, PdCl$_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stille coupling) may be useful. This experience can be transferred to N- and O-arylations. Numerous papers and methods are available and useful for the one skilled in the art in respect of N-arylation and even of electron deficient anilines, and with aryl chlorides and anilines as well as for O-arylation by using Cu catalysis and Pd catalysis.

In the final step of the processes above, a salt of the compounds, preferably those of formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as magnesium hydroxide, calcium hydroxide and barium hydroxide; alkali metal alkoxides, for example potassium ethoxide and sodium propoxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. The aluminum salts of the compounds according to the invention are likewise included. In the case of certain compounds of the formula i, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as methanesulfonate, ethanesulfonate, toluenesulfonate and benzenesulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprate, caprylate, chloride, chlorobenzoate, citrate, cyclamate, cinnamate, cyclopentanepropionate, digluconate, dihydrogenphosphate, dinitrobenzoate, dodecylsulfate, ethanesulfonate, formate, glycolate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Both types of salts may be formed or interconverted preferably using ion-exchange resin techniques.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine. This is not intended to represent a restriction.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, di-O-p-toluoyl-tartaric acid, mandelic acid, malic acid, lactic acid, suitable N-protected amino acids (for example N-benzoylproline or N-benzenesulfonylproline), or the various optically active camphorsulfonic acids. The suitably formed salt with optically active acid is crystallized using various combinations of solvents, such as but not limited to methanol, ethanol, isopropanol, THF, water, diethyl ether, acetone, methyl tert-butyl ethers and other solvents known to the person skilled in the art. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

When discovering and developing therapeutic agents, the person skilled in the art attempts to optimize pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

A further aspect of the invention relates to the use of compounds according to formula (I) and/or physiologically acceptable salts thereof for inhibiting a glycosidase. Such use may be therapeutic or non-therapeutic in character. The term "inhibition" denotes any reduction in glycosidase activity, which is based on the action of the specific inventive compounds capable to interact with the target glycosidase in such a manner that makes recognition, binding and blocking possible. It shall be understood that the compounds of the invention finally interact with the target to unfold the effect. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-β-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-β-D-glucopyranoside (O-GlcNAc) while they do not substantially inhibit a lysosomal β-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. $IC_{50}$ is the concentration of a compound that produces 50% of the maximal inhibition for that compound. The glycosidase target is especially half inhibited by the compounds described herein if the concentration of the compounds amounts to less than 100 μM, preferably less than 10 μM, more preferably less than 1 μM, most preferably less than 0.2 μM. Most preferably, compounds of Formula (I) exhibit an $IC_{50}$ less than 0.02 μM.

A further aspect of the present invention relates to a method for inhibiting a glycosidase, wherein a system capable of expressing the glycosidase, particularly expressing said glycosidase, is contacted with at least one compound of formula (I) according to the invention and/or physiologically acceptable salts thereof, under conditions such that said glycosidase is inhibited. In a preferred embodiment of the method, the glycosidase is contacted with a compound selectively inhibiting O-GlcNAcase and more preferably having an $IC_{50}$ of less than 0.2 µM. It is also preferred that the method is performed in-vitro and/or that the method is not practiced on the human body. A cellular system is preferred in the scope of the method. The cellular system is defined to be any subject provided that the subject comprises cells. The cell refers to any type of primary cells or genetically engineered cells, whether in the isolated status, in culture, as cell line, assembled in tissue, organs or intact laboratory mammals, provided that they are capable of expressing the glycosidase. It shall also be understood that the cell expresses the glycosidase as inherent pre-condition to put the methods of inhibition into practice. Although it is particularly preferred that the cells are capable of expressing or do express the glycosidase, it shall not be excluded that glycosidase-deficient cells can be used and the glycosidase is artificially added to the cellular system. The assay of the invention can be even completely performed in-vitro such that the cell is waived but a glycosidase is contacted with at least one compound of formula (I) according to the invention and/or physiologically acceptable salts thereof. Hence, an amount of isolated glycosidase is provided in crude or purified form for this purpose.

As discussed herein, the glycosidase-signaling pathways are relevant for various diseases, preferably neurodegenerative diseases, diabetes, cancer and stress. Accordingly, the compounds according to the invention are useful in the prophylaxis and/or treatment of diseases that are dependent on the said signaling pathways by interaction with one or more of them. The present invention therefore relates to the therapeutic and non-therapeutic use of compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer and stress. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

A further aspect of the invention relates to a medicament comprising at least one compound according to the invention and/or pharmaceutically usable derivatives, salts, solvates and stereoisomers thereof, including mixtures thereof in all ratios. A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (e.g., WO 2008/025170) and are useful with the compounds of the invention.

In some embodiments, a compound according to the invention, or for use according to the invention, may be provided in combination with any other active agents or pharmaceutical compositions where such combined therapy may be useful to modulate O-GlcNAcase activity, for example to treat neurodegenerative, inflammatory, cardiovascular, or immunoregulatory diseases or any condition described herein. In some embodiments, a compound according to the invention, or for use according to the invention, may be provided in combination with one or more agents useful in the prevention or treatment of tauopathies and Alzheimer's disease. Examples of such agents may include, without limitation,

- Acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Huperzine A, Phenserine, Debio-9902 SR (ZT-1 SR), Zanapezil (TAK0147), ganstigmine, NP7557, of nicotinic acetylcholine receptor agonists, 5-HT6 receptor antagonists, etc
- Tau aggregation inhibitors such as methylene blue, etc
- Microtubule stabilizers such as AL-108, AL-208, paclitaxel, etc
- Amyloid-β (A β) peptide lowering agents such as 1-secretase (BACE-1) inhibitors, senile plaque-clearing biologies such as Aβ antibodies and Aβ vaccines The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intra-dermal) methods. Such formulations can be prepared using processes known in the pharmaceutical art by, e.g., combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example tauopathies and Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer and stress, more preferably neurodegenerative diseases, most preferably one or more tauopathies, highly preferably Alzheimer's disease and dementia. It shall be understood that the host of the compound is included in the present scope of protection according to the present invention.

Another aspect of the present invention relates to compounds of formula (I) according to the invention and/or physiologically acceptable salts thereof for use in the prophylactic or therapeutic treatment and/or monitoring of diseases that are caused, mediated and/or propagated by OGA activity. Another aspect of the invention concerns compounds of formula (I) according to the invention and/or physiologically acceptable salts thereof for use in the prophylactic or therapeutic treatment and/or monitoring of neurodegenerative diseases, diabetes, cancer and stress. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer and stress.

Another aspect of the invention relates to a method for treating a disease that is caused, mediated and/or propagated by OGA activity, wherein an effective amount of at least one compound of formula (I) according to the invention and/or physiologically acceptable salts thereof is administered to a mammal in need of such treatment. Another aspect of the invention relates to a method for treating neurodegenerative diseases, diabetes, cancer and stress, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

The neurodegenerative disease or condition is more preferably selected from the group of one or more tauopathies and Alzheimer's disease, dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Dementia with Lewy Bodies, Diffuse neurofibrillary tangles with calcification, Down's syndrome, Familial British dementia, Familial Danish dementia, Frontotemporal dementia with parkinsonism linked to chromosome 17 (FTDP-17), Frontotemporal Lobe Degeneration (FTLD), Ganglioglioma, Gangliocytoma, Gerstmann-Straussler-Scheinker disease, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Pure Autonomic Failure, Richardson's syndrome, Subacute sclerosing panencephalitis, Tangle-only dementia, Tuberous Sclerosis, Huntington's disease and Parkinson's disease. Most preferred are one ore more tauopathies and Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer and stress.

In the meaning of the invention, prophylactic treatment is advisable if the subject possesses any preconditions for the aforementioned physiological or pathological conditions, such as a familial disposition, a genetic defect, or a previously passed disease.

In the scope of the present invention, compounds of formula (I) are provided for the first time. The low molecular weight compounds of the invention are strong and selective glycosidase inhibitors with improved passive permeability. The compounds of formula (I) have been shown to be competitive with PUGNAc, a known OGA inhibitor that binds in the substrate pocket. The endogenous substrate is an O-GlcNAcylated protein. O-GlcNAcylation of nuclear and cytoplasmic proteins is one of the most common post-translational modifications in animals and plants. O-GlcNAc cycling modulates a number of cellular processes, and evidence is mounting that dysregulation of O-GlcNAcylation plays a role in the etiology of several diseases, including tauopathies and Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in tauopathies and Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat tauopathies and Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims.

EXPERIMENTAL PART

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in CDCl$_3$). s (singlet), d (doublet), t (triplet), q (quadruplet), br (broad), quint (quintuplet).

The MS data provided in the examples described below were obtained as followed: Mass spectrum: LC/MS Agilent (ESI/APCI), Chemstration, 1200 Series.

LCMS Methods:
Method A
Method: A—0.1% TFA in H$_2$O, B—0.1% TFA in ACN: Flow—2.0 mL/min.
Column: XBridge C8 (50×4.6 mm, 3.5 pm +ve mode
Method B
Method: A—10 mM NH$_4$HCO$_3$ in H$_2$O, B—ACN: Flow—1.0 mL/min.
Column: XBridge C8 (50×4.6 mm, 3.5 pm), +ve mode
Method C
Method: A—10 mM NH$_4$HCO$_3$ in H$_2$O, B—ACN: Flow—1.0 mL/min.
Column: XBridge C8 (50×4.6 mm, 3.5 μm), -ve mode HPLC analyses were obtained using Agilent 1200 Series instruments as followed using % with UV detection (maxplot).
Method A
Method: A—0.1% TFA in H$_2$O, B—0.1% TFA in ACN: Flow—2.0 mL/min.
Column: XBridge C8 (50×4.6 mm, 3.5 μm).
Method B
Method: A—10 mM NH$_4$HCO$_3$ in H$_2$O, B—ACN: Flow—1.0 mL/min.
Column: XBridge C8 (50×4.6 mm, 3.5 μm).
Method C
Method: Gradient from 70% H$_2$O (10 mM K$_2$HPO$_4$): 30% MeCN to 70% MeCN over 15 minutes, Flow: 1 mL/min. Column: XTERRA RP18 (250×4.6) mm, 5 μm Chiral HPLC
Method A
Mobile Phase: 0.1% DEA in n-HEXANE:IPA: 60:40; COLUMN: CHIRALPAK AD-H (250×4.6) mm, 5μηι, FLOW: 1.0 mL/min
Method B:
Mobile Phase: n-HEXANE:EtOH: 90:10: FLOW: 1.0 mL\min; COLUMN: CHIRALPAK IC (250×4.6) mm, 5μηι
Method C:
Mobile Phase: 0.1% TFA in n-HEXANE:IPA: 60:40; COLUMN: CHIRALcell OD-H (250×4.6) mm, 5μηι, FLOW: 1.0 mL/min
Method D:
Mobile Phase: 0.1% DEA in Hexane:EtOH: 80:20; FLOW: 1.0 mL\min; COLUMN: Chiralcell OJ-H column (250×4.6) mm, 5 μηι
Method E:
Mobile Phase: 0.1% DEA in Hexane:EtOH: 80:20; FLOW: 1.0 mL\min; COLUMN: Chiralcell AY-H column (250×4.6) mm, 5μηι
Method F:
Mobile Phase: 0.1% DEA in Hexane:EtOH: 70:30; FLOW: 1.0 mL\min; COLUMN: Chiralpak IA (250×4.6) mm, 5 μm
Method G:
Mobile Phase: 0.1% DEA in Hexane:EtOH: 60:40; FLOW: 1.0 mL\min; COLUMN: Chiralcel OD-H (250×4.6) mm, 5 pm
Method H:
Mobile Phase: 0.1% DEA in n-Hexane:EtOH: 80:20; FLOW: 1.0 mL\min; COLUMN: CHIRALPAK IC (250×4.6) mm, 5 pm General flash chromatography conditions used for the purification of intermediates or compounds of Formula I: silica gel 230-400 mesh; gradients used as eluent: 10 to 80% EtOAc in Petroleum ether or 1 to 15% MeOH in DCM MD Autoprep Conditions
The mass directed preparative HPLC purifications were performed with a mass directed autopurification Fractionlynx from Waters.
Method A
0.1% HCOOH in H$_2$O, B-MeOH or ACN, Column: Symmetry C8 (300 mm×19 mm), 7 μm
Method B
0.1% TFA in H$_2$O, B-MeOH or ACN, Column: Symmetry C8 (300 mm×19 mm), 7 μm
Method C
10 mM NH$_4$HCO$_3$ in H$_2$O, B-MeOH or ACN, Column: Symmetry C8 (300 mm×19 mm), 7 μm
Method D
10 mM NH$_4$OAC in H$_2$O, B-MeOH or ACN, Column: Symmetry C8 (300 mm×19 mm), 7 μm Preparative HPLC Conditions
Method PA
0.1% TFA in H$_2$O, B-MeOH or ACN. Column: Sunfire C8 (19 mm×250 mm) 5 μm or Sunfire C18 (30 mm×250 mm) 10 pm.
Method PB
10 mM NH$_4$HCO$_3$ in H$_2$O, B-MeOH or ACN, Column: Sunfire C8 (19 mm×250 mm) 5 μm or Sunfire C18 (30 mm×250 mm) 10 pm.
Chiral Preparative Method PC
Mobile phase: n-Hexane, IPA; Column: Chiral pak AD-H (20×250) mm, 5 micron, Flow: 12 mL/min
Chiral Preparative Method PD:
Mobile phase: n-Hexane, IPA; Column: Chiral pak AD-H (20×250) mm, 5 micron, Flow: 12 mL/min
Chiral Preparative Method PE:
Mobile phase: n-Hexane, IPA; Column: Chiralcell OD-H (20×250) mm, 5 micron, Flow: 12 mL/min
Chiral Preparative Method PF:
Mobile Phase: 0.1% DEA in Hexane:EtOH: 80:20; FLOW: 12.0 mL\min; COLUMN: Chiralcell OJ-H column (250×20) mm, 5 pm
Chiral Preparative Method PG:
Mobile Phase: 0.1% DEA in Hexane:EtOH: 80:20; FLOW: 20.0 mL\min; COLUMN: Chiralcell AY-H column (250×30) mm, 5 μm
Chiral Preparative Method PH:
Mobile Phase: n-HEXANE:ETOH: 90:10: FLOW: 20.0 mL\min; COLUMN: CHIRALPAK IC (250×30) mm, 5 μm
Chiral Preparative Method PI:
Mobile Phase: 0.1% DEA in Hexane:EtOH: 80:20; FLOW: 12.0 mL\min; COLUMN: Lux Cellulose C4 (250×21.2) mm, 5 pm
Chiral Preparative Method PJ:
Mobile Phase: 0.1% DEA in Hexane:EtOH: 70:30; FLOW: 12.0 mL\min; COLUMN: Chiralpak IA (250×20) mm, 5 pm
Chiral Preparative Method PK:
Mobile Phase: 0.1% DEA In Hexane:EtOH: 50:50; FLOW: 10.0 ml_/min; COLUMN: Chiralpac IC (250×21) mm, 5 μm The SFC purifications were performed with a Prep SFC, THAR-SFC 80 and THAR-SFC 200.

The microwave chemistry was performed on a single mode microwave reactor Initiator™ Sixty from Biotage.

General procedure for ester reduction of heterocycles: Procedure A

To a stirred solution of ester (1 equiv) in dry THF (20 to 35 mL), lithium triethylborohydride (1 M solution in THF, 1.7 equiv) was added slowly at 0° C. The reaction mixture was stirred at room temperature for 2 h. The completion of the reaction was monitored by TLC. Reaction mixture was cooled to 0° C. and quenched using 10% ammonium chloride solution. Solvent was removed under vacuum and resulting residue was purified by flash column chromatography to afford the desired product.

General procedure for chlorination of hetrocyclic alcohol: Procedure B To a stirred solution of alcohol (1 equiv) in dry DCM (10 to 20 mL), thionyl chloride (1.7 to 3 equiv) was added slowly at 0° C. The reaction mixture was warmed to rt and was refluxed for 1 h. The reaction mixture was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum to give chloro compound.

General Procedure for Reductive Amination: Procedure C

To a solution of aldehyde (1 equiv) in dry THF (4 to 10 mL), amine (0.8 to 1.1 equiv), acetic acid (7 equiv) was added at room temperature and stirred for 30 min. Then the reaction mixture was cooled to 0° C. and sodium triacetoxy borohydride (1.2 equiv) was added slowly. The resulting reaction mixture was stirred at room temperature for 16 h. The reaction mixture was concentrated, the crude product was diluted with (10 to 20 mL) EtOAc and the organic layer was washed with (10-20 mL) of brine. The organic layer was separated, dried over anhydrous $Na_2SO_4$ and concentrated under vacuum. The crude products were purified by flash column chromatography to afford the desired product.

General Procedure for W-Alkylation: Procedure D

To a stirred solution of amine (1 mmol/0.8 to 1 equiv) in dry DMF (5 to 10 mL), chloro compound (1.0 to 1.2 equiv) and potassium carbonate (2 equiv) were added at rt. The resulting mixture was heated at 90° C. for 16 h. It was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum. The crude products were purified by flash chromatography to afford the desired product.

General Procedure for W-Alkylation: Procedure E

To a stirred solution of amine (1 mmol/1 equiv) in acetonitrile (5 to 10 mL), chloro compound (1.5 to 2 equiv), triethyl amine (2 equiv) were added at rt. The resulting mixture was stirred at rt to 60° C. for 16 h. It was diluted with water (15 mL) and extracted with EtOAc (2×20 mL). The organic layer was dried over anhydrous $Na_2SO_4$ and concentrated under reduced pressure. The resulting crude product was purified by flash chromatography to afford the desired product.

INTERMEDIATES SYNTHESIS

Intermediate 1: 5-(1-Chloroethyl)penzord1H,31dioxole

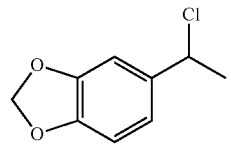

Step 1: 1-(Benzo[d][1,3]dioxol-5-yl)ethan-1-ol

To a stirred solution of 3,4-methylenedioxy acetophenone (4.5 g, 27 mmol, Alfa aesar) in dry MeOH (50 mL), $NaBH_4$ (1.08 g, 42 mmol, Loba chemie) was added slowly at 0° C. The reaction mixture was stirred at room temperature for 1 h. Then the reaction mixture was concentrated under vacuum and diluted with DCM. The DCM layer was washed with water, brine and dried over anhydrous $Na_2SO_4$. The solvent was removed under reduced pressure and resulting crude alcohol was used as such in the next step. Yield: 90% (4.0 g, colorless liquid). $^1$H NMR (400 MHz, $CDCl_3$): δ 6.89 (s, 1H), 6.89-6.75 (m, 2H), 5.95 (s, 2H), 4.81 (t, J=8.0 Hz, 1H), 1.46 (d, J=8.0 Hz, 3H). LCMS: (Method B) 149.0 (Hydroxy elimination mass), Rt. 2.51 min, 98.6% (Max). HPLC: (Method A) Rt. 2.499 min, 99.5% (Max).

Step 2: 5-(1-Chloroethyl)benzo[d][1,3]dioxole

The title compound was synthesized by following general procedure B. It was used for next step without further purification. Yield: 72% (1.2 g, colorless liquid). $^1$H NMR (400 MHz, DMSO-$d_6$): δ 7.06 (d, J=4.0 Hz, 1H), 6.93 (d, J=8.0 Hz. 1H), 6.86 (d, J=8.0 Hz, 1H), 6.01 (s, 2H), 2.49 (q, J=8.0 Hz, 1H), 1.74 (d, J=8.0 Hz, 3H). LCMS: (Method B) 149.0 (Cl-Elimination mass), Rt. 3.71 min, 80.15% (Max).

Intermediate 2: 1-(1-(Benzord1H,31 dioxol-5-yl)ethyl)piperazine Hydrochloride

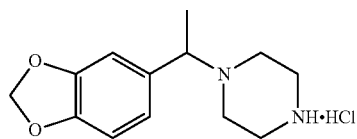

Step 1: tert-butyl 4-(1-(benzo[d][1,3]dioxol-5-yl) ethyl)piperazine-1-carboxylate The title compound was synthesized following general procedure D, starting with Intermediate 1 and N-boc piperazine. The crude product was purified by flash chromatography, affording the title compound (yellow solid). $^1$H NMR (400 MHz, DMSO-$d_6$): δ 6.85-6.82 (m, 2H), 6.74-6.71 (m, 1H), 5.98 (m, 2H), 3.37-3.36 (m, 1H), 3.27 (br. s, 4H), 2.28-2.21 (m, 4H), 1.37 (s, 9H), 1.25 (d, 3H, J=6.8 Hz). LCMS: (Method A) 335.2 (M+H), Rt. 3.10 min, 93.15% (Max). HPLC: (Method A) Rt. 3.12 min, 95.01% (Max).

Step 2: 1-(1-(Benzo[d][1,3]dioxol-5-yl)ethyl)piperazine hydrochloride

To a stirred solution of tert-butyl 4-(1-(benzo[d][1,3]dioxol-5-yl)ethyl)piperazine-1-carboxylate (1.8 g, 5.38 mmol) in dry dioxane (10 mL), HCl in dioxane (10 mL, 4 M, Spectrochem) was added at rt and stirred for 2 h at same temperature. The reaction mixture was concentrated under vacuum and the resulting crude product was washed with diethyl ether to afford the title product as hydrochloride salt. Yield: 82% (1.2 g, off white solid). $^1$H NMR (400 MHz, DMSO-$d_6$): δ 12.29 (s, 1H), 7.34 (s, 1H), 7.08 (d, 1H, J=7.7 Hz), 7.00 (d, 1H, J=7.9 Hz), 6.07 (s, 2H), 4.54 (br. s, 1H), 3.81 (br. s, 1H), 3.49-3.42 (m, 3H), 3.33 (br. s, 2H), 3.12 (br. s, 1H), 2.99 (br. s, 1H), 1.67 (d, 3H, J=5.7 Hz). LCMS: (Method A) 235.0 (M+H), Rt. 1.65 min, 98.08% (Max). HPLC: (Method A) Rt. 1.56 min, 99.86% (Max).

Intermediate 3: 6-(1-chloroethyl)-2,3-dihydrobenzorbiri,41 dioxine

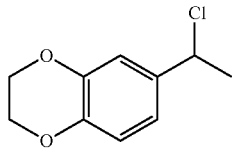

Step 1: 1-(2,3-dihydrobenzo[b][1,4]dioxin-6-yl)ethan-1-ol

The title compound was synthesized with same protocol as described for Intermediate 1, Step 1, using 1-(2,3-dihydrobenzo[b][1,4]dioxin-6-yl)ethan-1-one (2.0 g, 11.2 mmol) and NaBH$_4$ (0.49 g, 13 mmol). The resulting crude alcohol was used as such in the next step. Yield: 99% (2.0 g, colorless liquid). $^1$H NMR (400 MHz, DMSO-$d_6$): δ 6.80 (s, 1H), 6.79-6.76 (m, 2H), 4.59 (q, J=5.6 Hz, 1H), 4.20 (s, 4H), 1.26 (d, J=5.6 Hz, 3H). LCMS: (Method B) 163.0 (Hydroxy elimination mass), Rt. 2.51 min, 99.4% (Max).

Step 2: 6-(1-chloroethyl)-2,3-dihydrobenzo[b][1,4]dioxine

The title compound was synthesized according to the general procedure B. It was used in the next step without further purification. Yield: 90% (2.2 g, brown liquid). $^1$H NMR (400 MHz, DMSO-$d_6$): δ 6.97 (s, 1H), 6.96-6.92 (m, 1H), 6.84-6.82 (m, 1H), 5.26 (t, J=6.7 Hz, 1H), 4.23 (s, 4H), 1.75 (d, J=6.7 Hz, 3H). LCMS: (Method A) 163.0 (Cl-Elimination mass), Rt. 3.66 min, 95.3% (Max).

Intermediate 4: 1-(1-(2,3-dihydrobenzorbin,41dioxin-6-yl)ethyl)piperazine Hydrochloride

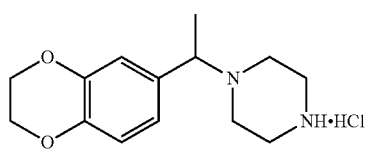

Step 1: t-Butyl 4-(1-(2,3-dihydrobenzo[b][1,4]dioxin-6-yl)ethyl)piperazine-1-carboxylate The title compound was synthesized according to the general procedure D, starting with Intermediate 3 (5 g, 25.2 mmol) and N-boc piperazine (3.96 g, 21.2 mmol). The crude product was purified by flash chromatography, affording the title compound. Yield: 52% (4.6 g, brown liquid). $^1$H NMR (400 MHz, DMSO-$d_6$): δ 6.80-6.71 (m, 3H), 4.21 (s, 5H), 3.34-3.26 (m, 4H), 2.27-2.24 (m, 4H), 1.37 (s, 9H), 1.23 (d, J=6.7 Hz, 3H). LCMS: (Method A) 349.2 (M+H), Rt. 3.19 min, 80.9% (Max).

Step 2: 1-(1-(2,3-dihydrobenzo[b][1,4]dioxin-6-yl)ethyl)piperazine Hydrochloride To a stirred solution of fert-butyl 4-(1-(2,3-dihydrobenzo[b][1,4]dioxin-6-yl)ethyl)piperazine-1-carboxylate (4.6 g, 13.20 mmol) in dry dioxane (5.0 ml_), HCl in dioxane (10.0 ml_, 4 M, Spectrochem) was added at 0° C. The reaction mixture was stirred at rt for 2 h. The completion of the reaction was monitored by TLC. The reaction mixture was concentrated. Diethyl ether was added and was evaporated again, affording the title compound. Yield: 89% (3.8 g, off white solid). $^1$H NMR (400 MHz, DMSO-$d_6$): δ 12.08 (br. s, 1H), 9.48-9.18 (m, 2H), 7.18 (s, 1H), 7.03 (s, 1H), 6.92 (d, J=10.6 Hz, 1H), 4.49 (s, 1H), 4.24 (s, 4H), 3.41-3.15 (m, 4H), 2.91-2.71 (m, 4H), 1.64 (s, 3H). LCMS: (Method A) 249.2 (M+H), Rt. 1.64 min, 92.6% (Max).

Intermediate 5: 5-(1-chloroethyl)-2,3-dihydrobenzofuran

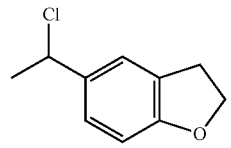

Step 1: 1-(2,3-dihydrobenzofuran-5-yl)ethan-1-ol

To a stirred solution of 1-(2,3-dihydrobenzofuran-5-yl)ethan-1-one (2.0 g, 13.0 mmol) in dry MeOH (20 mL), NaBH$_4$ (0.68 g, 26.0 mmol, Loba chemie) was added slowly at 0° C. The reaction mixture was stirred at rt for 1 h. It was then concentrated under vacuum and the resulting crude product was dissolved in DCM (50 mL), washed with water, brine, dried over anhydrous Na$_2$SO$_4$ and concentrated under reduced pressure. The crude product was used in the next step without further purification. Yield: 91% (1.83 g).

Step 2: 5-(1-chloroethyl)-2,3-dihydrobenzofuran

The title compound was synthesized following the general procedure B. The reaction mixture was concentrated under vacuum and the resulting crude mixture was used without further purification. Yield: 72% (0.6 g, colorless liquid). LCMS: (Method B) 149.0 (chloro elimination mass), Rt. 3.705 min, 80.15% (Max).

117

Intermediate 6: 6-(1-chloroethyl)quinoxaline

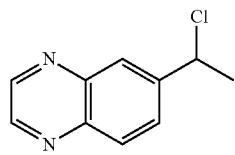

Step 1: 1-(quinoxalin-6-yl)ethan-1-one

6-Bromo quinoxaline (2.0 g, 9.5 mmol) in toluene (20 ml.) was degassed for 30 min. To this solution, 1-ethoxy vinyl tributyltin (3.8 g, 10.5 mmol) and bis(triphenylphosphine)palladium dichloride (0.67 g, 0.95 mmol) were added at rt and stirred for 16 hours at 90° C. The reaction mixture was cooled to rt and filtered through celite. After evaporation of the solvent, 6 N HCl solution in water (20 ml.) was added and the mixture was stirred for 1 hour at rt. It was concentrated and neutralized with sat. NaHCO$_3$. The desired product was extracted with DCM (100 ml_), dried over Na$_2$SO$_4$ and concentrated. The crude product was purified by flash column chromatography to afford the title compound (brown solid). $^1$H NMR (400 MHz, DMSO-d$_6$): δ 9.06-9.04 (m, 2H), 8.70 (d, J=2.4 Hz, 1H), 8.28 (t, J=2.8 Hz, 1H), 8.16 (d, J=11.6 Hz, 1H), 2.97 (s, 3H). LCMS: (Method A) 173 (M+H), Rt. 2.25 min, 99.06% (Max).

Step 2: 1-(quinoxalin-6-yl)ethan-1-ol

To a stirred solution of 1-(quinoxalin-6-yl)ethan-1-one (0.8 g, 4.65 mmol) in dry MeOH (20 mL), sodium borohydride (0.36 g, 9.3 mmol) was added portion wise at 0° C. and the resulting mixture was stirred for 1 h. It was then concentrated, diluted with DCM (80 mL), washed with water (20 mL), dried over Na$_2$SO$_4$ and concentrated. The crude product was taken for next step without further purification. Yield: 75% (600 mg, dark brown liquid). $^1$H NMR (400 MHz, DMSO-d$_6$): δ 8.91-8.89 (m, 2H), 8.03 (t, J=11.6 Hz, 2H), 7.87-7.86 (m, 1H), 5.49 (d, J=5.9 Hz, 1H), 4.97 (t, J=6.2 Hz, 1H), 1.42 (d, J=8.6 Hz, 3H). LCMS: (Method A) 175.0 (M+H), Rt. 1.89 min, 95.0% (Max).

Step 3: 6-(1-chloroethyl)quinoxaline

To a stirred solution of 1-(quinoxalin-6-yl)ethan-1-ol (0.6 g, 3.46 mmol) in dry DCM (10 mL), thionyl chloride (0.5 mL, 6.93 mmol) was added dropwise at 0° C. and stirred at rt for 1 hour. The reaction mixture was evaporated to dryness and was used without further purification. Yield: 97% (650 mg, off white solid). $^1$H NMR (400 MHz, DMSO-d$_6$): δ 8.74 (s, 2H), 7.93 (s, 1H), 7.70-7.68 (m, 2H), 4.46-4.23 (m, 1H), 1.87 (s, 3H). LCMS: (Method A) 193 (M+H), Rt. 3.41 min, 71.4% (Max).

118

Intermediate 7: N-(5-(piperazin-1-yl)-1,3,4-thiadiazol-2-yl)acetamide Hydrochloride

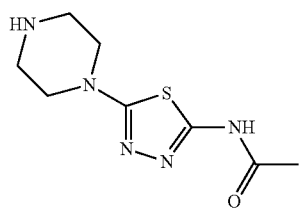

Step 1: tert-Butyl 4-(5-amino-1,3,4-thiadiazol-2-yl)piperazine-1-carboxylate To a stirred solution of 2-amino 5-bromo-1,3,4-thiadiazole (10.0 g, 55.5 mmol) in dry DMF (100 mL), K$_2$CO$_3$ (15.3 g, 111.1 mmol) and 1-boc piperazine (12.4 g, 66.65 mmol) were added at 0° C. The reaction mixture was stirred overnight at 80° C. The reaction mixture was concentrated under vacuum. To the resulting crude solids, DCM (200 mL) was added. The DCM layer was washed with water (100 mL), brine (100 mL) and, dried over anhydrous Na$_2$SO$_4$ and concentrated. The crude product was purified by silica gel column chromatography to afford the title compound. Yield: 76% (12 g, pale brown solid). $^1$H NMR (400 MHz, DMSO-d$_6$): δ 6.51 (s, 2H), 3.39 (d, J=6.9 Hz, 4H), 3.19 (d, J=7.7 Hz, 4H), 1.39 (s, 9H). LCMS: (Method A) 286.1 (M+H), Rt. 2.71 min, 97.6% (Max).

Step 2: tert-Butyl 4-(5-acetamido-1,3,4-thiadiazol-2-yl)piperazine-1-carboxylate To a stirred solution of fert-butyl 4-(5-amino-1,3,4-thiadiazol-2-yl)piperazine-1-carboxylate (12.0 g, 42.09 mmol) in pyridine (120 mL), acetic anhydride (5.1 g, 50.5 mmol) was added at 0° C. The reaction mixture was stirred overnight at 50° C. The reaction mixture was concentrated under vacuum and triturated with diethyl ether (100 mL). The solid obtained was filtered, washed with diethyl ether (20 mL), dried and taken for next step without any further purification. Yield: 87% (12 g, off white solid). $^1$H NMR (400 MHz, DMSO-d$_6$): δ 12.07 (br.s, 1H), 3.45-3.34 (m, 8H), 2.11 (s, 3H), 1.42 (s, 9H). LCMS: (Method A) 328.0 (M+H), Rt. 3.11 min, 86.3% (Max).

Step 3: N-(5-(Piperazin-1-yl)-1,3,4-thiadiazol-2-yl)acetamide Hydrochloride

To a stirred solution of fert-butyl 4-(5-acetamido-1,3,4-thiadiazol-2-yl)piperazine-1-carboxylate (12.0 g) in dry dioxane (100 mL), HCl in dioxane (100 mL, 4 N) was added and the reaction mixture was stirred at rt for 3 h. The reaction mixture was concentrated under vacuum and the resulting crude product was suspended diethyl ether (50 mL). The title compound was obtained after evaporation of the solvent. Yield: 93% (9 g, white solid). $^1$H NMR (400 MHz, DMSO-d$_6$): δ 12.07 (br. s, 1H), 3.67 (s, 4H), 3.21 (s, 4H), 2.13 (s, 3H). LCMS: (Method A) 228.0 (M+H), Rt. 0.71 min, 85.3% (Max).

Intermediate 8: Ethyl 2-(piperazin-1-yl)thiazole-5-carboxylate Hydrochloride

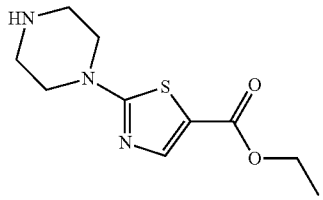 [SMILES: CCOC(=O)c1cnc(N2CCNCC2)s1]

Step 1: Ethyl 2-(4-(tert-butoxycarbonyl)piperazin-1-yl)thiazole-5-carboxylate To a stirred solution of ethyl 2-bromothiazole-5-carboxylate (4.0 g, 17.0 mmol) in dry DMF (40 mL), triethylamine (7.3 mL, 51.0 mmol, Spectrochem), followed by N-Boc piperazine (3.6 g, 19.0 mmol, GLRscientific) were added. The resulting mixture was heated at 90° C. for 12 h. It was then concentrated, diluted with DCM (200 ml_), washed with water (100 ml.) and dried over Na$_2$SO$_4$. After evaporation of the solvents, the crude product was purified by flash chromatography (3% methanol in DCM) to afford the title compound. Yield: 77% (4.5 g, white solid). LCMS: (Method A) 342.0 (M+H), Rt. 4.42 min, 99.5% (Max). $^1$H NMR (400 MHz, CDCl$_3$): δ 7.88 (s, 1H), 4.30 (q, J=7.2 Hz, 2H), 3.57 (s, 8H), 1.49 (s, 9H), 1.35 (t, J=7.2 Hz, 3H).

Step 2: Ethyl 2-(piperazin-1-yl)thiazole-5-carboxylate Hydrochloride

To a stirred solution of ethyl 2-(4-(fert-butoxycarbonyl)piperazin-1-yl)thiazole-5-carboxylate (4.5 g, 13.0 mmol) in dry dioxane (20 ml_), HCl in dioxane (4 N, 50 ml.) was added at 0° C. and the reaction mixture was stirred at rt for 2 h. The reaction mixture was concentrated and the resulting solid was washed with diethyl ether and dried under vacuum. Yield: 90% (5.4 g, off white solid). $^1$H NMR (400 MHz, DMSO-d$_6$): δ 9.32 (s, 2H), 7.88 (s, 1H), 4.21 (q, J=9.4 Hz, 2H), 3.96-3.73 (m, 4H), 3.55-2.41 (m, 4H), 1.24 (t, J=7.0 Hz, 3H). LCMS: (Method B) 242.0 (M+H), Rt. 2.11 min, 99.8% (Max).

Intermediate 9: 7-(1-chloroethyl)quinoline

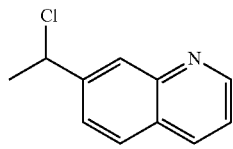

Step 1: 1-(quinolin-7-yl)ethan-1-one

The title compound was synthesized according to the protocol described for the synthesis of Intermediate 6, step 1, using 7-bromo quinoline (2 g, 9.56 mmol, Harvechem) as starting material. The crude product was purified by flash chromatography to afford the title compound (brown solid). $^1$H NMR (300 MHz, DMSO-d$_6$): δ 9.02 (d, J=3.2 Hz, 1H), 8.63 (s, 1H), 8.46-8.10 (m, 1H), 8.08-8.03 (m, 2H), 7.68-7.50 (m, 1H), 2.68 (s, 3H). LCMS: (Method A) 172.0 (M+H), Rt. 1.49 min, 84.1% (Max).

Step 2: 1-(quinolin-7-yl)ethan-1-ol

The title compound was synthesized according to the protocol described for the synthesis of Intermediate 6, step 2, using 1-(quinolin-7-yl)ethan-1-one as starting material. The crude product was taken for next step without further purification (brown solid). $^1$H NMR (400 MHz, DMSO-d$_6$): δ 8.86-8.85 (m, 1H), 8.31 (d, J=8.1 Hz, 1H), 7.92 (t, J=8.5 Hz, 2H), 7.60 (d, J=8.4 Hz, 1H), 7.47 (dd, J=4.2, 8.2 Hz, 1H), 5.39 (d, J=4.2 Hz, 1H), 4.90-4.96 (m, 1H), 1.41 (d, J=6.4 Hz, 3H). LCMS: (Method A) 174.0 (M+H), Rt. 1.34 min, 99.2% (Max).

Step 3: 7-(1-chloroethyl)quinoline

The title compound was synthesized according to the protocol described for the synthesis of Intermediate 6, step 3, using 1-(quinolin-7-yl)ethan-1-ol as starting material. The crude product was taken for next step without further purification. Yield: 96% (260 mg, grey solid). $^1$H NMR (400 MHz, DMSO-d$_6$): δ 9.19 (d, J=3.5 Hz, 1H), 8.88 (d, J=7.6 Hz, 1H), 8.27 (d, J=6.6 Hz, 2H), 7.60 (d, J=8.4 Hz, 1H), 7.93 (dt, J=6.0, Hz, 2H), 5.71-5.68 (m, 1H), 1.91 (d, J=6.7 Hz, 3H). LCMS: (Method A) 192.0 (M+H), Rt. 2.27 min, 98.7% (Max).

Intermediate 10: N-(2-(piperazin-1-yl)pyrimidin-5-yl)acetamide, Hydrochloride

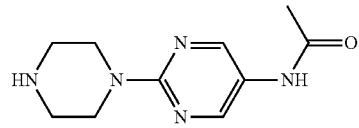 [SMILES: CC(=O)Nc1cnc(N2CCNCC2)nc1]

Step 1: Tert-butyl 4-(5-nitropyrimidin-2-yl)piperazine-1-carboxylate

To a stirred solution of 2-chloro-5-nitro-pyrimidine (2.2 g, 13.7 mmol) in dry DMF (25 ml_), triethylamine (5.7 ml_, 41.3 mmol, Spectrochem) followed by N-Boc piperazine (2.8 g, 15.7 mmol) were added and the resulting mixture was heated at 90° C. for 12 h. It was concentrated and the residue was diluted with DCM (50 ml_), washed with water (15 ml.) and dried over Na$_2$SO$_4$. After evaporation of the solvents, the crude product was washed with ACN with 5% methanol to afford the title compound (brown solid). $^1$H NMR (400 MHz, DMSO-d$_6$): δ 9.12 (s, 2H), 3.92-3.88 (m, 4H), 3.45-3.42 (m, 4H), 1.4 (s, 9H). LCMS: (Method A) 254.0 (M-(t-butyl)+H), Rt. 4.43 min, 98.03% (Max).

Step 2: Tert-butyl 4-(5-aminopyrimidin-2-yl)piperazine-1-carboxylate

To a stirred solution of fert-butyl 4-(5-nitropyrimidin-2-yl)piperazine-1-carboxylate (2.1 g, 6.79 mmol) in methanol (25 ml_), Pd/C (10%, 0.210 g, Aldrich) was added and the reaction mixture was stirred under H₂ atmosphere for 3 h. The reaction completion was monitored by TLC. The reaction mixture was filtered through celite and evaporated under vacuum. The crude product was used without further purification. Yield: 95% (1.8 g, pale brown solid). $^1$H NMR (400 MHz, DMSO-d$_6$): δ 7.88 (s, 2H), 4.62 (s, 2H), 3.48-3.45 (m, 4H), 3.35-3.28 (m, 4H), 1.33 (s, 9H). LCMS: (Method A) 280 (M+H), Rt. 2.66 min, 98.82% (Max).

Step 3: Tert-butyl 4-(5-acetamidopyrimidin-2-yl) piperazine-1-carboxylate

To a stirred solution of fert-butyl 4-(5-aminopyrimidin-2-yl)piperazine-1-carboxylate (1.8 g, 6.44 mmol) in dry DCM (18 ml_), pyridine (0.7 ml_, 9.67 mmol, spectrochem), acetic anhydride (0.9 ml_, 9.67 mmol, spectrochem) and dimethyl aminopyridine (0.036 g, 2%, spectrochem) were added. The resulting mixture was stirred at rt for 12 h. The reaction mixture was concentrated under reduced pressure and the resulting solid was suspended in HCl (1.5 N in water, 15 ml_). The solid was filtered and washed with water (200 ml.) to afford the title compound. Yield: 87% (1.8 g, off white solid). $^1$H NMR (400 MHz, DMSO-d$_6$): δ 9.85 (s, 1H), 8.51 (s, 2H), 3.66-3.61 (m, 4H), 3.33-3.31 (m, 4H), 2.00 (s, 3H), 1.41 (s, 9H). LCMS: (Method A) 322 (M+H), Rt. 3.1 min, 98.4% (Max).

Step 4: N-(2-(piperazin-1-yl)pyrimidin-5-yl)acetamide

To a stirred solution of fert-butyl 4-(5-acetamidopyrimidin-2-yl)piperazine-1-carboxylate (1.8 g, 5.6 mmol) in dry dioxane (5 mL) at 0° C., a solution of HCl in dioxane (4 N, 15 mL) was added and the reaction mixture was stirred 3 h at rt. It was concentrated and the resulting product washed with diethyl ether, affording the title compound. Yield: 83% (1.8 g, off white solid). $^1$H NMR (400 MHz, DMSO-d$_6$): δ 10.9 (s, 1H), 9.92 (s, 1H), 8.86 (s, 2H), 3.22-3.17 (m, 4H), 3.02-2.78 (m, 4H), 2.06 (s, 3H). LCMS: (Method B) 222.0 (M+H), Rt. 2.36 min, 95.34% (Max)

Intermediate 11: 6-(1-(piperazin-1-yl)ethyl)quinoxaline Hydrochloride

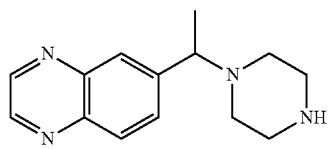 [SMILES: CC(c1ccc2nccnc2c1)N1CCNCC1]

Step 1: tert-butyl 4-(1-(quinoxalin-6-yl) ethyl) piperazine-1-carboxylate

To a stirred solution of 1-boc piperazine (3.8 g, 20.83 mmol) in dry DMF (40 mL), TEA (8.7 mL, 62.4 mmol) and Intermediate 6 (4 g, 20.83 mmol) were added at rt and the reaction mixture was stirred overnight at 90° C. The reaction mixture was cooled to rt and concentrated under vacuum. To this crude mixture, water (50 mL) was added and the product was extracted with DCM (150 mL). Organic layer was dried over anhydrous Na₂SO₄ and concentrated to get the crude product. The crude product was purified by flash column chromatography to afford the title compound (brown solid). LCMS: (Method A) 343.2 (M+H), Rt. 2.59 min, 75.3% (Max).

Step 2: 6-(1-(piperazin-1-yl) ethyl) quinoxaline Hydrochloride

To a solution of fert-butyl 4-(1-(quinoxalin-6-yl) ethyl) piperazine-1-carboxylate (3.5 g, 10.23 mmol) in methanol (5 mL), dioxane HCl (35 mL, 10 V) was added at rt and the reaction mixture was stirred at for 2 h. The reaction mixture was concentrated under reduced pressure and then triturated with diethyl ether (15 mL) to afford the title compound. Yield: 87% (2.1 g, brown solid). $^1$H NMR (400 MHz, DMSO-d$_6$): 8.94 (d, J=6.0 Hz, 2H), 8.09 (d, J=8.8 Hz, 1H), 8.01 (s, 1H), 7.88 (d, J=8.8 Hz, 1H), 3.85 (d, J=6.8 Hz, 1H), 3.54 (t, J=5.2 Hz, 2H), 3.16 (d, J=3.6 Hz, 2H), 3.06-2.96 (m, 1H), 2.92-3.02 (m, 1H), 2.67 (s, 2H), 2.55-2.58 (m, 2H), 1.42 (d, J=6.8 Hz, 3H). LCMS: (Method A) 243.3 (M+H), Rt. 1.36 min, 95.02% (Max).

Intermediate 12: 4-chloro-7-(1-chloroethyl)quinoline

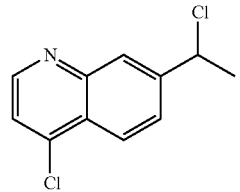

Step 1—1-(4-chloroquinolin-7-yl)ethan-1-one

7-Bromo-4-chloroquinoline (1 g, 4.12 mmol, combi-block) in toluene (5 mL) was degassed for 30 min. To this solution, 1-ethoxy vinyl tributyltin (1.6 mL, 4.53 mmol) and bis(triphenylphosphine)palladium dichloride (3.38 g, 4.76 mmol) were added at rt and stirred for 12 hours at 90° C. The reaction mixture was cooled to rt and filtered through celite. The resulting crude product was suspended in 6 N HCl in water (10 mL) and stirred for 1 hour at rt. The mixture was concentrated and neutralized with saturated aqueous solution of NaHCO₃. The desired product was extracted with DCM (50 mL), dried over Na₂SO₄ and concentrated. The crude product was purified by flash column chromatography to afford the title compound (pale yellow solid). $^1$H NMR (400 MHz, DMSO-d$_6$): 8.98 (d, J=4.6 Hz, 2H), 8.72 (s, 1H), 8.33 (d, J=8.7 Hz, 1H), 8.21 (d, J=8.7 Hz, 1H), 7.92 (d, J=4.6 Hz, 1H), 2.78 (s, 3H). LCMS: (Method A) 206.0 (M+H), Rt. 2.98 min, 96.8% (Max).

Step-2—1-(4-chloroquinolin-7-yl)ethan-1-ol

To a stirred solution of 1-(4-chloroquinolin-7-yl)ethan-1-one (0.39 g, 1.92 mmol) in dry MeOH (5 mL), sodium borohydride (0.108 g, 2.88 mmol) was added portion wise at 0° C. and stirred for 1 h. The reaction mixture was concentrated, diluted with DCM (50 mL) and washed with water (20 mL). The organic layer was dried over Na₂SO₄ and concentrated. The crude product was taken for next step without further purification. Yield: 95% (0.38 g, colourless liquid). $^1$H NMR (400 MHz, DMSO-d$_6$): δ 8.81 (d, J=6.3

Hz, 1H), 8.15-8.30 (m, 1H), 8.02 (s, 1H), 7.69-7.78 (m, 2H), 5.47 (d, J=5.8 Hz, 1H), 4.92-5.00 (m, 1H), 1.42 (t, J=8.6 Hz, 3H).

Step-3: 4-chloro-7-(1-chloroethyl)quinoline

To a stirred solution of 1-(4-chloroquinolin-7-yl)ethan-1-ol (0.38 g, 1.82 mmol) in dry DCM (10 mL), thionyl chloride (0.4 mL, 5.4 mmol) was added dropwise at 0° C. and stirred at rt for 1 hour. The reaction mixture was concentrated and dried under vacuum and used as such for next step without any further purification. Yield: 97% (0.4 g, colourless liquid). $^1$H NMR (400 MHz, DMSO-d$_6$): 8.89 (d, J=6.3 Hz, 1H), 8.21-8.26 (m, 2H), 7.87-7.92 (m, 2H), 5.63 (q, J=8.8 Hz, 1H), 1.91 (s, 3H). LCMS: (Method A) 226.0 (M+H), Rt. 3.54 min, 94.58% (Max).

Intermediate 13: 5-(1-chloroethyl)benzorc1H,2,5]oxadiazole

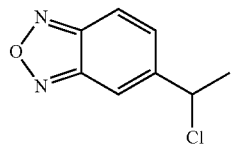

Step 1: 1-(benzo[c][1,2,5]oxadiazol-5-yl)ethan-1-one

A solution of 5-bromobenzo[c][1,2,5]oxadiazole (3 g, 15.0 mmol, Combiblocks) in toluene (10 mL) was degassed for 30 min. 1-Ethoxy vinyl tributyltin (6.01 mL, 16.5 mole, Frontier Scientific) and bis(triphenylphosphine)palladium (II) dichloride (1.16 g, 1.65 mmol) were added at rt and the resulting mixture was stirred at 90° C. overnight. It was cooled to rt and filtered through celite. HCl aqueous solution (20 mL, 6N) was added and the mixture was stirred for 1 hour at rt. It was concentrated and neutralized with sat. NaHCO$_3$ solution (25 mL). The product was extracted with DCM (100 mL), dried over Na$_2$SO$_4$ and concentrated. The crude product was purified by flash column chromatography to afford the title compound. Yield: 60% (1.5 g, pale yellow solid). $^1$H NMR (400 MHz, DMSO-d$_6$): δ 8.90 (s, 1H), 8.14 (d, J=9.6 Hz, 1H), 7.98-7.39 (m, 1H), 2.72 (s, 3H). LCMS: (Method B) 162.0 (M+H), Rt. 4.6 min, 98.01% (Max).

Step 2: 1-(benzo[c][1,2,5]oxadiazol-5-yl)ethan-1-ol

To a stirred solution of 1-(benzo[c][1,2,5]oxadiazol-5-yl)ethan-1-one (1.4 g, 8.53 mmol) in dry MeOH (20 mL), sodium borohydride (0.48 g, 12.7 mmol, spectrochem) was added portion wise at 0° C. and stirred for 1 h. The reaction mixture was concentrated, diluted with DCM (60 mL) and washed with water (10 mL). The organic layer was dried over Na$_2$SO$_4$ and concentrated. The crude product was taken for next step without any further purification. Yield: 98% (1.3 g, pale yellow solid). $^1$H NMR (400 MHz, DMSO-d$_6$): δ 6.85-6.82 (m, 2H), 6.71 (s, 1H), 4.36-4.30 (m, 1H), 1.43 (d, J=6.4 Hz, 3H).

Step 3: 5-(1-chloroethyl) benzo[c][1,2,5]oxadiazole

To a stirred solution of 1-(benzo[c][1,2,5]oxadiazol-5-yl)ethan-1-ol (1 g, 6.09 mmol) in dry DCM (10 mL), thionyl chloride (1.3 mL, 1.82 mmol, spectrochem) was added dropwise at 0° C. and stirred at rt for 1 hour. The reaction mixture was concentrated and used for next step without any further purification. Yield: 91% (1.01 g, brown liquid). $^1$H NMR (400 MHz, DMSO-d$_6$): δ 7.77-7.75 (m, 1H), 7.64 (s, 1H), 7.24-7.19 (m, 1H), 4.86-4.82 (m, 1H), 1.87 (d, J=6.7 Hz, 3H).

Intermediate 14: 7-(1-chloroethyl)-3,4-dihydro-2H-benzo[b][1,4]dioxepine

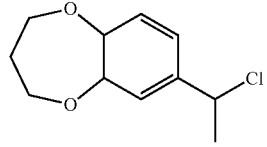

Step 1: 1-(3,4-dihydro-2H-benzo[b][1,4]dioxepin-7-yl) ethan-1-one

The title compound was synthesized following the same protocol as Intermediate 13, Step 1, using 7-bromo-3,4-dihydro-2H-benzo[b][1,4]dioxepine (3 g, 13.0 mmol, Alfa aesar) as starting material. The crude product was purified by flash column chromatography to afford the title compound. Yield: 50% (1.25 g, yellow solid). $^1$H NMR (400 MHz, DMSO-d$_6$): δ 7.57-7.52 (m, 2H), 7.05 (d, J=8.3 Hz, 1H), 4.25-4.18 (m, 4H), 2.16 (t, J=5.7 Hz, 2H), 1.73 (s, 3H). LCMS: (Method A) 193.0 (M+H), Rt. 3.2 min, 91.5% (Max).

Step 2: 1-(3,4-dihydro-2H-benzo[b][, 4]dioxepin-7-yl)ethan-1-ol

The title compound was synthesized following the same protocol as Intermediate 13, Step 2, using 1-(3,4-dihydro-2H-benzo[b][1,4]dioxepin-7-yl)ethan-1-one (1.21 g, 6.2 mmol) as starting material. The crude product was taken for next step without any further purification. Yield: 94% (1.1 g, Brown liquid). $^1$H NMR (400 MHz, DMSO-d$_6$): δ 7.57-7.52 (m, 2H), 7.03 (d, J=8.1 Hz, 1H). 5.65 (s, 1H), 5.28-5.23 (m, 1H), 4.13-4.10 (m, 4H), 2.14 (t, J=11.2 Hz, 2H), 1.71 (d, J=6.7 Hz, 3H).

Step 3: 7-(1-chloroethyl)-3,4-dihydro-2H-benzo[b][1,4]dioxepine

The title compound was synthesized following the same protocol as Intermediate 13, Step 3, using 1-(3,4-dihydro-2H-benzo[b][1,4]dioxepin-7-yl)ethan-1-ol (1.15 g, 5.92 mmol) as starting material. The crude product was used without any further purification. Yield: 90% (1.0 g, brown liquid). $^1$H NMR (400 MHz, DMSO-d$_6$): δ 7.06-7.02 (m, 2H), 6.93 (d, J=8.1 Hz, 1H), 5.28-5.23 (m, 1H), 4.13-4.10 (m, 4H), 2.14 (t, J=11.2 Hz, 2H), 1.73 (d, J=6.7 Hz, 3H).

Intermediate 15: 8-(1-chloroethyl)quinolone

Step 1: 1-(quinolin-8-yl) ethan-1-one

A solution of 8-bromo quinoline (3 g, 14.4 mmol, Combiblock) in toluene (10 mL) was degassed for 30 min. To this solution, 1-ethoxy vinyl tributyltin (5.72 mL, 15.8 mmol, Frontier Scientific) and bis(triphenylphosphine)palladium (II) dichloride (1.01 g, 1.44 mmol) were added at rt and stirred overnight at 90° C. The reaction mixture was cooled to rt and filtered through celite. HCl aqueous solution (20 mL, 6 N) was added and the mixture was stirred for 1 hour at rt. It was concentrated and neutralized with saturated NaHCO$_3$ solution (25 mL). The desired product was extracted with DCM (100 mL), dried over anhydrous Na$_2$SO$_4$ and concentrated. The crude product was purified by flash column chromatography to afford the title compound. Yield: 60% (1.5 g, brown liquid). $^1$H NMR (300 MHz, DMSO-d$_6$): δ 9.01-8.99 (m, 1H), 8.46 (d, J=8.3 Hz, 1H), 8.16 (d, J=8.1 Hz, 1H), 7.86 (d, J=7.1 Hz, 1H), 7.70-7.62 (m, 2H), 2.82 (s, 3H). LCMS: (Method A) 172.0 (M+H), Rt. 0.82 min, 98.9% (Max).

Step 2: 1-(quinolin-8-yl) ethan-1-ol

To a stirred solution of 1-(quinolin-8-yl) ethan-1-one (1.5 g, 8.72 mmol) in dry MeOH (20 mL), sodium borohydride (0.49 g, 13.0 mmol, Spectrochem) was added portion wise at 0° C. and the resulting mixture was stirred for 1 h. It was concentrated, diluted with DCM (60 mL), washed with water (10 mL) and dried over Na$_2$SO$_4$. After evaporation of the solvents, the crude product was taken for next step without any further purification. Yield: 79% (1.2 g, brown liquid). $^1$H NMR (400 MHz, DMSO-d$_6$): δ 9.02-8.95 (m, 1H), 8.49 (d, J=8.1 Hz, 1H), 7.90 (t, J=8.5 Hz, 2H), 7.75 (d, J=8.4 Hz, 1H), 7.63-7.60 (m, 1H), 5.17 (d, J=4.2 Hz, 1H), 4.90-4.95 (m, 1H), 1.41 (d, J=6.4 Hz, 3H). LCMS: (Method A) 174.0 (M+H), Rt. 1.31 min, 95.4% (Max).

Step 3: 8-(1-chloroethyl)quinoline

To a stirred solution of 1-(quinolin-8-yl) ethan-1-ol (0.30 g, 1.72 mmol) in dry DCM (10 ml), thionyl chloride (0.4 ml, 2.89 mmol, spectrochem) was added dropwise at 0° C. and the resulting mixture was stirred at rt for 1 hour. It was concentrated and the resulting product was used in the next step without any further purification. Yield: 96% (0.28 g, grey liquid). $^1$H NMR (400 MHz, DMSO-d$_6$): δ 9.02 (d, J=1.7 Hz, 1H), 8.50 (d, J=4.1 Hz, 1H), 8.08-8.02 (m, 2H), 7.73-7.64 (m, 2H), 6.64 (t, J=8.0 Hz, 1H), 1.96 (d, J=6.7 Hz, 3H). LCMS: (Method A) 192.0 (M+H), Rt 2.81 min, 95.7% (Max).

Intermediate 16: (S)-1-(1-(benzordin,31 dioxol-5-yl) ethyl)piperazine Hydrochloride

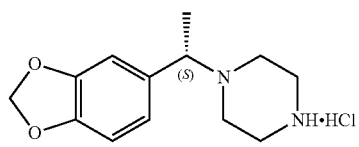

Step 1: (R)—N-(1-(benzo[d][1,3]dioxol-5-yl)ethylidene)-2-methylpropane-2-sulfinamide To a mixture of 1-(benzo[d][1,3]dioxol-5-yl)ethan-1-one (105.7 g, 644.6 mmol), (R)-(+)-2-methyl-2-propanesulfinamide (85.79 g, 709 mmol) in THF (1.0 L), titanium(IV) ethoxide (294.06 g, 1289.2 mmol) was added at rt over 30 min and refluxed for 35 h. The reaction was monitored by HPLC.

The reaction mixture was cooled to rt and slowly quenched with water (500 ml). The precipitate observed was filtered through celite bed (100 g) and washed with EtOAc (2.0 L). The organic layer was washed with water (500 ml), brine solution (300 ml.) and dried over Na$_2$SO$_4$ (100 g) and evaporated under vacuum at 50° C. The resulting crude product was codistilled with toluene (2×500 ml.) and used as such for next step without any further purification (164 g, brown liquid). LCMS: (Method A) 268.0 (M+H), Rt. 3.87 min, 83.05% (Max). HPLC: (Method A) Rt. 3.81 min, 57.62% (Max).

Step 2: (R)—N—((S)-1-(benzo[d][, 3]dioxol-5-yl)ethyl)-2-methylpropane-2-sulfinamide To a stirred solution of (R)—N-(1-(benzo[d][1,3]dioxol-5-yl)ethylidene)-2-methylpropane-2-sulfinamide (96 g, 359 mmol) in THF (960 mL), L-Selectride (539 mL, 539 mmol, 1 M solution in THF) was added under nitrogen atmosphere at −50° C. over 30 min and stirred for 1 h. The completion of the reaction was confirmed by TLC. The reaction mixture was quenched with methanol (150 mL), water (750 mL) and stirred overnight at rt. The aqueous layer was extracted with EtOAc (2×300 mL). The combined organic layer was washed with sat. NH$_4$Cl (2×250 mL), brine (250 mL), dried over Na$_2$SO$_4$ and evaporated under vacuum at 50° C. The resulting crude product (as light brown thick oil) was diluted with pet ether (250 mL) and stirred at −20° C. for 30 min. The resulting precipitate was filtered and washed with pet ether (2×100 mL). It was dried under vacuum to give the title compound. Yield: 70.2% (68 g, Off white solid). $^1$H NMR (400 MHz, DMSO-d$_6$): δ 6.89 (s, 1H), 6.83-6.77 (m, 2H), 5.99-5.95 (m, 2H), 5.25 (d, J=5.2 Hz, 1H), 4.30 (q, J=6.0 Hz, 1H), 1.39 (d, J=1.6 Hz, 3H), 1.11-1.06 (m, 9H). LCMS: (Method A) 270.0 (M+H), Rt. 3.66 min, 99.65% (Max). HPLC: (Method A) Rt. 3.62 min, 99.69% (Max). Chiral HPLC: (Method C) Rt. 9.71 min, 100%.

Step 3: (S)-1-(benzo[d][1,3]dioxol-5-yl)ethan-1-amine

To a stirred solution of (R$_s$)—N—((S)-1-(benzo[d][1,3]dioxol-5-yl)ethyl)-2-methylpropane-2-sulfinamide (68 g, 252 mmol) in MeOH (680 mL), thionyl chloride (74.3 g, 630 mmol) was added at 0° C. over 15 min and the resulting mixture was stirred at rt for 1 h. The completion of the reaction was confirmed by TLC. The reaction mixture was concentrated under vacuum at 50° C. The resulting residue was suspended in EtOAc (300 mL), filtered and washed with EtOAc (150 mL). The product was basified with 30% aqueous ammonia solution (300 mL) and extracted with EtOAc (2×250 mL). The combined organic layer was washed with brine solution (1×150 mL) and dried over Na$_2$SO$_4$. The solvent was evaporated at under vacuum to give the title compound. Yield: 92.84% (38.3 g, brown liquid). $^1$H NMR (400 MHz, DMSO-d$_6$): δ 6.95 (s, 1H), 6.81-6.77 (m, 2H), 5.95 (s, 2H), 3.90 (q, J=6.56 Hz, 1H), 1.85 (s, 2H), 1.19 (m, J=6.56 Hz, 3H). LCMS: (Method A) 149.0 (M-16), Rt. 1.65 min, 99.56% (Max). HPLC: (Method A) Rt. 1.60 min, 99.61% (Max). Chiral HPLC: (Method B) Rt 11.11 min, 100%.

Step 4: (S)-1-(1-(benzo[d][1,3]dioxol-5-yl)ethyl)-4-tosylpiperazine

To a stirred solution of (S)-1-(benzo[d][1,3]dioxol-5-yl)ethan-1-amine (41 g, 248 mmol) in DIPEA (86.6 mL, 496 mmol), N,N-bis(2-chloroethyl)-p-toluene sulfonamide (80.74 g, 273 mmol) was added at rt and the resulting mixture was heated at 105° C. overnight. The completion of the reaction was confirmed by TLC and the reaction mixture was diluted with water (1000 mL) and extracted with EtOAc (2×500 mL). The combined organic layer was washed with water (200 mL), brine solution (200 mL) and dried over Na$_2$SO$_4$. After evaporation of the solvent, the resulting crude solid was suspended in pet ether (350 mL) and stirred for 10 min at rt. The suspension was filtered and was washed with Et$_2$O (2×200 mL) and dried under vacuum to give the title compound. Yield: 63.2% (61 g, Off white solid). $^1$H NMR (400 MHz, DMSO-d$_6$): δ 7.59 (d, J=8.2 Hz, 2H), 7.45 (d, J=8.2 Hz, 2H), 6.81-6.77 (m, 1H), 6.69 (d, J=7.4 Hz, 1H), 5.96 (s, 2H), 3.32 (q, J=7.76 Hz, 1H), 2.81-2.80 (m, 4H), 2.42 (s, 3H), 2.36-2.32 (m, 4H), 1.18 (d, J=6.4 Hz, 3H). LCMS: (Method A) 389.2 (M+H), Rt. 3.40 min, 98.09% (Max). HPLC: (Method A) Rt. 3.30 min, 98.69% (Max). Chiral HPLC: (Method D) Rt. 15.79 min, 100.00%

Step 5: (S)-1-(1-(benzo[d][1,3]dioxol-5-yl)ethyl)piperazine Hydrochloride

To a mixture of (S)-1-(1-(benzo[d][1,3]dioxol-5-yl)ethyl)-4-tosylpiperazine (61 g, 157 mmol) and 4-hydroxy benzoic acid (65.01 g, 471 mmol), HBr in acetic acid (244 mL) was added at 0° C. and the reaction mixture was stirred at rt overnight. The completion of the reaction was confirmed by TLC. The reaction mixture was diluted with water (400 mL). The precipitate was filtered through celite bed and washed with water (200 mL). The aqueous filterate was washed with EtOAc (4×300 mL) and basified up to pH 11 with NaOH pellet (30 g) at 0° C. (during basification the colour of aqueous was converted to light back). The product was extracted with EtOAc (4×300 mL). The combined organic layer was dried over Na$_2$SO$_4$ and evaporated under vacuum. The resulting light black oil was diluted in 1,4 Dioxane (50 mL) and cooled to 0° C. and 4.5 N HCl solution in dioxane (100 mL) was added and stirred for 15 min at rt. The solvent was evaporated at 45° C. under reduced pressure to get the title compound (pale brown solid). $^1$H NMR (400 MHz, DMSO-d$_6$): δ 12.11 (s, 1H), 7.32 (s, 1H), 7.06-6.99 (m, 2H), 6.07 (s, 2H), 4.55-4.52 (m, 1H), 3.80-3.61 (m, 2H), 3.05-2.95 (m, 2H), 2.51-2.50 (m 4H), 1.68 (s, 3H). LCMS: (Method A) 235.3 (M+H), Rt. 1.53 min, 95.85% (Max). HPLC: (Method A) Rt. 1.52 min, 95.06% (Max). Chiral HPLC: (Method A) Rt. 8.11 min, 100%.

Intermediate 17: 5-(1-chloroethyl)benzord1thiazole

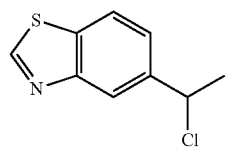

Step 1: 1-(benzo[d]thiazol-5-yl)ethan-1-one

The title compound was prepared according to the procedure described for Intermediate 6, Step 1, using 5-bromobenzo[d]thiazole (3 g, 14 mmol) as starting material. The crude product was purified by flash chromatography to give the title compound. Yield: 64.5% (1.6 g, pale yellow solid). LCMS: (Method A) 178.0 (M+H), Rt. 2.61 min, 81.8% (Max).

Step 2: 1-(benzo[d]thiazol-5-yl)ethan-1-ol

To a stirred solution of 1-(benzo[d]thiazol-5-yl)ethan-1-one (1.6 g, 9.0 mmol) in methanol (20 mL), sodium borohydride (683 mg, 18 mmol) was added slowly at 0° C. and stirred 1.5 h. The completion of the reaction was monitored by TLC and the solvents were evaporated at 45° C. under vacuum. The residue was diluted with EtOAc (50 mL) and washed with water (50 mL), brine solution (50 mL) and dried over Na$_2$SO$_4$. The organic layer was evaporated at 40° C. to give the title compound. Yield: 91.9% (1.49 g, pale brown solid). LCMS: (Method A) 180.0 (M+H), Rt. 2.35 min, 92.8% (Max).

Step 3: 5-(1-chloroethyl)benzo[d]thiazole

The title was synthesized from 1-(benzo[d]thiazol-5-yl)ethan-1-ol (1.49 g, 8.3 mmol), according the general procedure B. The crude product was used in the next step without further purification. Yield: quantitative (1.64 g, pale yellow solid). $^1$H NMR (400 MHz, DMSO-d$_6$): δ 9.43 (s, 1H), 8.19-8.17 (m, 2H), 7.63-7.61 (m, 1H), 5.57-5.52 (m, 1H), 1.87 (d, J=6.7 Hz, 3H). LCMS: (Method A) 198.0 (M+H), Rt. 3.98 min, 62.0% (Max).

Intermediate 18: 5-(1-chloroethyl)-2,2-difluorobenzordiri,31 dioxole

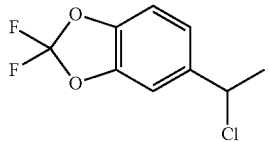

Step 1: 1-(2,2-difluorobenzo[d][1,3]dioxol-5-yl)ethan-1-one

The title compound was prepared according to the procedure described for Intermediate 6, Step 1, using 5-bromo-2,2-difluorobenzo[d][1,3]dioxole (3 g, 12.6 mmol) as starting material. The crude product was purified by flash chromatography to give the title compound. Yield: 94.86% (2.4 g, pale brown solid). $^1$H NMR (400 MHz, DMSO-d$_6$): δ 7.94-7.91 (m, 1H), 7.90-7.88 (m, 1H), 7.55 (d, J=8.4 Hz), 2.57 (s, 3H).

Step 2: 1-(2,2-difluorobenzo[d][1,3]dioxol-5-yl)ethan-1-ol

The title compound was prepared according to the procedure described for Intermediate 17, Step 2, using 1-(2,2-difluorobenzo[d][1,3]dioxol-5-yl)ethan-1-one (2.5 g, 12.4 mmol) as starting material. After evaporation of the solvent, the title product was isolated and used in the next without further purification. Yield: 91.08% (2.3 g, Black liquid). $^1$H NMR (400 MHz, DMSO-d$_6$): δ 7.34-7.30 (m, 2H), 7.17-7.14 (m, 1H), 4.75-4.69 (m, 1H), 1.29 (d, J=6.4 Hz, 3H).

Step 3: 5-(1-chloroethyl)-2,2-difluorobenzo[d][1,3]dioxole

The title compound was synthesized from 1-(2,2-difluorobenzo[d][1,3]dioxol-5-yl)ethan-1-ol (1 g, 4.9 mmol), according the general procedure B. Yield: 92.5% (1 g, black gel). $^1$H NMR (400 MHz, DMSO-$d_6$): δ 7.59 (d, J=2 Hz, 1H), 7.41-7.38 (m, 1H), 7.34-7.31 (m, 1H), 5.38 (q, J=6.8 Hz, 1H), 1.78 (d, J=8 Hz, 3H).

Intermediate 19: 5-(1-chloroethyl)benzorcin,2,5]thiadiazole

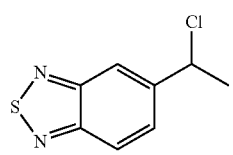

Step 1: 1-(benzo[c][1,2,5]thiadiazol-5-yl)ethan-1-one

The title compound was prepared according to the procedure described for Intermediate 6, Step 1, using 5-bromobenzo[c][1,2,5]thiadiazole (3 g, 13.9 mmol) as starting material. The crude product was purified by flash chromatography to give the title compound. Yield: 76.61% (1.9 g, pale brown solid). $^1$H NMR (400 MHz, DMSO-$d_6$): δ 8.84 (s, 1H), 8.20-8.13 (m, 2H), 2.76 (s, 3H). LCMS: (Method A) 178.9 (M+H), Rt. 4.81 min, 43.23% (Max).

Step 2: 1-(benzo[c][1,2,5]thiadiazol-5-yl)ethan-1-ol

The title compound was prepared according to the procedure described for Intermediate 17, Step 2, using 1-(benzo[c][1,2,5]thiadiazol-5-yl)ethan-1-one (1.9 g, 10.6 mmol) as starting material. After evaporation of the solvent, the title compound was isolated and used without further purification. Yield: 88.5% (1.7 g, dark brown liquid). $^1$H NMR (400 MHz, DMSO-$d_6$): δ 8.02 (d, J=9.08 Hz, 1H), 7.95 (s, 1H), 7.74-7.71 (m, 1H), 5.50 (d, J=4.36 Hz, 1H), 4.93-4.88 (m, 1H), 1.40 (d, J=6.48 Hz, 3). LCMS: (Method A) 181.0 (M+H), Rt. 2.05 min, 95.01% (Max).

Step 3: 5-(1-chloroethyl)benzo[c][1,2,5]thiadiazole

The title compound was synthesized from 1-(benzo[c][1,2,5]thiadiazol-5-yl)ethan-1-ol (1.7 g, 9.4 mmol), according the general procedure B. The crude product was used in the next step without further purification. Yield: quantitative (1.9 g, brown oil). $^1$H NMR (400 MHz, DMSO-$d_6$): δ 8.17-8.12 (m, 2H), 7.88-7.85 (m, 1H), 5.62-5.57 (m, 1H), 1.89 (d, J=6.76 Hz, 3H).

Intermediate 20: 3-chloro-7-(1-chloroethyl)quinoline

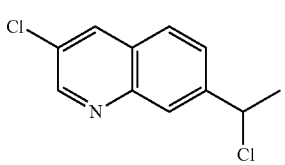

Step 1: 1-(3-chloroquinolin-7-yl)ethan-1-one

The title compound was prepared according to the procedure described for Intermediate 6, Step 1, using 7-bromo-3-chloroquinoline (1 g, 4.12 mmol) as starting material. The crude product was purified by flash chromatography to give the title compound. Yield: 71.5% (0.6 g, pale yellow solid). $^1$H NMR (400 MHz, DMSO-$d_6$): δ 9.02 (s, 1H), 8.69-8.66 (m, 2H), 8.14-8.07 (m, 2H), 2.75 (s, 3H).

Step 2: 1-(3-chloroquinolin-7-yl)ethan-1-ol

The title compound was prepared according to the procedure described for Intermediate 17, Step 2, using 1-(3-chloroquinolin-7-yl)ethan-1-one (0.6 g, 2.9 mmol) as starting material. After evaporation of the solvent, the title compound was isolated and used without further purification. Yield: 99.2% (0.6 g, pale yellow oil). $^1$H NMR (400 MHz, DMSO-$d_6$): δ 8.87-8.86 (d, J=2.48 Hz, 1H), 8.54 (s, 1H), 7.98-7.93 (m, 2H), 7.69-7.67 (m, 1H), 5.45 (d, J=4.4 Hz, 1H), 4.95-4.93 (m, 1H), 1.41 (d, J=6.48 Hz, 3H). LCMS: (Method A) 208.0 (M+H), Rt. 2.59 min, 96.46% (Max).

Step 3: 3-chloro-7-(1-chloroethyl)quinoline

The title was synthesized from 1-(3-chloroquinolin-7-yl)ethan-1-ol (0.600 g, 2.89 mmol), according to the general procedure B. The crude product was used in the next step without further purification. Yield: quantitative (0.655 g, pale yellow oil). LCMS: (Method A) 227.9 (M+H), Rt. 4.55 min, 90.09% (Max).

Intermediate 21: 6-(1-chloroethyl)-2,3-di hydrobenzofuran

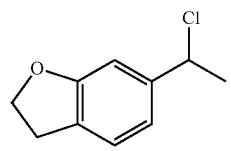

Step 1: 1-(2,3-dihydrobenzofuran-6-yl)ethan-1-one

The title compound was prepared according to the procedure described for Intermediate 6, Step 1, using 6-bromo-2,3-dihydro-1-benzofuran (1 g, 5.03 mmol) as starting material. The crude product was purified by flash chromatography to give the title compound. Yield: 73.7% (0.6 g, pale yellow solid). $^1$H NMR (400 MHz, DMSO-$d_6$): δ 7.48 (d, J=7.64 Hz, 1H), 7.37-7.35 (d, J=7.68 Hz, 1H), 7.26 (s, 1H), 4.58 (t, J=8.76 Hz, 2H), 3.24 (t, J=8.76 Hz, 2H), 2.53 (s, 3H). LCMS: (Method A) 163.2 (M+H), Rt. 3.01 min, 97.60% (Max).

Step 2: 1-(2,3-dihydrobenzofuran-6-yl)ethan-1-ol

The title compound was prepared according to the procedure described for Intermediate 17, Step 2, using 1-(2,3-dihydrobenzofuran-6-yl)ethan-1-one (0.6 g, 3.7 mmol) as starting material. After evaporation of the solvent, the title compound was isolated and used without further purification. Yield: 88.30% (0.53 g, colourless liquid). $^1$H NMR (400 MHz, DMSO-$d_6$): δ 7.11 (d, J=7.6 Hz, 1H), 6.77-6.75

(m, 1H), 6.71 (s, 1H), 5.04 (d, J=4.4 Hz, 1H), 4.63-4.61 (m, 1H), 4.48 (t, J=8.8 Hz, 2H), 3.11 (t, J=8.8 Hz, 2H), 1.25 (d, J=6.4 Hz, 3H). LCMS: (Method A) 147.0 (M-17H), Rt. 2.64 min, 89.95% (Max).

Step 3: 6-(1-chloroethyl)-2,3-dihydrobenzofuran

The title compound was synthesized from 1-(2,3-dihydrobenzofuran-6-yl)ethan-1-ol (0.53 g, 3.23 mmol), according to the general procedure B. The crude product was used in the next step without further purification. Yield: quantitative (0.58 g, brown oil). $^1$H NMR (400 MHz, DMSO-$d_6$): δ 7.20 (d, J=7.56 Hz, 1H), 6.93-6.91 (m, 1H), 6.87 (s, 1H), 5.29-5.24 (m, 1H), 4.53 (t, J=8.72 Hz, 2H), 3.15 (t, J=8.76 Hz, 2H), 1.75 (d, J=6.76 Hz, 3H). LCMS: (Method A) 147.0 (M-35H), Rt. 3.76 min, 83.62% (Max).

Intermediate 22: 1,2-Dichloro-4-(1-chloroethyl)benzene

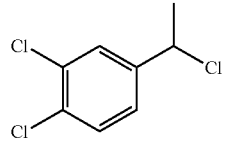

Step 1: 1-(3,4-Dichlorophenyl)ethan-1-ol

To a stirred solution of 3,4-dichloroacetophenone (4 g, 21.15 mmol, Aldrich) in dry MeOH (80 mL), sodium borohydride (0.96 g, 25.39 mmol, spectrochem) was added portionwise at 0° C. The reaction mixture was stirred at rt overnight. It was cooled to 0° C. and quenched using ice water (10 mL). Solvents were removed under reduced pressure and resulting residue was dissolved in DCM (50 mL). The organic layer was washed with water (25 mL), brine (20 mL), dried over Na$_2$SO$_4$ and concentrated. The crude product was used for next step without further purification. Yield: 95% (3.8 g, colorless liquid). $^1$H NMR (400 MHz, DMSO-$d_6$): δ 7.57-7.55 (m, 2H), 7.33 (d, J=1.9 Hz, 1H), 5.38 (d, J=4.4 Hz, 1H), 4.76-4.70 (m, 1H), 1.30 (d, J=6.4 Hz, 3H).

Step 2: 1,2-Dichloro-4-(1-chloroethyl) benzene

The title compound was synthesized by following general procedure B, using 1-(3,4-dichlorophenyl)ethan-1-ol (1.5 g, 7.85 mmol) and thionyl chloride (1.14 mL, 15.7 mmol) as starting materials. It was used in the next step without further purification. Yield: 97% (1.6 g, colorless liquid). $^1$H NMR (400 MHz, DMSO-$d_6$): δ 7.75 (s, 1H), 7.65-7.43 (m, 2H), 5.74-5.32 (m, 1H), 1.35 (d, J=8.5 Hz, 3H).

Intermediate 23: 3-(1-chloroethyl)quinoline

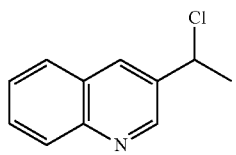

Step 1: 1-(quinolin-3-yl)ethan-1-ol

To a stirred solution of 1-(quinolin-3-yl)ethan-1-one (1 g, 5.85 mmol) in methanol (10 mL), sodium borohydride (442 mg, 11.7 mmol) was added slowly at 0° C. The reaction was stirred for 2 h at rt. The completion of reaction was monitored by TLC. The reaction mixture was evaporated at 45° C. under vacuum. The resulting mixture was diluted with EtOAc (100 mL), washed with water (50 mL), brine (50 ml.) and dried over anhydrous Na$_2$SO$_4$. After evaporation of the solvents, the title compound was isolated and used for the next step without any further purification. Yield: 89.1% (900 mg, pale brown solid). LCMS: (Method A) 174.0 (M+H), Rt. 1.37 min, 99.3% (Max).

Step 2: 3-(1-chloroethyl)quinoline

The compound 3-(1-chloroethyl)quinoline was synthesized from 1-(quinolin-3-yl)ethan-1-ol (900 mg, 5.2 mmol), according to the general procedure B. Yield: quantitative (993 mg, off white solid). $^1$H NMR (400 MHz, DMSO-$d_6$): δ 8.64 (s, 1H), 6.90-6.85 (m, 2H), 6.77-6.73 (m, 1H), 5.78-5.75 (m, 2H), 4.13-4.09 (m, 1H), 3.19-3.15 (m, 4H), 2.53-2.49 (m, 4H), 1.27 (d, J=6.6 Hz, 3H). LCMS: (Method A) 192.0 (M+H), Rt. 2.28 min, 99.4% (Max).

Intermediate 24: (R)-1-(1-(benzord1H,31dioxol-5-yl)ethyl)piperazine

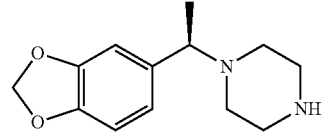 [SMILES: C[C@H](c1ccc2c(c1)OCO2)N1CCNCC1]

Step 1: (R)—N-(1-(benzo[d][1,3]dioxol-5-yl)ethylidene)-2-methylpropane-2-sulfinamide To a mixture of 1-(benzo[d][1,3]dioxol-5-yl)ethan-1-one (260 g, 1584 mmol), (f?)-(+)-2-Methyl-2-propanesulfinamide (210.3 g, 1742 mmol) in THF (2.3 L) titanium(IV) ethoxide (722 g, 3168 mmol) was added at rt over 30 min and refluxed for 30 h. Reaction was monitored by HPLC. The reaction mass was cooled to rt and slowly quenched with water (1000 mL). The precipitate observed was filtered through celite bed (350 g) and the filtration cake was washed with ethylacetate (2×1.5 L). The combined organic layer was washed with water (1.5 L), brine solution (1.5 L) and dried over sodium sulfate (250 g) and evaporated under vacuum at 50° C. The resulted crude was co-distilled with toluene (2×1000 mL) and used as such for next step. Yield: quantitative (580 g, brown liquid). HPLC: (Method A) Rt. 3.83 min, 53.3% (Max).

Step 2: (R)—N—((R)-1-(benzo[d][1,3]dioxol-5-yl) ethyl)-2-methylpropane-2-sulfinamide To a stirred solution of (R)—N-(1-(benzo[d][1,3]dioxol-5-yl)ethylidene)-2-methylpropane-2-sulfinamide (6 g, 22.0 mmol) in THF (100 mL), sodium borohydride (2.5 g, 67.4 mmol) was added slowly at 0° C. and then stirred at rt for 1 h. Completion of the reaction was confirmed by TLC. The precipitate observed was filtered through celite bed (30 g)

and was washed with EtOAc (2×50 mL). The organic layer was washed with water (50 mL), brine (50 mL) and dried over Na$_2$SO$_4$ (20 g) and evaporated under vacuum at 50° C. The resulting crude product was purified by flash chromatography (25% EtOAc in pet ether) to give the title compound. Yield: 66.2% (4 g, off white solid). $^1$H NMR (400 MHz, DMSO-d$_6$): δ 6.97 (s, 1H), 6.83-6.77 (m, 2H), 5.97-5.96 (m, 2H), 5.25 (d, J=7.1 Hz, 1H), 4.30-4.23 (m, 1H), 1.33 (d, J=6.8 Hz, 3H), 1.08 (s, 9H). LCMS: (Method A) 270.0 (M+H), Rt. 3.79 min, 96.41% (Max). HPLC: (Method A) Rt. 3.76 min, 96.84% (Max). Chiral HPLC: (Method C) Rt. 7.71 min, 97.5%.

Step 3: (R)-1-(benzo[d][1,3]dioxol-5-yl)ethan-1-amine

To a stirred solution of (R)—N—((R)-1-(benzo[d][1,3]dioxol-5-yl)ethyl)-2-methylpropane-2-sulfinamide (4 g, 14.86 mmol) in MeOH (20 mL), methanolic hydrochloride (18.5 mL, 74.3 mmol, 4M) was added at 0° C. over 15 min and stirred at rt for 1 h. Completion of the reaction was confirmed by TLC. Then the reaction mixture was concentrated under vacuum at 50° C. To the resulting crude, EtOAc (50 mL) was added and filtered and Alteration cake was washed with EtOAc (50 mL). The solid hydrochloride salt was basified by aq.ammonia (30% w/v, 25 mL) and extracted with EtOAC (2×50 mL). The combined organic layer was washed with brine solution (1×50 mL) and dried over Na$_2$SO$_4$. The solvent was evaporated at under vacuum to give the title compound. Yield: 85% (2.1 g, brown liquid). $^1$H NMR (400 MHz, DMSO-d$_6$): δ 6.95 (s, 1H), 6.81-6.77 (m, 2H), 5.95-5.93 (m, 2H), 3.90 (q, J=6.5 Hz, 1H), 1.86-1.85 (brs, 2H), 1.17 (d, J=6.5 Hz, 3H). LCMS: (Method A) 149.0 (M-16), Rt. 1.66 min, 96.9% (Max). HPLC: (Method A) Rt. 1.59 min, 96.86% (Max). Chiral HPLC: (Method B) Rt. 7.12 min, 97.76%.

Step 3: (R)-1-(1-(benzo[d][1,3]dioxol-5-yl)ethyl)-4-tosylpiperazine

To a stirred solution of (R)-1-(benzo[d][1,3]dioxol-5-yl)ethan-1-amine (2 g, 12.1 mmol) in DIPEA (4.22 mL, 24.2 mmol), N,N-bis(2-chloroethyl)-p-toluene sulfonamide (3.9 g, 13.3 mmol) was added at rt and the resulting mixture was heated to 105° C. for 18 h. Completion of the reaction was confirmed by TLC. Reaction mixture was diluted with water (30 mL) and extracted with EtOAc (2×50 mL). The combined organic layer was dried over Na$_2$SO$_4$ and evaporated under vacuum. To the resulting crude solid hexane (50 mL) was added, and the resulting mixture was stirred for 10 min at rt. It was filtered and the solid was washed with Et$_2$O (2×50 mL) and dried under vacuum to give the title compound. Yield: 63.8% (3 g, off white solid). $^1$H NMR (400 MHz, DMSO-d$_6$): δ 7.59 (d, J=8.4 Hz, 2H), 7.45 (d, J=8.0 Hz, 2H), 6.81-6.77 (m, 2H), 6.69-6.6 (m, 1H), 5.97-5.95 (m, 2H), 3.35-3.31 (m, 1H), 2.81-2.80 (m, 4H), 2.42 (s, 3H), 2.36-2.32 (m, 4H), 1.18 (d, J=6.8 Hz, 3H). LCMS: (Method A) 389.0 (M+H), Rt. 3.39 min, 98.9% (Max). HPLC: (Method A) Rt. 3.30 min, 99.53% (Max), Chiral HPLC: (Method A) Rt. 15.54 min, 97.58%.

Step 5: (R)-1-(1-(benzo[d][1,3]dioxol-5-yl)ethyl)piperazine

To the reaction mixture of (R)-1-(1-(benzo[d][1,3]dioxol-5-yl)ethyl)-4-tosylpiperazine (2.7 g, 6.9 mmol) and 4-hydroxy benzoic acid (2.8 g, 20.8 mmol), HBr in acetic acid (30% w/v, 14 mL) was added at 0° C. and stirred overnight at rt. Completion of the reaction was confirmed by TLC. Reaction mixture was diluted with water (60 mL) and the resulting precipitate was filtered through a celite bed. The celite bed was washed with water (50 mL). The aqueous layer was washed with EtOAc (4×50 mL) and basified up to pH 11 with NaOH pellet (10 g) at 0° C. The product was extracted with EtOAc (3×30 mL). The combined organic layer was dried over Na$_2$SO$_4$ and evaporated under vacuum to give the title compound. Yield: 92% (1.5 g, Dark brown solid). $^1$H NMR (400 MHz, DMSO-d$_6$): δ 6.84-6.81 (m, 2H), 6.72-6.71 (m, 1H), 5.97-5.95 (m, 2H), 3.29-3.23 (m, 2H), 2.64-2.62 (m, 4H), 2.26-2.19 (m, 4H), 1.22 (d, J=6.8 Hz, 3H). LCMS: (Method A) 235.3 (M+H), Rt. 1.56 min, 96.9% (Max). HPLC: (Method A) Rt. 1.50 min, 96.9% (Max). Chiral HPLC: (Method A) Rt. 10.13 min, 98.04%.

Intermediate 25: 2-(piperazin-1-yl)-6,7-dihydrothiazolo[5,4-c]pyridin-4(5H)-one Dihydrochloride

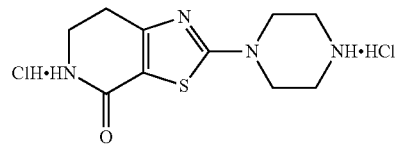

Step 1: tert-butyl 3-bromo-2,4-dioxopiperidine-1-carboxylate

To a stirred solution of fert-butyl 2,4-dioxopiperidine-1-carboxylate (1 g, 4.69 mmol) in dry CCl$_4$ (10 mL), /v-bromosuccinimide (0.83 g, 4.69 mmol) was added at 10° C. The reaction mixture was stirred at 10-15° C. for 2 h. It was then evaporated under reduced pressure. Water (10 mL) was added and the desired product was extracted with EtOAc (2×30 mL). The combined organic layer was dried over Na$_2$SO$_4$ and concentrated. The resulting crude product was purified by flash column chromatography, affording the title product. Yield: 99% (1.4 g, off white solid). $^1$H NMR (400 MHz, DMSO-d$_6$): δ 5.50 (s, 1H), 3.74-3.71 (m, 2H), 2.69-2.66 (m, 2H), 1.46 (s, 9H). LCMS: (Method A) 193.8 (M-Boc+H), Rt. 2.93 min, 81.51% (Max).

Step 2: tert-butyl-2-(4-(tert-butoxycarbonyl)piperazin-1-yl)-4-oxo-6J-dfoˆdrothiazolo[5,4-c]pyridine-5(4H)-carboxylate To a stirred solution of fert-butyl 4-carbamothioylpiperazine-1-carboxylate (synthesized according to Example 5, Step 1, 1.31 g, 5.36 mmol) in isopropanol (15 mL), fert-butyl 3-bromo-2,4-dioxopiperidine-1-carboxylate obtained in the first step (1.3 g, 4.46 mmol) was added at rt. The reaction mixture was stirred overnight at 90° C. It was cooled down to rt and evaporated under reduced pressure. Water (10 mL) was added and the desired product was extracted with diethyl ether (2×30 mL), dried over Na$_2$SO$_4$ and concentrated, affording the title product. Yield: 74% (1.42 g, yellow solid). LCMS: (Method A) 239.0 (M-Boc+H), Rt. 0.70 min, 48.39% (Max).

Step 3: 2-(piperazin-1-yl)-6,7-dihydrothiazolo[5,4-c]pyridin-4(5H)-one Dihydrochloride To a stirred solution of fert-butyl-2-(4-(tert-butoxycarbonyl)piperazin-1-yl)-4-oxo-6,7-dihydrothiazolo[5,4-c]pyridine-5(4H)-carboxylate obtained in previous step (1.3 g, 2.96 mmol) in 1,4-dioxane (10 mL), HCl in dioxane (4 M solution, 13 mL, 10 V) was added at 0° C. The reaction mixture was stirred for 2 h at rt. It was evaporated and DCM (15 mL) was added and evalopated. This procedure was repeated twice, affording the title product which was used without any further purification. Yield: 99% (0.82 g, off white solid).

Intermediate 26:
5-(1-chloroethyl)-2-methylbenzordlthiazole

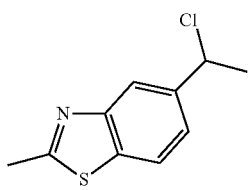

Step 1: 2-methylbenzo[d]thiazole-5-carboxylic Acid

4-Chloro-3-nitrobenzoic acid (10 g, 50.25 mmol) and sodium sulfide (33.3 g, 427 mmol) were heated up to melting and stirred for 20 min. Then reaction mixture was cooled to rt and acetic anhydride (11.7 mL, 115 mmol) and acetic acid (4.3 mL, 75.3 mmol) were added. The resulting reaction mixture was refluxed for 20 min and cooled to rt. Water (50 mL) and EtOAc (100 mL) were added and the mixture was stirred for 20 min. The resulting mass was filtered through celite, washed with EtOAc (50 mL). The combined filtrate was washed with brine (30 mL), dried over $Na_2SO_4$ and concentrated. The celite plug was further washed with EtOH (3×100 mL) and the filtrate was filtered through silica gel and concentrated under reduced pressure. Both fractions were mixed and taken for next step without further purification (brown solid). $^1$H NMR (400 MHz, DMSO-$d_6$): δ 9.88 (s, 1H), 8.33 (s, 1H), 7.92-7.88 (m, 2H), 2.79 (s, 3H). LCMS: (Method A) 194.0 (M+H), Rt. 2.73 min, 59.03% (Max).

Step 2: (2-methylbenzo[d]thiazol-5-yl)methanol

To a stirred solution of 2-methylbenzo[d]thiazole-5-carboxylic acid obtained in the previous step (3.7 g, 19.7 mmol) in dry THF (35 mL), lithium aluminium hydride (2 M in THF, 19.2 mL, 38.34 mmol) was added at 0° C. and the resulting mixture was stirred at rt for 1 h. It was cooled to 0° C., quenched with saturated $Na_2SO_4$ solution and filtered through celite. The filtrate was diluted with EtOAc (50 ml_), washed with brine (10 ml_), water (10 mL) and dried over $Na_2SO_4$. After evaporation of the solvent, the resulting crude product was taken for next step without further purification (yellow oil). LCMS: (Method A) 180.0 (M+H), Rt. 1.95 min, 40.76% (Max).

Step 3: 2-methylbenzo[d]thiazole-5-carbaldehyde

To a stirred solution of (2-methylbenzo[d]thiazol-5-yl) methanol (0.6 g, 3.35 mmol) in dry DCM (6 mL), $NaHCO_3$ (1.12 g, 13.4 mmol) followed by Dess-Martin periodinane (2.84 g, 6.70 mmol) were added and the reaction mixture was stirred at rt for 2 h. It was diluted with DCM (50 mL) and washed with water (15 mL), 10% $NaHCO_3$ solution (15 mL), brine (15 mL) and dried over $Na_2SO_4$. The title product was obtained after evaporation of the solvents. Yield: 99% (0.65 g, brown liquid). $^1$H NMR (400 MHz, DMSO-$d_6$): δ 10.12 (s, 1H), 8.25 (s, 1H), 7.80-7.79 (m, 2H), 2.86 (s, 3H). LCMS: (Method A) 178.0 (M+H), Rt. 2.84 min, 81.57% (Max).

Step 4: 1-(2-methylbenzo[d]thiazol-5-yl)ethan-1-ol

To a stirred solution of 2-methylbenzo[d]thiazole-5-carbaldehyde (0.65 g, 3.67 mmol) in THF (6 mL), methyl magnesium bromide (1.4M in THF Toluene 1:3 mixture, 3.9 mL, 5.50 mmol) was added at 0° C. The reaction mixture was stirred for 1 h at rt and was then quenched with saturated N $H_4Cl$ (5 mL) at 0° C. It was diluted with EtOAc (30 mL), washed with water (10 mL), brine (10 mL) and dried over $Na_2SO_4$. The title product was obtained after evaporation of the solvents (brown liquid). $^1$H NMR (400 MHz, DMSO-$d_6$): δ7.97-7.95 (m, 1H), 7.51-7.50 (m, 2H), 5.29 (d, J=4.4 Hz, 1H), 4.87-4.86 (m, 1H), 2.78 (s, 3H), 1.37 (d, J=6.4 Hz, 3H). LCMS: (Method A) 194.0 (M+H), Rt. 2.53 min, 73.53% (Max).

Step 5: 5-(1-chloroethyl)-2-methylbenzo[d]thiazole

To a stirred solution of 1-(2-methylbenzo[d]thiazol-5-yl) ethan-1-ol (0.35 g, 3.67 mmol) in DCM (5 mL), thionyl chloride (0.27 mL, 3.62 mmol) was added at 0° C. The reaction mixture was stirred for 1 h at rt and concentrated. DCM (15 mL) was added and was evaporated. This procedure was repeated a second time, affording the title product. It was used in the next step without any further purification. Yield: 90% (0.38 g, brown liquid). $^1$H NMR (400 MHz, DMSO-$d_6$): δ 8.01-8.00 (m, 2H), 7.54-7.52 (m, 1H), 5.53-5.51 (m, 1H), 2.80 (s, 3H), 1.86 (d, J=6.8 Hz, 3H). LCMS: (Method A) 212.0 (M+H), Rt. 2.61 min, 58.89% (Max).

Intermediate 27: 6-(1-chloroethyl)benzordlthiazole

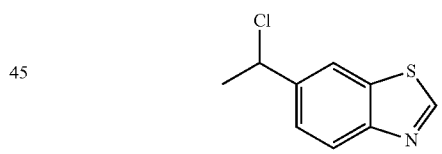

Step 1: 1-(benzo[d]thiazol-6-yl)ethan-1-one

A solution of 6-bromobenzo[d]thiazole (1.2 g, 5.61 mmol) in dry toluene was put under inter atmosphere. 1-Ethoxy vinyl tributyltin (3.0 g, 8.41 mmol) and bis(triphenylphosphine)palladium dichloride (0.39 g, 0.56 mmol) were added at rt and the resulting mixture was stirred overnight at 90° C. It was cooled to rt and filtered through celite. The filtrate was concentrated under vacuum and the resulting crude product was stirred in HCl aqueous solution (6 N, 20 ml.) for 1 h at rt. The solution was concentrated and neutralized with saturated $NaHCO_3$ solution. The desired product was extracted with DCM (60 ml_), dried over anhydrous $Na_2SO_4$ and concentrated under reduced pressure. It was purified by flash column chromatography to afford the title compound. Yield: 60% (0.6 g, yellow solid). $^1$H NMR (400 MHz, DMSO-$d_6$): δ 9.59 (s, 1H), 8.88 (s, 1H), 8.17 (d, J=8.0 Hz, 1H), 8.06 (d, J=8.0 Hz, 1H), 2.75 (s, 3H). LCMS: (Method A) 178.0 (M+H), Rt. 1.97 min, 94.50% (Max).

Step 2: 1-(benzo[d]thiazol-6-yl)ethan-1-ol

To a stirred solution of 1-(benzo[d]thiazol-6-yl)ethan-1-one, obtained in the previous step (0.6 g, 3.39 mmol) in dry MeOH (20 mL), sodium borohydride (0.38 g, 10.2 mmol) was added portion wise at 0° C. and the mixture was stirred at rt for 1 h. It was concentrated, diluted with DCM (50 mL), washed with water (15 mL), brine (10 ml.) and dried over $Na_2SO_4$. After evaporation of the solvent, the title product was obtained and was used in the next step without any further purification. Yield: 66% (0.4 g, brown liquid). $^1$H NMR (400 MHz, DMSO-$d_6$): δ 9.39 (s, 1H), 8.40 (s, 1H), 7.80 (d, J=2.0 Hz, 1H), 7.78 (d, J=2.0 Hz, 1H), 4.88 (d, J=2.8 Hz, 1H), 4.37 (d, J=2.8 Hz, 1H), 1.92 (s, 3H).

Step 3: 6-(1-chloroethyl)benzo[d]thiazole

To a stirred solution of 1-(benzo[d]thiazol-6-yl)ethan-1-ol (0.4 g, 2.25 mmol) in dry DCM (20 mL), thionyl chloride (0.3 mL, 4.5 mmol) was added dropwise at 0° C. and the resulting reaction mixture was stirred at rt for 1 h. It was concentrated. DCM (5 ml.) was added and was evaporated again. This procedure was repeated twice, affording the title product that was used without any further purification. Yield: 98% (430 mg, brown liquid).

Intermediate 28: 7-(1-Chloroethyl)-3-methylquinoline

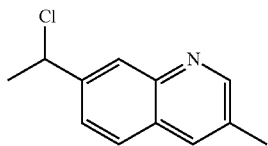

Step 1: 7-Bromo-3-methylquinoline

To a solution of 4-bromo-2-nitrobenzaldehyde (5 g, 21.7 mmol) in ethanol (50 mL), iron powder (4.85 g, 86.9 mmol) was added followed by HCl aqueous solution (0.1 N, 15 mL). The resulting reaction mixture was vigorously stirred at 95° C. for 2 h. The reaction progression was followed by TLC. When the reduction was completed, propionaldehyde (1.5 mL, 21.7 mmol) and KOH (1.46 g, 26.0 mmol, in two portions) were added at rt. The reaction mixture was stirred at 95° C. overnight. It was cooled to rt, diluted with DCM (30 mL) and filtered through celite. The filtrate was washed with water (50 mL) and the aqueous layer was extracted with DCM (2×100 mL). The combined organic layer was dried over anhydrous $Na_2SO_4$ and concentrated under reduced pressure. The resulting crude product was purified by flash chromatography, affording the title compound. Yield: 52% (2.5 g, Pale yellow solid). $^1$H NMR (400 MHz, DMSO-$d_6$): δ 8.81 (s, 1H), 8.18-8.17 (m, 2H), 7.89 (d, J=8.7 Hz, 1H), 7.72 (dd, J=1.9, 8.7 Hz, 1H), 2.50 (s, 3H). LCMS: (Method D) 223.9 (M+H), Rt. 2.48 min, 99.58% (Max).

Step 2: 1-(3-Methylquinolin-7-yl)ethan-1-one

A stirred solution of 7-bromo-3-methylquinoline obtained in previous step (2 g, 9.0 mmol) in toluene (20 mL) was flushed with nitrogen for 15-20 min. 1-Ethoxy-1-(tributylstannyl) ethylene (3.9 mL, 11.7 mmol) and bis(triphenylphosphine)palladium dichloride (0.31 g, 0.45 mmol) were added and the resulting reaction mixture was stirred at 90° C. for 12 h. It was cooled to rt, filtered through celite and concentrated under reduced pressure. HCl aqueous solution (6 N, 30 mL) was added and the mixture was stirred at room temperature for 1 h. The solution was neutralized with the addition of solid sodium bicarbonate and was extracted with EtOAc (2×50 mL). The combined organic layer was dried over anhydrous $Na_2SO_4$ and concentrated. The crude product was purified by flash chromatography, affording the title compound. Yield: 60% (1.1 g, pale yellow solid). $^1$H NMR (400 MHz, DMSO-$d_6$): δ 8.90 (s, 1H), 8.61 (s, 1H), 8.21 (s, 1H), 8.04-7.98 (m, 2H), 2.76 (s, 3H), 2.52 (s, 3H). LCMS: (Method D) 186.0 (M+H), Rt. 1.88 min, 99.85% (Max).

Step 3: 1-(3-Methylquinolin-7-yl)ethan-1-ol

To a stirred solution of 1-(3-methylquinolin-7-yl)ethan-1-one obtained in previous step (1.1 g, 5.9 mmol) in MeOH (12 mL), sodium borohydride (0.26 g, 7.1 mmol) was added portion wise at 0° C. and the reaction mixture was stirred at room temperature for 1 h. The reaction mixture was concentrated under reduced pressure and the resulting cude water was added and extracted with DCM (2×50 mL). The combined organic layer was dried over anhydrous sodium sulphate, concentrated under reduced pressure and the crude mass was purified by column chromatography to afford the title compound. Yield: 55% (0.8 g, yellow solid). $^1$H NMR (400 MHz, DMSO-$d_6$): δ 8.73 (s, 1H), 8.07 (s, 1H), 7.89 (s, 1H), 7.82 (d, J=8.4 Hz, 1H), 7.56 (d, J=8.4 Hz, 1H), 5.33 (d, J=4.4 Hz, 1H), 4.94-4.89 (m, 1H), 2.47 (s, 3H), 1.41 (d, J=6.4 Hz, 3H). LCMS: (Method D) 188.1 (M+H), Rt. 0.83 min, 94.19% (Max).

Step 4: 7-(1-Chloroethyl)-3-methylquinoline

To a stirred solution of 1-(3-methylquinolin-7-yl)ethan-1-ol obtained in previous step (0.8 g, 4.2 mmol) in DCM (8 mL), thionyl chloride (0.61 mL, 8.5 mmol) was added drop wise at 0° C. and the resulting mixture stirred at room temperature for 1 h. The reaction completion was confirmed by TLC. The reaction mixture was concentrated under reduced pressure and the resulting crude product was used in the next step without any further purification. Yield: 85% (0.75 g, brown solid). $^1$H NMR (400 MHz, DMSO-$d_6$): δ 9.06 (s, 1H), 8.60 (s, 1H), 8.18 (s, 1H), 8.13 (d, J=8.8 Hz, 1H), 7.90 (d, J=8.4 Hz, 1H), 5.68-5.63 (m, 1H), 2.57 (s, 3H), 1.90 (d, J=6.8 Hz, 3H). LCMS: (Method D) 206.0 (M+H), Rt. 2.12 min, 91.94% (Max).

Intermediate 29: 1-(3-(Trifluoromethyl)pyridin-2-yl)piperazine

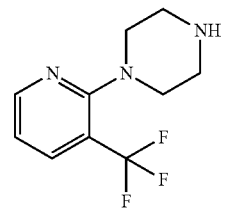 [SMILES: FC(F)(F)c1cccnc1N1CCNCC1]

To a stirred solution of 2-chloro-3-(trifluoromethyl)pyridine (1 g, 5.50 mmol) in n-Butanol (10 mL), 1-piperazine (6.63 g, 77.12 mmol) was added and the reaction mixture was stirred at 100° C. for 24 h. The reaction completion was confirmed by TLC. The reaction mixture was cooled to room temperature and concentrated under reduced pressure. The resulting mixture was diluted with ethyl acetate (30 mL) and neutralized with saturated sodium bicarbonate solution (4 mL), and extracted with EtOAc (2×50 mL). The combined organic layer was dried over anhydrous $Na_2SO_4$ and concentrated under reduced pressure. The crude was purified by column chromatography to afford the title compound. Yield: 63% (0.8 g, colorless gum). $^1$H NMR (400 MHz, DMSO-d$_6$): δ 8.50 (d, J=3.6 Hz, 1H), 8.03 (dd, J=7.8, 2.0 Hz, 1H), 7.16-7.13 (m, 1H), 3.11-3.08 (m, 4H), 2.81-2.79 (m, 4H). LCMS: (Method F) 232.0 (M+H), Rt. 2.10 min, 96.01% (Max).

EXAMPLES

Example 1: 2-(1-(1-(Benzord1H,31dioxol-5-yl)ethyl)piperidin-4-yl)-4-methylthiazole Step 1: 1-(tert-Butoxycarbonyl)piperidine-4-carboxylic acid

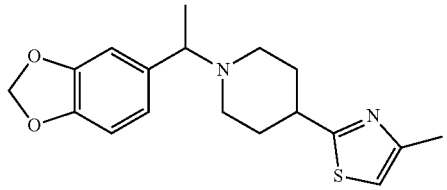 [SMILES: Cc1csc(C2CCN(C(C)c3ccc4c(c3)OCO4)CC2)n1]

To a stirred solution of isonipecotic acid (6.0 g, 46.6 mmol) in fert-BuOH (18 mL), NaOH solution (12 mL, 3.71 g, 92.8 mmol in 12 mL water) was added at 10-15° C., followed by di-fert-butyl dicarbonate (10.1 g, 46.6 mmol) and the mixture was stirred at rt for 3 h. The completion of the reaction was monitored by TLC. The reaction mixture was diluted with water and washed with petroleum ether (3×25 mL). The pH of the aqueous layer was adjusted to 6-6.5 using citric acid and was extracted with DCM. The organic layer was dried over anhydrous $Na_2SO_4$ and concentrated under reduced pressure to afford the title compound. Yield: 73% (10.0 g, white solid). $^1$H NMR (400 MHz, DMSO-d$_6$): δ 12.25 (s, 1H), 3.83-3.80 (m, 2H), 2.80-2.49 (m, 2H), 2.39-2.36 (m, 1H), 1.79-1.75 (m, 2H), 1.41-1.34 (m, 11H).

Step 2: tert-Butyl 4-carbamoylpiperidine-1-carboxylate

To a stirred solution of 1-(fert-butoxycarbonyl)piperidine-4-carboxylic acid (10.0 g, 43.6 mmol) in dry THF (150 ml_), CDI (9.95 g, 65.6 mmol) was added at 0-5° C. and the reaction mixture was stirred at rt for 16 h. Then the reaction mixture was cooled to 0-5° C. and a continuous flow of ammonia was applied to the solution for 2 h. MeOH (30 ml.) was added and the flow of ammonia was applied for 2 additional hours at the same temperature. The reaction mixture was then stirred at rt for 16 h. It was concentrated under reduced pressure and the resulting crude mixture was dissolved in EtOAc and washed with 10% citric acid, 10% sodium bicarbonate, water, dried over anhydrous $Na_2SO_4$ and concentrated under vacuum to afford the title compound (white solid). $^1$H NMR (400 MHz, DMSO-de): δ 6.77 (s, 2H), 3.91-3.88 (m, 2H), 2.71-2.49 (m, 2H), 2.25-2.17 (m, 1H), 1.66-1.62 (m, 2H), 1.39-1.35 (m, 13H). LCMS: (Method A) 130.2 (M+H), Rt. 2.62 min, 99.0% (Max).

Step 3: tert-Butyl 4-carbamothioylpiperidine-1-carboxylate

To a stirred solution of fert-butyl 4-carbamoylpiperidine-1-carboxylate (1.3 g, 5.7 mmol) in THF (16 ml_), Lawssen's reagent 2.53 g, 6.27 mmol) was added. The reaction mixture was refluxed for 6 h and then stirred at rt for 16 h. The completion of the reaction was monitored by TLC. The reaction mixture was diluted with ethyl acetate and was washed with 10% citric acid, 10% sodium bicarbonate, water and brine, dried over anhydrous $Na_2SO_4$ and concentrated under vacuum to afford the title compound. Yield: 78% (1.09 g, colorless oil). $^1$H NMR (400 MHz, DMSO-d$_6$): δ 9.41 (s, 1H), 9.11 (s, 1H), 4.03-3.97 (m, 1H), 2.66-2.61 (m, 2H), 1.64-1.52 (m, 4H), 1.40 (s, 9H), 1.38-1.34 (m, 2H). LCMS: (Method A) 245.2 (M+H), Rt. 3.38 min, 93.5% (Max).

Step 4: tert-Butyl 4-(4-methylthiazol-2-yl)piperidine-1-carboxylate

To a stirred solution of fert-butyl 4-carbamothioylpiperidine-1-carboxylate (1.0 g, 4.1 mmol) in dioxane (10 ml_), triethyl amine (0.62 g, 6.5 mmol) and bromo acetone (0.84 g, 6.5 mmol) were added and stirred at 90° C. for 16 h. The completion of the reaction was monitored by TLC. The reaction mixture was quenched with water and extracted with DCM with 10% MeOH (5×25 mL). The organic layer was separated, dried over anhydrous $Na_2SO_4$, concentrated under vacuum and was purified by flash chromatography (30% EtOAc in petroleum ether) to afford the title compound (colorless oil). LCMS: (Method A) 283.0 (M+H), Rt. 3.35 min, 93.5% (Max).

Step 5: 4-Methyl-2-(piperidin-4-yl)thiazole hydrochloride

To a stirred solution of fert-butyl 4-(4-methylthiazol-2-yl)piperidine-1-carboxylate (0.39 g, 1.38 mmol) in dry dioxane (2 mL), HCl in dioxane (3 N, 10 mL) was added at rt and the reaction mixture was stirred for 2 h. It was then concentrated under reduced pressure and the crude product was triturated in diethyl ether, filtrated and dried under vacuum to afford the title compound. Yield: 99% (0.3 g, white oil).

LCMS: (Method B) 183.0 (M+H), Rt. 3.21 min, 92.5% (Max).

Step 6: 2-(1-(1-(Benzo[d][1,3]dioxol-5-yl)ethyl)piperidin-4-yl)-4-mˆthylthiazole The title compound was synthesized by following general procedure E, using 4-methyl-2-(piperidin-4-yl)thiazole hydrochloride (0.3 g, 1.37 mmol) and Intermediate 1 (0.379 g, 2.0 mmol). The reaction mixture was stirred at 60° C. for 16 h. The crude product was purified by flash chromatography, affording the title compound (colorless oil). $^1$H NMR (400 MHz, CDCl$_3$): δ 6.90 (s, 1H), 6.76-6.74 (m, 3H), 5.96 (s, 2H), 3.41-3.39 (m, 1H), 3.17-3.14 (m, 1H), 2.94-2.92 (m, 2H), 2.42 (s, 3H), 2.14-2.02 (m, 4H), 1.92-1.74 (m, 2H), 1.37 (d, J=6.8 Hz, 3H). LCMS: (Method A) 331.0 (M+H), Rt. 2.54 min, 95.5% (Max). HPLC: (Method A) Rt. 2.54 min, 97.3% (Max).

Example 2: 2-(1-(1-(benzordiri,31dioxol-5-yl)ethyl) piperidin-4-yl)-5-methyl-1,3,4-oxadiazole

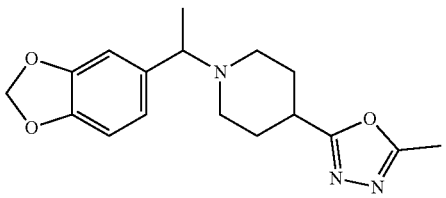 [SMILES: Cc1nnc(C2CCN(C(C)c3ccc4c(c3)OCO4)CC2)o1]

Step 1: Ethyl 1-(1-(benzo[d][1,3]dioxol-5-yl)ethyl) piperidine-4-carboxylate

The title compound was synthesized by following general procedure D, using 4-piperidine carboxylic acid ester (25 g, 159 mmol) and Intermediate 1 (49.87 g, 271 mmol). The crude product was purified by flash chromatography, affording the title compound (pale brown liquid). LCMS: (Method A) 306.0 (M+H), Rt. 2.71 min, 29.4% (Max).

Step 2: 1-(1-(Benzo[d][1,3]dioxol-5-yl)ethyl)piperidine-4-carbohydrazide

To a stirred solution of ethyl 1-(1-(benzo[d][1,3]dioxol-5-yl)ethyl)piperidine-4-carboxylate (4.3 g, 3.79 mmol) in ethanol (4 ml_), hydrazine hydrate (3.79 g, 75 mmol) was added at rt and stirred at 90° C. for 3 h. The completion of the reaction was monitored by TLC. The reaction mixture was concentrated under reduced pressure and the resulting crude product was dissolved in EtOAc, washed with water and dried over anhydrous $Na_2SO_4$. After evaporation of the solvents, the crude product was purified by flash chromatography to afford the title compound (colorless oil). $^1$H NMR (400 MHz, DMSO-$d_6$): δ 8.88 (s, 1H), 6.83-6.81 (m, 2H), 6.73-6.71 (m, 1H), 5.98 (s, 2H), 4.12 (m, 2H), 2.93-2.91 (m, 1H), 2.76-2.73 (m, 1H), 1.94 (m, 1H), 1.87-1.83 (m, 1H), 1.74 (m, 1H), 1.57-1.48 (m, 4H), 1.24-1.22 (d, J=6.5 Hz, 3H). LCMS: (Method A) 292.0 (M+H), Rt. 1.71 min, 96.0% (Max).

Step 3: 2-(1-(1-(benzo[d][1,3]dioxol-5-yl)ethyl) piperidin-4-yl)-5-methyl-1,3,4-oxadiazole A solution of 1-(1-(benzo[d][1,3]dioxol-5-yl)ethyl)piperidine-4-carbohydrazide (0.18 g, 0.62 mmol) in triethyl ortho acetate (1.8 mL) was stirred at 110° C. for 16 h. The reaction mixture was concentrated under reduced pressure. The resulting crude product was dissolved in EtOAc, washed with water and dried over anhydrous $Na_2SO_4$. After evaporation of the solvents, the crude product was purified by flash chromatography to afford the title compound (pale brown oil). $^1$H NMR (400 MHz, DMSO-$d_6$): δ 6.86 (s, 1H), 6.82 (d, J=8.0 Hz, 1H), 6.73 (d, J=8.0 Hz, 1H), 5.97 (m, 2H), 3.42-3.39 (m, 1H), 2.90-2.88 (m, 1H), 2.83-2.75 (m, 2H), 2.43 (s, 3H), 2.06-1.86 (m, 4H), 1.72-1.59 (m, 2H), 1.25 (d, J=6.8 Hz, 3H). LCMS: (Method A) 316.0 (M+H), Rt. 2.10 min, 95.5% (Max). HPLC: (Method A) Rt. 2.10 min, 96.9% (Max).

Example 3: 1-(1-(benzo[di[131dioxol-5-yl)ethyl)-4-(4-methyl-1H-pyrazol-1-yl)piperidine

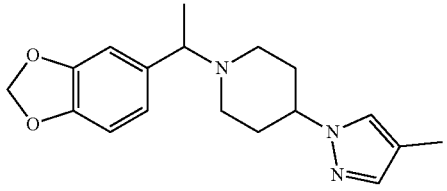 [SMILES: Cc1cnn(C2CCN(C(C)c3ccc4c(c3)OCO4)CC2)c1]

Step 1: tert-Butyl 4-((methylsulfonyl)oxy)piperidine-1-carboxylate

To a stirred solution of 1-boc-4-hydroxy piperidine (6.0 g, 29.8 mmol) in dry DCM (100 mL), TEA (8.48 g, 89.5 mmol) and mesyl chloride (5.12 g, 44.78 mmol) were added slowly at 0° C. The reaction mixture was stirred at rt for 1 h. It was concentrated under vacuum and the resulting crude product was dissolved in DCM. The resulting solution was washed with brine, water, dried over anhydrous $Na_2SO_4$ and concentrated under vacuum to afford the title compound. Yield: 99% (8.32 g, off white solid). LCMS: (Method A) 180.2 (M+H), Rt. 3.79 min, 99.2% (Max).

Step 2: tert-Butyl 4-(4-methyl-1H-pyrazol-1-yl) piperidine-1-carboxylate

To a stirred solution of fert-butyl 4-((methylsulfonyl)oxy) piperidine-1-carboxylate (6.8 g, 24 mmol) in dry DMF (80 mL), $Cs_2CO_3$ (23.45 g, 72 mmol) and 4-methyl pyrazole (2 g, 24 mmol) were added and the reaction mixture was stirred at 80° C. for 4 h. The completion of the reaction was monitored by TLC. The reaction mixture was concentrated under vacuum and resulting crude product was dissolved in DCM. The resulting solution washed with brine, water, dried over anhydrous $Na_2SO_4$ and concentrated under vacuum to afford the title compound (colorless oil). LCMS: (Method A) 166.3 (Boc elimination mass), Rt. 3.92 min, 96.3% (Max).

Step 3: 4-(4-Methyl-1H-pyrazol-1-yl)piperidine hydrochloride

To a stirred solution of fert-butyl 4-(4-methyl-1H-pyrazol-1-yl)piperidine-1-carboxylate (0.81 g, 3.06 mmol) in dry dioxane (2 mL), HCl in dioxane (10 mL) was added and the reaction mixture was stirred at rt for 2 h. The reaction mixture was concentrated under vacuum and the crude product was washed with diethyl ether to afford the title compound. Yield: 82% (0.61 g, white oil). LCMS: (Method A) 166.3 (M+H), Rt. 1.41 min, 95.2% (Max).

Step 4: 1-(1-(benzo[d][1,3]dioxol-5-yl)ethyl)-4-(4-methyl-1H-pyrazol-1-yl)piperidine The title compound was synthesized by following general procedure D, using 4-(4-methyl-1H-pyrazol-1-yl)piperidine hydrochloride and Intermediate 1. The crude product was purified by flash chromatography, affording the title compound (brown oil). $^1$H NMR (400 MHz, DMSO-$d_6$): δ 7.29 (s, 1H), 7.20 (s, 1H), 6.89 (s, 1H), 6.76 (s, 1H), 5.95 (m, 2H), 4.06-4.00 (m, 1H), 3.43-3.42 (m, 1H), 3.16-3.14 (m, 1H), 2.97-2.94 (m, 1H), 2.15-2.07 (m, 2H), 2.04-2.00 (m, 4H),

Example 4: 5-(1-(1-(Benzordiri,31 dioxol-5-yl)ethyl)piperidin-4-yl)-3-methyl-1,2,4-oxadiazole

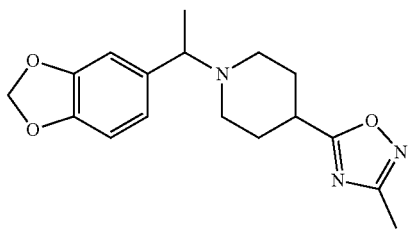 [SMILES: Cc1noc(C2CCN(C(C)c3ccc4c(c3)OCO4)CC2)n1]

Step 1: Ethyl 1-(1-(benzo[d][,3]dioxol-5-yl)ethyl)piperidine-4-carboxylate

The title compound was synthesized by following general procedure D, using 4-piperidine carboxylic acid ester (25 g, 159 mmol) and Intermediate 1 (49.87 g, 271 mmol). The crude product was purified by flash chromatography, affording the title compound (pale brown liquid). LCMS: (Method A) 306.0 (M+H), Rt. 2.71 min, 29.4% (Max).

Step 2: 1-(1-(Benzo[d][1,3]dioxol-5-yl)ethyl)piperidine-4-carboxylic acid

To a stirred solution of ethyl 1-(1-(benzo[d][1,3]dioxol-5-yl)ethyl)piperidine-4-carboxylate (1.0 g, 3.2 mmol) in dioxane (15 ml_), NaOH in water (0.256 g, 6.5 mmol, 1 mL water) was added at 0° C. and stirred for 20 h at rt. Reaction mixture was evaporated at 40° C. To the resulting crude product, DCM (30 ml.) and water (15 ml.) were added and pH was adjusted to 6.5-7.0 using citric acid. The reaction mixture was extracted with 10% MeOH in DCM (30 ml.) and evaporated under reduced pressure to afford the title compound. (pale brown oil). $^1$H NMR (400 MHz, DMSO-$d_6$): δ 7.04-6.72 (m, 3H), 5.99-5.95 (m, 2H), 5.08-5.06 (m, 1H), 4.64-4.50 (m, 1H), 2.15-2.08 (m, 4H), 1.90-1.50 (m, 2H), 1.46-1.44 (m, 2H), 1.35 (d, J=7.6 Hz, 3H). LCMS: (Method B) 278.0 (M+H), Rt. 2.721 min, 70.13% (Max).

Step 3: 5-(1-(1-(Benzo[d][1,3]dioxol-5-yl)ethyl)piperidin-4-yl)-3-m^thyl-1,2,4-oxadiazole To a stirred solution of 1-(1-(benzo[d][1,3]dioxol-5-yl)ethyl)piperidine-4-carboxylic acid (290 mg, 1.05 mmol) in ACN (5 mL), HOBt (163 mg, 1.21 mmol) and EDC.HCl (241 mg, 1.26 mmol) were added at rt and stirred for 30 min. Then N'-hydroxyacetimidamide was added and stirred for overnight at rt. The reaction mixture was concentrated under vacuum and the resulting residue was dissolved in EtOAc (50 mL). The EtOAc layer was washed with water (10 mL), brine solution (10 mL), dried over anhydrous Na$_2$SO$_4$ and concentrated under vacuum. The crude product was purified by preparative HPLC (Method PB) to afford the title compound (pale brown oil). $^1$H NMR (400 MHz, CDCl$_3$): δ 6.87 (s, 1H), 6.75 (s, 2H), 5.95 (m, 2H), 3.40-3.38 (m, 1H), 3.07-3.02 (m, 1H), 2.90-2.85 (m, 2H), 2.38 (s, 3H), 2.13-1.85 (m, 6H), 1.35 (d, J=6.4 Hz, 3H). LCMS: (Method A) 1.99-1.92 (m, 3H), 1.37 (d, J=6.8 Hz, 3H). LCMS: (Method A) 314.0 (M+H), Rt. 2.76 min, 93.6% (Max). HPLC: (Method A) Rt 2.78 min, 97.0% (Max).

Example 5: 2-(4-(1-(Benzordiri,31dioxol-5-yl)ethyl)piperazin-1-yl)-4-phenylthiazole

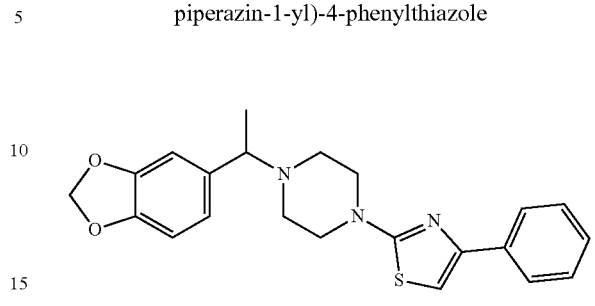

Step 1: tert-butyl 4-carbamothioylpiperazine-1-carboxylate

To a solution of 1-boc piperazine (5.0 g, 26.88 mmol) in dry THF (50 mL), 1,1-thio carbonylimidazole (5.48 g, 29.56 mmol) was added at room temperature and stirred for 2 h. The reaction mixture was heated at 50° C. for 1 h. It was cooled down to 0° C. and methanolic ammonia solution (50 mL, 7 N) was added. The mixture was stirred at 60° C. for 20 h. It was then diluted with water and extracted with EtOAc. The organic layer was dried over anhydrous Na$_2$SO$_4$ and concentrated under vacuum. The crude product was purified by flash chromatography to give the title compound. Yield: 92% (4.0 g, white solid). $^1$H NMR (400 MHz, DMSO-$d_6$): δ 9.2 (m, 2H), 3.16-3.14 (m, 2H), 2.49-2.48 (m, 6H), 1.30 (s, 9H). LCMS: (Method A) 246.2 (M+H), Rt. 2.93 min, 95.3% (Max).

Step 2: tert-Butyl 4-(4-phenylthiazol-2-yl)piperazine-1-carboxylate

To a stirred solution of fert-butyl 4-carbamothioylpiperazine-1-carboxylate (0.5 g, 2.08 mmol) in dioxane (10 mL), triethyl amine (0.22 mL, 2.6 mmol) and 2-bromo-1-phenylethan-1-one (0.52 g, 2.6 mmol) were added at rt. The resulting mixture was stirred at 90° C. for 20 h. The completion of the reaction was monitored by TLC. It was diluted with water and extracted with EtOAc. The organic layer was separated, dried over anhydrous Na$_2$SO$_4$, concentrated under vacuum. The resulting crude product was taken as such for the next step. Yield: 86% (0.5 g, colorless liquid).

Step 3: 4-Phenyl-2-(piperazin-1-yl)thiazole hydrochloride

To a stirred solution of fert-butyl 4-(4-phenylthiazol-2-yl)piperazine-1-carboxylate (0.5 g) in dry dioxane (2 mL), HCl in dioxane (10 mL, 4 N) was added at room temperature and stirred for 3 h at same temperature. The reaction mixture was concentrated under reduced pressure and the resulting crude product was suspended in diethyl ether (10 mL). It was filtered and dried under vacuum to afford the title compound. Yield: 75% (350 mg, yellow solid). LCMS: (Method A) 246.2 (M+H), Rt. 2.85 min, 71.5% (Max).

Step 4: 2-(4-(1-(Benzo[d][1,3]dioxol-5-yl)ethyl)piperazin-1-yl)-4-phenylthiazole The title compound was synthesized by following general procedure E, using 4-phenyl-2-(piperazin-1-yl)thiazole hydrochloride (0.2 g, 0.8 mmol) and Intermediate 1 (0.3 g, 1.6 mmol). The reaction mixture was stirred at rt for 16 h. The crude product was purified by flash chromatography, affording the title compound (yellow solid). $^1$H NMR (400 MHz, DMSO-d$_6$): δ 7.84-7.82 (m, 2H), 7.40-7.36 (m, 3H), 7.30-7.26 (m, 1H), 7.14-6.99 (m, 3H), 6.06 (s, 2H), 4.61-4.48 (m, 1H), 4.18-3.98 (m, 2H), 3.43-3.33 (m, 2H) 3.12-2.98 (m, 2H), 2.59-2.49 (m, 2H), 1.63 (br.s, 3H). LCMS: (Method A) 394.0 (M+H), Rt. 3.87 min, 98.3% (Max). HPLC: (Method A) Rt. 3.89 min, 99.3% (Max).

Example 6: 2-(4-(1-(Benzordin,31dioxol-5-yl)ethyl)piperazin-1-yl)-4-(4-methoxyphenvDthiazole

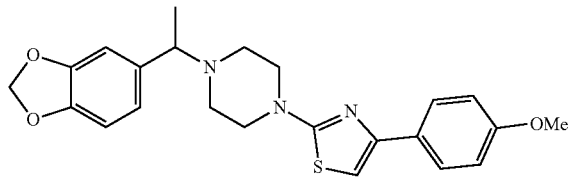 [SMILES: COc1ccc(-c2csc(N3CCN(C(C)c4ccc5c(c4)OCO5)CC3)n2)cc1]

Step 1: tert-butyl 4-(4-(4-methoxyphenyl)thiazol-2-yl)piperazine-1-carboxylate

To a stirred solution of fert-butyl 4-carbamothioylpiperazine-1-carboxylate (synthesized according to Example 5, Step 1, 1.0 g, 4.0 mmol) in dioxane (20 mL), triethyl amine (0.6 mL, 8.3 mmol) and 2-bromo-1-(4-methoxyphenyl)ethan-1-one (1.2 g, 5.3 mmol) was added at rt and stirred at 90° C. for 20 h. The completion of the reaction was monitored by TLC. The reaction mixture was diluted with water (10 mL) and extracted with EtOAc (2×25 mL). The organic layer was separated, dried over anhydrous Na$_2$SO$_4$. After evaporation of the solvents, the resulting crude product was taken as such for the next step. Yield: 53% (0.8 g, pale yellow liquid).

Step 2: 4-(4-Methoxyphenyl)-2-(piperazin-1-yl)thiazole hydrochloride

To a stirred solution of fert-butyl 4-(4-(4-methoxyphenyl)thiazol-2-yl)piperazine-1-carboxylate (0.8 g) in dry dioxane (5 mL), HCl in dioxane (4 M, 10 mL) was added at rt and stirred for 3 h. The reaction mixture was concentrated under vacuum. The resulting crude product was triturated in diethyl ether (10 mL), filtrated and dried under vacuum to afford the title compound. Yield: 68% (400 mg, yellow solid). LCMS: (Method A) 276.0 (M+H), Rt. 2.82 min, 69.9% (Max).

Step 3: 2-(4-(1-(Benzo[d][1,3]dioxol-5-yl)ethyl)piperazin-1-yl)-4-(4-methoxyphenyl)thiazole The title compound was synthesized by following general procedure E, using 4-(4-methoxyphenyl)-2-(piperazin-1-yl)thiazole hydrochloride (0.5 g, 2.7 mmol) and Intermediate 1 (0.9 g, 5.4 mmol). The reaction mixture was stirred at rt for 16 h. The crude product was purified by flash chromatography, affording the title compound (pale yellow solid). $^1$H NMR (400 MHz, DMSO-d$_6$): δ 7.76 (d, J=8.4 Hz, 2H), 7.07 (s, 1H), 6.94-6.91 (m, 3H), 6.86-6.84 (m, 1H), 6.78-6.76 (m, 1H), 5.99 (m, 2H), 3.76 (s, 3H), 3.43-3.42 (m, 5H), 2.50 (m, 2H) 2.42-2.41 (m, 2H), 1.30 (d, J=6.8 Hz, 3H). LCMS: (Method A) 424.0 (M+H), Rt. 3.86 min, 98.7% (Max). HPLC: (Method A) Rt. 3.85 min, 99.3% (Max).

Example 7: 2-(4-(1-(Benzordiri,31dioxol-5-yl)ethyl)piperazin-1-yl)thiazole

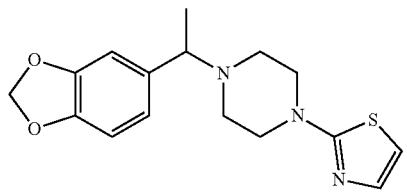 [SMILES: CC(c1ccc2c(c1)OCO2)N1CCN(c2nccs2)CC1]

To a stirred solution of Intermediate 2 (0.1 g, 0.37 mmol) in dry DMSO (5 mL), K$_2$CO$_3$ (0.15 g, 11.11 mmol) and 2-bromo thiazole (0.066 g, 0.407 mmol) were added. The reaction mixture was heated in a microwave at 150° C. for 3 h. The reaction mixture was cooled and concentrated under vacuum. The resulting crude product was purified by MD Autoprep (Method B) to afford the title compound (off white solid). $^1$H NMR (400 MHz, CDCl$_3$): δ 7.20 (d, J=4.0 Hz, 1H), 6.90 (s, 1H), 6.77 (s, 2H), 6.57 (s, 1H), 5.97 (s, 2H), 3.48 (s, 4H), 3.36 (s, 1H), 2.60-2.53 (m, 4H), 1.37 (s, 3H). LCMS: (Method A) 318.0 (M+H), Rt. 2.04 min, 94.4% (Max). HPLC: (Method A) Rt. 2.04 min, 98.6% (Max).

Example 8: -5-(4-(1-(benzordlH,31dioxol-5-yl)ethyl)piperazin-1-yl)-2-iodopyrimidine

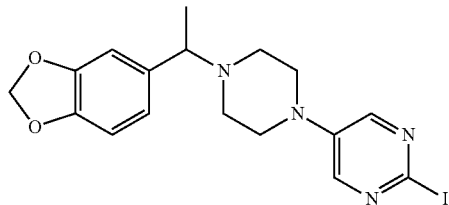 [SMILES: CC(c1ccc2c(c1)OCO2)N1CCN(c2cnc(I)nc2)CC1]

To a stirred solution of Intermediate 2 (0.14 g, 0.51 mmol) in 1-propyl alcohol (5 mL), TEA (0.22 g, 2.20 mmol) and 2-iodo-5-chloro-pyrimidine (0.1 g, 0.415 mmol) were added and the reaction mixture was heated in a microwave at 140° C. for 40 min. The reaction mixture was cooled down to rt and concentrated under vacuum. The resulting crude product was purified by flash chromatography to afford the title compound. Yield: 60% (83.46 mg, pale brown oil). $^1$H NMR (400 MHz, CDCl$_3$): δ 8.47 (s, 2H), 6.89 (d, J=1.6 Hz, 1H), 6.83 (d, J=8.0 Hz, 1H), 6.74 (d, J=8.0 Hz, 1H), 5.99 (s, 2H), 3.66-3.64 (m, 4H), 3.37-3.35 (m, 1H), 2.44-2.38 (m, 2H) 2.35-2.30 (m, 2H), 1.27 (d, J=6.4 Hz, 3H). LCMS: (Method A) 439.0 (M+H), Rt. 3.40 min, 98.3% (Max). HPLC: (Method A) Rt. 3.43 min, 98.6% (Max).

Example 9: 2-(4-(1-(Benzo[d][1,3]dioxol-5-yl)ethyl)piperazin-1-yl)-4-methylpyrimidine

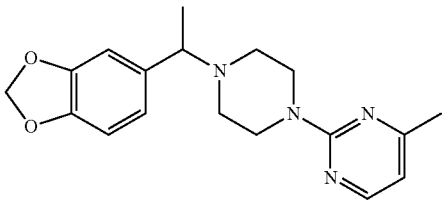 [SMILES: Cc1ccnc(N2CCN(C(C)c3ccc4c(c3)OCO4)CC2)n1]

To a stirred solution of Intermediate 2 (0.1 g, 0.37 mmol) in dry DMF (5 mL), DIPEA (0.22 g, 1.7 mmol) and 2-chloro-4-methyl pyrimidine (0.109 g, 0.8 mmol) were added at rt and the reaction mixture was stirred at 120° C. for 12 h. It was cooled down to rt and concentrated under vacuum. The resulting crude product was purified by flash chromatography to afford the title compound (brown oil). $^1$H NMR (400 MHz, DMSO-$d_6$): δ 8.17 (d, J=4.8 Hz, 1H), 6.89 (s, 1H), 6.84 (d, J=8.0 Hz, 1H), 6.76-6.74 (m, 1H), 6.48 (d, J=4.8 Hz, 1H), 5.99 (m, 2H), 3.70-3.66 (m, 4H), 3.40-3.34 (m, 1H), 2.43-2.39 (m, 2H), 2.34-2.31 (m, 2H) 2.24 (s, 3H), 1.28 (d, J=6.4 Hz, 3H). LCMS: (Method A) 327.0 (M+H), Rt. 2.57 min, 98.1% (Max). HPLC: (Method A) Rt. 2.59 min, 98.6% (Max).

Example 10: 1-(1-(Benzo[d][1,3]dioxol-5-yl)ethyl)-4-(pyridin-2-yl)piperazine

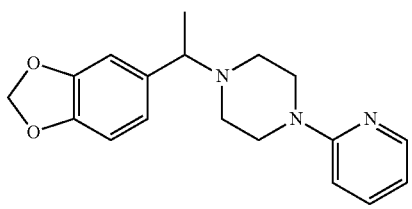 [SMILES: CC(c1ccc2c(c1)OCO2)N1CCN(c2ccccn2)CC1]

The title compound was synthesized by following general procedure D, using 1-pyridyl-2-piperazine (0.2 g, 1.3 mmol) and Intermediate 1 (0.3 g, 1.63 mmol). The resulting crude product was purified by silicagel column, affording the title compound (colorless oil). $^1$H NMR (400 MHz, DMSO-$d_6$): δ 8.07 (dd, J=2.0, 4.8 Hz, 1H), 7.51-7.46 (m, 1H), 6.88 (s, 1H), 6.84-6.82 (m, 1H), 6.76-6.74 (m, 2H), 6.61-6.58 (m, 1H), 5.98 (m, 2H), 3.43-3.40 (m, 4H), 3.34-3.33 (m, 1H), 2.47-2.44 (m, 2H), 2.39-2.35 (m, 2H), 1.28 (d, J=6.8 Hz, 3H). LCMS: (Method A) 312.0 (M+H), Rt. 1.83 min, 98.0% (Max). HPLC: (Method A) Rt. 1.82 min, 98.4% (Max).

Example 11: 2-(4-(1-(Benzo[d][1,3] dioxol-5-yl)ethyl)piperazin-1-yl)pyrimidine

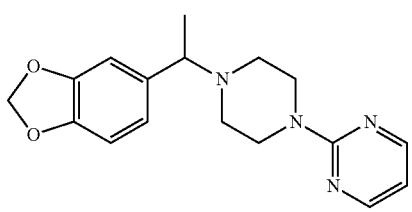 [SMILES: CC(c1ccc2c(c1)OCO2)N1CCN(c2ncccn2)CC1]

The title compound was synthesized by following general procedure D, using 2-(piperazin-1-yl)pyrimidine (0.2 g, 1.21 mmol) and Intermediate 1 (0.366 g, 1.82 mmol). The resulting crude product was purified by MD Autoprep (Method B), affording the title compound (colourless oil). $^1$H NMR (400 MHz, MeOH-$d_4$): δ 8.36 (d, J=4.8 Hz, 2H), 6.96 (s, 1H), 6.90-6.84 (m, 2H), 6.66 (t, J=4.8 Hz, 1H), 5.99 (s, 2H), 3.92-3.90 (m, 4H), 3.33 (m, 1H), 2.83 (m, 4H), 1.59 (d, J=6.0 Hz, 3H). LCMS: (Method A) 313.2 (M+H), Rt. 2.45 min, 99.4% (Max). HPLC: (Method A) Rt. 2.44 min, 99.8% (Max).

As can be seen from the following comparison, the compound of Example 11 exhibits a highly increased OGA inhibitor activity as compared to the similar compound of Example 1 of U.S. Pat. No. 3,299,067, and is thus significantly more effective than said compound of U.S. Pat. No. 3,299,067 in the indications mentioned in this specification:

| U.S. Pat. No. 3,299,067 (Example 1) | 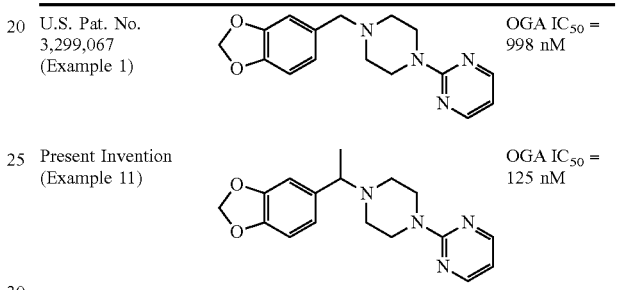 | OGA IC$_{50}$ = 998 nM |
|---|---|---|
| Present Invention (Example 11) | 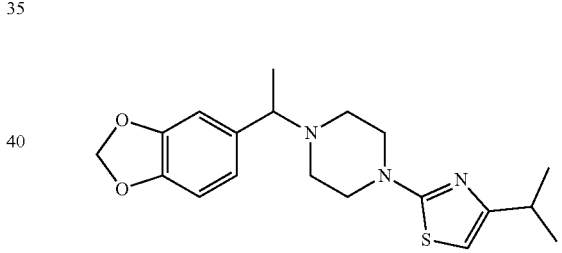 | OGA IC$_{50}$ = 125 nM |

Example 12: 2-(4-(1-(Benzo[d][1,3]dioxol-5-yl)ethyl)piperazin-1-yl)-4-isopropylthiazole

Step 1: t-Butyl 4-(4-isopropylthiazol-2-yl)piperazine-1-carboxylate

To a stirred solution of tert-butyl 4-carbamothioylpiperazine-1-carboxylate (synthesized according to Example 5, Step 1, 1.2 g, 4.01 mmol) in THF (10 ml), triethyl amine (0.5 ml, 5.3 mmol) and 1-bromo-3-methylbutan-2-one (1.0 ml, 5.3 mmol) were added at rt. The resulting mixture was stirred for 16 h at 90° C. The completion of the reaction was monitored by TLC. The reaction mixture was quenched with water and extracted with EtOAc. The organic layer was dried over anhydrous Na$_2$SO$_4$, concentrated under vacuum and the resulting crude product was taken as such for next step. Yield: 80% (0.8 g, pale yellow oil). LCMS: (Method A) 312.0 (M+H), Rt. 3.24 min, 95.2% (Max).

Step 2: 4-Isopropyl-2-(piperazin-1-yl)thiazole hydrochloride

To a stirred solution of tert-butyl 4-(4-isopropylthiazol-2-yl)piperazine-1-carboxylate (0.8 g, 2.4 mmol) in dry dioxane (2 ml_), HCl in dioxane (4 N, 10 ml.) was added at rt and stirred for 2 h at same temperature. The reaction mixture was concentrated under vacuum and the crude product was washed with diethyl ether to afford the title compound. Yield: 93% (1.2 g, pale yellow oil).

Step 3: 2-(4-(1-(Benzo[d][1,3]dioxol-5-yl)ethyl)piperazin-1-yl)-4-isopropylthiazole The title compound was synthesized by following general procedure D, using 4-isopropyl-2-(piperazin-1-yl)thiazole hydrochloride (0.57 g, 2.3 mmol) and Intermediate 1 (0.5 g, 2.3 mmol). The resulting crude product was purified by MD Autoprep (Method C), affording the title compound (pale yellow oil). $^1$H NMR (400 MHz, DMSO-$d_6$): δ 6.89 (s, 1H), 6.84 (d, J=8.0 Hz, 1H), 6.76 (d, J=8.0 Hz, 1H), 6.33 (s, 1H), 5.98 (m, 2H), 3.41-3.11 (m, 5H), 2.74-2.72 (m, 1H), 2.46-2.38 (m, 4H), 1.27 (d, J=6.8 Hz, 3H), 1.15 (d, J=6.8 Hz, 3H). LCMS: (Method A) 360.0 (M+H), Rt. 2.71 min, 94.5% (Max). HPLC: (Method A) Rt. 2.69 min, 98.8% (Max).

Example 13: 2-(4-(1-(Benzordiri,31dioxol-5-yl)ethyl)piperazin-1-yl)-4-(trifluoromethyl)thiazole

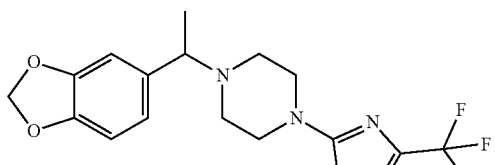

Step 1: tert-Butyl 4-(4-(trifluoromethyl)thiazol-2-yl)piperazine-1-carboxylate To a stirred solution of fert-butyl 4-carbamothioylpiperazine-1-carboxylate (synthesized according to Example 5, Step 1, 2 g, 13.75 mmol) in dioxane (20 mL), triethyl amine (1.7 mL, 12.24 mmol) and 1-bromo-3,3,3-trifluoro acetone (3.2 g, 16.5 mmol) were added and stirred at 90° C. for 3 h. The completion of the reaction was monitored by TLC. The reaction mixture was quenched with water (10 mL) and extracted with ethyl acetate (2×25 mL). The organic layer was separated, dried over anhydrous $Na_2SO_4$, concentrated under vacuum and was used as such for next step. Yield: 75% (1.0 g, white solid). $^1$H NMR (300 MHz, DMSO-$d_6$): δ 7.57 (s, 1H), 3.42 (m, 8H), 1.40 (s, 9H). LCMS: (Method A) 338.0 (M+H), Rt. 5.37 min, 99.0% (Max).

Step 2: 2-(Piperazin-1-yl)-4-(trifluoromethyl)thiazole hydrochloride

To a stirred solution of fert-butyl 4-(4-(trifluoromethyl)thiazol-2-yl)piperazine-1-carboxylate (1.0 g, 2.93 mmol) in dry dioxane, HCl in dioxane (4 N, 15 mL) was added and the reaction mixture was stirred at rt for 1 h. The reaction mixture was concentrated under vacuum and the resulting crude product was triturated in diethyl ether, filtrated and dried under vacuum to afford the title compound. Yield: 99% (700 mg, white solid). $^1$H NMR (400 MHz, DMSO-$d_6$): δ 9.22 (br. s, 2H), 7.66 (s, 1H), 3.68-3.64 (m, 4H), 3.21 (m, 4H). LCMS: (Method A) 238.0 (M+H), Rt. 2.33 min, 99.7% (Max).

Step 3: 2-(4-(1-(Benzo[d][1,3]dioxol-5-yl)ethyl)piperazin-1-yl)-4-(trifluoroˆethyl)thiazole To a stirred solution of 2-(piperazin-1-yl)-4-(trifluoromethyl)thiazole hydrochloride (0.26 g, 1.07 mmol) in dry DMF (3 mL), Intermediate 1 (0.19 g, 1.07 mmol) and triethyl amine (0.272 g, 2.69 mmol) were added and the reaction mixture was stirred at 80° C. for 16 h. The reaction mixture was concentrated, the crude product was diluted with ethyl acetate (10 mL) and the organic layer was washed with brine (10 mL). The organic layer was separated, dried over anhydrous $Na_2SO_4$ and concentrated to afford the title compound (colorless oil). $^1$H NMR (400 MHz, DMSO-$d_6$): δ 6.96 (s, 1H), 6.88 (s, 1H), 6.76-7.75 (m, 2H), 5.91 (s, 2H), 3.55-3.45 (m, 4H), 3.38 (q, J=6.4 Hz, 1H), 2.62-2.49 (m, 4H), 2.56-2.51 (m, 4H), 1.36 (d, J=6.4 Hz, 3H). LCMS: (Method A) 386.0 (M+H), Rt. 3.55 min, 97.4% (Max). HPLC: (Method A) Rt. 3.54 min, 98.7% (Max).

Example 14: 1-(1-(Benzordiri,31 dioxol-5-yl)ethyl)-4-(5-methylpyridin-2-yl)piperazine

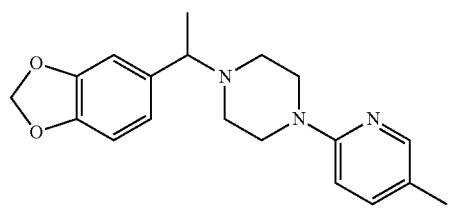 [SMILES: Cc1ccc(N2CCN(C(C)c3ccc4c(c3)OCO4)CC2)nc1]

The title compound was synthesized according the general procedure D, using Intermediate 2 and 2-fluoro-5-methyl pyridine. The crude product was purified by flash chromatography to afford the title compound (off white solid). $^1$H NMR (400 MHz, DMSO-$d_6$): δ 7.92 (s, 1H), 7.36-7.33 (m, 1H), 6.89 (s, 1H), 6.84 (d, J=8.0 Hz, 1H), 6.76 (d, J=7.6 Hz, 1H), 6.70 (d, J=8.4 Hz, 1H), 5.99 (m, 2H), 3.37-3.35 (m, 5H), 2.47-2.44 (m, 2H), 2.38-2.36 (m, 2H), 2.12 (s, 3H), 1.28 (d, J=6.8 Hz, 3H). LCMS: (Method A) 326.2 (M+H), Rt. 1.96 min, 97.6% (Max). HPLC: (Method A) Rt. 1.96 min, 98.1% (Max).

Example 15: (R)-2-(4-(1-(benzordiri,31dioxol-5-yl)ethyl)piperazin-1-yl)-4-methylthiazole or (S)-2-(4-(1-(benzordiri,31 dioxol-5-yl)ethyl)piperazin-1-yl)-4-methylthiazole

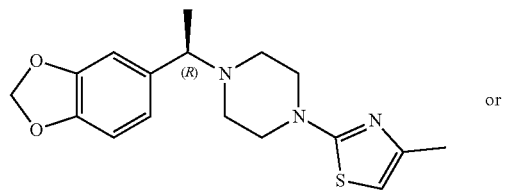 or

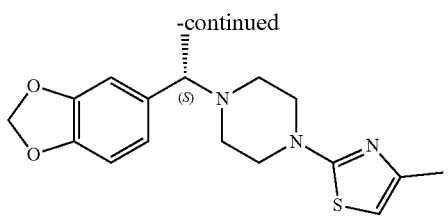

The two enantiomers of Example A were separated by chiral preparative HPLC (Method PE). The first eluting compound has Rt. 5.76 min (Method C) (colorless oil). $^1$H NMR (400 MHz, DMSO-d$_6$): δ 6.89 (s, 1H), 6.84 (d, J=8.0 Hz, 1H), 6.76 (d, J=8.0 Hz, 1H), 6.35 (s, 1H), 5.99-5.98 (m, 2H), 3.40-3.36 (m, 1H), 3.32-3.29 (m, 4H), 2.47-2.44 (m, 2H), 2.41-2.37 (m, 2H), 2.11 (s, 3H), 1.26 (d, J=6.4 Hz, 3H). LCMS: (Method A) 332.0 (M+H), Rt. 2.06 min, 96.3% (Max). HPLC: (Method A) Rt 2.05 min, 99.5% (Max), 99.4% (254 nm). HPLC chiral purity: (Method C) Rt. 5.76 min, 100% (Max). Example 15 is the second eluting compound with Rt. 7.44 min (Method C) (colorless oil). $^1$H NMR (400 MHz, DMSO-d$_6$): δ 6.89 (s, 1H), 6.84 (d, J=8.0 Hz, 1H), 6.76 (d, J=8.0 Hz, 1H), 6.35 (s, 1H), 5.99 (s, 2H), 3.42-3.37 (m, 1H), 3.32-3.30 (m, 4H), 2.47-2.44 (m, 2H), 2.40-2.36 (m, 2H), 2.11 (s, 3H), 1.26 (d, J=6.8 Hz, 3H). LCMS: (Method A) 332.0 (M+H), Rt. 2.04 min, 99.2% (Max). HPLC: (Method A) Rt. 2.05 min, 99.2% (Max). HPLC chiral purity: (Method C) Rt. 7.44 min, 99.83% (Max).

Example 16: 2-(4-(1-(benzofdlH,31dioxol-5-yl)ethyl)piperazin-1-yl)-4-(teit-butyl)thiazole

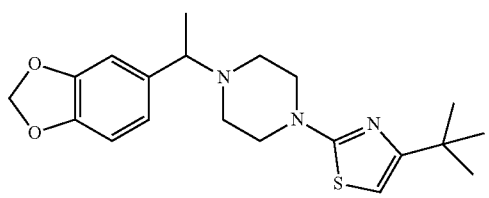 [SMILES: CC(c1ccc2c(c1)OCO2)N1CCN(c2nc(C(C)(C)C)cs2)CC1]

Step 1: tert-butyl 4-(4-(tert-butyl)thiazol-2-yl)piperazine-1-carboxylate

To a stirred solution of ferf-butyl 4-carbamothioylpiperazine-1-carboxylate (synthesized according to Example 5, Step 1, 1.3 g, 5.3 mmol) in dioxane (10 ml_), TEA (1 ml_, 7 mmol) and 1-bromo-3,3-dimethylbutan-2-one (0.94 ml_, 6.8 mmol) were added at rt and stirred for 16 h at 90° C. The completion of the reaction was monitored by TLC. The reaction mixture was quenched with water and extracted with EtOAc. The organic layer was dried over anhydrous Na$_2$SO$_4$, concentrated under vacuum and the resulting crude product was taken as such for next step without further purification. Yield: 88% (1.5 g, black liquid). LCMS: (Method A) 326.2 (M+H), Rt. 3.75 min, 60.4% (Max).

Step 2: 4-(tert-Butyl)-2-(piperazin-1-yl)thiazole hydrochloride

To a stirred solution of ferf-butyl 4-(4-(tert-butyl)thiazol-2-yl)piperazine-1-carboxylate (1.5 g, 4.61 mmol) in dry dioxane (2 mL), HCl in dioxane (4 N, 10 mL) was added and the reaction mixture was stirred at rt for 2 h. The reaction mixture was concentrated under vacuum and the resulting crude product was triturated in diethyl ether (100 mL), filtered and dried under vacuum to afford the title compound. Yield: 63% (1.02 g, black solid).

Step 3: 2-(4-(1^enzo[d][1,3]dioxol-5-yl)ethyl)piperazin-1-yl)-4-(tert-brt yl) thiazole The title compound was synthesized following the general procedure D, using 4-(terf-butyl)-2-(piperazin-1-yl)thiazole hydrochloride (0.732 g, 2.8 mmol) and Intermediate 1 (0.28 g, 2.8 mmol) and the crude product was purified by flash chromatography (pale yellow oil). $^1$H NMR (400 MHz, DMSO-d$_6$): δ 6.89 (s, 1H), 6.85 (d, J=7.6 Hz), 6.76 (d, J=7.6 Hz, 1H), 6.33 (s, 1H), 5.99 (m, 2H), 3.40 (m, 1H), 3.37-3.30 (m, 4H), 2.49-2.46 (m, 2H), 2.43-2.40 (m, 2H), 1.28 (d, J=6.8 Hz, 3H), 1.19 (s, 9H). LCMS: (Method A) 374.0 (M+H), Rt. 3.40 min, 98.6% (Max). HPLC: (Method A) Rt. 3.39 min, 99.7% (Max).

Example 17: Ethyl 2-(4-(1-(benzordiri,31 dioxol-5-yl)ethyl)piperazin-1-yl)thiazole-4-carboxylate

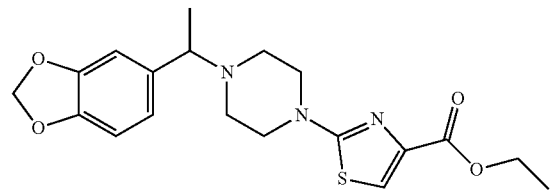 [SMILES: CCOC(=O)c1csc(N2CCN(C(C)c3ccc4c(c3)OCO4)CC2)n1]

Step 1: Ethyl 2-(4-(tert-butoxycarbonyl)piperazin-1-yl)thiazole-4-carboxylate

To a stirred solution of ferf-butyl 4-carbamothioylpiperazine-1-carboxylate (synthesized according to Example 5, Step 1, 3.0 g, 12 mmol) in dioxane (10 mL), TEA (2.6 mL, 16 mmol) and 3-bromo-ethyl pyruvate (2.1 mL, 16 mmol) were added at rt and the mixture was stirred at 90° C. for 16 h. The completion of the reaction was monitored by TLC. The reaction mixture was quenched with water and extracted with EtOAc. The organic layer was dried over anhydrous Na$_2$SO$_4$, concentrated under vacuum and the resulting crude product was taken as such for next step. Yield: 95% (4 g, black solid).

Step 2: Ethyl 2-(piperazin-1-yl)thiazole-4-carboxylate hydrochloride

To a stirred solution of ethyl 2-(4-(fert-butoxycarbonyl)piperazin-1-yl)thiazole-4-carboxylate (4.0 g, 11.73 mmol) in dry dioxane (2 mL), HCl in dioxane (4 N, 10 mL) was added at rt and stirred for 2 h. The reaction mixture was concentrated under vacuum and the resulting crude product was triturated in diethyl ether (25 mL), filtered and dried under vacuum to afford the title compound. Yield: 90% (3.2 g, black solid). LCMS: (Method A) 242.0 (M+H), Rt. 1.88 min, 90.7% (Max).

Step 3: Ethyl 2-(4-(1-(benzo[d][1,3]dioxol-5-yl)ethyl)piperazin-1-yl)thiazole-4-carboxylate The title compound was synthesized following the general procedure D, using ethyl 2-(piperazin-1-yl)thiazole-4-carboxylate hydrochloride and Intermediate 1 and the crude product was purified by flash chromatography followed by MD Autoprep (Method B) (yellow solid). ¹HNMR (400 MHz, DMSO-d₆): δ 7.66 (d, J=2.0 Hz, 1H), 6.88 (s, 1H), 6.84 (d, J=8.0 Hz, 1H), 6.75 (d, J=8.0 Hz, 1H), 5.98 (m, 2H), 4.21-4.20 (m, 2H), 3.38-3.32 (m, 5H), 2.49-2.40 (m, 4H), 1.26-1.23 (m, 6H). LCMS: (Method A) 390.0 (M+H), Rt. 2.99 min, 97.8% (Max). HPLC: (Method A) Rt. 2.95 min, 98.9% (Max).

Example 18: 2-(4-(1-(Benzordiri,31dioxol-5-yl)ethyl)piperazin-1-yl)thiazole-4-carboxylic acid

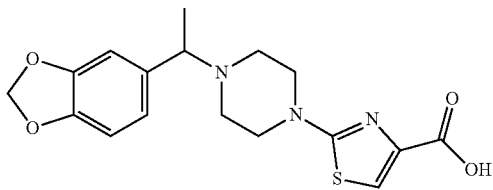 [SMILES: CC(c1ccc2c(c1)OCO2)N1CCN(c2nc(C(=O)O)cs2)CC1]

To a stirred solution of Example 17 (0.2 g) in dry THF (10 mL), 5% NaOH in water (5 mL) was added slowly at rt and the mixture was stirred for 16 h at same temperature. It was then concentrated under vacuum, neutralised to pH=6 with 2N HCl and extracted with DCM (20 mL). The organic layer was washed with brine (10 mL), water (10 mL), dried over anhydrous Na₂SO₄ and concentrated under reduced pressure. The crude product was purified by flash chromatography followed by MD Autoprep (Method B) to afford the title compound (off white solid). ¹H NMR (400 MHz, DMSO-d₆): δ 7.58 (s, 1H), 6.90 (s, 1H), 6.88 (d, J=8.0 Hz, 1H). 6.76 (d, J=8.0 Hz, 1H), 6.00-5.99 (m, 2H), 3.35-3.36 (m, 5H), 2.51-2.49 (m, 2H), 2.44-2.40 (m, 2H), 1.29-1.27 (d, J=6.8 Hz, 3H). LCMS: (Method A) 362.0 (M+H), Rt. 2.29 min, 95.5% (Max). HPLC: (Method A) Rt. 2.30 min, 95.9% (Max).

Example 19: 2-(4-(1-(Benzordiri,31 dioxol-5-yl)ethyl)piperazin-1-yl)-4-ethylthiazole

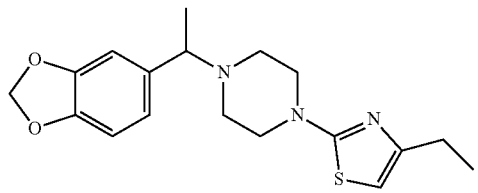 [SMILES: CCc1csc(N2CCN(C(C)c3ccc4c(c3)OCO4)CC2)n1]

Step 1: t-Butyl 4-(4-ethylthiazol-2-yl)piperazine-1-carboxylate

To a stirred solution of fert-butyl 4-carbamothioylpiperazine-1-carboxylate (synthesized according to Example 5, Step 1, 2.0 g, 8.16 mmol) in dioxane (20 mL), TEA (1.7 mL, 10.6 mmol) and 1-bromobutan-2-one (1.2 mL, 10 mmol) were added and stirred at 80° C. for 16 h. The completion of the reaction was monitored by TLC. The reaction mixture was quenched with water (10 mL) and extracted with EtOAc (2×25 mL). The organic layer was separated, dried over anhydrous Na₂SO₄, concentrated under vacuum. The result-ing product was taken as such for next step. Yield: 86% (2.1 g, pale yellow solid). LCMS: (Method A) 298.0 (M+H), Rt. 2.94 min, 93.1% (Max).

Step 2: 4-Ethyl-2-(piperazin-1-yl)thiazole hydrochloride

To a stirred solution of fert-butyl 4-(4-ethylthiazol-2-yl)piperazine-1-carboxylate (1.9 g, 6.3 mmol) in dry dioxane (2 mL), HCl in dioxane (4 N, 10 mL) was added and the reaction mixture was stirred at rt for 2 h. The reaction mixture was concentrated under vacuum and the crude product was triturated in diethyl ether (15 mL), filtered and dried under vacuum to afford the title compound. Yield: 53% (0.8 g, black solid).

Step 3: 2-(4-(1-(Benzo[d][1,3]dioxol-5-yl)ethyl)piperazin-1-yl)-4-ethylthiazole

The title compound was synthesized following the general procedure D, using 4-ethyl-2-(piperazin-1-yl)thiazole hydrochloride (1.1 g, 4.7 mmol) and Intermediate 1 (0.9 g, 4.7 mmol). The crude product was purified by flash chromatography (pale yellow oil). ¹H NMR (400 MHz, DMSO-d₆): δ 6.89 (d, J=1.6 Hz, 1H), 6.84 (d, J=7.6 Hz, 1H), 6.75 (d, J=7.5 Hz, 1H), 6.35 (s, 1H), 5.98 (m, 2H), 3.40-3.37 (m, 1H), 3.37-3.30 (m, 4H), 2.51-2.38 (m, 6H), 1.28 (d, J=6.8 Hz, 3H), 1.23 (t, J=7.6 Hz, 3H). LCMS: (Method A) 346.0 (M+H), Rt. 2.31 min, 98.0% (Max). HPLC: (Method A) Rt. 2.34 min, 99.4% (Max).

Example 20: 1-(1-(Benzordiri,31 dioxol-5-yl)ethyl)-4-(6-chloropyridin-3-yl)piperazine

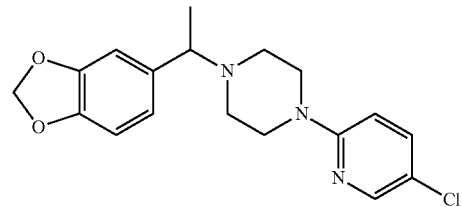 [SMILES: CC(c1ccc2c(c1)OCO2)N1CCN(c2ccc(Cl)cn2)CC1]

The title compound was synthesized following the general procedure D, using Intermediate 1 and 1-(5-chloro-2-pyridyl) piperazine. The crude product was purified by flash chromatography (off white solid). ¹H NMR (400 MHz, DMSO-d₆): δ 8.07 (d, J=2.4 Hz, 1H), 7.57-7.54 (m, 1H), 6.88-6.74 (m, 4H), 5.98 (m, 2H), 3.42 (q, J=6.4 Hz, 1H), 2.46-2.43 (m, 2H), 2.37-2.34 (m, 2H), 1.28 (d, J=6.4 Hz, 3H). LCMS: (Method A) 346.0 (M+H), Rt. 3.27 min, 98.7% (Max). HPLC: (Method A) Rt 3.25 min, 99.2% (Max).

Example 21: 1-(1-(Benzordiri,31 dioxol-5-yl)ethyl)-4-(6-methylpyridin-2-yl)piperazine

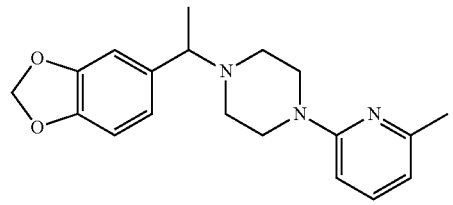 [SMILES: Cc1cccc(N2CCN(C(C)c3ccc4c(c3)OCO4)CC2)n1]

To a stirred solution of Intermediate 2 (0.12 g, 0.5 mmol) in dry DMF (2 mL), 2-fluoro-6-methyl pyridine (0.11 g, 0.99 mmol) and DIPEA (0.26 g, 2.4 mmol) were added at rt and the reaction mixture was stirred at 120° C. for 16 h. The reaction mixture was cooled to rt and concentrated under vacuum. The resulting crude product was purified by flash chromatography followed by preparative HPLC (Method PA) to afford the title compound (brown liquid). $^1$H NMR (400 MHz, DMSO-$d_6$): δ 7.40-7.36 (m, 1H), 6.90 (s, 1H), 6.85 (d, J=7.6 Hz, 1H), 6.77 (d, J=7.6 Hz, 1H), 6.55-6.46 (m, 2H), 5.98 (s, 2H), 3.410-3.415 (m, 5H), 2.38-2.37 (m, 4H), 2.28-2.30 (m, 3H), 1.29 (d, J=7.2 Hz, 3H). LCMS: (Method A) 326.2 (M+H), Rt. 1.89 min, 94.9% (Max). HPLC: (Method A) Rt 1.91 min, 96.6% (Max).

Example 22: 2-(4-(1-(Benzo[d][1,3]dioxol-5-yl)ethyl)piperazin-1-yl)pyrimidin-4-amine

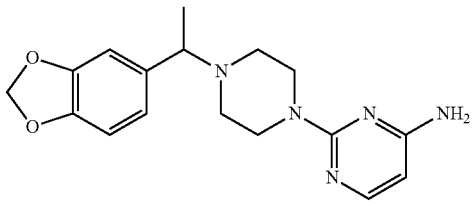 [SMILES: CC(c1ccc2c(c1)OCO2)N1CCN(c2nccc(N)n2)CC1]

The title compound was synthesized by following procedure D, using Intermediate 2 (0.228 g, 0.85 mmol) and 4-amino-2-chloro pyrimidine (0.1 g, 0.77 mmol). The crude product was purified by flash chromatography followed by MD Autoprep (Method B) (white solid). $^1$H NMR (400 MHz, DMSO-$d_6$): δ 7.70 (d, J=5.2 Hz, 1H), 6.88 (s, 1H), 6.83 (d, J=8.0 Hz, 1H), 6.75 (d, J=7.6 Hz, 1H), 6.36 (s, 2H), 5.98 (m, 2H), 5.69 (d, J=5.6 Hz, 1H), 3.6-3.58 (m, 4H), 3.33-3.32 (m, 1H), 2.38-2.34 (m, 2H), 2.31-2.27 (m, 2H), 1.27 (d, J=6.8 Hz, 3H). LCMS: (Method A) 328.0 (M+H), Rt. 1.85 min, 97.2% (Max). HPLC: (Method A) Rt. 1.84 min, 97.1% (Max).

Example 23: N-(2-(4-(1-(Benzo[d][1,3]dioxol-5-yl)ethyl)piperazin-1-yl)pyrimidin-4-yl)acetamide

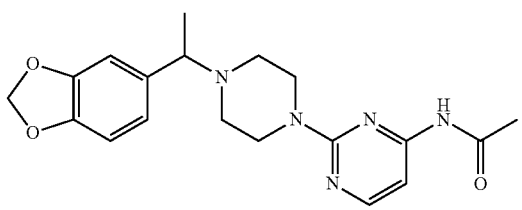 [SMILES: CC(=O)Nc1ccnc(N2CCN(C(C)c3ccc4c(c3)OCO4)CC2)n1]

Step 1: N-(2-Chloropyrimidin-4-yl)acetamide

To a stirred solution of 4-amino-2-chloro pyrimidine (0.6 g, 4.65 mmol) in DCM (5 mL), pyridine (1.8 mL) and acetic anhydride (0.71 g, 6.9 mmol) were added at 0° C. and stirred at 75° C. for 6 h. The reaction mixture was concentrated under vacuum and the resulting crude product was dissolved in EtOAc (15 mL). The organic layer was washed with water (10 mL), brine (10 mL) and dried over anhydrous Na$_2$SO$_4$. After concentration under vacuum, the crude product was taken as such for next step. Yield: 56.9% (0.45 g, pale brown solid). LCMS: (Method A) 172.0 (M+H), Rt. 1.58 min, 80.2% (Max).

Step 2: N-(2-(4-(1-(Benzo[d][1,3]dioxol-5-yl)ethyl)piperazin-1-yl)pyrimidin-4-yl)acetamide The title compound was synthesized following procedure D and using Intermediate 2 (0.25 g, 0.93 mmol) and N-(2-chloropyrimidin-4-yl)acetamide (0.19 g, 1.12 mmol). The crude product was purified by flash chromatography followed by MD Autoprep (Method B) (white solid). $^1$H NMR (400 MHz, DMSO-$d_6$): δ 10.30 (s, 1H), 8.18 (d, J=5.6 Hz, 1H), 7.21 (d, J=5.6 Hz, 1H), 6.89 (d, J=1.6 Hz, 1H), 6.84 (d, J=7.6 Hz, 1H), 6.75 (dd, J=1.6, 8 Hz, 1H), 5.98 (m, 2H), 3.68-3.66 (m, 4H), 3.37-3.36 (m, 1H), 2.42-2.38 (m, 2H), 2.35-2.31 (m, 2H), 2.07 (s, 3H), 1.28 (d, J=6.8 Hz, 3H). LCMS: (Method A) 370.0 (M+H), Rt. 2.26 min, 97.5% (Max). HPLC: (Method A) Rt. 2.21 min, 98.9% (Max).

Example 24: 4-(4-(1-(Benzo[d][1,3]dioxol-5-yl)ethyl)piperazin-1-yl)-6-chloropyrimidine

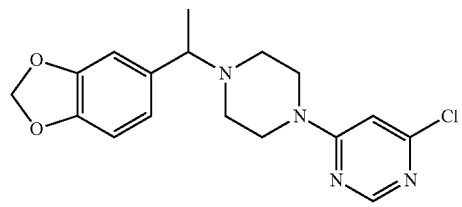 [SMILES: CC(c1ccc2c(c1)OCO2)N1CCN(c2cc(Cl)ncn2)CC1]

To a stirred solution of Intermediate 2 (0.2 g, 0.74 mmol) in DMF (5 mL), TEA (0.5 mL, 3.70 mmol) and 4,6-dichloro pyrimidine (0.11 g, 0.74 mmol) were added and the resulting mixture was stirred at 120° C. for 2 h. It was concentrated under vacuum and the resulting crude product was dissolved in DCM and washed with water, dried over anhydrous Na$_2$SO$_4$, and concentrated under vacuum. The crude product was purified by flash chromatography to afford the title product (brown oil). $^1$H NMR (400 MHz, DMSO-$d_6$): δ 8.30 (s, 1H), 6.91 (s, 1H), 6.89 (s, 1H), 6.84 (d, J=8.0 Hz, 1H), 6.75 (d, J=8.0 Hz, 1H), 5.98 (m, 2H), 3.55-3.52 (m, 4H), 3.39-3.37 (m, 1H), 2.43-2.39 (m, 2H), 2.36-2.32 (m, 2H), 1.27 (d, J=6.8 Hz, 3H).

LCMS: (Method A) 347.0 (M+H), Rt. 2.55 min, 98.7% (Max). HPLC: (Method A) Rt. 2.57 min, 99.7% (Max).

Example 25: 2-(4-(1-(Benzo[d][1,3]dioxol-5-yl)ethyl)piperazin-1-yl)-6-chloropyrazine

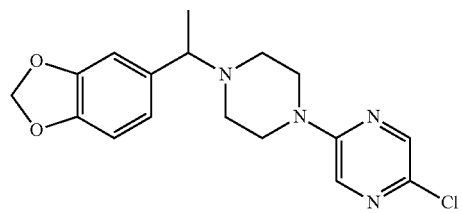 [SMILES: CC(c1ccc2c(c1)OCO2)N1CCN(c2cnc(Cl)cn2)CC1]

To a stirred solution of Intermediate 2 (0.2 g, 0.74 mmol) in DMF (5 mL), TEA (0.5 mL, 3.70 mmol) and 2,5-dichloro pyrazine (0.11 g, 0.74 mmol) was added and stirred at 120°

C. for 2 h. The reaction mixture was concentrated under vacuum and the resulting crude product was dissolved in DCM. It was washed with water, dried over anhydrous Na$_2$SO$_4$, and concentrated under vacuum. The crude product was purified by flash chromatography to afford the title compound (brown oil). $^1$H NMR (400 MHz, DMSO-d$_6$): δ 8.23 (s, 1H), 7.81 (s, 1H), 6.88 (d, J=1.2 Hz, 1H), 6.84 (d, J=8.0 Hz, 1H), 6.74 (dd, J=1.6, 8.0 Hz, 1H), 5.97 (s, 2H), 3.54-3.52 (m, 4H), 3.39-3.37 (m, 1H), 2.45-2.44 (m, 2H), 2.39-2.37 (m, 2H), 1.27 (d, J=6.4 Hz, 3H). LCMS: (Method A) 347.0 (M+H), Rt. 3.03 min, 97.9% (Max). HPLC: (Method A) Rt. 3.05 min, 97.6% (Max).

Example 26: (R)-2-(4-(1-(Benzordiri,31dioxol-5-yl)ethyl)piperazin-1-yl)pyrimidine or (S)-2-(4-(1-(Benzordiri,31 dioxol-5-yl)ethyl)piperazin-1-yl)pyrimidine

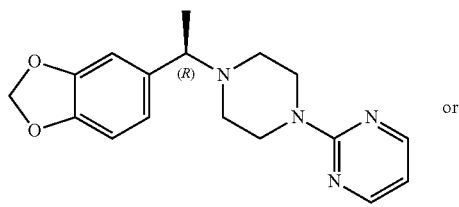

or

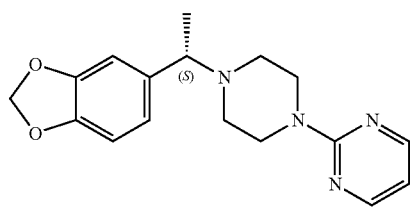

The two enantiomers of Example 11 were separated by chiral preparative HPLC (Method PF). The first eluting compound has Rt. 8.50 min (colorless oil). $^1$H NMR (400 MHz, DMSO-d$_6$): δ 8.32 (d, J=4.8 Hz, 2H), 6.88 (s, 1H), 6.83 (d, J=8.0 Hz, 1H), 6.74 (d, J=8.0 Hz, 1H), 6.58 (t, J=4.4 Hz, 1H), 5.97 (m, 2H), 3.68-3.67 (m, 4H), 3.37-3.35 (m, 1H), 2.49-2.38 (m, 2H), 2.35-2.30 (m, 2H), 1.27 (d, J=6.4 Hz, 3H). LCMS: (Method A) 313.0 (M+H), Rt. 2.45 min, 99.5% (Max). HPLC: (Method A) Rt. 2.47 min, 99.5% (Max). HPLC chiral purity: (Method D) Rt. 8.50 min, 100% (Max). Example 26 is the second eluting compound, with Rt. 13.33 min (colorless oil). 1H NMR (400 MHz, DMSO-d$_6$): δ 8.32 (d, J=4.8 Hz, 2H), 6.88 (s, 1H), 6.83 (d, J=8.0 Hz, 1H), 6.74 (d, J=8.0 Hz, 1H), 6.58 (t, J=4.4 Hz, 1H), 5.97 (m, 2H), 3.68-3.67 (m, 4H), 3.36-3.33 (m, 1H), 2.49-2.38 (m, 2H), 2.35-2.30 (m, 2H), 1.27 (d, J=6.4 Hz, 3H). LCMS: (Method A) 313.0 (M+H), Rt. 2.44 min, 99.5% (Max). HPLC: (Method A) Rt. 2.47 min, 99.8% (Max). HPLC chiral purity: (Method D) Rt. 13.33 min, 100% (Max).

Example 27: Ethyl 2-(4-(1-(benzordiri,31 dioxol-5-yl)ethyl)piperazin-1-yl)thiazole-5-carboxylate

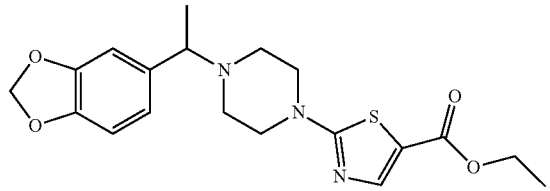 [SMILES: CCOC(=O)c1cnc(N2CCN(C(C)c3ccc4c(c3)OCO4)CC2)s1]

Step 1: Ethyl 2-bromothiazole-5-carboxylate

To a stirred solution of ethyl-2-amino thiazole-5-carboxylate (10.0 g, 46.45 mmol, Combi block) in 48% HBr (75 mL), sodium nitrite (4.80 g, 69.68 mmol) in water (50 mL) was added dropwise at 0° C. and the reaction mixture was stirred at 0° C. for 15 min. Copper (I)bromide (6.66 g, 46.45 mmol) in 48% HBr (75 ml.) was added dropwise at 0° C. and the reaction mixture was stirred at rt for 4 h. The reaction mixture was diluted with DCM (200 ml.) and washed with water (50 ml_), brine (50 ml_), dried over Na$_2$SO$_4$ and concentrated under reduced pressure. The crude product was purified by flash chromatography (100% CHCl$_3$) to afford the title compound. Yield: 50.18% (5.5 g, yellow liquid). $^1$H NMR (400 MHz, DMSO-d$_6$): δ 8.16 (s, 1H), 4.38 (q, J=7.16 Hz, 2H), 1.40 (t, J=7.12 Hz, 3H). LCMS: (Method A) 235.9 (M+H), Rt. 3.85 min, 98.6% (Max).

Step 2: Ethyl 2-(4-(1-(benzo[d][1,3]dioxol-5-yl)ethyl)piperazin-1-yl)thiazole-5-carboxylate To a stirred solution of Intermediate 2 (1.5 g, 6.40 mmol) in dry DMF (15 ml_), ethyl 2-bromothiazole-5-carboxylate (1.96 g, 8.32 mmol) and TEA (3.5 ml_, 25.6 mmol) were added at rt and the reaction mixture was stirred at 120° C. for overnight. The reaction mixture was cooled to rt and was diluted with EtOAc. The organic layer was washed with brine (10 ml_), water (10 ml_), dried over anhydrous Na$_2$SO$_4$ and concentrated under vacuum. The crude product was purified by column chromatography to afford the title compound (off white solid). $^1$H NMR (400 MHz, DMSO-d$_6$): δ 7.83 (s, 1H), 6.89 (s, 1H), 6.89 (d, J=8.0 Hz, 1H). 6.76 (d, J=8.0 Hz, 1H), 5.99 (s, 2H), 4.19 (q, J=6.8 Hz, 2H), 3.50-3.42 (m, 5H), 2.51-2.46 (m, 2H), 2.44-2.33 (m, 2H), 1.30-1.22 (m, 6H). LCMS: (Method A) 247.2 (M+H), Rt. 3.17 min, 78.6% (Max).

Example 28: (2-(4-(1-(Benzordiri,31dioxol-5-yl)ethyl)piperazin-1-yl)thiazol-5-yl)methanol

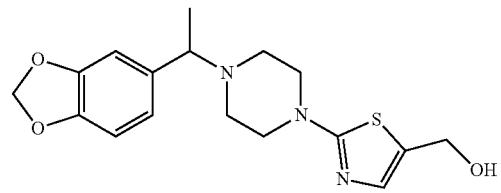 [SMILES: CC(c1ccc2c(c1)OCO2)N1CCN(c2ncc(CO)s2)CC1]

The title compound was synthesized following the general procedure A starting from Example 27. The crude product was purified by flash chromatography followed by MD Autoprep (Method B) (off white solid). ¹H NMR (400 MHz, DMSO-d₆): δ 6.96 (s, 1H), 6.89 (s, 1H), 6.84 (d, J=7.6 Hz, 1H), 6.75 (d, J=7.6 Hz, 1H), 5.98 (m, 2H), 5.21 (t, J=5.6 Hz, 1H), 4.44 (d, J=5.6 Hz, 2H), 3.40-3.37 (m, 1H), 3.34-3.31 (m, 4H), 2.46-2.42 (m, 2H), 2.41-2.38 (m, 2H), 1.28 (d, J=6.4 Hz, 3H). LCMS: (Method A) 348.0 (M+H), Rt. 1.91 min, 96.3% (Max). HPLC: (Method A) Rt. 1.89 min, 95.1% (Max).

Example 29: (2-(4-(1-(Benzordiri,31dioxol-5-yl)ethyl)piperazin-1-yl)thiazol-4-yl)methanol

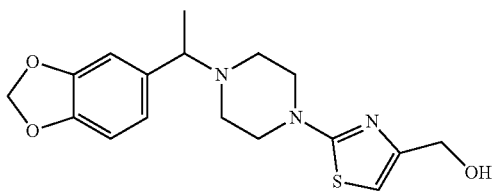 [SMILES: CC(c1ccc2c(c1)OCO2)N1CCN(c2nc(CO)cs2)CC1]

The title compound was synthesized following general procedure A, starting with Example 17 (0.5 g) and the crude product was purified by flash chromatography (pale yellow oil). ¹H NMR (400 MHz, DMSO-d₆): δ 6.89 (s, 1H), 6.85 (d, J=8.0 Hz, 1H), 6.75 (dd, J=1.6, 8.0 Hz, 1H), 6.52 (s, 1H), 5.99 (m, 2H), 5.11-5.09 (t, J=8.0 Hz, 1H), 4.31 (d, J=8.0 Hz, 2H), 3.40-3.34 (m, 5H). 2.51-2.49 (m, 2H), 2.42-2.32 (m, 2H), 1.28 (d, J=6.8 Hz, 3H). LCMS: (Method A) 348.0 (M+H), Rt. 1.98 min, 94.8% (Max). HPLC: (Method A) Rt. 1.99 min, 96.0% (Max).

Example 30: 2-(4-(1-(Benzordiri,31 dioxol-5-yl)ethyl)piperazin-1-yl)-N-methylthiazole^4-carboxamide

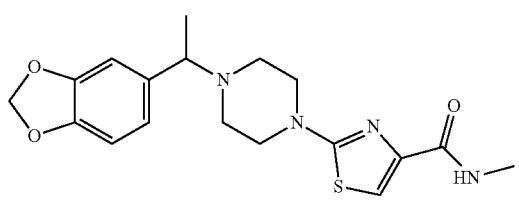 [SMILES: CNC(=O)c1csc(N2CCN(C(C)c3ccc4c(c3)OCO4)CC2)n1]

To a stirred solution of Example 18 (0.3 g, 0.5 mmol) in DCM (10 mL), DIPEA (0.6 mL, 2 mmol) and HATU (0.56 g, 1.48 mmol) were added slowly at 0° C. The reaction mixture was stirred at 0° C. for 20 min. Methyl amine in THF (0.6 mL, 1.48 mmol) was added and the reaction mixture was stirred overnight at room temperature. The reaction mixture was diluted with EtOAc (10 mL) and washed with water (10 mL) and brine (10 mL). The organic layer was dried over anhydrous Na₂SO₄, concentrated under vacuum. The crude product was purified by flash chromatography followed by MD Autoprep (Method B) to afford the title compound (off white solid). ¹H NMR (400 MHz, DMSO-d₆): δ 7.96 (d, J=4.8 Hz, 1H), 7.33 (s, 1H), 6.89 (s, 1H). 6.85 (d, J=8.0 Hz, 1H), 6.75 (dd, J=1.6, 8.0 Hz, 1H), 5.98 (m, 2H), 3.43-3.38 (m, 5H), 2.72 (d, J=4.8 Hz, 3H), 2.41-2.39 (m, 4H), 1.27 (d, J=6.4 Hz, 3H). LCMS: (Method A) 375.0 (M+H), Rt. 2.34 min, 98.2% (Max). HPLC: (Method A) Rt. 2.32 min, 99.0% (Max).

Example 31: 3-(4-(1-(Benzordiri,31dioxol-5-yl)ethyl)piperazin-1-yl)-6-chloropyridazine

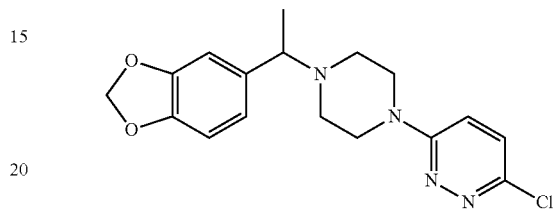

The title compound was synthesized following general procedure D, using Intermediate 2 and 3,6-dichloro pyridazine. The crude product was purified by flash chromatography (off white solid). 1H NMR (DMSO-d₆): δ 7.65 (d, J=9.6 Hz, 1H), 7.46 (d, J=9.6 Hz, 1H), 7.21 (s, 1H), 7.01-6.98 (m, 2H), 6.08 (s, 2H), 4.50-4.44 (m, 1H), 4.39-4.36 (m, 1H), 3.80-3.75 (m, 1H), 3.45-3.42 (m, 1H), 3.28-3.25 (m, 1H), 3.18-3.15 (m, 1H), 3.11-3.08 (m, 1H), 3.01-2.98 (m, 1H), 2.92-2.86 (m, 1H), 1.67 (d, J=6.8 Hz, 3H). LCMS: (Method A) 347.0 (M+H), Rt. 2.55 min, 96.5% (Max). HPLC: (Method A) Rt. 2.58 min, 95.5% (Max).

Example 32: 2-(4-(1-(Benzordiri,31dioxol-5-yl)ethyl)piperazin-1-yl)-N-isopropylthiazole-4-carboxamide

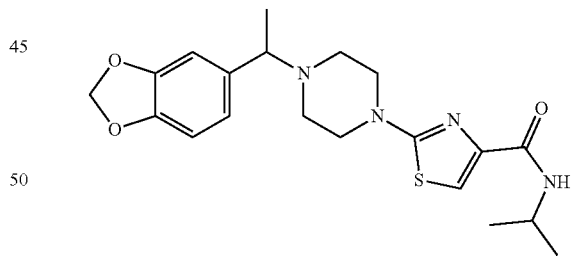

The title compound was synthesized by following the same procedure as described for Example 30, using Example 18 (0.3 g, 0.9 mmol) and isopropyl amine (0.09 mL, 1.08 mmol) as starting material (off white solid). ¹H NMR (400 MHz, DMSO-d₆): δ 7.62 (d, J=8.4 Hz, 1H), 7.35 (s, 1H), 6.90 (s, 1H), 6.85 (d, J=8.0 Hz, 1H), 6.77 (d, J=8.0 Hz, 1H), 5.99 (m, 2H), 4.04-3.99 (m, 1H), 3.43-3.34 (m, 5H), 2.50-2.42 (m, 4H), 1.29 (d, J=6.8 Hz, 3H), 1.14-1.07 (m, 6H). LCMS: (Method A) 403.0 (M+H), Rt. 2.90 min, 95.5% (Max). HPLC: (Method A) Rt. 2.91 min, 96.5% (Max).

Example 33: 2-(4-(1-(Benzordiri,31dioxol-5-yl)ethyl)piperazin-1-yl)-N-cyclohexylthiazole-4-carboxamide

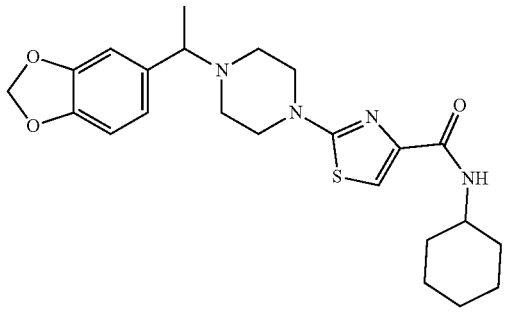 [SMILES: CC(c1ccc2c(c1)OCO2)N1CCN(c2nc(C(=O)NC3CCCCC3)cs2)CC1]

The title compound was synthesized by following the same procedure as described for Example 30, using Example 18 (0.3 g, 0.9 mmol) and cyclohexyl amine (0.12 mL, 1.08 mmol) as starting material (off white solid). $^1$H NMR (400 MHz, DMSO-d$_6$): δ 7.60 (d, J=8.4 Hz, 1H), 7.35 (s, 1H), 6.90 (s, 1H), 6.85 (d, J=7.6 Hz, 1H), 6.77 (d, J=7.6 Hz, 1H), 5.99 (s, 2H), 3.68-3.67 (m, 1H), 3.42 (br.s, 4H), 2.50-2.42 (m, 4H), 1.74-1.70 (m, 4H), 1.59-1.56 (m, 1H), 1.36-1.23 (m, 8H), 1.13-1.09 (m, 1H). LCMS: (Method A) 443.0 (M+H), Rt. 3.57 min, 97.9% (Max). HPLC: (Method A) Rt. 3.62 min, 99.3% (Max).

Example 34: (R)-2-(4-(1-(2,3-Dihydrobenzorbiri,41dioxin-6-yl)ethyl)piperazin-1-yl)pyrimidine or (S)-2-(4-(1-(2,3-Dihydrobenzorbiri^1dioxin-6-yl)ethyl)piperazin-1-yl)pyrimidine

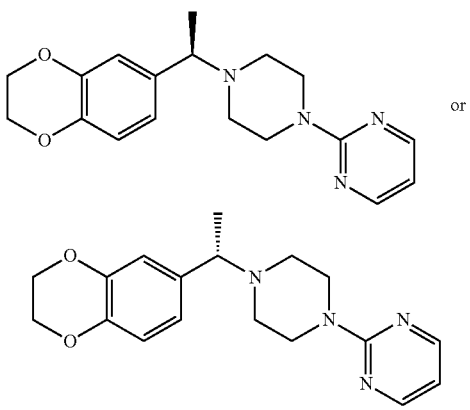

The title compound was synthesized by following procedure D, using Intermediate 3 (2.2 g, 11 mmol) and 1-(2-pyrimidyl) piperazine (1.8 g, 11 mmol). The crude product was purified by flash chromatography followed by preparative chiral HPLC (Method PF) to separate the two enenatiomers. The first eluting compound has Rt. 7.90 min (Method D) (off white solid). $^1$H NMR 400 MHz, DMSO-d$_6$): δ 8.32 (d, J=4.4 Hz, 2H), 6.78-6.75 (m, 3H), 6.59 (t, J=9.6 Hz, 1H), 4.21-4.20 (m, 4H), 3.68-3.67 (m, 4H), 3.36-3.26 (m, 1H), 2.49-2.39 (m, 2H), 2.34-2.32 (m, 2H), 1.25 (d, J=6.4 Hz, 3H). LCMS: (Method A) 327.2 (M+H), Rt. 2.51 min, 98.7% (Max). HPLC: (Method A) Rt. 2.54 min, 99.3% (Max). HPLC chiral purity: (Method D) Rt. 7.90 min, 100.0% (Max). Example 34 corresponds to the second eluting compound, with Rt. 13.92 min (Method D) (off white solid). $^1$H NMR (400 MHz, DMSO-d$_6$): δ 8.32 (d, J=4.4 Hz, 2H), 6.80-6.75 (m, 3H), 6.59 (t, J=9.6 Hz, 1H), 4.21-4.20 (m, 4H), 3.69-3.66 (m, 4H), 3.33-3.32 (m, 1H), 2.44-2.38 (m, 2H), 2.36-2.31 (m, 2H), 1.26 (d, J=6.8 Hz, 3H). LCMS: (Method A) 327.0 (M+H), Rt. 2.51 min, 99.1% (Max). HPLC: (Method A) Rt. 2.49 min, 99.2% (Max). HPLC chiral purity: (Method D) Rt. 13.92 min, 99.88% (Max).

Example 35: 2-(4-(1-(Benzordiri,31dioxol-5-yl)ethyl)piperazin-1-yl)thiazole-4-carboxamide

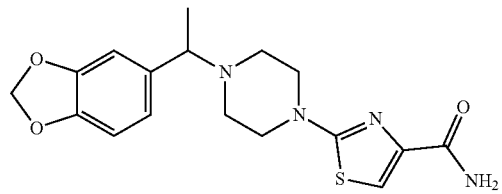 [SMILES: CC(c1ccc2c(c1)OCO2)N1CCN(c2nc(C(N)=O)cs2)CC1]

The title compound was synthesized by following the same procedure as described for Example 30, using Example 18 (0.3 g, 0.9 mmol) and ammonia in THF (4.5 mL, 9 mmol, 2 M in THF) as starting material. The crude mixture was purified by flash chromatography (off white solid). H NMR (400 MHz, DMSO-d$_6$): δ 7.39 (br s, 2H), 7.37 (s, 1H), 6.90 (s, 1H), 6.85 (d, J=7.6 Hz, 1H), 6.77 (d, J=7.2 Hz, 1H), 5.99 (br s, 2H), 3.41-3.34 (m, 5H), 2.50-2.43 (m, 4H), 1.30 (d, J=6.8 Hz, 3H). LCMS: (Method A) 361.0 (M+H), Rt. 2.19 min, 94.8% (Max). HPLC: (Method A) Rt. 2.17 min, 98.0% (Max).

Example 36: 5-(4-(1-(Benzordiri,31 dioxol-5-yl)ethyl)piperazin-1-yl)-2-methylthiazole

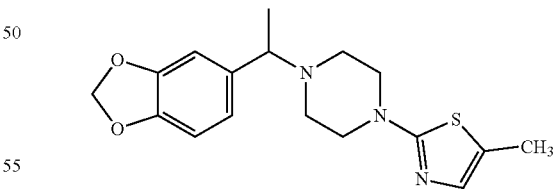

The title compound was synthesized following general procedure D, using 2-bromo-5-methyl thiazole and Intermediate 2. The crude product was purified by flash chromatography (brown solid). $^1$H NMR (DMSO-d$_6$): δ 6.89 (s, 1H), 6.85 (d, J=7.6 Hz, 1H), 6.80 (d, J=7.6 Hz, 1H), 6.76-6.74 (m, 1H), 5.99 (m, 2H), 3.40-3.36 (m, 1H), 3.29-3.26 (m, 4H), 2.46-2.45 (m, 2H), 2.42-2.38 (m, 2H), 2.23 (s, 3H), 1.28-1.27 (m, 3H). LCMS: (Method A) 332.0 (M+H), Rt. 2.13 min, 96.0% (Max). HPLC: (Method A) Rt. 2.11 min, 97.4% (Max).

Example 37: 5-(4-(1-(Benzordiri,31dioxol-5-yl)ethyl)piperazin-1-yl)-2-methylthiazole

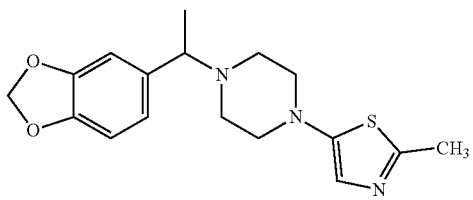 [SMILES: Cc1ncc(N2CCN(C(C)c3ccc4c(c3)OCO4)CC2)s1]

The mixture of 5-bromo-2-methyl thiazole (150 mg, 0.84 mmol), Intermediate 2 (200 mg, 0.84 mmol) and TEA (344 mg, 3.4 mmol) in DMF (4 mL) was heated at 130° C. for overnight. It was concentrated under vacuum and to the resulting crude product was dissolved in EtOAc (10 mL) and washed with water (10 mL). The organic layer was dried over $Na_2SO_4$ and concentrated. The crude product was purified by flash column chromatography (brown solid). $^1$H NMR (DMSO-$d_6$): δ 6.90 (s, 1H), 6.85-6.78 (m, 3H), 5.95 (br s, 2H), 3.55-3.51 (m, 1H), 3.12-3.11 (m, 4H), 2.80-2.65 (m, 4H), 2.54 (s, 3H), 1.44 (d, J=5.6 Hz, 3H). LCMS: (Method A) 332.0 (M+H), Rt. 5.71 min, 97.35% (Max). HPLC: (Method B) Rt. 5.64 min, 96.8% (Max).

Example 38: 5-(4-(1-(Benzordiri,31dioxol-5-yl)ethyl)piperazin-1-yl)-2-chloropyrimidine

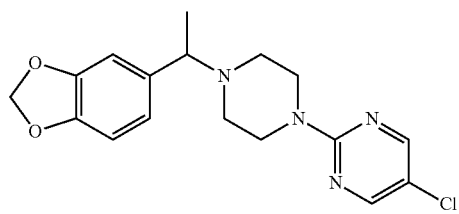

The title compound was synthesized following the general procedure D, using Intermediate 2 and 2,5-dichloropyrimidine. The crude product was purified by flash chromatography (off white solid). $^1$H NMR (400 MHz, DMSO-$d_6$): δ 8.38 (s, 2H), 6.88 (s, 1H), 6.83 (d, J=8.0 Hz, 1H), 6.75 (m, J=8.0 Hz, 1H), 5.98 (m, 2H), 3.68-3.65 (m, 4H), 3.38-3.369 (m, 1H), 2.44-2.39 (m, 1H), 2.36-2.32 (m, 2H), 1.27 (d, J=6.8 Hz, 3H). LCMS: (Method A) 347.0 (M+H), Rt. 3.24 min, 98.3% (Max). HPLC: (Method A) Rt. 3.22 min, 99.6% (Max).

Example 39: 2-(4-(1-(Benzordiri,31dioxol-5-yl)ethyl)piperazin-1-yl)-4-methoxypyrimidine

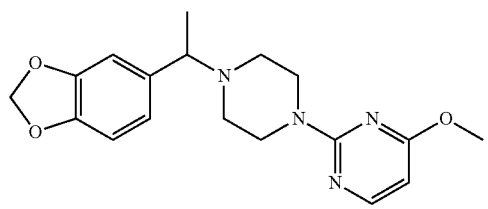 [SMILES: COc1ccnc(N2CCN(C(C)c3ccc4c(c3)OCO4)CC2)n1]

The title compound was synthesized following general procedure D, using Intermediate 2 and 2-chloro-5-methoxy pyrimidine. The crude product was purified by flash chromatography (white solid). $^1$H NMR (400 MHz, DMSO-$d_6$): δ 8.04 (d, J=5.6 Hz, 1H), 6.88-0 (s, 1H), 6.83 (d, J=8.0 Hz, 1H), 6.74 (d, J=8.0 Hz, 1H), 6.02 (d, J=5.6 Hz, 1H), 5.98 (br s, 2H), 3.79 (s, 3H), 3.72-3.66 (m, 4H), 3.37-3.39 (m, 1H), 2.43-2.39 (m, 2H), 2.34-2.30 (m, 2H), 1.28-1.26 (d, J=6.4 Hz, 3H). LCMS: (Method A) 343.0 (M+H), Rt. 2.27 min, 99.6% (Max). HPLC: (Method A) Rt. 2.27 min, 99.4% (Max).

Example 40: 4-(4-(1-(Benzordiri,31dioxol-5-yl)ethyl)piperazin-1-yl)-2-chloropyrimidine

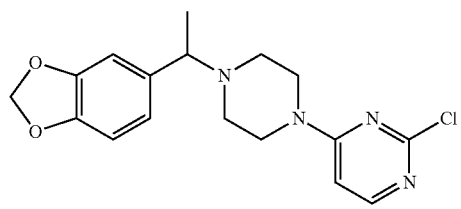 [SMILES: CC(c1ccc2c(c1)OCO2)N1CCN(c2ccnc(Cl)n2)CC1]

The title compound was synthesized following the general procedure D, using Intermediate 2 and 2,4-dichloropyrimidine. The crude product was purified by flash chromatography (yellow oil). $^1$H NMR (400 MHz, DMSO-$d_6$): δ 8.04 (d, J=7.6 Hz, 1H), 6.89 (s, 1H), 6.85 (d, J=8.0 Hz, 1H), 6.80-6.75 (m, 2H), 5.99 (m, 2H), 3.59 (br.s, 4H), 3.39 (q, J=6.4 Hz, 1H), 2.45-2.42 (m, 2H), 2.38-2.33 (m, 2H), 1.29-1.27 (d, J=6.8 Hz, 3H). LCMS: (Method A) 347.0 (M+H), Rt. 2.59 min, 96.4% (Max). HPLC: (Method A) Rt. 2.51 min, 98.2% (Max).

Example 41: 5-(4-(1-(benzordiri,31dioxol-5-yl)ethyl)piperazin-1-yl)-1,3,4-thiadiazol-2-amine

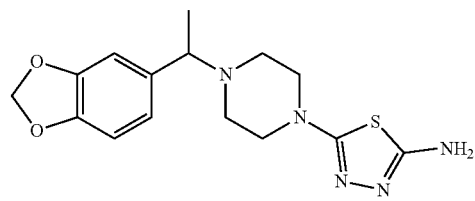 [SMILES: CC(c1ccc2c(c1)OCO2)N1CCN(c2nnc(N)s2)CC1]

The title compound was synthesized following the general procedure D, using Intermediate 2 and 2-amino-5-bromo-1,3,4-thiadiazole. The crude product was purified by recrystallisation. Yield: 81% (2.0 g, off white solid). $^1$H NMR (400 MHz, DMSO-$d_6$): δ 6.88-6.87 (m, 1H), 6.85-6.83 (m, 1H), 6.76-6.73 (m, 1H), 6.47 (s, 2H) 5.99 (s, 2H), 3.40-3.34 (m, 1H), 3.19-3.17 (m, 4H), 2.47-2.43 (m, 2H), 2.40-2.36 (m, 2H), 1.27 (d, J=6.4 Hz, 3H). LCMS: (Method A) 334.0 (M+H), Rt. 1.84 min, 96.5% (Max). HPLC: (Method A) Rt. 1.83 min, 98.2% (Max).

Example 42: 2-(4-(1-(benzordlH,31dioxol-5-yl) ethyl)piperazin-1-yl)-N,N-dimethylthiazole-4-carboxamide

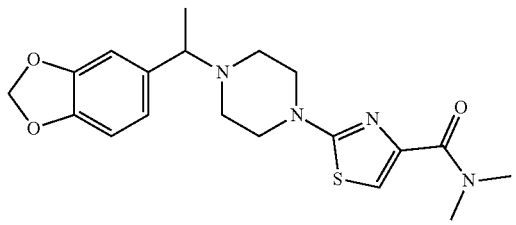 [SMILES: CC(c1ccc2c(c1)OCO2)N1CCN(c2nc(C(=O)N(C)C)cs2)CC1]

The title compound was synthesized following the same procedure as described for Example 30, using Example 18 (0.3 g, 0.9 mmol) and dimethyl amine (0.9 mL, 1.8 mmol, 2 M in THF) as starting material (pale yellow solid). $^1$H NMR (400 MHz, DMSO-$d_6$): δ 7.16 (s, 1H), 6.89 (s, 1H), 6.85 (d, J=7.6 Hz, 1H), 6.76 (d, J=8.0 Hz, 1H), 5.99 (br s, 2H), 3.41-3.34 (m, 5H), 3.30 (s, 3H), 2.90 (s, 3H), 2.43-2.42 (m, 4H), 1.28 (d, J=6.8 Hz, 3H). LCMS: (Method A) 389.0 (M+H), Rt. 2.41 min, 95.1% (Max). HPLC: (Method A) Rt. 2.38 min, 94.3% (Max).

Example 43: 2-(4-(1-(Benzordiri,31dioxol-5-yl) ethyl)piperazin-1-yl)-N-isopropylthiazole-5-carboxamide

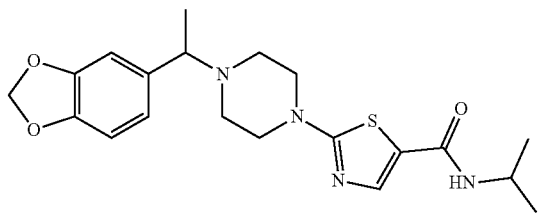 [SMILES: CC(C)NC(=O)c1cnc(N2CCN(C(C)c3ccc4c(c3)OCO4)CC2)s1]

Step 1: 2-(4-(1-(Benzo[d][1,3]dioxol-5-yl)ethyl) piperazin-1-yl)thiazole-5-carboxylic acid To a stirred solution of Example 27 (0.8 g, 2.05 mmol) in dioxane (24 mL), NaOH (2M in water, 3 mL) was added slowly. The reaction mixture was stirred overnight at room temperature. It was then concentrated under vacuum and neutralized with HCl (1.5 N) up to pH=6 and was extracted with DCM (25 mL). The organic layer was washed with water (15 mL), brine (15 mL), dried over anhydrous Na$_2$SO$_4$ and concentrated under reduced pressure to afford the title compound (off white solid). LCMS: (Method A) 362.0 (M+H), Rt. 2.30 min, 77.6% (Max).

Step 2: 2-(4-(1-(Benzo[d][1,3]dioxol-5-yl)ethyl) piperazin-1-yl)^-isopropylthiazole-5-carboxamide To a solution of 2-(4-(1-(benzo[d][1,3]dioxol-5-yl)ethyl) piperazin-1-yl)thiazole-5-carboxylic acid (0.1 g, 0.277 mmol) in dry DCM (2 mL), HATU (0.16 g, 0.41 mmol) was added and the resulting mixture was stirred at room temperature for 1 h. Isopropyl amine (0.02 g, 0.36 mmol) and DIPEA (0.14 mL, 0.83 mmol) were added at 0° C. and the mixture was stirred overnight at room temperature. The reaction was quenched with water (10 mL) and extracted with EtOAc (25 mL). The organic layer was dried over anhydrous Na$_2$SO$_4$ and concentrated under vacuum. The resulting crude product was purified by MD Autoprep (Method B) to afford the title compound (off white solid). $^1$H NMR (400 MHz, DMSO-$d_6$): δ 7.96 (d, J=7.6 Hz, 1H), 7.78 (s, 1H), 6.89 (s, 1H), 6.85 (d, J=7.6 Hz, 1H), 6.75 (d, J=8.0 Hz, 1H), 5.99 (br s, 2H), 3.98-3.96 (m, 1H), 3.42-3.41 (m, 5H), 2.42-2.38 (m, 4H), 1.28 (d, J=6.8 Hz, 3H), 1.11 (d, J=6.8 Hz, 6H). LCMS: (Method A) 403 (M+H), Rt. 2.72 min, 97.81% (Max). HPLC: (Method A) Rt. 2.70 min, 98.62% (Max).

Example 44: N-(5-(4-(1-(BenzofdlH,31dioxol-5-yl) ethyl)piperazin-1-yl)-1,3,4-thiadiazol-2-vOacetamide

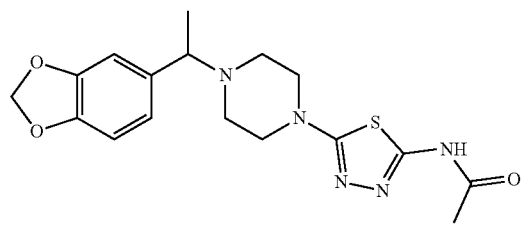 [SMILES: CC(=O)Nc1nnc(N2CCN(C(C)c3ccc4c(c3)OCO4)CC2)s1]

To a stirred solution of Example 41 (0.06 g, 0.7 mmol), diisopropylethylamine (0.4 mL, 0.32 mmol) in dry DCM (4.0 mL), acetic anhydride (0.96 mL, 1.05 mmol) was added at 0° C. and the resulting mixture was stirred for 5 h at rt. The completion of the reaction was monitored by TLC. The reaction mixture was concentrated and the crude products were purified by flash chromatography to afford the title compound (colorless oil). $^1$H NMR (400 MHz, DMSO-$d_6$): δ 12.03 (m, 1H), δ 6.89 (m, 1H), 6.86-6.84 (m, 1H), 6.77-6.75 (m, 1H), 5.99 (m, 2H), 3.41-3.40 (m, 5H), 2.51-2.50 (m, 2H), 2.43-2.40 (m, 2H), 2.10 (s, 3H), 1.28 (d, J=6.8 Hz, 3H). LCMS: (Method A) 376.0 (M+H), Rt. 2.512 min, 96.77% (Max). HPLC: (Method A) Rt. 2.262 min, 98.69% (Max).

Example 45: 2-(4-(1-(Benzordiri,31 dioxol-5-yl) ethyl)piperazin-1-yl)-N-propylpyrimidin-4-amine

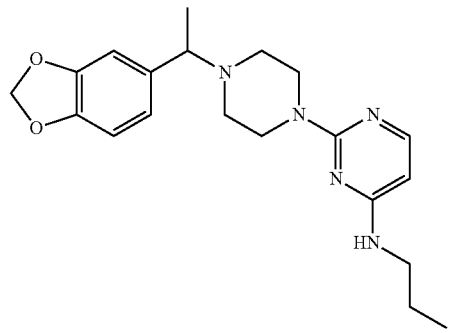 [SMILES: CCCNc1ccnc(N2CCN(C(C)c3ccc4c(c3)OCO4)CC2)n1]

Step 1: 2-chloro-N-propylpyrimidin-4-amine

To a stirred solution of 2,4-dichloro pyrimidine (0.2 g, 1.34 mmol) in dry THF (10 mL), TEA (0.54 g, 5.36 mmol)

and propyl amine (0.088 g, 1.34 mmol) were added and the resulting mixture was stirred at room temperature for 10 h. It was diluted with water and extracted with EtOAc. The organic layer was dried over anhydrous Na$_2$SO$_4$ and concentrated under vacuum to afford the title compound. Yield: 70% (0.18 g, colorless oil). $^1$H NMR (400 MHz, DMSO-d$_6$): δ 7.92-7.85 (m, 2H), 6.49-6.41 (m, 1H), 3.21 (t, J=6.4 Hz 2H), 1.56-1.47 (m, 2H), 0.91-0.87 (t, J=7.36 Hz, 3H). LCMS: (Method A) 172.0 (M+H), Rt. 2.07 min, 99.5% (Max).

Step 2: 2-(4-(1-(Benzo[d][1,3]dioxol-5-yl)ethyl)piperazin-1-yl)-N^ropylpyrimidin-4-amine To a stirred solution of Intermediate 2 (0.2 g, 0.9 mmol) in dry DMF (4.0 mL), 2-chloro-N-propylpyrimidin-4-amine (0.18 g, 1.04 mmol) and TEA (0.5 mL, 3.2 mmol) were added at 0° C. The reaction mixture was stirred at 130° C. for overnight. It was then concentrated and the crude product was purified by flash chromatography to afford the title compound (colorless oil). $^1$H NMR (400 MHz, DMSO-d$_6$): δ 7.65 (s, 1H), 6.89-6.75 (m, 3H), 6.12-5.95 (m, 3H), 5.83 (br. s, 1H), 3.62 (m, 4H), 3.20 (s, 3H), 2.51-2.49 (m, 4H), 1.50 (qm, 2H), 1.28-1.24 (m, 3H), 0.88 (t, J=8.0 Hz, 3H). LCMS: (Method A) 370.0 (M+H), Rt. 2.604 min, 97.37% (Max). HPLC: (Method A) Rt. 2.54 min, 99.78% (Max).

Example 46: 4-(4-(1-(Benzordiri,31dioxol-5-yl)ethyl)piperazin-1-yl)pyrimidin-2-amine

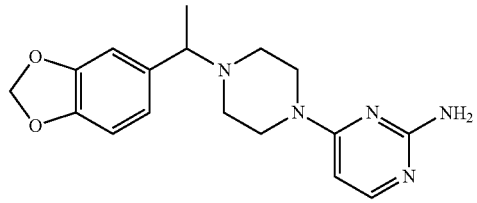 [SMILES: CC(c1ccc2c(c1)OCO2)N1CCN(c2ccnc(N)n2)CC1]

The title compound was synthesized following the general procedure D, using Intermediate 2 and 2-amino-4-chloropyrimidine. The crude product was purified by flash chromatography (off white solid). $^1$H NMR (400 MHz, DMSO-d$_6$): δ 7.72 (d, 1H, J=6.0 Hz), 6.88 (s, 1H), 6.84 (d, J=8.0 Hz, 1H), 6.75 (d, J=8.0 Hz, 1H), 5.98-5.95 (m, 5H), 3.46-3.45 (m, 4H), 3.37-3.35 (m, 1H), 2.40-2.37 (m, 2H), 2.33-2.29 (m, 2H), 1.27 (d, J=6.4 Hz, 3H). LCMS: (Method A) 328.0 (M+H), Rt. 1.86 min, 97.06% (Max). HPLC: (Method A) Rt. 1.81 min, 97.5% (Max).

Example 47: 2-(4-(1-(Benzord1(1,3)dioxol-5-yl)ethyl)piperazin-1-yl)-N,N-dimethylthiazole-5-carboxamide

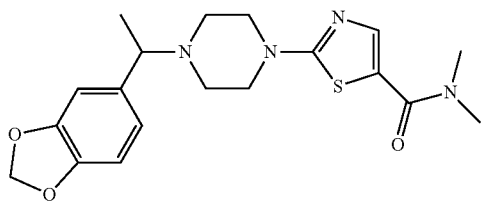 [SMILES: CC(c1ccc2c(c1)OCO2)N1CCN(c2ncc(C(=O)N(C)C)s2)CC1]

To a stirred solution of 2-(4-(1-(benzo[d][1,3]dioxol-5-yl)ethyl)piperazin-1-yl)thiazole-5-carboxylic acid (Example 43, Step 1, 0.155 g, 0.4 mmol) and HATU (0.206 g, 1.2 mmol) in dry DMF (3 ml_), DIPEA (0.1 ml, 0.8 mmol) was added and the resulting mixture was stirred for 30 min at room temperature. Dimethylamine in THF (0.5 ml, 8.4 mmol) was then added at 0° C. The reaction mixture was stirred overnight at room temperature. Solvents were evaporated and the resulting crude mixture was diluted with EtOAc, washed with water, 10% sodium bicarbonate solution, brine and dried over Na$_2$SO$_4$. After evaporation of the solvents, the resulting crude product was purified by MD Autoprep (Method B) to afford the title compound (off white solid). $^1$H NMR (400 MHz, CDCl$_3$): δ 7.47 (s, 1H), 6.87 (s, 1H), 6.77-6.76 (m, 2H), 5.96 (s, 2H), 3.52-3.51 (m, 4H), 3.37-3.36 (m, 1H), 3.17 (s, 6H), 2.57-2.52 (m, 4H), 2.26 (s, 3H). LCMS: (Method B) 389 (M+H), Rt. 5.049 min, 98.02% (Max). HPLC: (Method A) Rt. 2.42 min, 98.49% (Max).

Example 48: 2-(4-(1-(Benzord1(1,3)dioxol-5-yl)ethyl)piperazin-1-yl)thiazole-5-carboxamide

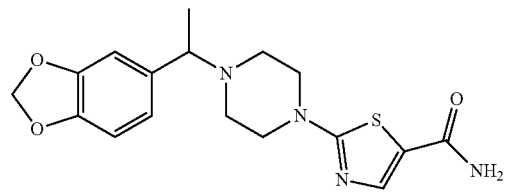 [SMILES: CC(c1ccc2c(c1)OCO2)N1CCN(c2ncc(C(N)=O)s2)CC1]

To a solution of 2-(4-(1-(benzo[d][1,3]dioxol-5-yl)ethyl)piperazin-1-yl)thiazole-5-carboxylic acid (Example 43, Step 1, 0.15 g, 0.4 mmol) in dry DMF (3 ml_), HATU (0.206 g, 1.2 mmol) was added and stirred at room temperature for 20 min. Ammonia in THF (5 ml.) and DIPEA (0.14 ml_, 0.83 mmol) were then added at 0° C. The resulting reaction mixture was stirred at room temperature overnight. It was concentrated under reduced pressure. EtOAc was added to the resulting mixture and was washed with water, 10% sodium bicarbonate solution, brine and dried over Na$_2$SO$_4$. After evaporation of the solvents, the crude product was purified by MD Autoprep (Method C) to afford the title compound (off white solid). $^1$H NMR (400 MHz, DMSO-d$_6$): δ 7.76 (s, 1H), 7.67 (br s, 1H), 7.11 (br s, 1H), 6.89 (s, 1H), 6.84 (d, J=7.6 Hz, 1H), 6.76 (d, J=7.6 Hz, 1H), 5.99 (br s, 2H), 3.41-3.40 (m, 5H), 2.50-2.39 (m, 4H), 1.28 (d, J=8.0 Hz, 3H). LCMS: (Method A) 361.0 (M+H), Rt. 2.01 min, 99.2% (Max). HPLC: (Method A) Rt. 2.03 min, 98.5% (Max).

Example 49: 2-(4-(1-(2,3-Dihydrobenzorbiri,41 dioxin-6-yl)ethyl)piperazin-1-yl)thiazole-4-carboxamide

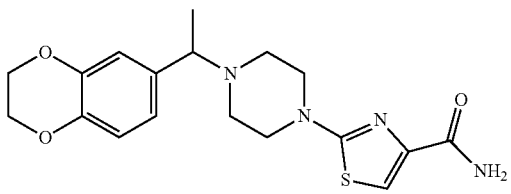 [SMILES: CC(c1ccc2c(c1)OCCO2)N1CCN(c2nc(C(N)=O)cs2)CC1]

Step 1: Ethyl-2-(4-(1-(2,3-dihydrobenzo[b][1,4] dioxin-6-yl)ethyl)piperazin-1-yl) thiazole-4-carboxylate The title compound was synthesized following general procedure D, using ethyl 2-(piperazin-1-yl)thiazole-4-carboxylate hydrochloride (Example 17, Step 2, 5.0 g, 20.4 mmol) and Intermediate 3 (4.97 g, 24 mmol). The crude product was purified by flash chromatography. Yield: 54% (4.5 g, black oil).

Step 2: 2-(4-(1-(2,3-Dihydrobenzo[b][1A]dioxin-6-yl)ethyl)piperazin-1-yl)thiazole-4-car^^xylic acid To a stirred solution of ethyl-2-(4-(1-(2,3-dihydrobenzo[b][1,4]dioxin-6-yl)ethyl)piperazin-1-yl)thiazole-4-carboxylate (4.5 g, 11.1 mmol) in THF (20 ml_), 10% NaOH (50 mL) was added slowly. The reaction mixture was stirred at room temperature for overnight. It was concentrated under vacuum, neutralized with HCl (2 N in water) to pH=6 and extracted with DCM (25 mL). The organic layer was washed with water (10 mL), brine (25 mL), dried over anhydrous $Na_2SO_4$ and concentrated under reduced pressure afford the title compound (pale yellow solid). $^1H$ NMR (400 MHz, $CDCl_3$): δ 7.44 (s, 1H), 6.94-6.76 (m, 3H), 4.26 (s, 4H), 3.65-3.49 (m, 5H), 2.59-3.54 (m, 4H), 2.49-2.45 (m, 4H), 1.26 (d, J=4.8 Hz, 3H), LCMS: (Method A) 376.0 (M+H), Rt. 2.36 min, 79.7% (Max).

Step 3: 2-(4-(1-(2,3-Dihydrobenzo[b][1A]dioxin-6-yl)ethyl)piperazin-1-yl)thiazole-4-car^^xamide The title compound was synthesized according to the same procedure as described for Example 30, using 2-(4-(1-(2,3-dihydrobenzo[b][1,4]dioxin-6-yl)ethyl)piperazin-1-yl)thiazole-4-carboxylic acid and $NH_3$ in THF. The crude product was purified by flash chromatography (off white solid). $^1H$ NMR (400 MHz, DMSO-de): $^1H$ NMR (400 MHz, DMSO-$d_6$): δ 7.39 (br s, 2H), 7.35 (s, 1H), 6.80-6.76 (m, 3H), 4.21 (s, 4H), 3.38-3.38 (m, 5H), 2.49-2.45 (m, 4H), 1.27-1.23 (m, 3H). LCMS: (Method A) 375.0 (M+H), Rt. 2.21 min, 96.1% (Max). HPLC: (Method A) Rt. 2.28 min, 96.6% (Max).

Example 50: 2-(4-(1-(2,3-dihydrobenzorbin,4] dioxin-6-yl)ethyl)piperazin-1-yl)-N-methylthiazole-4-carboxamide

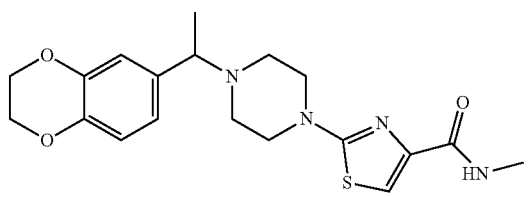 [SMILES: CNC(=O)c1csc(N2CCN(C(C)c3ccc4c(c3)OCCO4)CC2)n1]

The title compound was synthesized according to the same procedure as described for Example 30, using 2-(4-(1-(2,3-dihydrobenzo[b][1,4]dioxin-6-yl)ethyl)piperazin-1-yl)thiazole-4-carboxylic acid and $MeNH_2$ in THF. The crude product was purified by flash chromatography (yellow oil). $^1H$ NMR (400 MHz, DMSO-$d_6$): δ 8.07 (q, J=4.0 Hz, 1H), 7.33 (s, 1H), 6.76-6.39 (m, 3H), 4.21 (s, 4H), 3.38-3.32 (m, 5H), 2.75-2.71 (m, 3H), 2.49-2.48 (m, 4H), 1.26-1.25 (m, 3H). LCMS: (Method A) 389.0 (M+H), Rt. 2.38 min, 95.9% (Max). HPLC: (Method A) Rt. 2.46 min, 97.7% (Max).

Example 51: Ethyl 2-(4-(1-(benzordin,31 dioxol-5-yl)ethyl)piperazin-1-yl)pyrimidine-5-carboxylate

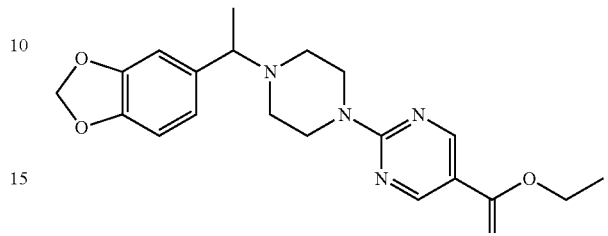

Step 1: tert-Butyl 4-(5-bromopyrimidin-2-yl)piperazine-1-carboxylate

To a stirred solution of 1-boc-piperazine (6.0 g, 31.5 mmol) in DMF (50 mL), triethyl amine (7 mL, 46.00 mmol) and 5-bromo-2-chloropyrimidine (6.3 g, 37.00 mmol) were added and the reaction mixture was stirred at 90° C. for 8 h. The reaction mixture was concentrated under reduced pressure. Water (50 mL) was added and the desired product was extracted with DCM (150 mL). The organic layer was dried over $Na_2SO_4$ and concentrated under reduced pressure. The crude product was purified by flash chromatography (10% EtOAc in pet ether) to afford the title compound. Yield: 76% (7 g, white). $^1H$ NMR (400 MHz, DMSO-$d_6$): δ 8.46 (s, 2H), 3.68-3.67 (m, 4H), 3.39-3.37 (m, 4H), 1.40 (s, 9H). LCMS: (Method A) 289.0 (M+H), Rt. 5.19 min, 99.05% (Max).

Step 2: 2-(4-(t-Butoxycarbonyl)piperazin-1-yl)pyrimidine-5-carboxylic acid

To a stirred solution of fert-butyl 4-(5-bromopyrimidin-2-yl)piperazine-1-carboxylate (5 g, 14.5 mmol) in dry THF (50 mL), n-BuLi (13.5 mL, 21.7 mmol, 1.6 M in THF) was added dropwise at −75° C. and stirred for 2 h at the same temperature. Dry $CO_2$ gas was passed through the reaction mixture for 1 h. The reaction was stirred for 30 min at same temperature and 30 min at rt. It was cooled to 0° C. and quenched by using 10% ammonium chloride solution. The product was extracted with DCM (150 mL). The organic layer was washed with water (50 mL), brine (50 mL) and dried over anhydrous $Na_2SO_4$. After evaporation of the solvents, the title compound was isolated and used in the next step without further purification. Yield: 55% (2.5 g, pale yellow oil). LCMS: (Method A) 308.0 (M+H), Rt. 3.61 min, 55.64% (Max).

Step 3: Ethyl 2-(piperazin-1-yl)pyrimidine-5-carboxylate

To a stirring solution of 2-(4-(fert-butoxycarbonyl)piperazin-1-yl)pyrimidine-5-carboxylic acid (2.0 g, 6.0 mmol) in EtOH (250 mL), $SOCl_2$ (1.7 mL, 16.23 mmol) was added slowly at 0° C. and the mixture was stirred at 90° C. for 15 h. It was concentrated under reduced pressure to afford the title compound (off white solid). LCMS: (Method A) 236 (M+H), Rt. 2.14, 49.8% (Max).

Step 4: Ethyl 2-(4-(1-(benzo[d][1,3]dioxol-5-yl)ethyl)piperazin-1-yl)pyrimidine-5-carboxylate To a stirring solution of ethyl 2-(piperazin-1-yl)pyrimidine-5-carboxylate (2.5 g, 9.0 mmol), diisopropyl ethyl amine (5.9 mL, 27.0 mmol) in dry acetonitrile (50 mL), Intermediate 1 (2.08 g, 11.0 mmol) was added at rt and the reaction mixture was stirred at 80° C. overnight. The reaction mixture was concentrated under vacuum and the resulting crude product was purified by flash chromatography (50% EtOAC in pet ether) to afford the title compound (yellow solid). $^1$H NMR (400 MHz, DMSO-d$_6$): δ 8.75 (s, 2H), 6.90 (s, 1H), 6.85-6.83 (d, J=7.6 Hz, 1H), 6.75 (d, J=7.6 Hz, 1H), 6.05 (d, J=2.8 Hz, 1H), 5.91 (d, J=2.8 Hz, 1H), 4.28-4.23 (q, J=7.2 Hz, 2H), 3.82-3.81 (m, 4H), 3.49 (q, J=6.8 Hz, 1H), 2.55-2.44 (m, 2H), 2.43-2.33 (m, 2H), 1.29-1.24 (m, 6H). LCMS: (Method A) 385 (M+H), Rt. 3.23 min, 94.1% (Max). HPLC: (Method A) Rt. 3.23 min, 99.14% (Max).

Example 52: (2-(4-(1-(benzordiri,31 dioxol-5-yl)ethyl)piperazin-1-yl)pyrimidin-5-yl)methanol

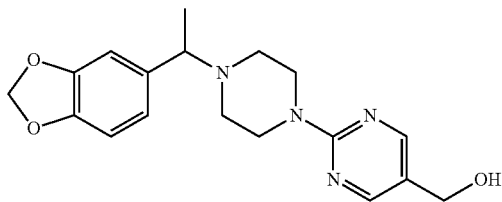 [SMILES: CC(c1ccc2c(c1)OCO2)N1CCN(c2ncc(CO)cn2)CC1]

The title compound was synthesized following general procedure A from Example 51. The crude product was purified by flash chromatography (30% EtOAc in pet ether) to afford the title compound (off white solid). $^1$H NMR (400 MHz, DMSO-d$_6$): δ 8.27 (s, 2H), 6.89 (s, 1H), 6.84 (d, J=8 Hz, 1H), 6.75 (d, J=8.0 Hz, 1H), 5.99 (m, 2H), 5.05 (t, J=5.2 Hz, 1H), 4.30 (d, J=5.2 Hz, 2H), 3.67 (s, 4H), 3.36-3.34 (m, 1H), 2.43-3.32 (m, 4H), 1.27 (d, J=6.8 Hz, 3H). LCMS: (Method A) 343.0 (M+H), Rt. 2.16 min, 95.05% (Max). HPLC: (Method A) Rt. 2.11 min, 97.35% (Max).

Example 53: 2-(4-(1-(2,3-dihydrobenzofuran-5-yl)ethyl)piperazin-1-yl)pyrimidine

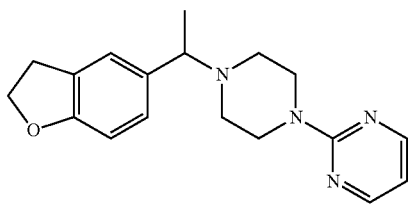 [SMILES: CC(c1ccc2c(c1)CCO2)N1CCN(c2ncccn2)CC1]

To a solution of 2-(piperazin-1-yl)pyrimidine (0.8 g, 4.8 mmol), diisopropylethylamine (3.0 mL, 5.7 mmol) in ACN (20 mL), Intermediate 5 (1.04 g, 5.7 mmol) was added at rt and the resulting mixture was stirred overnight. It was diluted with water (5 mL) and extracted with DCM (2×50 mL).

The combined organic layer was dried over Na$_2$SO$_4$ and concentrated under vacuum. The crude product was purified by MD Autoprep (Method B) to afford the title compound (white solid). $^1$H NMR (400 MHz, DMSO-d$_6$): δ 8.31 (d, J=4.8 Hz, 2H), 7.16 (s, 1H), 6.99 (d, J=8.4 Hz, 1H), 6.67 (d, J=8.0 Hz, 1H), 6.58 (t, J=4.8 Hz, 1H), 4.48 (t, J=8.8 Hz, 2H), 3.67 (m, 4H), 3.34 (t, J=6.8 Hz, 1H), 3.14 (m, 2H), 2.42-2.38 (m, 2H), 2.35-2.31 (m, 2H), 1.28 (d, J=6.8 Hz, 3H). LCMS: (Method A) 311.2 (M+H), Rt. 2.511 min, 98.68% (Max). HPLC: (Method A) Rt. 2.52 min, 99.82% (Max).

Example 54: N-(4-(4-(1-(Benzordiri,31dioxol-5-yl)ethyl)piperazin-1-yl)pyrimidin-2-vQacetamide

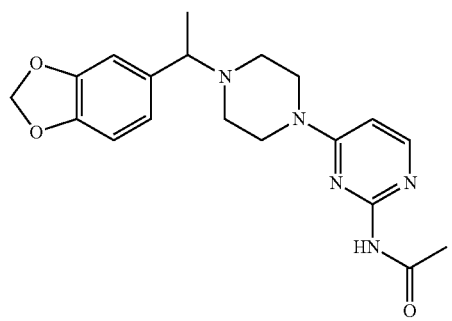 [SMILES: CC(=O)Nc1nccc(N2CCN(C(C)c3ccc4c(c3)OCO4)CC2)n1]

To a stirred solution of Example 46 (0.35 g, 1.0 mmol) in dry DCM (3.5 mL), pyridine (0.2 mL, 2.1 mmol), acetic anhydride (0.12 mL, 1.3 mmol) and DMAP (0.006 g, 0.5 mmol) were added at rt. The resulting mixture was stirred for 5 h at rt and overnight at 50° C. It was diluted with ethyl acetate (100 mL) and washed with HCl (1.5N), water, brine, dried over Na$_2$SO$_4$ and concentrated under vacuum. The resulting crude product was purified by MD Autoprep (Method C) to afford the title compound (off white solid). $^1$H NMR (400 MHz, MeOH-d$_4$): δ 7.99 (s, 1H), 6.88 (s, 1H), 6.77 (s, 2H), 6.54 (br. s, 1H), 5.93 (s, 2H), 3.71 (s, 4H), 3.40 (q, J=6.8 Hz, 1H), 2.61-2.57 (m, 2H), 2.51-2.47 (m, 2H), 2.24 (s, 3H), 1.38 (d, J=6.8 Hz, 3H). LCMS: (Method A) 370.2 (M+H), Rt. 1.88 min, 95.01% (Max). HPLC: (Method A) Rt. 1.83 min, 98.7% (Max).

Example 55: 1-(1-(benzordiri,31dioxol-5-yl)ethyl)-4-(5-nitropyridin-2-yl)piperazine

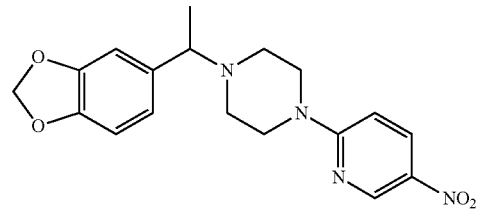 [SMILES: CC(c1ccc2c(c1)OCO2)N1CCN(c2ccc([N+](=O)[O-])cn2)CC1]

To a stirred solution of Intermediate 2 (0.2 g, 2.1 mmol), Et$_3$N (1.2 mL, 8.5 mmol) in dry DMF (5 mL), 2-chloro-5-nitropyridine (0.44 g, 2.8 mmol) was added at rt. The resulting mixture was stirred at 120° C. for 20 h. The completion of the reaction was monitored by TLC. The reaction mixture was diluted with water (10 mL) and extracted with EtOAc (25 mL). The organic layer was dried over anhydrous Na$_2$SO$_4$ and concentrated under vacuum. The resulting crude product was purified by flash chromatography to afford the title compound (yellow solid). ¹H NMR (400 MHz, DMSO-d₆): δ 8.93 (d, J=2.8 Hz, 1H), 8.19 (dd, J=9.6, 2.8 Hz, 1H), 6.91-6.89 (m, 2H), 6.85 (d, J=8.0 Hz, 1H), 6.76 (d, J=8.0 Hz, 1H), 5.99 (br s, 2H), 3.73 (s, 4H), 3.40 (q, J=6.4 Hz, 1H), 2.41-2.38 (m, 4H), 1.29 (d, J=6.4 Hz, 3H). LCMS: (Method A) 357.0 (M+H), Rt. 2.98 min, 96.03% (Max). HPLC: (Method A) Rt. 3.03 min, 95.35% (Max).

Example 56: (/?)-2-(4-(1-(Benzordiri,31dioxol-5-yl) ethyl)piperazin-1-yl)-N-methylthiazole^4-carboxamide or ^S)-2-(4-(1-(benzordiri,31dioxol-5-yl)ethyl) piperazin-1-yl)-N-methylthiazole^4-carboxamide

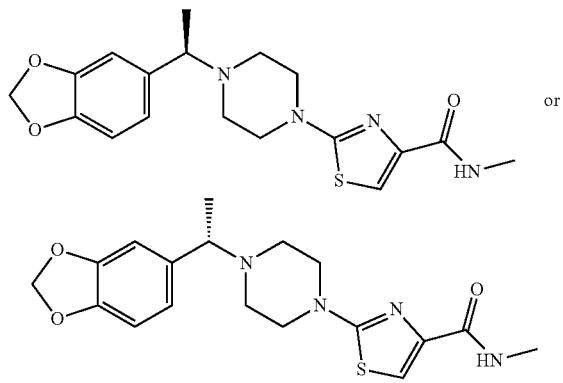

The two enantiomers of Example 30 were separated by chiral preparative HPLC (Method PG). The first eluting compound has a Rt. 15.74 min (white solid). ¹H NMR (400 MHz, DMSO-d₆): δ 7.99 (q, J=4.8 Hz, 1H), 7.34 (s, 1H), 6.90 (d, J=1.2 Hz, 1H), 6.85 (d, J=8.0 Hz, 1H), 6.76 (dd, J=8.0, 1.2 Hz, 1H), 5.99 (s, 2H), 3.50-3.42 (m, 5H), 2.72 (d, J=4.8 Hz, 3H), 2.50-2.49 (m, 4H), 1.29 (d, J=6.8 Hz, 3H). LCMS: (Method A) 375 (M+H), Rt. 2.35 min, 98.15% (Max). HPLC: (Method A) Rt. 2.38 min, 97.08% (Max), 96.58% (254 nm). Chiral HPLC: (Method E) Rt. 15.74 min, 100.00%. Example 56 corresponds to the second eluting compound, with Rt. 28.85 min (white solid). ¹HNMR (400 MHz, DMSO-d₆): δ 7.99 (q, J=4.8 Hz, 1H), 7.34 (s, 1H), 6.90 (d, J=1.2 Hz, 1H), 6.85 (d, J=7.6 Hz, 1H), 6.76 (dd, J=8.0, 1.2 Hz, 1H), 5.99 (s, 2H), 3.50-3.41 (m, 5H), 2.72 (d, J=4.8 Hz, 3H), 2.50-2.43 (m, 4H), 1.29 (d, J=6.8 Hz, 3H). LCMS: (Method A) 375.0 (M+H), Rt. 2.34 min, 99.94% (Max). HPLC: (Method A) Rt. 2.37 min, 99.77% (Max). Chiral HPLC: (Method E) Rt. 28.85 min, 100.00%

Example 57: (R)-2-(4-(1-(2,3-dihydrobenzorbin, 41dioxin-6-yl)ethyl)piperazin-1-yl)-N-methylthiazole-4-carboxamide or (S)-2-(4-(1-(2,3-dihydrobenzorbiri,41dioxin-6-yl)ethyl)piperazin-1-yl)-N-methylthiazole-4-carboxamide

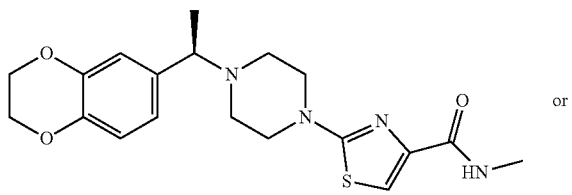

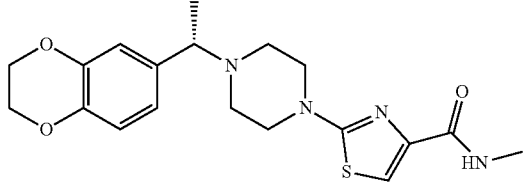

The two enantiomers of Example 50 were separated by chiral preparative HPLC (Method PG). The first eluting compound has a Rt. 16.29 min (yellow solid). ¹H NMR (400 MHz, DMSO-d₆): δ 7.98 (q, J=4.4 Hz, 1H), 7.34 (s, 1H), 6.81-6.74 (m, 3H), 4.22 (s, 4H), 3.42-3.39 (m, 5H), 2.73 (d, J=4.8 Hz, 3H), 2.48-2.41 (m, 4H), 1.27 (t, J=6.4 Hz, 3H). LCMS: (Method A). 389.0 (M+H), Rt. 2.40 min, 99.14% (Max). HPLC: (Method A) Rt. 2.36 min, 99.63% (Max). Chiral HPLC: (Method E) Rt, 16.29 min, 100% (max). Example 57 corresponds to the second eluting compound, with Rt. 33.49 min (yellow solid). ¹H NMR (400 MHz, DMSO-d₆): δ 7.98 (d, J=4.4 Hz, 1H), 7.34 (s, 1H), 6.81-6.74 (m, 3H), 4.21 (s, 4H), 3.42-3.37 (m, 5H), 2.73 (d, J=4.8 Hz, 3H), 2.46-2.41 (m, 4H), 1.26 (t, J=6.4 Hz, 3H). LCMS: (Method A). 389.0 (M+H), Rt. 2.34 min, 98.58% (Max). HPLC: (Method A) Rt. 2.37 min, 99.28% (Max). Chiral HPLC: (Method E) Rt. 33.49 min, 99.66% (max).

Example 58: 6-(4-(1-(Benzordiri,31dioxol-5-yl) ethyl)piperazin-1-yl)pyridin-3-amine

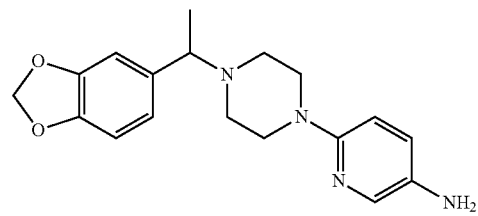

To a stirred solution of Example 55 (0.20 g, 5.6 mmol) in methanol (4.0 mL), Pd/C (0.02 g, 10% w/w) was added at rt and the mixture was stirred overnight under hydrogen atmosphere (5 Kg/cm²) at rt. The reaction mixture was filtered through celite and washed with methanol (10 mL). The organic layer was dried over anhydrous Na₂SO₄ and concentrated under vacuum. The resulted crude product was purified by MD Autoprep (Method C) to afford the title compound (dark oil). ¹H NMR (400 MHz, DMSO-d₆): δ 7.57 (d, J=2.8 Hz, 1H), 6.90-6.88 (m, 2H), 6.84 (d, J=8.0 Hz, 1H), 6.76 (d, J=8.0 Hz, 1H), 6.57 (d, J=8.8 Hz, 1H), 5.98 (m, 2H), 4.55 (s, 2H), 3.33 (br m, 1H), 3.18 (s, 4H), 2.38-2.36 (m, 4H), 1.27 (d, J=6.4 Hz, 3H). LCMS: (Method A) 327.2 (M+H), Rt. 1.85 min, 98.76% (Max). HPLC: (Method A) Rt. 1.81 min, 99.66% (Max).

Example 59 and Example 60: (R)-2-(4-(1-(Benzo-rdiri,31dioxol-5-yl)ethyl)piperazin-1-yl)-N-ethylthiazole-5-carboxamide and (S)-2-(4-(1-(benzordiri,31dioxol-5-yl)ethyl)piperazin-1-yl)-N-ethylthiazole-5-carboxamide

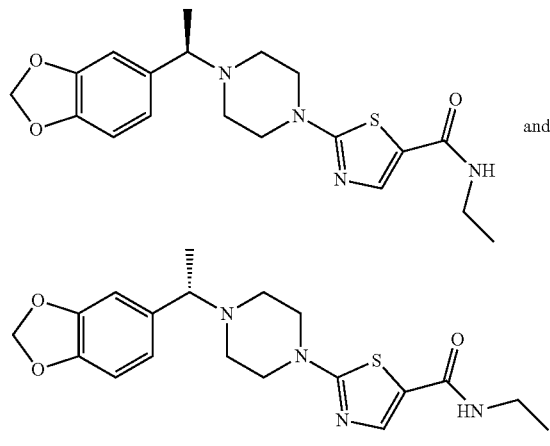

and

Step 1: Lithium 2-(4-(1-(benzo[d][1,3]dioxol-5-yl)ethyl)piperazin-1-yl)thiazole-5-carboxylate To a stirred solution of Example 27 (1.8 g, 3.86 mmol) in THF (14 mL) MeOH (4 mL) and H$_2$O (2 mL) was added LiOH.H$_2$O (395 mg, 9.65 mmol). The reaction mixture was stirred at 50° C. for 3 h.

The completion of the reaction was monitored by TLC. The reaction mixture was concentrated under vacuum. The resulting crude product was suspended in toluene and the solvents were evaporated again. It was used in the next step without any further purification. Yield: 89% (1.5 g, off white solid). $^1$H NMR (400 MHz, DMSO-d$_6$): δ 7.73 (s, 1H), 6.88-6.82 (m, 2H), 6.75-6.73 (m, 1H), 5.97 (s, 2H), 3.67-3.32 (m, 5H), 2.87-2.59 (m, 4H), 1.32-1.15 (m, 3H). LCMS: (Method A) 362.0 (M+H), Rt. 2.26 min, 88.6% (Max).

Step 2: (R)-2-(4-(1-(Benzo[d][1,3]dioxol-5-yl)ethyl)piperazin-1-yl)-N-ethylthiazole-5-carboxamide and (S)-2-(4-(1-(benzo[d][1,3]dioxol-5-yl)ethyl)piperazin-1-yl)^-ethylthiazole-5-carboxamide To a stirred solution of lithium 2-(4-(1-(benzo[d][1,3]dioxol-5-yl)ethyl)piperazin-1-yl)thiazole-5-carboxylate (500 mg, 1.33 mmol) in DMF (10 mL), DIPEA (0.7 mL, 3.99 mmol), ethyl amine (2 M in THF, 1 mL, 2.00 mmol) and HATU (607 mg, 1.60 mmol) were added at 0° C. The reaction mixture was stirred at room temperature overnight. The reaction mixture was concentrated under vacuum and diluted with DCM. It was washed with water, brine and dried over anhydrous Na$_2$SO$_4$. The crude product was purified by flash chromatography. Both enantiomers were separated by chiral preparative HPLC (Method PF). Example 59 corresponds to the first eluting compound with a Rt. 17.99 min (white solid). $^1$H NMR (400 MHz, DMSO-d$_6$): δ 8.19 (t, J=5.6 Hz, 1H), 7.74 (s, 1H), 6.90 (s, 1H), 6.85 (d, J=8.0 Hz, 1H), 6.76 (d, J=6.4 Hz, 1H), 5.99 (s, 2H), 3.21-3.17 (m, 2H), 2.48-2.39 (m, 4H), 1.28 (d, J=6.4 Hz, 3H), 1.07 (t, J=7.2 Hz, 3H). LCMS: (Method A) 389.2 (M+H), Rt. 2.47 min, 97.4% (Max). HPLC: (Method A) Rg. 2.43 min, 99.9% (Max). Chiral HPLC: (Method D) Rt. 17.99 min, 100.00%. Example 60 corresponds to the second eluting compound with a Rt. 19.92 min (white solid). $^1$H NMR (400 MHz, DMSO-d$_6$): δ 8.19 (t, J=5.6 Hz, 1H), 7.74 (s, 1H), 6.90 (s, 1H), 6.85 (d, J=8.0 Hz, 1H), 6.76 (d, J=6.8 Hz, 1H), 5.99 (s, 2H), 3.21-3.17 (m, 2H), 2.48-2.33 (m, 4H), 1.28 (d, J=6.8 Hz, 3H), 1.07 (t, J=7.2 Hz, 3H). LCMS: (Method A) 389.0 (M+H), Rt. 2.46 min, 99.3% (Max). HPLC: (Method A) Rt. 2.43 min, 99.9% (Max). Chiral HPLC: (Method D) Rt. 19.92 min, 100.00%.

Example 61: (R)-2-(4-(1-(benzofdlH,31dioxol-5-yl)ethyl)piperazin-1-yl)-N,N-dimethylthiazole-5-carboxamide or (S)-2-(4-(1-(benzordlH,31dioxol-5-yl)ethyl)piperazin-1-yl)-N,N-dimethylthiazole-5-carboxamide

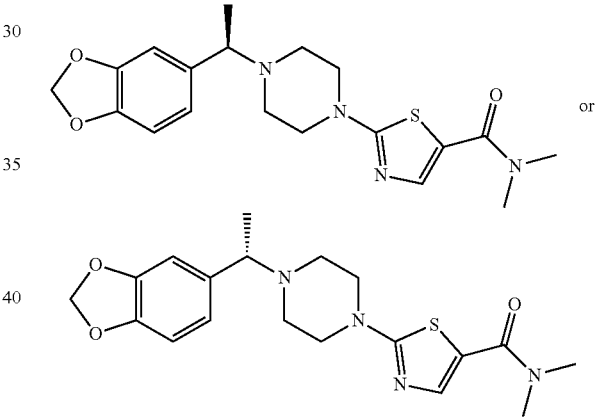

or

The two enantiomers of Example 47 were separated by chiral preparative HPLC (Method PF). The first eluting compound has a Rt. 14.07 min (white solid). $^1$H NMR (400 MHz, DMSO-d$_6$): δ 7.58 (s, 1H), 6.90 (s, 1H), 6.85 (s, 1H), 6.76 (s, 1H), 5.99 (s, 2H), 3.44-3.42 (m, 5H), 3.07 (br m, 6H), 2.47-2.39 (m, 4H), 1.28 (d, J=6.8 Hz, 3H). LCMS: (Method A) 389.0 (M+H), Rt. 2.39 min, 99.5% (Max). HPLC: (Method A) Rt. 2.37 min, 99.6% (Max). Chiral HPLC: (Method D) Rt. 14.07 min, 100.00%. Example 61 corresponds to the second eluting compound with Rt. 16.06 min (white solid). $^1$H NMR (400 MHz, DMSO-d$_6$): δ 7.58 (s, 1H), 6.90 (s, 1H), 6.85 (s, 1H), 6.76 (s, 1H), 5.99 (s, 2H), 3.44-3.42 (m, 5H), 3.07 (br m, 6H), 2.50-2.39 (m, 4H), 1.28 (d, J=6.4 Hz, 3H). LCMS: (Method A) 389.2 (M+H), Rt. 2.44 min, 95.3% (Max). HPLC: (Method A) Rt. 2.37 min, 99.9% (Max). Chiral HPLC: (Method D) Rt. 16.06 min, 99.7%.

Example 62: (S)-2-(4-(1-(2,3-dihydrobenzorbiri,
41dioxin-6-yl)ethyl)piperazin-1-yl)-N-ethylthiazole-
5-carboxamide or (R)-2-(4-(1-(2,3-dihydrobenzor-
bIH,41dioxin-6-yl)ethyl)piperazin-1-yl)-N-
ethylthiazole-5-carboxamide

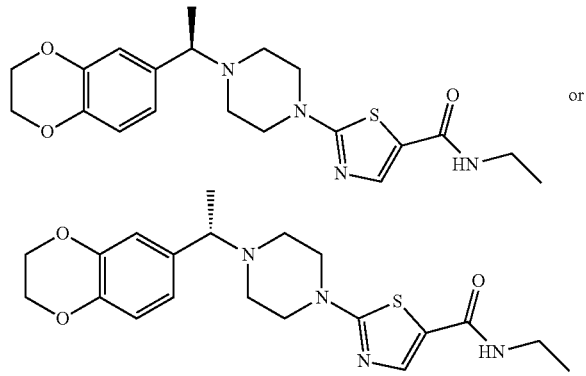

Step 1: Ethyl 2-(4-(1-(2,3-dihydrobenzo[b][1,4]
dioxin-6-yl)ethyl)piperazin-1-yl)thiazole-5-carboxy-
late To a stirred solution of Intermediate 4 (3.4 g, 11.94 mmol) in dry DMF (50 mL), ethyl 2-bromothiazole-5-carboxylate (Example 27, Step 1, 2.8 g, 11.94 mmol) and TEA (5.0 mL, 35.82 mmol) were added at 0° C. The resulting mixture was stirred at 120° C. overnight. It was cooled to rt, diluted with EtOAc, washed with water, brine, dried over anhydrous $Na_2SO_4$ and concentrated under vacuum. The resulting crude product was purified by flash chromatography to afford the title compound. Yield: 64% (3.1 g, pale brown solid). $^1$H NMR (400 MHz, DMSO-$d_6$): δ 7.81 (s, 1H), 6.79-6.74 (m, 3H), 4.19-4.14 (m, 7H), 3.48-3.32 (m, 4H), 2.42-2.36 (m, 4H), 1.26-1.19 (m, 6H). LCMS: (Method A) 404.0 (M+H), Rt. 3.19 min, 96.5% (Max).

Step 2: Lithium 2-(4-(1-(2,3-dihydrobenzo[b][1A]
dioxin-6-yl)ethyl)piperazin-1-yl)thiazole-5-carboxy-
late The title compound was synthesized according to the protocol described for Example 60, Step 1, using ethyl 2-(4-(1-(2,3-dihydrobenzo[b][1,4]dioxin-6-yl)ethyl)piper-azin-1-yl)thiazole-5-carboxylate as starting material. The resulting product was used in the next step without further purification. Yield: 86% (2.5 g, off white solid). $^1$H NMR (400 MHz, DMSO-$d_6$): δ 7.16 (s, 1H), 6.79-6.72 (m, 3H), 4.20 (s, 4H), 3.34-3.29 (m, 5H), 2.44-2.28 (m, 4H), 1.24 (d, J=8.8 Hz, 3H). LCMS: (Method A) 376.0 (M+H), Rt. 2.34 min, 97.4% (Max).

Step 3: (S)-2-(4-(1-(2,3-dihydrobenzo[b][1A]dioxin-
6-yl)ethyl)piperaz^-yl)-N-ethylthiazole-5-carboxam-
ide or (R)-2-(4-(1-(2,3-dihydrobenzo[b][1,4]dioxin-
6-yl)ethyl)piperazin-1-yl)-N-ethylthiazole-5-
carboxamide The title compound was synthesized according to the protocol described for Example 60, Step 2, using lithium 2-(4-(1-(2,3-dihydrobenzo[b][1,4]dioxin-6-yl)ethyl)piper-azin-1-yl)thiazole-5-carboxylate as starting material. The crude mixture was purified by flash chromatography followed by chiral preparative HPLC (Method PE) to separate both enantiomers. The first fraction was concentrated to give Example 62 (Rt. 19.00 min) (white solid). $^1$H NMR (400 MHz, DMSO-$d_6$): δ 8.19 (t, J=5.2 Hz, 1H), 7.74 (s, 1H), 6.81-6.74 (m, 3H), 4.22 (s, 4H), 3.42-3.35 (m, 5H), 3.22-3.16 (m, 2H), 2.50-2.33 (m, 4H), 1.27 (d, J=6.8 Hz, 3H), 1.07 (t, J=7.2 Hz, 3H). LCMS: (Method A) 403.0 (M+H), Rt. 2.50 min, 98.4% (Max). HPLC: (Method A) Rt. 2.47 min, 98.2% (Max). Chiral HPLC: (Method A) Rt. 19.00 min, 100%. The second enantiomer had a Rt. 29.37 min (white solid). $^1$H NMR (400 MHz, DMSO-$d_6$): δ 8.19 (t, J=5.6 Hz, 1H), 7.74 (s, 1H), 6.81-6.74 (m, 3H), 4.22 (s, 4H), 3.42-3.37 (m, 5H), 3.22-3.17 (m, 2H), 2.50-2.41 (m, 4H), 1.27 (d, J=6.4 Hz, 3H), 1.07 (t, J=7.2 Hz, 3H). LCMS: (Method A) 403.2 (M+H), Rt. 2.51 min, 99.6% (Max). HPLC: (Method A) Rt. 2.47 min, 98.9% (Max). Chiral HPLC: (Method A) Rt. 29.37 min, 100%.

Example 63 and Example 64: (R)-2-(4-(1-(2,3-di-
hydrobenzorbiri,41dioxin-6-yl)ethyl)piperazin-1-yl)-
N,N-dimethylthiazole-5-carboxamide and (S)-2-(4-
(1-(2,3-dihydrobenzorbin,41dioxin-6-yl)ethyl)
piperazin-1-yl)-N,N-dimethylthiazole-5-
carboxamide

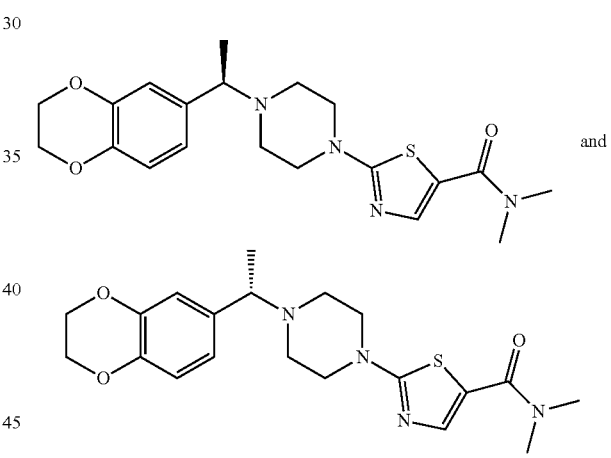

The title compounds were synthesized according to the protocol described for Example 59 and Example 60, Step 2, using lithium 2-(4-(1-(2,3-dihydrobenzo[b][1,4]dioxin-6-yl) ethyl)piperazin-1-yl)thiazole-5-carboxylate (Example 62, Step 2) and dimethyl amine as starting material. The crude mixture was purified by flash chromatography. Both enantiomers were separated by chiral preparative HPLC (Method PF). The first fraction corresponds to Example 63 (Rt. 17.78 min) (white solid). $^1$H NMR (400 MHz, DMSO-$d_6$): δ 7.58 (s, 1H), 6.81-6.75 (m, 3H), 4.22 (s, 4H), 3.44-3.38 (m, 5H), 3.06 (br. s, 6H), 2.47-2.39 (m, 4H), 1.27 (d, J=6.8 Hz, 3H). LCMS: (Method A) 403.0 (M+H), Rt. 2.42 min, 99.3% (Max). HPLC: (Method A) Rt. 2.41 min, 99.6% (Max). Chiral HPLC: (Method D) Rt. 17.78 min, 100.00%. The second fraction corresponds to Example 64 (Rt. 21.09 min) (white solid). $^1$H NMR (400 MHz, DMSO-$d_6$): δ 7.58 (s, 1H), 6.81-6.77 (m, 3H), 4.22 (s, 4H), 3.44-3.38 (m, 5H), 3.12-2.99 (m, 6H), 2.46-2.39 (m, 4H), 1.27 (d, J=6.40 Hz, 3H). LCMS: (Method A) 403.0 (M+H), Rt. 2.43 min, 99.8%

(Max). HPLC: (Method A) Rt. 2.40 min, 99.8% (Max). Chiral HPLC: (Method D) Rt. 21.09 min, 97.38%.

Example 65 and Example 66: (R)-2-(4-(1-(benzordin,31dioxol-5-yl)ethyl)piperazin-1-yl)-N-methylthiazole-5-carboxamide and (S)-2-(4-(1-(benzordiri,31 dioxol-5-yl)ethyl)piperazin-1-yl)-N-methylthiazole-5-carboxamide

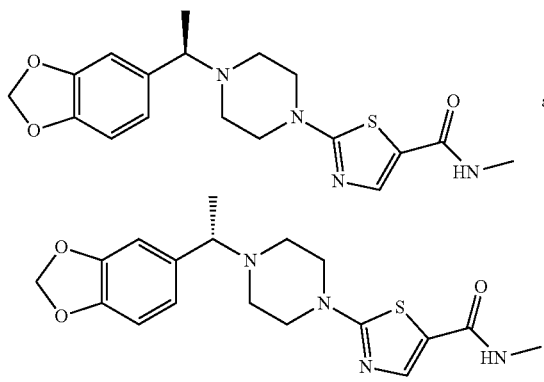

The title compounds were synthesized according to the procedure described for Example 59 and Example 60 using methyl amine (2M in THF) as reagent. The crude mixture was purified by flash chromatography followed by chiral preparative HPLC (Method PF) to separate enantiomers. The first fraction was concentrated to give Example 65 (white solid). 1H NMR (400 MHz, DMSO-$d_6$): 8.16 (d, J=4.4 Hz, 1H), 7.72 (s, 1H), 6.89 (s, 1H), 6.85 (d, J=7.6 Hz, 1H), 6.76 (d, J=8.0 Hz, 1H), 5.99 (br s, 2H), 3.43-3.42 (m, 5H), 2.69 (d, J=4.4 Hz, 3H), 2.47-2.33 (m, 4H), 1.28 (d, J=6.4 Hz, 3H). LCMS: (Method A) 375.0 (M+H), Rt. 2.23 min, 99.0% (Max). HPLC: (Method A) Rt. 2.19 min, 99.6% (Max). Chiral HPLC: (Method D) Rt. 15.48 min, 98.91%.

The second fraction was concentrated to give Example 66 (white solid). 1H NMR (400 MHz, DMSO-$d_6$): δ 8.16 (q, J=4.8 Hz, 1H), 7.72 (s, 1H), 6.90 (s, 1H), 6.85 (d, J=8.0 Hz, 1H), 6.76 (d, J=8.0 Hz, 1H), 5.99 (br s, 2H), 3.43-3.41 (m, 5H), 2.69 (d, J=4.8 Hz, 3H), 2.48-2.39 (m, 4H), 1.28 (d, J=6.8 Hz, 3H). LCMS: (Method A) 375.0 (M+H), Rt. 2.23 min, 97.4% (Max). HPLC: (Method A) Rt. 2.19 min, 96.9% (Max). Chiral HPLC: (Method D) Rt. 18.44 min, 100.00%

Example 67: (2-(4-(1-(Benzordiri.31 dioxol-5-vhethvnpiperazin-1-vnthiazol-5-yl)(morpholino)methanone

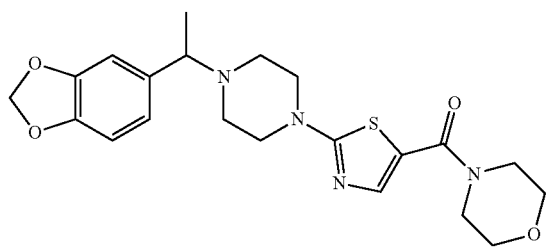

The title compound was synthesized according to the procedure described for Example 59 and Example 60 using morpholine as reagent. Both enantiomers were not separated in this example (pale brown solid). $^1$H NMR (400 MHz, DMSO-$d_6$): δ 7.55 (s, 1H), 6.90 (s, 1H), 6.85 (d, J=8.0 Hz, 1H), 6.76 (d, J=7.6 Hz, 1H), 5.99 (s, 2H), 3.61 (br m, 8H), 3.45-3.42 (m, 5H), 2.47-2.40 (m, 4H), 1.29 (d, J=6.4 Hz, 3H). LCMS: (Method A) 431.0 (M+H), Rt. 2.41 min, 98.6% (Max). HPLC: (Method A) Rt. 2.38 min, 97.1% (Max).

Example 68 and Example 69: (R)—N-(5-(4-(1-(benzordin,31dioxol-5-yl)ethyl)piperazin-1-yl)-1,3,4-thiadiazol-2-yl)acetamide and (S)—N-(5-(4-(1-(benzofdlH,31dioxol-5-yl)ethyl)piperazin-1-yl)-1,3,4-thiadiazol-2-yl)acetamide

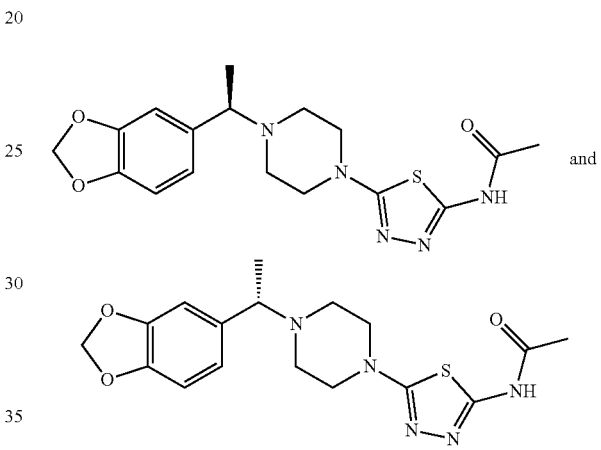

To a stirred solution of Example 41 (0.6 g, 1.8 mmol) in dry DCM (10 mL), acetic anhydride (0.22 mL, 2.3 mmol) and DIPEA (0.615 mL, 3.6 mmol) were added at 0° C. and the reaction mixture was stirred at room temperature for 4 h. It was concentrated under vacuum and the crude product was purified by recrystallization followed by enantiomer separation by SFC. The first fraction was collected as Example 68 (off white solid). $^1$H NMR (400 MHz, DMSO-$d_6$): δ 11.66 (br s, 1H), 6.89 (s, 1H), 6.85 (d, J=8.0 Hz, 1H), 6.76 (d, J=8.0 Hz, 1H), 5.99 (m, 2H), 3.42-3.34 (m, 5H), 2.51-2.50 (m, 2H), 2.43-2.33 (m, 2H), 2.09 (s, 3H), 1.27 (d, J=6.4 Hz, 3H). LCMS: (Method A) 376.0 (M+H), Rt. 2.27 min, 97.4% (Max). HPLC: (Method A) Rt. 2.29 min, 98.2% (Max). HPLC chiral purity: (Method D) Rt. 24.02 min, 99.3% (Max). The second fraction was collected as Example 69 (off white solid). $^1$H NMR (400 MHz, DMSO-$d_6$): δ 11.66 (br s, 1H), 6.89 (s, 1H), 6.85 (d, J=8.0 Hz, 1H), 6.76 (dd, J=8.0, 1.2 Hz, 1H), 5.99 (m, 2H), 3.41-3.34 (m, 5H), 2.55-2.47 (m, 2H), 2.43-2.39 (m, 2H), 2.09 (s, 3H), 1.27 (d, J=6.4 Hz, 3H). LCMS: (Method A) 376.0 (M+H), Rt. 2.28 min, 95.8% (Max). HPLC: (Method A) Rt. 2.29 min, 97.1% (Max). HPLC chiral purity: (Method D) Rt. 26.57 min, 97.5% (Max).

Example 70: 2-(4-(1-(Benzord in,31dioxol-5-yl)ethyl)piperazin-1-yl)pyrimidin-5-amine

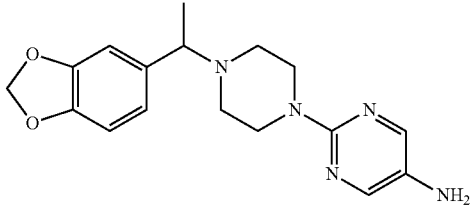 [SMILES: CC(c1ccc2c(c1)OCO2)N1CCN(c2ccc(N)cn2)CC1]

Step 1: 2-(4-(1-(Benzo[d][1,3]dioxol-5-yl)ethyl)piperazin-1-yl)-4-nitropyrimidine To a stirred solution of Intermediate 2 (1 g, 4.2 mmol) in dry DMF (10 ml_), Et₃N (2.3 ml, 16.8 mmol) and 2-chloro-5-nitropyrimidine (0.74 g, 4.6 mmol) were added at rt and the resulting mixture was stirred at 120° C. for 20 h. It was diluted with water and extracted with EtOAc. The organic layer was dried over anhydrous $Na_2SO_4$ and concentrated under vacuum. The resulting crude product was purified by flash chromatography to give the title compound (yellow solid). ¹H NMR (400 MHz, DMSO-d₆): δ 9.08 (s, 2H), 6.92 (s, 1H), 6.85-6.83 (m, 1H), 6.77 (s, 1H), 5.98 (m, 2H), 3.89 (s, 4H), 3.50 (s, 1H), 2.45-2.44 (m, 4H), 1.30 (br s, 3H). LCMS: (Method A) 358.0 (M+H), Rt. 3.00 min, 94.23% (Max).

Step 2: 2-(4-(1-(Benzo[d][1,3]dioxol-5-yl)ethyl)piperazin-1-yl)pyrimidin-5-amine To a stirred solution of 2-(4-(1-(benzo[d][1,3]dioxol-5-yl)ethyl)piperazin-1-yl)-4-nitropyrimidine (0.70 g, 1.9 mmol) in methanol (14 ml_), Pd/C (0.07 g, 10% w/w) was added at rt and the resulting mixture was stirred under hydrogen atmosphere (5 kg/cm²) overnight at rt. The reaction mixture was filtered through celite and washed with methanol. The filtrate was dried over anhydrous $Na_2SO_4$ and concentrated under vacuum. The crude product was purified by flash chromatography to afford the title compound (yellow solid). ¹H NMR (400 MHz, DMSO-d₆): δ 7.86 (s, 2H), 6.88 (s, 1H), 6.84 (d, J=8.0 Hz, 1H), 6.75 (d, J=7.6 Hz, 1H), 6.46 (s, 2H), 5.98 (m, 2H), 3.48-3.45 (m, 4H), 2.43-2.42 (m, 2H), 2.34-2.31 (m, 2H), 1.27 (d, J=6.8 Hz, 3H). LCMS: (Method A) 328.2 (M+H), Rt. 1.91 min, 96.83% (Max). HPLC: (Method A) Rt. 1.88 min, 95.85% (Max).

Example 71: (R)-2-(4-(1-(2,3-Dihydrobenzorb1H,41dioxin-6-yl)ethyl)piperazin-1-yl)-N-(2-(dimethylamino)ethyl)-N-methylthiazole-5-carboxamide or (S)-2-(4-(1-(2,3-dihydrobenzorbiri^1dioxin-6-yl)ethyl)piperazin-1-yl)-N-(2-(dimethylamino)ethyl)-N-methylthiazole-5-carboxamide

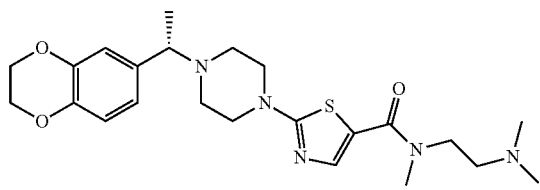 or 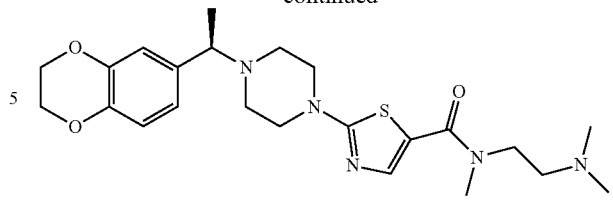

The title compound was synthesized according to the procedure described for Example 62, using N,N,N trimethyl ethylene diamine as reagent. The crude product was purified by flash chromatography, followed by chiral preparative HPLC using (Method PF) to separate both enantiomers. The first eluting compound had Rt. 14.56 min (pale brown oil). ¹H NMR (400 MHz, DMSO-d₆): δ 7.57 (s, 1H), 6.80-6.73 (m, 3H), 4.21 (s, 4H), 3.52 (t, J=6.4 Hz, 2H), 3.50-3.38 (m, 5H), 3.16-3.11 (m, 3H), 2.56-2.50 (m, 1H), 2.49-2.38 (m, 5H), 2.32-2.10 (m, 6H), 1.26 (d, J=6.8 Hz, 3H). LCMS: (Method A) 460.2 (M+H), Rt. 2.12 min, 95.2% (Max). HPLC: (Method A) Rt. 2.02 min, 96.9% (Max). Chiral HPLC: (Method D) Rt. 14.56 min, 97.43%. The second eluting compound corresponds to Example 71 (Rt. 16.81 min) (pale brown oil). ¹H NMR (400 MHz, DMSO-d₆): δ 7.56 (s, 1H), 6.80-6.73 (m, 3H), 4.21 (s, 4H), 3.50 (t, J=6.8 Hz, 2H), 3.48-3.36 (m, 5H), 3.09 (br. s, 3H), 2.55-2.50 (m, 1H), 2.49-2.38 (m, 5H), 2.13 (s, 6H), 1.26 (d, J=6.8 Hz, 3H). LCMS: (Method A) 460.2 (M+H), Rt. 2.13 min, 95.4% (Max). HPLC: (Method A) Rt. 2.03 min, 97.5% (Max). Chiral HPLC: (Method D) Rt. 16.81 min, 98.36%.

Example 72: N-(2-(4-(1-(benzordlH,31dioxol-5-yl)ethyl)piperazin-1-yl)pyrimidin-5-yl)acetamide

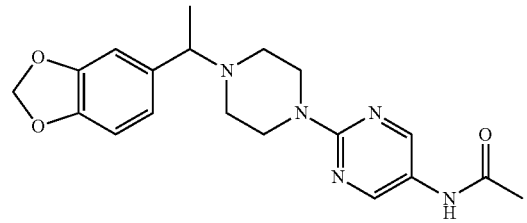 [SMILES: CC(=O)Nc1cnc(N2CCN(C(C)c3ccc4c(c3)OCO4)CC2)nc1]

To a stirred solution of Example 70 (180 mg, 0.54 mmol) in dry pyridine (1.35 mL), acetic anhydride (0.06 mL, 0.65 mmol) was added at room temperature and the resulting mixture was stirred at 50° C. overnight. It was diluted with ethyl acetate (100 mL) and washed with HCl (1.5 N), water, brine and dried over $Na_2SO_4$. After evaporation of the solvents, the crude product was purified by flash chromatography to afford the title compound (yellow solid). ¹H NMR (400 MHz, DMSO-d₆): δ 9.82 (s, 1H), 8.46 (d, J=0.4 Hz, 2H), 6.89 (s, 1H), 6.84 (d, J=7.6 Hz, 1H), 6.76 (d, J=7.6 Hz, 1H), 5.98 (m, 2H), 3.64-3.62 (m, 4H), 3.36-3.34 (m, 1H), 2.45-2.32 (m, 4H), 2.00 (s, 3H), 1.25 (d, J=6.8 Hz, 3H). LCMS: (Method A) 370.2 (M+H), Rt. 2.30 min, 94.42% (Max). HPLC: (Method A) Rt. 2.22 min, 95.29% (Max).

183

Example 73: (2-(4-(1-(2,3-Dihydrobenzo[b][1,4]di-oxin-6-yl)ethyl)piperazin-1-yl)thiazol-5-yl)(4-hydroxypiperidin-1-yl)methanone

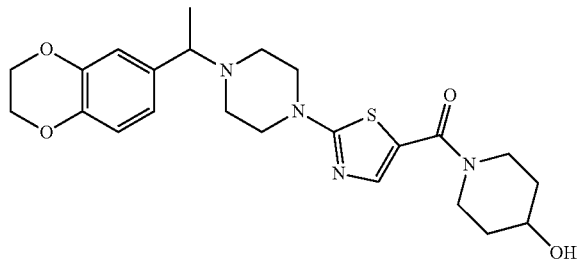 [SMILES: CC(c1ccc2c(c1)OCCO2)N1CCN(c2ncc(C(=O)N3CCC(O)CC3)s2)CC1]

Step 1: 1-(2-(4-(1-(2,3-dihydrobenzo[b][1,4]dioxin-6-yl)ethyl)piperazin-1-yl)thiazole-5-carbonyl) piperidin-4-one The title compound was synthesized according to the same procedure as described for Example 62 using piperidine-4-one, hydrochloride, mono hydrate as starting material (off white solid). 1H NMR (400 MHz, DMSO-d$_6$): δ 7.61 (s, 1H), 6.81-6.77 (m, 3H), 4.22 (s, 4H), 3.89 (t, J=6.1 Hz, 4H), 3.71 (t, J=6.1 Hz, 1H), 3.60 (t, J=4.2 Hz, 4H), 2.34-2.33 (m, 8H), 1.27 (d, J=6.7 Hz, 3H). LCMS: (Method A) 457.0 (M+H), Rt. 2.42 min, 90.5% (Max).

Step 2: (2-(4-(1-(2,3-Dihydrobenzo[b][1,4]dioxin-6-yl)ethyl)piperazin-1-yl)thiazol-5-yl)(4-hydroxy'piperidin-1-yl)methanone To a stirred solution of 1-(2-(4-(1-(2,3-dihydrobenzo[b][1,4]dioxin-6-yl)ethyl)piperazin-1-yl)thiazole-5-carbonyl) piperidin-4-one (480 mg, 1.0 mmol) in dry MeOH (100 mL), NaBH$_4$ (59 mg, 1.5 mmol) was added slowly at 0° C. The reaction mixture was stirred at room temperature for 2 h. It was then concentrated under vacuum and the resulting crude product was dissolved in DCM, washed with water, brine and dried over anhydrous Na$_2$SO$_4$. The solvent was removed under reduced pressure to get the title compound. Yield: 69% (325 mg, off white solid). $^1$H NMR (400 MHz, DMSO-d$_6$): δ 7.48 (s, 1H), 6.80-6.73 (m, 3H), 4.78 (br. s, 1H), 4.21 (s, 4H), 3.92-3.88 (m, 2H), 3.72 (br s, 1H), 3.42-3.35 (m, 4H), 3.33-3.25 (m, 2H), 2.46-2.38 (m, 4H), 1.75-1.74 (m, 2H), 1.34-1.31 (m, 2H), 1.25 (d, J=6.8 Hz, 3H). LCMS: (Method A) 459.0 (M+H), Rt. 2.32 min, 95.8% (Max). HPLC: (Method A) Rt. 2.33 min, 97.7% (Max).

184

Example 74 and Example 75: (R)-(2-(4-(1-(2,3-dihydrobenzo[b][1,4]dioxin-6-yl)ethyl)piperazin-1-yl)thiazol-5-yl)(4-methylpiperazin-1-yl)methanone and (S)-(2-(4-(1-(2,3-dihydrobenzo[b][1,4]dioxin-6-yl)ethyl)piperazin-1-yl)thiazol-5-yl)(4-methylpiperazin-1-yl)methanone

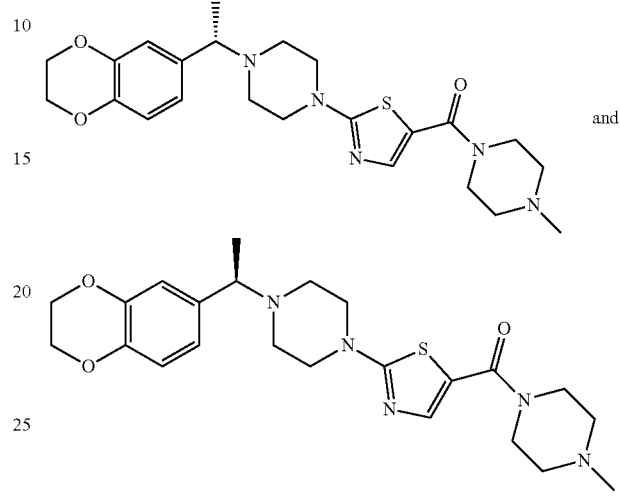

and

The title compounds were synthesized according to the same procedure as described for Example 62, using N-methyl piperazine as starting material. The crude mixture was purified by column chromatography followed by chiral preparative HPLC using (Method PF) to separate both enantiomers. The first eluting fraction was concentrated to give Example 74 (off white solid). $^1$H NMR (400 MHz, DMSO-d$_6$): δ 7.52 (s, 1H), 6.81-6.77 (m, 3H), 4.22 (s, 4H), 3.60 (br. s, 4H), 3.43-3.38 (m, 5H), 2.45-2.33 (m, 8H), 2.19 (s, 3H), 1.27 (d, J=6.4 Hz, 3H). LCMS: (Method A) 458.2 (M+H), Rt. 2.02 min, 99.2% (Max). HPLC: (Method A) Rt. 2.01 min, 99.7% (Max). Chiral HPLC: (Method D) Rt. 14.95 min, 98.36%. The second eluting fraction was concentrated to give Example 75 (pale brown oil). $^1$H NMR (400 MHz, DMSO-d$_6$): δ 7.52 (s, 1H), 6.81-6.74 (m, 3H), 4.22 (s, 4H), 3.60-3.59 (m, 4H), 3.43-3.37 (m, 5H), 2.50-2.31 (m, 8H), 2.19 (s, 3H), 1.27 (d, J=6.4 Hz, 3H). LCMS: (Method A) 458.2 (M+H), Rt. 2.02 min, 98.3% (Max). HPLC: (Method A) Rt. 2.01 min, 99.2% (Max). Chiral HPLC: (Method D) Rt. 17.10 min, 97.39%.

Example 76: N-(5-(4-(1-(3,4-difluorophenyl)ethyl)piperazin-1-yl)-1,3,4-thiadiazol-2-yl)acetamide

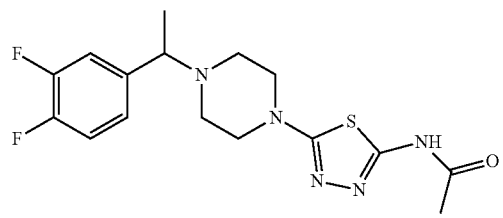 [SMILES: CC(=O)Nc1nnc(N2CCN(C(C)c3ccc(F)c(F)c3)CC2)s1]

Step 1: 1-(3,4-Difluorophenyl)ethan-1-ol

To a stirred solution of 1-(3,4-difluorophenyl)ethan-1-one (2.0 g, 12.81 mmol, Combi Blocks) in dry MeOH (40.0 mL), sodium borohydride (0.58 g, 15.32 mmol, Loba chemie) was added portion wise at 0° C. The reaction mixture was stirred at rt for 4 h. The reaction mixture was concentrated. The residue was dissolved in DCM, washed with water, brine solution, dried over anhydrous sodium sulfate and concentrated to afford the title compound. Yield: 98% (2.0 g, colorless liquid). $^1$H NMR (400 MHz, DMSO-$d_6$): δ 7.38-7.29 (m, 2H), 7.17-7.13 (m, 1H), 5.31 (d, J=5.9 Hz, 3H), 4.68 (q, J=8.3 Hz, 1H), 1.27 (d, J=8.3 Hz, 3H).

Step 2: 4-(1-chloroethyl)-1,2-difluorobenzene

To a stirred solution of 1-(3,4-difluorophenyl)ethan-1-ol (2.0 g, 12.64 mmol) in dry DCM (100.0 mL), thionyl chloride (1.9 mL, 34.81 mmol, Spectrochem) was added slowly at 0° C. The reaction mixture was stirred at rt for 1 h. The completion of the reaction was monitored by TLC. The reaction mixture was concentrated and resulting crude product was taken as such for next step. Yield: 90% (2.0 g, colorless liquid). $^1$H NMR (400 MHz, DMSO-$d_6$): δ 7.64-7.58 (m, 1H), 7.48-7.41 (m, 1H), 7.37-7.34 (m, 1H), 5.36 (q, J=6.6 Hz, 1H), 1.78 (d, J=6.6 Hz, 3H).

Step 3: N-(5-(4-(1-(3A-difluorophenyl)ethyl)piperazin-1-yl)-1,3A-thiadiazol-2-yl)acetamide The title compound was synthesized by using general procedure D, using 4-(1-chloroethyl)-1,2-difluorobenzene and Intermediate 7 as starting materials. The crude product was purified by flash chromatography (off white solid). 1H NMR (400 MHz, DMSO-$d_6$): δ 12.02 (s, 1H), 7.42-7.35 (m, 2H), 7.18-7.16 (m, 1H), 3.53 (q, J=6.4 Hz, 1H), 3.36-3.34 (m, 4H), 2.51-2.40 (m, 4H), 2.09 (s, 3H), 1.30 (d, J=6.4 Hz, 3H). LCMS: (Method A) 368.0 (M+H), Rt. 2.48 min, 97.02% (Max). HPLC: (Method A) Rt. 2.51 min, 98.31% (Max).

Example 77 and Example 78: (R)—N-(2-(4-(1-(benzordiri,31dioxol-5-yl)ethyl)piperazin-1-yl)pyrimidin-5-yl)acetamide and (S)—N-(2-(4-(1-(benzordiri,31 dioxol-5-yl)ethyl)piperazin-1-yl)pyrimidin-5-yl)acetamide

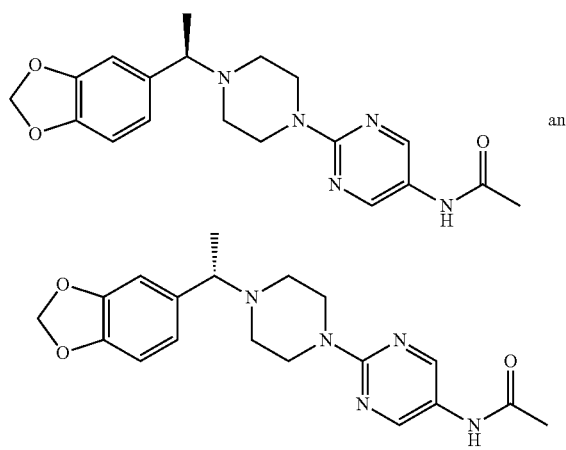

Example 72 was submitted to chiral preparative HPLC (Method PD). The first eluting fraction was concentrated, affording Example 77 (pale yellow solid). $^1$H NMR (400 MHz, DMSO-d6): δ 9.81 (s, 1H), 8.46 (s, 2H), 6.89 (s, 1H), 6.84 (d, J=8.0 Hz, 1H), 6.76 (d, J=8.0 Hz, 1H), 5.98 (m, 2H), 3.63 (t, J=4.8 Hz, 4H), 3.31 (s, 1H), 2.44-2.33 (m, 4H), 2.00 (s, 3H), 1.26 (d, J=6.0 Hz, 3H). LCMS: (Method A) 370.2 (M+H), Rt. 2.33 min, 99.5% (Max). HPLC: (Method A) Rt. 2.24 min, 99.7% (Max). Chiral HPLC: (Method F) Rt. 31.24 min, 99.05%. The second eluting fraction was concentrated, affording Example 78 (pale yellow solid). 1H NMR (400 MHz, DMSO-$d_6$): δ 9.81 (s, 1H), 8.46 (s, 2H), 6.89 (s, 1H), 6.84 (d, J=8.0 Hz, 1H), 6.76 (d, J=8.0 Hz, 1H), 5.98 (m, 2H), 3.63 (t, J=4.8 Hz, 4H), 3.31 (s, 1H), 2.41-2.32 (m, 4H), 2.00 (s, 3H), 1.26 (d, J=6.0 Hz, 3H). LCMS: (Method A) 370.2 (M+H), Rt. 2.31 min, 99.5% (Max). HPLC: (Method A) Rt. 2.25 min, 99.8% (Max). Chiral HPLC: (Method F) Rt. 21.26 min, 100.00%.

Example 79: 4-((2-(4-(1-(Benzofdin,31dioxol-5-yl)ethyl)piperazin-1-yl)thiazol-5-vQmethyQmorpholine

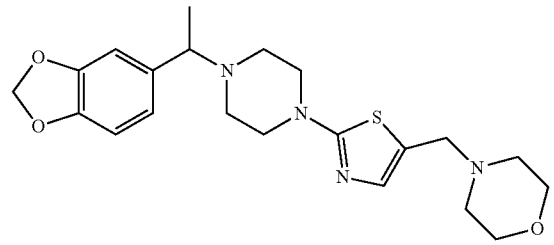 [SMILES: CC(c1ccc2c(c1)OCO2)N1CCN(c2ncc(CN3CCOCC3)s2)CC1]

Step 1: (2-(4-(1-(benzo[d][1,3]dioxol-5-yl)ethyl)piperazin-1-yl)thiazol-5-yl)methanol To a stirred solution of Example 27 (6.0 g, 16.4 mmol) in dry THF (70 mL), Super hydride (65 mL, 65.0 mmol) was added slowly at 0° C. The reaction mixture was stirred at rt for 2 h. The reaction mixture was quenched with saturated N H$_4$Cl and extracted with ethyl acetate. The organic layer was separated, dried over anhydrous Na$_2$SO$_4$, concentrated under vacuum. The crude product was purified by silica gel column chromatography (10% MeOH in DCM) to afford the title compound (white solid). $^1$H NMR (400 MHz, DMSO-$d_6$): δ 6.93 (s, 1H), 6.87-6.84 (d, J=12.8 Hz, 1H), 6.81-6.75 (m, 1H), 6.74-6.72 (d, J=8.8 Hz, 1H), 5.96-5.96 (d, J=1.2 Hz, 2H), 5.18-5.16 (d, J=7.8 Hz, 1H), 3.41-3.28 (m, 3H), 2.52-2.37 (m, 8H), 2.25 (s, 1H). LCMS: (Method A) 348.0 (M+H), Rt. 1.95 min, 97.02% (Max).

Step 2: 2-(4-(1-(benzo[d][1,3]dioxol-5-yl)ethyl)piperazin-1-yl)-5-(chloromethyl)thiazole To a stirred solution of (2-(4-(1-(benzo[d][1,3]dioxol-5-yl)ethyl)piperazin-1-yl)thiazol-5-yl)methanol (4.0 g, 11.5 mmol) in DCM (50 ml_), SOCl$_2$ (1.6 ml_, 23.0 mmol) was added slowly at 0° C. and the resulting mixture was stirred at rt for 1 h. It was concentrated under vacuum. The resulting crude product was taken for next step reaction without further purification. Yield: 96% (4.8 g, Yellow solid). $^1$H NMR (400 MHz, DMSO-$d_6$): δ 11.69 (s, 1H), 7.36-7.33 (m, 1H), 7.13-6.98 (m, 2H), 6.07 (s, 2H), 4.46 (d, J=12.8 Hz, 2H), 4.04-3.69 (m, 4H), 3.54-3.27 (m, 1H), 3.12-292 (m, 3H), 1.69 (d, J=6.0 Hz, 3H). LCMS: (Method A) 363 (M+H), Rt. 2.49 min, 86.01% (Max).

Step 3: 4-((2-(4-(1-(Benzo[d][1,3]dioxol-5-yl)ethyl)piperazin-1-yl)thiazol-5-yl)methyl)mor^holine To a stirred solution of 2-(4-(1-(benzo[d][1,3]dioxol-5-yl)ethyl)piperazin-1-yl)-5-(chloromethyl)thiazole (0.8 g, 2.0 mmol) in dry ACN (20 ml_), DIPEA (1.8 ml_, 8.0 mmol) and morpholine (0.22 ml_, 2.4 mmol) were added and the reaction mixture was stirred at rt overnight. The reaction mixture was diluted with EtOAc and washed with water. It was dried over anhydrous $Na_2SO_4$ and concentrated under vacuum. The crude product was purified by flash chromatography (10% MeOH in DCM) to afford the title compound (pale yellow solid). $^1$H NMR (400 MHz, DMSO-$d_6$): δ 6.95 (s, 1H), 6.88 (s, 1H), 6.84 (d, J=8.0 Hz, 1H), 6.75 (d, J=8.0 Hz, 1H), 5.99 (m, 2H), 3.54-3.53 (m, 4H), 3.48 (s, 2H), 3.39 (q, J=6.8 Hz, 1H), 3.25-3.40 (m, 4H), 2.40-2.33 (m, 4H), 1.28-1.27 (d, J=6.4 Hz, 3H). LCMS: (Method A) 418.0 (M+H), Rt. 1.99 min, 97.82% (Max). HPLC: (Method A) Rt. 1.78 min, 95.19% (Max).

Example 80: N-((2-(4-(1-(benzordiri,31dioxol-5-yl) ethyl)piperazin-1-yl)thiazol-5-yl)methyl)-N-methyl-acetamide

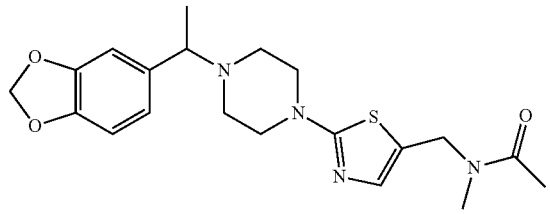 [SMILES: CC(=O)N(C)Cc1cnc(N2CCN(C(C)c3ccc4c(c3)OCO4)CC2)s1]

Step 1: 1-(2-(4-(1-(benzo[d][1,3]dioxol-5-yl)ethyl) piperazin-1-yl)thiazol-5-yl)-N-methylmethanamine To a stirred solution of 2-(4-(1-(benzo[d][1,3]dioxol-5-yl)ethyl)piperazin-1-yl)-5-(chloromethyl)thiazole (Example 79, Step 3, 1.2 g, 3.1 mmol) in dry ACN (20 ml_), DIPEA (2.3 ml_, 12.4 mmol) and methyl amine (5.0 ml_, 9.3 mmol, 2 M in THF) were added dropwise. The resulting mixture was stirred at rt overnight. It was diluted with water and extracted with ethyl acetate. The organic layer was separated, dried over anhydrous $Na_2SO_4$, concentrated under vacuum. The crude product was purified by flash chromatography (10% MeOH in DCM) to afford the title compound (yellow solid). LCMS: (Method A) 362.0 (M+H), Rt. 1.96 min, 25.6% (Max).

Step 2: N-((2-(4-(1^enzo[d][1,3]dioxol-5-yl)ethyl) piperazin-1-yl)thiaz^^-5-yl)methyl)-N-methylacet-amide To a stirred solution of 1-(2-(4-(1-(benzo[d][1,3]dioxol-5-yl)ethyl)piperazin-1-yl)thiazol-5-yl)-N-methylmeth-anamine (0.1 g, 0.27 mmol), DIPEA (0.3 mL, 0.8 mmol) in dry DCM (10 mL), acetic anhydride (0.3 mL, 0.8 mmol) was added portion wise and the reaction mixture was stirred at rt for 12 h. It was quenched with water (10 mL) and extracted with ethyl acetate (25 mL). The organic layer was dried over anhydrous $Na_2SO_4$ and concentrated under vacuum. The resulting crude product was purified by flash chromatography (10% MeOH in DCM) to afford the title compound (pale yellow solid). $^1$H NMR (400 MHz, DMSO-$d_6$): δ 7.05 (d, J=9.6 Hz, 1H), 6.88 (s, 1H), 6.84 (d, J=8.0 Hz, 1H), 6.75 (d, J=8.0 Hz, 1H), 5.99-5.98 (m, 2H), 4.40 (s, 2H), 3.39 (q, J=6.0 Hz, 1H), 3.33-3.30 (m, 4H), 2.88 (s, 3H), 2.50-2.37 (m, 4H), 1.97 (s, 3H), 1.27 (d, J=6.8 Hz, 3H). LCMS: (Method A) 403.0 (M+H), Rt. 2.19 min, 97.19% (Max). HPLC: (Method A) Rt. 2.14 min, 98.5% (Max).

Example 81: (/?)-(2-(4-(1-(2,3-Dihydrobenzorbin, 41dioxin-6-yl)ethyl)piperazin-1-yl)thiazol-5-yl)(4-hydroxypiperidin-1-yl)methanone or (S)-(2-(4-(1-(2, 3-Dihydrobenzorbin,41dioxin-6-yl)ethyl)piperazin-1-yl)thiazol-5-yl)(4-hydroxypiperidin-1-yl) methanone

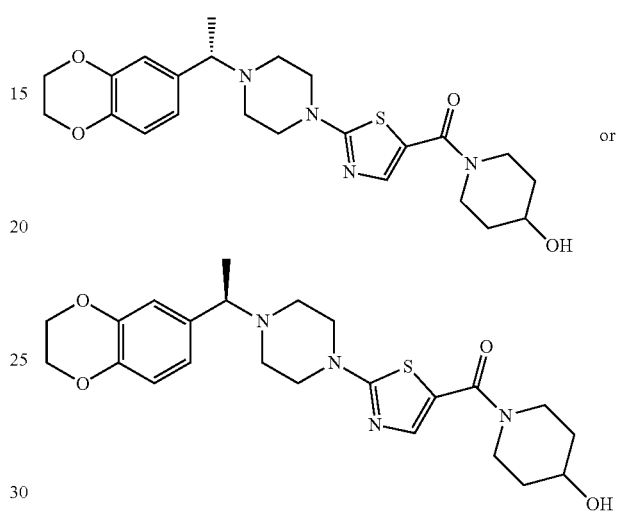

The two enantiomers of Example 73 were separated by chiral preparative HPLC, (Method PH). The first eluting compound had Rt. 32.84 min (pale brown solid). $^1$H NMR (400 MHz, DMSO-$d_6$): δ 7.49 (s, 1H), 6.79-6.77 (m, 3H), 4.78 (br. s, 1H), 4.22 (s, 4H), 3.93-3.90 (m, 2H), 3.73-3.72 (m, 1H), 3.42-3.38 (m, 5H), 3.34-3.28 (m, 2H), 2.50-2.39 (m, 4H), 1.78-1.74 (m, 2H), 1.38-1.26 (m, 5H). LCMS: (Method A) 459.0 (M+H), Rt. 2.32 min, 95.9% (Max). HPLC: (Method A) Rt. 2.21 min, 94.4% (Max). Chiral HPLC: (Method B) Rt. 32.84 min, 100%. The second eluting compound was isolated as Example 81 with Rt. 36.77 min (off white solid). $^1$H NMR (400 MHz, DMSO-$d_6$): δ 7.49 (s, 1H), 6.80-6.74 (m, 3H), 4.78 (br. s, 1H), 4.22 (s, 4H), 3.94-3.88 (m, 2H), 3.74-3.72 (m, 1H), 3.43-3.38 (m, 5H), 3.33-3.26 (m, 2H), 2.50-2.39 (m, 4H), 1.78-1.74 (m, 2H), 1.36-1.32 (m, 2H), 1.27 (d, J=6.4 Hz, 3H). LCMS: (Method A) 459.0 (M+H), Rt. 2.32 min, 98.9% (Max). HPLC: (Method A) Rt. 2.23 min, 99.8% (Max). Chiral HPLC: (Method B) Rt. 36.77 min, 94.52%.

Example 82: N-(5-(4-(1-(quinoxalin-6-yl)ethyl)pip-erazin-1-yl)-1,3,4-thiadiazol-2-yl)acetamide

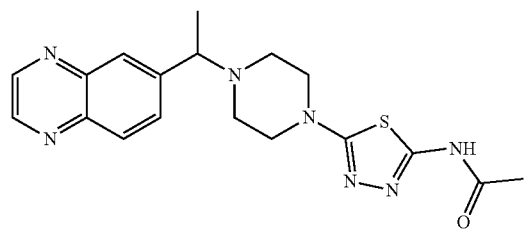 [SMILES: CC(=O)Nc1nnc(N2CCN(C(C)c3ccc4nccnc4c3)CC2)s1]

To a stirred solution of Intermediate 7 (0.4 g, 1.52 mmol) in dry ACN (10 mL), DIPEA (0.9 mL, 4.9 mmol) and Intermediate 6 (0.29 g, 1.52 mmol) were added at rt and the reaction mixture was stirred at 80° C. for 16 h. It was cooled to rt and concentrated. The resulting mixture was dissolved in ethyl acetate (70 mL), washed with water (10 mL), brine (10 mL), dried over anhydrous sodium sulfate and concentrated. The crude product was purified by flash chromatography to afford the title compound (orange solid). $^1$H NMR (400 MHz, DMSO-d$_6$): δ 12.03 (s, 1H), 8.94 (dd, J=1.6, 7.0 Hz, 2H), 8.09 (d, J=8.8 Hz, 1H), 8.01 (d, J=1.6 Hz, 1H), 7.91 (dd, J=2.0, 8.6 Hz, 1H), 3.83-3.78 (m, 1H), 3.39-3.33 (m, 4H), 2.67-2.60 (m, 2H), 2.56-2.50 (m, 2H), 2.09 (s, 3H), 1.44 (d, J=6.8 Hz, 3H). LCMS: (Method A) 384.2 (M+H), Rt. 1.87 min, 98.4% (Max). HPLC: (Method A) Rt. 1.76 min, 99.0% (Max).

Example 83: 6-(1-(4-(pyrimidin-2-yl)piperazin-1-yl)ethyl)quinoxaline

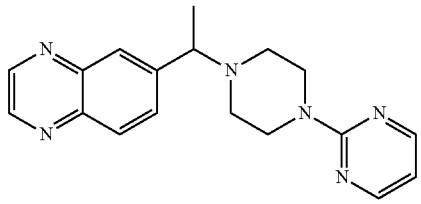 [SMILES: CC(c1ccc2nccnc2c1)N1CCN(c2ncccn2)CC1]

To a stirred solution of 2-(piperazin-1-yl)pyrimidine hydrochloride (0.25 g, 1.52 mmol) in dry ACN (10 mL), DIPEA (0.9 mL, 4.9 mmol) and Intermediate 6 (0.29 g, 1.52 mmol) were added at rt and the reaction mixture was stirred at 80° C. for 16 h. It was cooled to rt and concentrated. The crude mixture was dissolved in ethyl acetate (70 mL), washed with water (10 mL), brine (10 mL) and dried over anhydrous sodium sulfate. After evaporation of the solvents, the crude product was purified by flash chromatography to afford the title compound (orange solid). $^1$H NMR (400 MHz, DMSO-d$_6$): δ 8.95-8.92 (m, 2H), 8.33 (d, J=4.8 Hz, 2H), 8.09 (d, J=8.8 Hz, 1H), 8.00 (d, J=2.0 Hz, 1H), 7.92 (dd, J=1.6, 8.8 Hz, 1H), 6.60 (t, J=4.8 Hz, 1H), 3.77-3.71 (m, 5H), 2.60-2.55 (m, 2H), 2.45-2.35 (m, 2H), 1.44 (d, J=6.8 Hz, 3H). LCMS: (Method A) 321.0 (M+H), Rt. 2.01 min, 98.45% (Max). HPLC: (Method A) 1.92 min, 99.1% (Max).

Example 84: (2-(4-(1-(benzordin,31 dioxol-5-yl)ethyl)piperazin-1-yl)thiazol-4-yl)methanamine

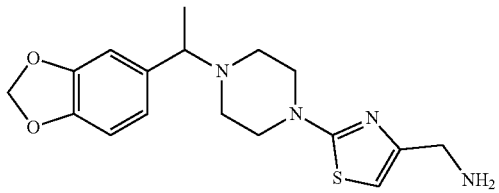 [SMILES: CC(c1ccc2c(c1)OCO2)N1CCN(c2nc(CN)cs2)CC1]

Step 1: 2-(4-(1-(benzo[d][1,3]dioxol-5-yl)ethyl)piperazin-1-yl)-4-(chloromethyl)thiazole To a stirred solution of Example 29 (1 g, 2.88 mmol) in dry DCM at 0° C., thionylchloride (0.4 ml_, 8.64 mmol, spectrochem) was added dropwise. The reaction mixture was stirred at rt for 2 h. It was then concentrated and the resulting crude product was used without further purification. Yield: quantitative (1.2 g, pink solid). $^1$H NMR (400 MHz, DMSO-d$_6$): δ 7.73-7.35 (m, 1H), 7.31-6.95 (m, 2H), 6.05 (s, 2H), 5.74 (s, 1H), 5.01-4.96 (m, 1H), 4.46 (s, 1H), 3.97-3.58 (m, 4H), 3.35-3.07 (m, 4H), 1.21 ((d, J=8.8 Hz, 3H). LCMS: (Method A) 362.0 (M–H), Rt. 2.45 min, 77.9% (Max).

Step 2: 4-(azidomethyl)-2-(4-(1-(benzo[d][1,3]dioxol-5-yl)ethyl)piperazin-1-yl)thiazole To a stirred solution of 2-(4-(1-(benzo[d][1,3]dioxol-5-yl)ethyl)piperazin-1-yl)-4-(chloromethyl)thiazole (1.2 g, 3.28 mmol) in dry DCM at 0° C., sodium azide (0.32 g, 4.9 mmol, spectrochem) was added in portion. The resulting mixture was heated at 80° C. for 12 h. It was then concentrated. The residue was dissolved in DCM (50 ml_), washed with water (15 ml.) and dried over Na$_2$SO$_4$. After evaporation of the solvents, the crude product was used without further purification. Yield: (1.1 g, colorless liquid). LCMS: (Method A) 373.0 (M+H), Rt. 2.96 min, 78.9% (Max).

Step 3: (2-(4-(1-(benzo[d][1,3]dioxol-5-yl)ethyl)piperazin-1-yl)thiazol-4-yl)methanamine To a stirred solution of 4-(azidomethyl)-2-(4-(1-(benzo[d][1,3]dioxol-5-yl)ethyl)piperazin-1-yl)thiazole (1.1 g, 2.95 mmol) in THF (18 ml.) and water (2 ml_), triphenylphosphine (1.16 g, 4.4 mmol, spectrochem) was added in portion and the resulting mixture was heated at 60° C. for 12 h. The reaction mixture was concentrated in a vacuum. The residue was dissolved in DCM (25 ml_), washed with water (10 ml.) and dried over Na$_2$SO$_4$. After evaporation of the solvents, the crude product was purified by MD Autoprep (Method B) (off white solid). $^1$H NMR (400 MHz, DMSO-d$_6$): δ 6.88 (t, J=2.4 Hz, 2H), 6.86-6.83 (m, 1H), 6.75 (d, J=8.0 Hz, 1H), 5.98 (m, 2H), 3.70 (s, 2H), 3.40 (t, J=6.8 Hz, 1H), 3.33-3.28 (m, 4H), 2.42-2.37 (m, 4H), 1.90 (s, 2H), 1.26 (d, J=6.8 Hz, 3H). LCMS: (Method A) 347.0 (M+H), Rt. 2.59 min, 98.65% (Max). HPLC: (Method A) Rt. 1.86 min, 98.9% (Max).

Example 85: N-((2-(4-(1-(benzordiri,31dioxol-5-yl)ethyl)piperazin-1-yl)thiazol-4-yl)methyl)acetamide

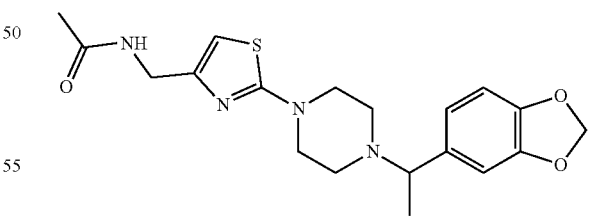

To a solution of Example 84 (0.08 g, 0.23 mmol) in dry dichloromethane (5 mL), pyridine (0.01 mL, 0.11 mmol, spectrochem) and acetic anhydride (0.01 mL, 0.11 mmol, spectrochem) were added and the resulting mixture was stirred at rt for 12 h. It was concentrated. The crude residue was dissolved in DCM (15 mL), washed with water (5 mL) and dried over Na$_2$SO$_4$. After evaporation of the solvents, the crude product was purified by MD Autoprep (Method C) (off white solid). $^1$H NMR (400 MHz, CDCl3): δ 7.00 (s, 1H), 6.90 (s, 1H), 6.77 (s, 2H), 5.97 (s, 2H), 5.77 (s, 1H), 4.43 (d, J=4.6 Hz, 2H), 3.48 (t, J=3.6 Hz, 5H), 2.56 (s, 4H), 2.00 (s, 3H), 1.41 (s, 3H). LCMS: (Method A) 389.2 (M+H), Rt. 2.02 min, 94.37% (Max). HPLC: (Method A) Rt. 1.94 min, 92.8% (Max).

Example 86: N-(5-(4-(1-(benzordlH,3ldioxol-5-yl)ethyl)piperazin-1-yl)thiazol-2-yl)acetamide

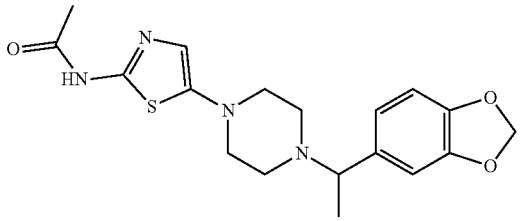 [SMILES: CC(=O)Nc1ncc(N2CCN(C(C)c3ccc4c(c3)OCO4)CC2)s1]

Step 1: 5-(4-(1-(benzo[d][1,3]dioxol-5-yl)ethyl)piperazin-1-yl)thiazol-2-amine

The title compound was synthesized following the general procedure D, using Intermediate 2 and 2-amino-5-bromo thiazole, hydrobromide salt as starting materials. Yield: 66% (0.85 g, black solid). LCMS: (Method A) 333.0 (M+H), Rt. 1.99 min, 57.8% (Max).

Step 2: N-(5-(4-(1-(benzo[d][1,3]dioxol-5-yl)ethyl)piperazin-1-yl)thiazol-2-yl)acetamide The title compound was synthesized via same procedure as described for Example 44, using 5-(4-(1-(benzo[d][1,3]dioxol-5-yl)ethyl)piperazin-1-yl)thiazol-2-amine as starting material (off white solid). $^1$H NMR (400 MHz, DMSO-d$_6$): δ 11.68 (s, 1H), 6.89 (s, 1H), 6.85 (d, J=8.0 Hz, 1H), 6.76 (d, J=7.6 Hz, 1H), 6.57 (s, 1H), 5.99 (s, 2H), 3.38-3.33 (m, 1H), 3.02-2.92 (m, 4H), 2.50-2.43 (m, 4H), 2.06 (s, 3H), 1.27 (d, J=6.4 Hz, 3H). LCMS: (Method A) 375.0 (M+H), Rt. 2.49 min, 97.9% (Max). HPLC: (Method A) Rt. 2.41 min, 97.5% (Max).

Example 87: N-(2-(4-(1-(3,4-Dichlorophenyl)ethyl)piperazin-1-yl)thiazol-5-yl)acetamide

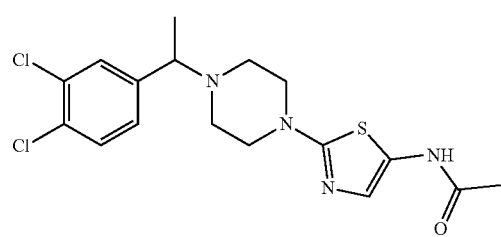 [SMILES: CC(=O)Nc1cnc(N2CCN(C(C)c3ccc(Cl)c(Cl)c3)CC2)s1]

The title compound was synthesized according to the general procedure D, using Intermediate 22 and Intermediate 2 as starting materials. The crude product was purified by column chromatography (yellow solid). $^1$H NMR (400 MHz, DMSO-d$_6$): δ 11.68 (s, 1H), 7.61-7.57 (m, 2H), 7.33 (dd, J=8.4, 1.6 Hz, 1H), 6.58 (s, 1H), 3.53 (q, J=6.8 Hz, 1H), 2.99-2.96 (m, 4H), 2.44-2.41 (m, 4H), 2.06 (s, 3H), 1.29 (d, J=6.8 Hz, 3H). LCMS: (Method A) 399.0 (M+H), Rt. 3.26 min, 97.0% (Max), 96.7% (220 nm). HPLC: (Method A) Rt. 3.16 min, 97.5% (Max).

Example 88: N-(5-(4-(1-(4-chloro-3-methoxyphenyl)ethyl)piperazin-1-yl)-1,3,4-thiadiazol-2-vOacetamide

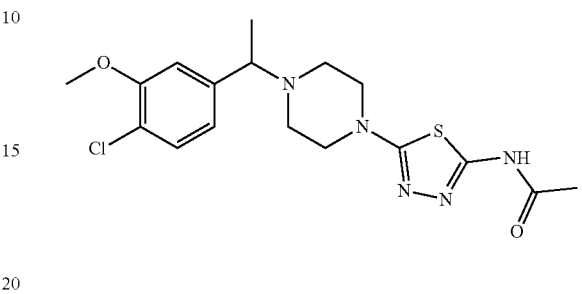

Step 1: 4-chloro-N,3-dimethoxy-N-methylbenzamide

To a stirred solution of 4-chloro-3-methoxy benzoic acid (2 g, 10.7 mmol) in dry DCM (20 mL), triethylamine (4.4 mL, 32.1 mmol), N,O-dimethylhydroxylamine, hydrochloride (1.15 g, 11.7 mmol), propylphosphonic anhydride (T$_3$P) were added successively at 0° C. The resulting mixture was stirred overnight at rt. It was diluted with ethylacetate (50 mL), washed with water and dried over anhydrous Na$_2$SO$_4$. After evaporation of the solvents, the resulting crude product was purified by flash chromatography (40% EtOAc in Hexane), affording the title compound. Yield: 73% (1.8 g, pale brown liquid). $^1$H NMR (400 MHz, DMSO-d$_6$): δ 7.49 (d, J=8.0 Hz, 1H), 7.30 (d, J=1.6 Hz, 1H), 7.18-7.15 (m, 1H), 3.88 (s, 3H), 3.56 (s, 3H), 3.25 (s, 3H). LCMS: (Method A) 230.0 (M+H), Rt. 3.43 min, 94.92% (Max).

Step 2: 1-(4-chloro-3-methoxyphenyl)ethan-1-one

To a stirred solution of 4-chloro-N,3-dimethoxy-N-methylbenzamide (2 g, 8.70 mmol) in dry tetrahydrofuran (20 mL), methyl magnesium bromide (3 M in Et$_2$O, 5.8 mL, 17.4 mmol) was added dropwise at 0° C. and the resulting mixture was stirred at rt for 1 h. It was quenched with saturated ammonium chloride solution (10 mL) and extracted with EtOAc (25 mL). The organic layer was washed with brine (15 mL), dried over anhydrous Na$_2$SO$_4$ and concentrated under vacuum. The crude product was purified by flash column chromatography (45% EtOAc in hexane) to afford the titled product (white solid). $^1$H NMR (300 MHz, DMSO-d$_6$): δ 7.71-7.60 (m, 1H), 7.52 (d, J=8.0 Hz, 3=1 H), 7.11 (s, 3H), 3.88 (s, 3H), 2.50 (s, 3H).

Step 3: 1-(4-chloro-3-methoxyphenyl)ethan-1-ol

The title compound was synthesized according to the general procedure A starting with 1-(4-chloro-3-methoxyphenyl)ethan-1-one. The resulting crude product was used without further purification. Yield: 98% (0.44 g, white solid). $^1$H NMR (400 MHz, DMSO-d$_6$): δ 7.45 (d, J=24.0 Hz, 1H), 6.91-6.90 (m, 2H), 4.58-4.42 (m, 1H), 3.88 (s, 3H), 1.48 (d, J=8.0, 3H).

Step 4: 1-chloro-4-(1-chloroethyl)-2-methoxybenzene

The title compound was synthesized using the general procedure B, starting with 1-(4-chloro-3-methoxyphenyl)

ethan-1-ol. The resulting crude product was used without further purification. Yield: 88% (0.3 g, colorless liquid). $^1$H NMR (400 MHz, DMSO-d$_6$): δ 7.43 (d, J=8.2 Hz, 1H), 7.25 (d, J=2.0 Hz, 1H), 7.10-7.07 (m, 1H), 5.38-5.36 (m, 1H), 3.88 (s, 3H), 1.80 (d, J=6.8 Hz, 3H).

Step 5: N-(5-(4-(1-(4-chloro-3-methoxyphenyl) ethyl)piperazin-1-yl)-1,3,4-thiadiazol-2-yl)acetamide The title compound was synthesized by following general procedure D, using 1-chloro-4-(1-chloroethyl)-2-methoxybenzene and Intermediate 2 as starting materials. The crude product was purified by flash chromatography (8% MeOH in DCM) to afford the title compound (off white solid). $^1$H NMR (400 MHz, DMSO-d$_6$): δ 12.02 (s, 1H), 7.37 (d, J=8.4 Hz, 1H), 7.09 (d, J=1.2 Hz, 1H), 6.92 (d, J=1.2, 8.4 Hz, 1H), 3.87 (s, 3H), 3.49 (q, J=6.4 Hz, 1H), 3.35 (t, J=4.8 Hz, 4H), 2.46-2.42 (m, 4H), 2.10 (s, 3H), 1.31 (d, J=6.8 Hz, 3H). LCMS: (Method A) 396.0 (M+H), Rt. 2.86 min, 98.8% (Max). HPLC: (Method A) Rt. 2.83 min, 98.9% (Max).

Example 89: (/?)-N-(5-(4-(1-(quinoxalin-6-yl)ethyl) piperazin-1-yl)-1,3,4-thiadiazol-2-vPacetamide or (S)—N-(5-(4-(1-(quinoxalin-6-yl)ethyl)piperazin-1-yl)-1,3,4-thiadiazol-2-vPacetamide

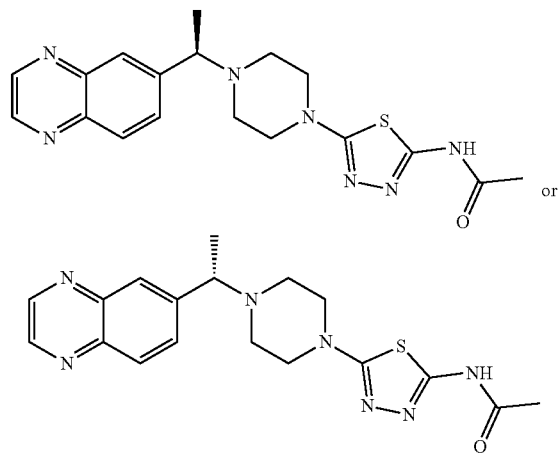

The two enantiomers of Example 82 were separated by chiral preparative HPLC (Method PF). The first eluting compound has a retention time of 15.34 min (Method D) (yellow solid). $^1$H NMR (400 MHz, DMSO-d$_6$): 12.02 (s, 1H), 8.93 (d, J=6.8 Hz, 2H), 8.09 (d, J=8.8 Hz, 1H), 8.01 (s, 1H), 7.91 (d, J=8.4 Hz, 1H), 3.80 (q, J=6.8 Hz, 1H), 3.39-3.37 (m, 4H), 2.63-2.60 (m, 2H), 2.47-2.46 (m, 2H), 2.09 (s, 3H), 1.43 (d, J=6.8 Hz, 3H). LCMS: (Method B) 384.2 (M+H), Rt. 1.88 min, 99.56% (Max). HPLC: (Method A) Rt. 1.77 min, 98.74% (Max). Chiral HPLC: (Method D) Rt. 15.34 min, 99.77%.

The second eluting compound corresponds to Example 89 (yellow solid). $^1$H NMR (400 MHz, DMSO-de): 11.94 (s, 1H), 8.93 (dd, J=1.6, 2.0 Hz, 2H), 8.09 (d, J=8.4 Hz, 1H), 8.00 (s, 1H), 7.91 (dd, J=1.6, 2.0 Hz, 1H), 3.80 (q, 1H, J=6.8 Hz), 3.39-3.37 (m, 4H), 2.63-2.60 (m, 2H), 2.47 (m, 2H), 2.09 (s, 3H), 1.43 (d, J=6.8 Hz, 3H). LCMS: (Method B) 384.2 (M+H), Rt. 1.88 min, 99.62% (Max). HPLC: (Method A) Rt. 1.77 min, 99.50% (Max). Chiral HPLC: (Method D) Rt. 17.11 min, 99.08%.

Example 90: Ethyl-2-(4-(1-(quinoxalin-6-yl)ethyl) piperazin-1-yl)thiazole-5-carboxylate

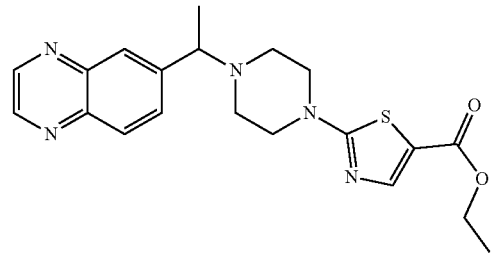 [SMILES: CCOC(=O)c1cnc(N2CCN(C(C)c3ccc4nccnc4c3)CC2)s1]

To a stirred solution of Intermediate 6 (0.5 g, 2.6 mmol) in dry ACN (18 mL), triethylamine (2.1 mL, 13.0 mmol, Spectrochem) and Intermediate 8 (1.08 g, 3.8 mmol) were added and the resulting mixture was heated at 90° C. for 12 h. It was concentrated, diluted with DCM (50 mL), washed with water (20 mL) and dried over anhydrous Na$_2$SO$_4$. After evaporation of the solvents, the resulting crude product was purified by flash chromatography (4% methanol in DCM) to afford the title compound. Yield: 58% (0.6 g, white solid). $^1$H NMR (400 MHz, DMSO-d$_6$): δ 8.86 (s, 2H), 8.12 (d, J=8.8 Hz, 1H), 8.03 (s, 1H), 7.90 (d, J=8.8 Hz, 1H), 7.87 (s, 1H), 4.30 (q, J=7.2 Hz, 2H), 3.76 (d, J=5.6 Hz, 1H), 3.59-3.58 (m, 4H), 2.71-2.70 (m, 2H), 2.60-2.59 (m, 2H), 1.51 (d, J=6.0 Hz, 3H), 1.34 (t, J=7.2 Hz, 3H). LCMS: (Method A) 398.2 (M+H), Rt. 2.61 min, 98.9% (Max). HPLC: (Method A) Rt. 2.64 min, 99.4% (Max).

Example 91: 7-(1-(4-(pyrimidin-2-yl)piperazin-1-yl) ethyl)quinoline

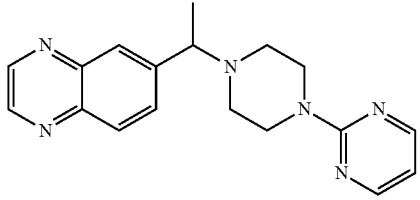 [SMILES: CC(c1ccc2nccnc2c1)N1CCN(c2ncccn2)CC1]

To a stirred solution of 2-(piperazin-1-yl)pyrimidine (0.17 g, 1.03 mmol) in dry DMF (10 mL), DIPEA (0.6 mL, 3.13 mmol) and Intermediate 9 (0.2 g, 1.03 mmol) were added at rt and the reaction mixture was stirred at 80° C. overnight. It was cooled to rt and concentrated. The resulting mixture was diluted in EtOAc (50 mL), washed with water (50 mL) and dried over anhydrous Na$_2$SO$_4$. After evaporation of the solvents, the crude product was purified by flash chromatography to afford the title compound (off white solid). $^1$H NMR (400 MHz, DMSO-d$_6$): δ 8.88 (t, J=2.8 Hz, 1H), 8.87-8.31 (m, 3H), 7.91-7.96 (m, 2H), 7.626-7.64 (m, 1H), 7.51-7.48 (m, 1H), 6.58 (t, J=4.8 Hz, 1H), 3.66-3.72 (m, 5H), 2.53-2.56 (m, 2H), 2.37-2.43 (m, 2H), 1.42 (d, J=6.8 Hz, 3H). LCMS: (Method A) 320.2 (M+H), Rt. 1.65 min, 99.0% (Max). HPLC: (Method A) Rt. 1.56 min, 98.7% (Max).

Example 92: N-methyl-2-(4-(1-(quinoxalin-6-yl)ethyl)piperazin-1-yl)thiazole-5-carboxamide

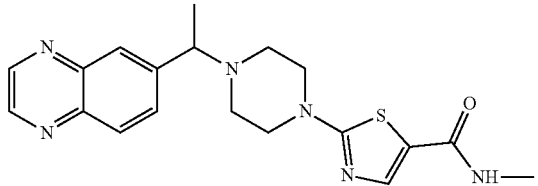 [SMILES: CNC(=O)c1cnc(N2CCN(C(C)c3ccc4nccnc4c3)CC2)s1]

Step 1: 2-(4-(1-(quinoxalin-6-yl)ethyl)piperazin-1-yl)thiazole-5-carboxylic acid To a stirred solution of Example 90 (0.5 g, 1.25 mmol) in dioxane (5 mL), NaOH (10% in water, 2 mL) was added and the mixture was stirred at rt for 12 h. It was neutralized with 5 N HCl solution (25 mL) and extracted with DCM (20 mL). The organic phase was dried over anhydrous $Na_2SO_4$. After evaporation of the solvents, the crude product was used without further purification. Yield: 50% (0.2 g, colourless oil). $^1$H NMR (400 MHz, DMSO-$d_6$): δ 10.9 (s, 1H), 9.92 (s, 1H), 8.86 (s, 2H), 3.22-3.17 (m, 4H), 3.02-2.78 (m, 4H), 2.06 (s, 3H). LCMS: (Method B) 370.0 (M+H), Rt. 1.90 min, 67.5% (Max).

Step 2: N-methyl-2-(4-(1-(quinoxalin-6-yl)ethyl)piperazin-1-yl)thiazole-5-carboxamide To a stirred solution of 2-(4-(1-(quinoxalin-6-yl)ethyl)piperazin-1-yl)thiazole-5-carboxylic acid (0.2 g, 0.5 mmol) in DCM (10 mL), DIPEA (0.5 mL, 2.0 mmol), methyl amine (2 M in THF, spectrochem, 0.03 mL, 1.00 mmol) and HATU (0.29 g, 0.7 mmol, spectrochem) were added at 0° C. The reaction mixture was stirred at room temperature for 12 h. The completion of the reaction was monitored by TLC. The reaction mixture was concentrated under vacuum, diluted with DCM (25 mL), washed with water, brine and dried over anhydrous $Na_2SO_4$. After evaporation of the solvents, the crude product was purified by flash chromatography to afford pure title product. Yield: 50% (100 mg, of off white solid). $^1$H NMR (400 MHz, DMSO-$d_6$): δ 8.94-8.93 (d, J=5.2 Hz, 2H), 8.15-8.14 (d, J=4.4 Hz, 1H), 8.10-8.08 (d, J=8.8 Hz, 1H), 8.00 (s, 1H), 7.92-7.90 (q, J=1.6 Hz, 1H), 7.71 (s, 1H), 3.82-3.81 (d, J=6.8 Hz, 1H), 3.46-3.45 (m, J=4.8 Hz, 4H), 2.69-2.68 (d, J=4.4 Hz, 3H), 2.60 (t, J=6.4 Hz, 2H), 2.46 (s, 2H), 1.44-1.43 (d, J=6.8 Hz, 3H). LCMS: (Method A) 383.2 (M+H), Rt. 1.86 min, 99.1% (Max). HPLC: (Method A) Rt. 1.73 min, 99.3% (Max).

Example 93: N-(2-(4-(1-(quinoxalin-6-yl)ethyl)piperazin-1-yl)pyrimidin-5-yl)acetamide

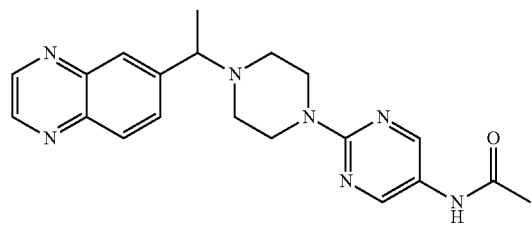 [SMILES: CC(=O)Nc1cnc(N2CCN(C(C)c3ccc4nccnc4c3)CC2)nc1]

To a stirred solution of Intermediate 10 (0.66 g, 2.6 mmol) in dry DMF (10 mL), triethylamine (1.4 mL, 10.4 mmol, Spectrochem) and Intermediate 6 (0.5 g, 2.6 mmol) were added and the resulting mixture was heated at 90° C. for 12 h. It was concentrated and the resulting residue was diluted with DCM (25 mL), washed with water (10 mL) and dried over $Na_2SO_4$. After evaporation of the solvents, the crude product was purified by MD Autoprep (Method B) to afford the title compound (off white solid). $^1$H NMR (400 MHz, DMSO-$d_6$): δ 9.80 (s, 1H), 8.91 (dd, J=2, 7.4 Hz, 2H), 8.45 (s, 2H), 8.08 (d, J=8.4 Hz, 1H), 7.99 (d, J=1.6 Hz, 1H), 7.92-7.90 (m, 1H), 3.82 (d, J=2 Hz, 1H), 3.65 (m, 4H), 2.55-2.51 (m, 2H), 2.49-2.42 (m, 2H), 1.99 (s, 3H), 1.42 (d, J=6.8 Hz, 3H). LCMS: (Method A) 378.3 (M+H), Rt. 1.71 min, 99.83% (Max). HPLC: (Method A) Rt 1.80 min, 99.66% (Max).

Example 94: 6-(1-(4-(4-(trifluoromethyl)pyrimidin-2-yl)piperazin-1-yl)ethyl)quinoxaline

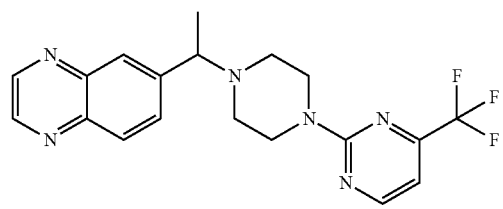 [SMILES: CC(c1ccc2nccnc2c1)N1CCN(c2nccc(C(F)(F)F)n2)CC1]

To a stirred solution of 2-(piperazin-1-yl)-4-(trifluoromethyl)pyrimidine hydrochloride (699 mg, 2.6 mmol) in DMF (10 mL), TEA (1.4 mL, 10.38 mmol) and Intermediate 6 (500 mg, 2.6 mmol) were added and the resulting mixture was stirred at 90° C. overnight. It was concentrated under vacuum and the residue was dissolved in DCM (15 mL), washed with water (10 mL) and dried over anhydrous $Na_2SO_4$. After evaporation of the solvents, the crude product was purified by flash chromatography to afford the title compound (brown oil). $^1$H NMR (400 MHz, DMSO-$d_6$): δ 8.92 (dd, J=8.8, 1.6 Hz, 2H), 8.64 (d, J=4.4 Hz, 1H), 8.07 (d, J=8.8 Hz, 1H), 7.99 (d, J=1.6 Hz, 1H), 7.91 (d, J=8.8, 1.6 Hz, 1H), 6.98 (d, J=4.4 Hz, 1H), 3.79-3.75 (m, 5H), 2.59-2.54 (m, 2H), 2.48-2.41 (m, 2H), 1.43 (d, J=6.8 Hz, 3H). LCMS: (Method A) 389.30 (M+H), Rt. 3.09 min, 99.40% (Max). HPLC: (Method A) Rt 3.07 min, 99.89% (Max).

Example 95: (S)-7-(1-(4-(pyrimidin-2-yl)piperazin-1-yl)ethyl)quinolone or (/?)-7-(1-(4-(pyrimidin-2-yl)piperazin-1-yl)ethyl)quinoline

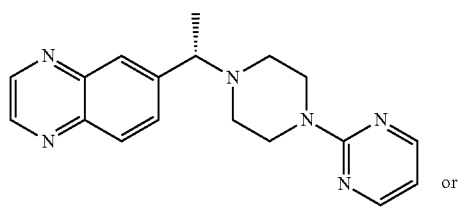

or

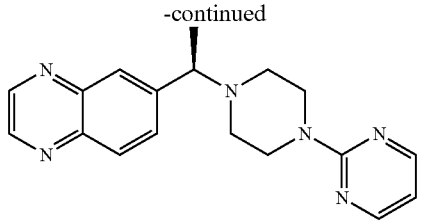

To a stirred solution of 1-(2-pyrimidylpiperazine) (1.11 g, 6.8 mmol) in dry DMF (20 mL), DIPEA (3.66 mL, 20.28 mmol) and Intermediate 9 (1.3 g, 6.8 mmol) were added and the reaction mixture was stirred at 80° C. overnight. It was concentrated under vacuum and the crude residue was dissolved in EtOAc (60 mL), washed with water (20 mL) and dried over anhydrous $Na_2SO_4$. After evaporation of the solvent, the crude product was purified by flash chromatography followed by chiral preparative HPLC (Method PF) to separate both enantiomers. Example 95 corresponds to the second eluting fraction (pale yellow solid). $^1$H NMR (400 MHz, DMSO-$d_6$): δ 8.89 (dd, J=4.4, 1.6 Hz, 1H), 8.35-8.31 (m, 3H), 7.95 (d, J=8.4 Hz, 1H), 7.91 (s, 1H), 7.66 (dd, J=8.4, 1.6 Hz, 1H), 7.49 (dd, J=8.0, 4.0 Hz, 1H), 6.59 (t, J=4.8 Hz, 1H), 3.72-3.68 (m, 5H), 2.56-2.51 (m, 2H), 2.43-2.37 (m, 2H), 1.42 (d, J=6.8 Hz, 3H). LCMS: (Method A) 320.2 (M+H), Rt. 1.63 min, 99.56% (Max). HPLC: (Method A) Rt. 1.54 min, 99.3% (Max). Chiral HPLC: (Method D) Rt 12.96 min, 100%.

Example 96: N-(2-(4-(1-(2,3-Dihydrobenzorbiri^1dioxin-6-yl)ethyl)piperazin-1-yl)pyrimidin-5-vQacetamide

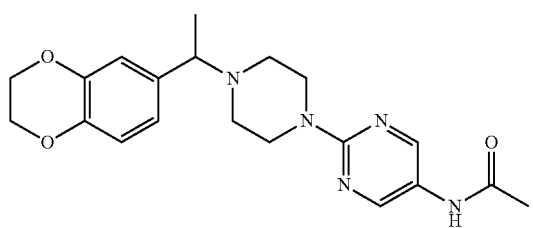 [SMILES: CC(=O)Nc1cnc(N2CCN(C(C)c3ccc4c(c3)OCCO4)CC2)nc1]

To a stirred solution of Intermediate 10 (320 mg, 1.24 mmol) in dry ACN (5 ml_), DIPEA (3.66 ml, 20.28 mmol) and Intermediate 3 (270 mg, 1.36 mmol) were added and the reaction mixture was stirred at 80° C. overnight. It was concentrated under vacuum and the crude product was dissolved in EtOAc (30 ml_), washed with water (10 ml.) and dried over anhydrous $Na_2SO_4$. After evaporation of the solvents, the crude product was purified by flash chromatography to afford the title compound (pale yellow solid). $^1$H NMR (400 MHz, DMSO-$d_6$): δ 9.79 (s, 1H), 8.44 (s, 2H), 6.76-6.74 (m, 3H), 4.19 (s, 4H), 3.61 (s, 4H), 2.38-2.31 (m, 4H), 1.98 (s, 3H), 1.24 (d, J=6.4 Hz, 3H). LCMS: (Method A) 384.2 (M+H), Rt. 2.27 min, 99.82% (Max). HPLC: (Method A) Rt. 2.26 min, 98.35% (Max).

Example 97: N-(5-(4-(1-(2,3-Dihydrobenzorb1H,41dioxin-6-yl)ethyl)piperazin-1-yl)-1,3,4-thiadiazol-2-yl)acetamide

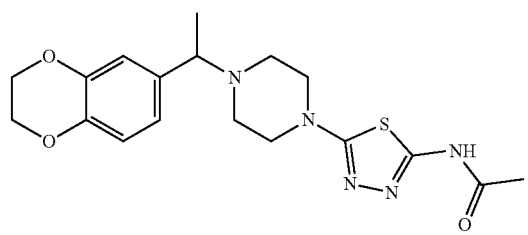 [SMILES: CC(=O)Nc1nnc(N2CCN(C(C)c3ccc4c(c3)OCCO4)CC2)s1]

The title compound was synthesized according the same procedure as Example 96, using Intermediate 7 and Intermediate 3 as starting materials. The crude product was purified by flash chromatography followed by MD Autoprep (Method B) to give the title compound (off white solid). $^1$H NMR (400 MHz, DMSO-$d_6$): δ 12.02 (s, 1H), 6.80-6.74 (m, 3H), 4.21 (s, 4H), 3.37-3.33 (m, 5H), 2.43-2.39 (m, 4H), 2.09 (s, 3H), 1.26 (d, J=6.8 Hz, 3H). LCMS: (Method A) 390.0 (M+H), Rt. 2.39 min, 98.62% (Max). HPLC: (Method A) Rt. 2.27 min, 97.05% (Max).

Example 98: 2-(4-(1-(Benzordiri,31dioxol-5-yl)ethyl)piperazin-1-yl)-N-methylpyrimidine-5-carboxamide

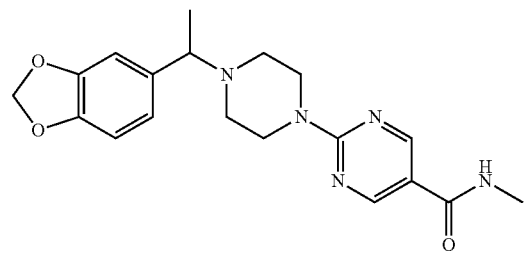 [SMILES: CNC(=O)c1cnc(N2CCN(C(C)c3ccc4c(c3)OCO4)CC2)nc1]

Step 1: Ethyl 2-(methylthio)pyrimidine-5-carboxylate

To a stirred solution of ethyl-4-chloro-(2-methyl thio pyrimidine) 5-carboxylate (10 g, 42.9 mmol) in THF/water (8:2, 100 ml_), zinc powder (14.0 g, 0.21 mmol) followed by f-BuOH (2 mL) were added and the resulting mixture was heated at 90° C. fo overnight. The reaction completion was monitored by LCMS. The mixture was filtered through celite and evaporated under vacuum. The crude product was dissolved in dichloromethane (100 mL), washed with water (50 mL) and dried over $Na_2SO_4$. After evaporation of the solvents, the crude product was purified by MD Autoprep (Method B) (colorless liquid). $^1$H NMR (400 MHz, DMSO-$d_6$): 9.03 (s, 2H), 4.35 (q, J=7.1 Hz, 2H), 2.58 (s, 3H), 1.33 (t, J=7.08 Hz, 3H). LCMS: (Method A) 199.0 (M+H), Rt. 3.50 min, 99.7% (Max).

Step 2: Ethyl 2-(methylsulfonyl)pyrimidine-5-carboxylate

To a stirred solution of ethyl 2-(methylthio)pyrimidine-5-carboxylate (2.8 g, 14.2 mmol) in tetrahydrofuran at 0° C., 3-chloroperbenzoic acid (7.8 g, 60.7 mmol, spectrochem) was added and the resulting solution was stirred at rt for 3 h. It was concentrated. DCM was added and was washed with water (25 mL) and 10% sodium bicarbonate solution (20 mL) and dried over Na$_2$SO$_4$. After evaporation of the solvents, the crude product was purified by flash chromatography to afford the titled product. Yield: 50.7% (1.65 g, off white solid). $^1$H NMR (400 MHz, DMSO-d$_6$): 9.48 (s, 2H), 4.43 (q, J=7.0 Hz, 2H), 3.48 (s, 3H), 1.37 (t, J=7.1 Hz, 3H), LCMS: (Method A) 230.9 (M+H), Rt. 2.33 min, 97.48% (Max).

Step 3: Ethyl 2-(4-(1-(benzo[d][1,3]dioxol-5-yl) ethyl)piperazin-1-yl)pyrimidine-5-carboxylate To a stirred solution of Intermediate 2 (1.87 g, 6.94 mmol) in dry acetonitrile, potassium carbonate (2.87 g, 20.8 mmol, spectrochem) and ethyl 2-(methylsulfonyl)pyrimidine-5-carboxylate were added and the resulting mixture was at rt for 12 h. It was filtered through celite and concentrated. Dichloromethane (25 mL) was added and the solution was washed with water, brine and dried over Na$_2$SO$_4$. After evaporation of the solvents, the crude product was purified by flash column chromatography to afford the title compound (white solid). $^1$H NMR (400 MHz, DMSO-d$_6$): 8.74 (s, 2H), 6.85 (t, J=7.8 Hz, 2H), 6.75 (d, J=7.8 Hz, 1H), 5.98 (s, 2H), 4.25 (q, J=6.8 Hz, 2H), 3.81 (s, 4H), 3.32 (s, 1H), 2.37-2.42 (m, 4H), 1.28 (d, J=6.6 Hz, 6H). LCMS: (Method A) 385.2 (M+H), Rt. 3.22 min, 98.88% (Max).

Step 4: Lithium 2-(4-(1-(benzo[d][1,3]dioxol-5-yl) ethyl)piperazin-1-yl)pyrimidine-5-carboxylate To a stirred solution of ethyl 2-(4-(1-(benzo[d][1,3]dioxol-5-yl)ethyl)piperazin-1-yl)pyrimidine-5-carboxylate (0.9 g, 2.34 mmol) in MeOH (2 mL), THF (7 mL) and water (1 mL) mixture, lithium hydroxide (0.24 g, 5.85 mmol, spectrochem) was added at 0° C. The resulting mixture was stirred at rt for 12 h. It was concentrated and the crude product was used without further purification. Yield: 90% (0.52 g, off white solid). LCMS: (Method A) 357.0 (M+H), Rt. 2.38 min, 99.21% (Max).

Step 5: 2-(4-(1-(Benzo[d][1,3]dioxol-5-yl)ethyl) piperazin-1-yl)-N-methylpyrimid^ne-5-carboxamide To a stirred solution of lithium 2-(4-(1-(benzo[d][1,3] dioxol-5-yl)ethyl)piperazin-1-yl)pyrimidine-5-carboxylate (300 mg, 0.82 mmol) in dry DMF (5 mL), methyl amine (0.09 mL, 0.988 mmol, 2M in THF), DIPEA (0.45 mL, 2.47 mmol) and HATU (471 mg, 1.29 mmol) were added and the resulting mixture was stirred at rt for 12 h. It was concentrated under vacuum and the crude product was diluted with DCM (20 mL), washed with water (15 mL) and dried over anhydrous Na$_2$SO$_4$. After evaporation of the solvents, the crude product was purified by MD Autoprep (Method B) to give the title compound (off white solid). $^1$H NMR (400 MHz, DMSO-d$_6$): δ 8.71 (s, 2H), 8.29 (q, J=4.4 Hz, 1H), 6.90 (d, J=1.6 Hz, 1H), 6.84 (d, J=7.6 Hz, 1H), 6.75 (dd, J=8.0, 1.2 Hz, 1H), 5.98 (m, 2H), 3.78-3.76 (m, 4H), 3.39 (q, J=6.4 Hz, 1H), 2.74 (d, J=4.8 Hz, 2H), 2.45-2.42 (m, 2H), 2.37-2.32 (m, 2H), 1.28 (d, J=6.4 Hz, 3H). LCMS: (Method A) 370.2 (M+H), Rt. 2.24 min, 97.69% (Max). HPLC: (Method A) Rt. 2.19 min, 99.52% (Max).

Example 99: 2-(4-(1-(benzo[d][1,3]dioxol-5-yl) ethyl)piperazin-1-yl)-N,N-dimethylpyrimidine-5-carboxamide

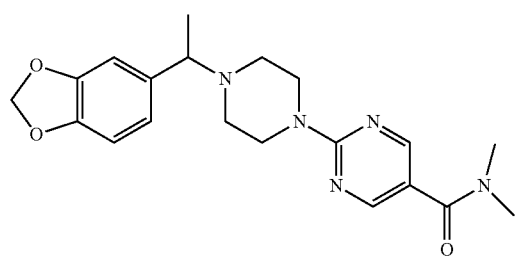 [SMILES: CC(c1ccc2c(c1)OCO2)N1CCN(c2ncc(C(=O)N(C)C)cn2)CC1]

The title compound was synthesized according the same protocol as Example 98, using dimethyl amine (2 M in THF) as reagent. The crude product was purified by MD Autoprep (Method B) to afford the title compound (white solid). $^1$H NMR (400 MHz, DMSO-d$_6$): δ 8.45 (s, 2H), 6.90 (d, J=1.2 Hz, 1H), 6.84 (d, J=7.6 Hz, 1H), 6.75 (dd, J=8.0, 1.2 Hz, 1H), 5.98 (m, 2H), 3.77-3.74 (m, 4H), 3.39 (q, J=6.4 Hz, 1H), 2.97 (s, 6H), 2.47-2.42 (m, 2H), 2.38-2.33 (m, 2H), 1.28 (d, J=6.4 Hz, 3H). LCMS: (Method A) 384.0 (M+H), Rt. 2.51 min, 99.94% (Max). HPLC: (Method A) Rt. 2.35 min, 99.85% (Max).

Example 100: N-(5-(4-(1-(4-chloroquinolin-7-yl) ethyl)piperazin-1-yl)-1,3,4-thiadiazol-2-vOacetamide

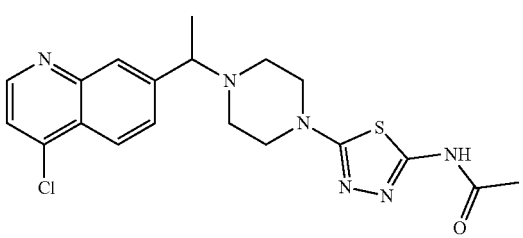 [SMILES: CC(=O)Nc1nnc(N2CCN(C(C)c3ccc4c(Cl)ccnc4c3)CC2)s1]

To a stirred solution of Intermediate 7 (231 mg, 0.88 mmol) in dry ACN (10 mL), DIPEA (0.5 mL, 2.64 mmol) and Intermediate 12 (200 mg, 0.88 mmol) were added at rt and the reaction mixture was stirred at 90° C. overnight. It was concentrated under vacuum and the resulting crude product was diluted with DCM (25 mL), washed with water (10 mL), brine (10 mL) and dried over anhydrous Na$_2$SO$_4$. After evaporation of the solvents, the crude product was purified by MD Autoprep (Method B) to give the title compound (off white solid). $^1$H NMR (400 MHz, DMSO-d$_6$): δ 12.00 (s, 1H), 8.83 (d, J=4.8 Hz, 1H), 8.19 (d, J=8.8 Hz, 1H), 8.0 (br s, 1H), 7.81 (dd, J=8.8, 1.6 Hz, 1H), 7.74 (d, J=4.8 Hz, 1H), 3.77 (q, J=6.4 Hz, 1H), 3.38-3.35 (m, 4H), 2.67-2.59 (m, 4H), 2.08 (s, 3H), 1.42 (d, J=6.4 Hz, 3H). LCMS: (Method A) 417.0 (M+H), Rt. 2.35 min, 96.55% (Max). HPLC: (Method A) Rt. 2.31 min, 96.43% (Max).

Example 101: N-(2-(4-(1-(4-chloroquinolin-7-yl)ethyl)piperazin-1-yl)pyrimidin-5-yl)acetamide

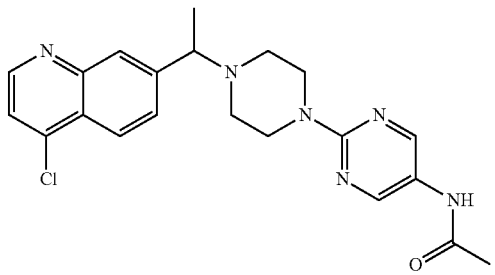 [SMILES: CC(=O)Nc1cnc(N2CCN(C(C)c3ccc4c(Cl)ccnc4c3)CC2)nc1]

The title compound was synthesized according the same protocol as described for the synthesis of Example 100, using Intermediate 10 and Intermediate 12 as starting materials. The crude product was purified by MD Autoprep (Method B) to give the title compound (off white solid). $^1$H NMR (400 MHz, DMSO-$d_6$): δ 9.8 (s, 1H), 8.82 (d, J=4.8 Hz, 1H), 8.46 (s, 2H), 8.19 (d, J=8.8 Hz, 1H), 7.99 (s, 1H), 7.82 (d, J=8.8 Hz, 1H), 7.73 (d, J=4.8 Hz, 1H), 3.77 (q, J=6.4 Hz, 1H), 3.67-3.65 (m, 4H), 2.53-2.41 (m, 4H), 1.99 (s, 3H), 1.41 (d, J=6.8 Hz, 3H). LCMS: (Method A) 411.0 (M+H), Rt. 2.35 min, 97.54% (Max). HPLC: (Method A) Rt. 2.29 min, 98.92% (Max).

Example 102: 6-(1-(4-(5-Methylpyrimidin-2-yl)piperazin-1-yl)ethyl)quinoxaline

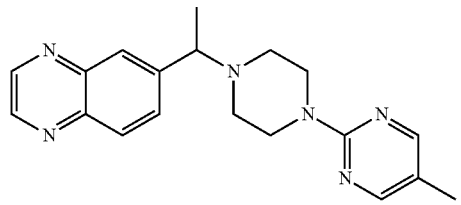 [SMILES: Cc1cnc(N2CCN(C(C)c3ccc4nccnc4c3)CC2)nc1]

To a stirred solution of Intermediate 11 (600 mg, 2.16 mmol) in dry DMF (10 mL), TEA (1.2 ml, 8.66 mmol) and 2-chloro-5-methylpyrimidine (280 mg, 2.16 mmol) were added at rt and the reaction mixture was stirred at 90° C. overnight. It was concentrated under vacuum and the resulting crude mixture was diluted with EtOAc (40 mL), washed with water (10 mL), brine (10 ml.) and dried over anhydrous Na$_2$SO$_4$. After evaporation of the solvents, the crude product was purified by flash chromatography to give the title compound (brown oil). $^1$H NMR (400 MHz, DMSO-$d_6$): δ 8.91 (d, J=7.2 Hz, 2H), 8.18 (s, 2H), 8.07 (s, J=8.8 Hz 1H), 7.99 (s, 1H), 7.90 (d, J=8.8 Hz, 1H), 3.67-3.66 (m, 4H), 2.54-2.49 (m, 2H), 2.40-2.38 (m, 2H), 2.05 (s, 3H), 1.42 (d, J=6.8 Hz, 3H). LCMS: (Method A) 335.2 (M+H), Rt. 2.14 min, 99.24% (Max). HPLC: (Method A) Rt. 2.21 min, 99.26% (Max).

Example 103: 6-(1-(4-(5-ethylpyrimidin-2-yl)piperazin-1-yl)ethyl)quinoxaline

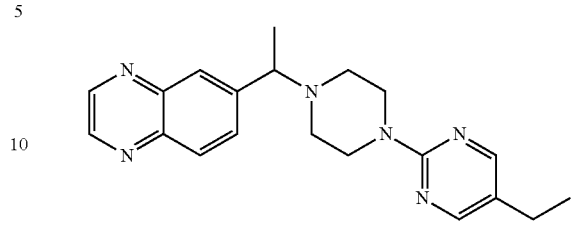

The title compound was synthesized according the same protocol as described for the synthesis of Example 102, using Intermediate 11 and 2-chloro-5-ethylpyrimidine as starting materials. The crude product was purified by flash chromatography to give the title compound (brown oil). $^1$HNMR (400 MHz, DMSO-$d_6$): δ 8.93 (d, J=6.0 Hz, 2H), 8.18 (s, 2H), 8.07 (d, J=8.4 Hz, 1H), 8.00 (s, 1H), 7.92 (d, J=8.4 Hz, 1H), 3.75 (q, J=6.8 Hz, 1H), 3.69-3.66 (m, 4H), 2.52-2.50 (m, 2H), 2.41-2.39 (m, 4H), 1.41 (d, J=6.8 Hz, 3H), 1.11 (t, J=7.2 Hz, 3H). LCMS: (Method A) 349.2 (M+H), Rt. 2.47 min, 98.68% (Max). HPLC: (Method A) Rt. 2.47 min, 99.26% (Max).

Example 104: (S)-6-(1-(4-(5-(trifluoromethyl)pyrimidin-2-yl)piperazin-1-yl)ethyl)quinoxaline or (R)-6-(1-(4-(5-(trifluoromethyl)pyrimidin-2-yl)piperazin-1-yl)ethyl)quinoxaline

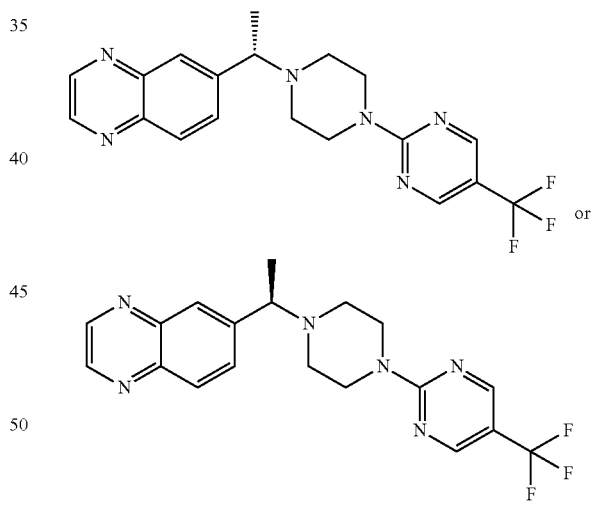

To a stirred solution of 2-(piperazin-1-yl)-5-(trifluoromethyl)pyrimidine hydrochloride (500 mg, 1.86 mmol) in dry DMF (10 mL), TEA (1.3 mL, 5.58 mmol) and Intermediate 6 (394 mg, 2.05 mmol) were added at rt and the reaction mixture was stirred at 90° C. overnight. The reaction mixture was concentrated under vacuum and the resulting residue was diluted with EtOAc (30 mL), washed with water (10 mL), brine (10 mL) and dried over anhydrous Na$_2$SO$_4$. After evaporation of the solvents, the crude product was purified by flash chromatography followed by chiral preparative HPLC (Method PJ) to separate both enantiomers. The second eluting fraction was concentrated to give the title compound (pale brown solid). $^1$H NMR (400 MHz, DMSO-d$_6$): δ 8.90 (dd, J=6.8, 1.6 Hz, 2H), 8.65 (d, J=0.8, Hz, 2H), 8.07 (d, J=8.4 Hz, 1H), 7.99 (d, J=1.6 Hz, 1H), 7.91 (d, J=8.4 Hz, 1H), 3.83-3.77 (m, 5H), 2.59-2.43 (m, 4H), 1.42 (d, J=6.8 Hz, 3H). LCMS: (Method A) 389.2 (M+H), Rt. 2.95 min, 99.43% (Max). HPLC: (Method A) Rt. 2.99 min, 99.71% (Max). Chiral HPLC: (Method F) Rt 17.91 min, 99.63%.

Example 105: N-(5-(4-(1-(benzo[d[1,3]dioxol-5-yl)ethyl)piperazin-1-yl)-1,3,4-thiadiazol-2-yl)propionamide

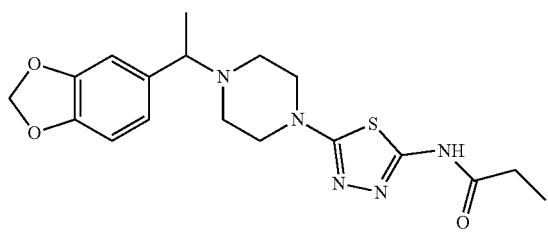 [SMILES: CCC(=O)Nc1nnc(N2CCN(C(C)c3ccc4c(c3)OCO4)CC2)s1]

To a stirred solution of Example 41 (310 mg, 1.2 mmol) in dry DCM (10 mL), TEA (0.4 mL, 2.78 mmol) and propionyl chloride (94 mg, 1.02 mmol) were added at 0° C. and the resulting mixture was stirred at rt overnight. The reaction mixture was concentrated under vacuum and the resulting crude product was purified by flash chromatography to give the title compound (white solid). $^1$H NMR (400 MHz, DMSO-d$_6$): δ 11.96 (s, 1H), 6.83 (s, 1H), 6.83 (d, J=8.0 Hz, 1H), 6.72 (d, J=8.0 Hz, 1H), 5.98 (m, 2H), 3.34-3.32 (m, 5H), 2.51-2.37 (m, 6H), 1.28 (d, J=6.8 Hz, 3H), 1.04 (d, J=7.2 Hz, 3H). LCMS: (Method A) 390.0 (M+H), Rt. 2.57 min, 99.27% (Max). HPLC: (Method A) Rt. 2.48 min, 99.7% (Max).

Example 106: N-(5-(4-(1-(benzo[d[1,3]dioxol-5-yl)ethyl)piperazin-1-yl)-1,3,4-thiadiazol-2-yl)butyramide

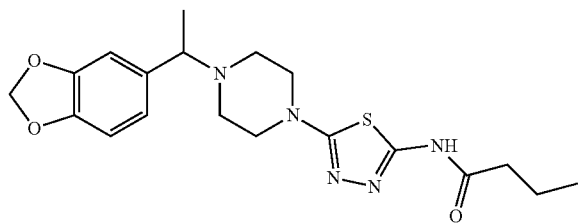 [SMILES: CCCC(=O)Nc1nnc(N2CCN(C(C)c3ccc4c(c3)OCO4)CC2)s1]

The title compound was synthesized according the same protocol as described for the synthesis of Example 105, using butyryl chloride as acylating agent. The resulting crude product was purified by flash column chromatography followed by MD Autoprep (Method B) to give the title compound (off white solid). $^1$H NMR (400 MHz, DMSO-d$_6$): δ 11.98 (s, 1H), 6.89 (d, J=1.6 Hz, 1H), 6.85 (d, J=8.0 Hz, 1H), 6.76 (dd, J=8.0, 1.6 Hz, 1H), 5.98 (m, 2H), 3.39 (q, J=5.6 Hz, 1H), 3.35-3.33 (m, 4H), 2.56-2.40 (m, 4H), 2.36 (t, J=7.6 Hz, 2H), 1.61-1.55 (m, 2H), 1.28 (d, J=6.4 Hz, 3H), 0.86 (t, J=7.2 Hz, 3H). LCMS: (Method A) 404.2 (M+H), Rt. 2.81 min, 97.58% (Max). HPLC: (Method A) Rt. 2.84 min, 99.12% (Max).

Example 107: N-(5-(4-(1-(benzo[d[1,3]dioxol-5-yl)ethyl)piperazin-1-yl)-1,3,4-thiadiazol-2-yl)isobutyramide

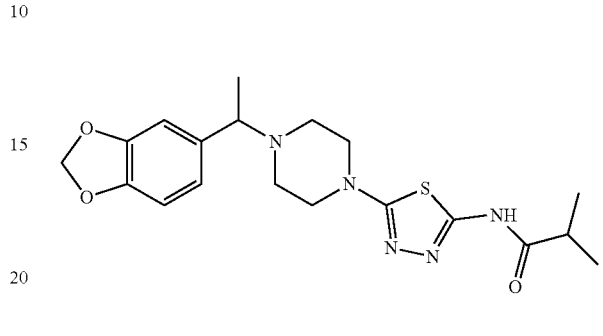

The title compound was synthesized according the same protocol as described for the synthesis of Example 105, using isobutryl chloride as acylating agent. The crude product was purified by flash chromatography to give the title compound (white solid). $^1$H NMR (400 MHz, DMSO-d$_6$): δ 11.99 (s, 1H), 6.89 (d, J=1.2 Hz, 1H), 6.85 (d, J=8.0 Hz, 1H), 6.76 (dd, J=8.0, 1.2 Hz, 1H), 5.99 (m, 2H), 3.43 (q, J=6.8 Hz, 1H), 3.80-3.33 (m, 4H), 2.72-2.65 (m, 1H), 2.44-2.32 (m, 4H), 1.28 (d, J=6.8 Hz, 3H), 1.09 (d, J=6.8 Hz, 6H). LCMS: (Method A) 404.2 (M+H), Rt. 2.82 min, 98.33% (Max). HPLC: (Method A) Rt. 2.75 min, 99.73% (Max).

Example 108: N-(5-(4-(1-(benzo[d[1,3]dioxol-5-yl)ethyl)piperazin-1-yl)-1,3,4-thiadiazol-2-yl)cyclo Propanecarboxamide

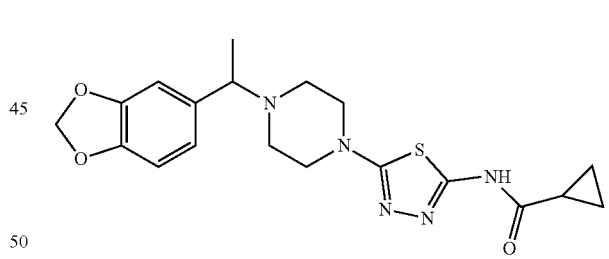

The title compound was synthesized according the same protocol as described for the synthesis of Example 105, using cyclopropane carbonyl chloride as acylating agent. The crude product was purified by flash chromatography followed by MD Autoprep (Method B) to give the title compound (off white solid). $^1$H NMR (400 MHz, DMSO-d$_6$): δ 12.30 (s, 1H), 6.89 (d, J=1.6 Hz, 1H), 6.84 (d, J=8.0 Hz, 1H), 6.76 (dd, J=8.0, 1.6 Hz, 1H), 5.99 (m, 2H), 3.39 (q, J=6.4 Hz, 1H), 3.33-3.28 (m, 4H), 2.56-2.39 (m, 4H), 1.88-1.87 (m, 1H), 1.28 (d, J=6.4 Hz, 3H), 0.90-0.83 (m, 4H). LCMS: (Method A) 402.2 (M+H), Rt. 2.63 min, 99.66% (Max). HPLC: (Method A) Rt. 2.66 min, 99.76% (Max).

Example 109: 2-(4-(1-(2,3-dihydrobenzorbiri,41dioxin-6-yl)ethyl)piperazin-1-yl)-N-methylthiazole-5-carboxamide

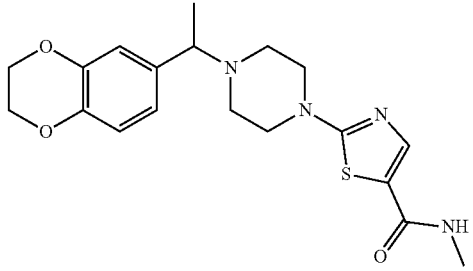 [SMILES: CNC(=O)c1cnc(N2CCN(C(C)c3ccc4c(c3)OCCO4)CC2)s1]

To a stirred solution of lithium 2-(4-(1-(2,3-dihydrobenzo[b][1,4]dioxin-6-yl)ethyl)piperazin-1-yl)thiazole-5-carboxylate (0.7 g, 18.37 mmol, Example 62, Step 2) in dry DMF (7 mL), methyl amine (2M in THF, 1.3 mL, 27.55 mmol), HATU (0.83 g, 22.0 mmol) and DIPEA (0.9 mL, 55.1 mmol) were added and the reaction mixture was stirred overnight at rt. It was cooled to rt and concentrated. Water (15 mL) was added to the resulting mixture and was extracted with EtOAc (2×30 mL). The organic layer was dried over anhydrous $Na_2SO_4$. After evaporation of the solvents, the crude product was purified by MD Autoprep HPLC (Method B) to afford the title compound as off white solid. $^1$H NMR (400 MHz, DMSO-$d_6$): δ 8.14 (q, J=4.0, 1H), 7.70 (s, 1H), 6.77-6.74 (m, 3H), 4.40 (s, 4H), 3.39-3.38 (m, 5H), 2.67 (d, J=4.4 Hz, 3H), 2.49-2.48 (m, 2H), 2.44-2.38 (m, 2H), 1.25 (d, J=6.4 Hz, 3H). LCMS: (Method A) 389.2 (M+H), Rt. 2.26 min, 97.94% (Max). HPLC: (Method A) Rt. 2.23 min, 98.53% (Max).

Example 110: N-(5-(4-(1-(benzordiri,31dioxol-5-yl)ethyl)piperazin-1-yl)-1,3,4-thiadiazol-2-yl)^4-chlorobenzamide

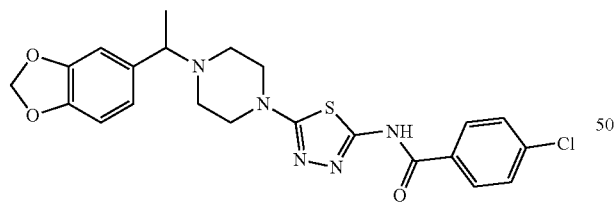

To a stirred solution of Example 41 (0.40 g, 1.2 mmol) in dry DCM (10 mL), TEA (0.4 mL, 0.45 mmol) and 4-chlorobenzoyl chloride (0.28 g, 1.65 mmol) were added at 0° C. and the resulting mixture was stirred overnight at rt. It was concentrated under vacuum and the resulting crude product was purified by flash chromatography to give the title compound (off white solid). $^1$H NMR (400 MHz, DMSO-$d_6$): 12.69 (s, 1H), 8.06 (d, J=8.4 Hz, 2H), 7.60 (d, J=8.8 Hz, 2H), 6.75-6.89 (m, 3H), 5.99 (t, J=0.4 Hz, 2H), 3.39-3.42 (m, 5H), 2.42-2.45 (m, 4H), 1.28 (d, J=6.80 Hz, 3H), LCMS: (Method A) 471.1 (M+H), Rt. 3.59 min, 98.8% (Max). HPLC: (Method A) Rt. 3.56 min, 98.7% (Max).

Example 111: 5-(4-(1-(benzordiri,31 dioxol-5-yl)ethyl)piperazin-1-yl)-N-(4-chlorobenzyl)-1,3,4-thiadiazol-2-amine

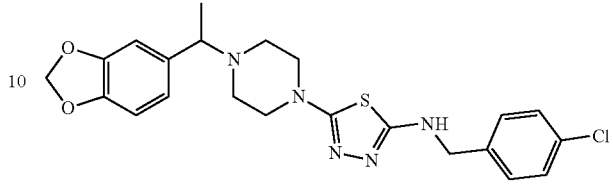

To a stirred solution of Example 41 (0.3 g, 0.90 mmol) in dry 1,2-dichloroethane (3 mL), titanium isopropoxide (0.8 mL, 2.71 mmol) and 4-chlorobenzaldehyde (0.19 g, 1.35 mmol) were added and the reaction mixture was refluxed for 8 h. It was cooled to 0° C. and sodium borohydride (0.17 g, 4.51 mmol) was added and the mixture was stirred at rt for 2 h. It was concentrated and water (15 mL) was added to the resulting crude product. It was extracted with EtOAc (2×30 mL). The organic layer was dried over anhydrous $Na_2SO_4$. After evaporation of the solvents, the crude product was purified by MD Autoprep HPLC (Method B) to afford the title compound as off white solid. $^1$H NMR (400 MHz, DMSO-$d_6$): δ 7.58 (t, J=6.0 Hz, 1H), 7.39-7.32 (m, 4H), 6.86 (s, 1H), 6.83 (d, J=8.0 Hz, 1H), 6.73 (d, J=8.0 Hz, 1H), 6.97-6.97 (m, 2H), 4.33 (m, 2H), 3.32-3.21 (m, 1H), 3.19-3.16 (m, 4H), 2.43-2.21 (m, 4H), 1.25 (d, J=6.4 Hz, 3H). LCMS: (Method B) 458.0 (M+H), Rt. 6.16 min, 96.93% (Max). HPLC: (Method A) Rt. 3.21 min, 96.02% (Max).

Example 112: 5-(4-(1-(benzordiri,31dioxol-5-yl)ethyl)piperazin-1-yl)-N-ethyl-1,3,4-thiadiazol-2-amine

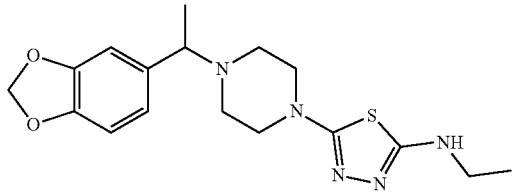 [SMILES: CCNc1nnc(N2CCN(C(C)c3ccc4c(c3)OCO4)CC2)s1]

The title compound was synthesized following the same procedure as Example 111, using acetaldehyde (0.17 mL, 1.35 mmol) as starting material. After evaporation of the solvents, the crude product was purified by flash chromatography to afford the title compound as off white solid. $^1$H NMR (400 MHz, DMSO-$d_6$): δ 6.99 (t, J=5.2 Hz, 1H), 6.88 (d, J=1.2 Hz, 1H), 6.84 (d, J=7.6 Hz, 1H), 6.74 (dd, J=7.6, 1.2 Hz, 1H), 5.99-5.98 (m, 2H), 3.37 (d, J=6.4 Hz, 1H), 3.19-3.13 (m, 6H), 2.45-2.32 (m, 4H), 1.25 (d, J=6.4 Hz, 3H), 1.11 (t, d, J=6.8 Hz, 3H). LCMS: (Method A) 362.0 (M+H), Rt. 2.01 min, 96.31% (Max). HPLC: (Method A) Rt. 1.98 min, 94.56% (Max).

Example 113: 2-(4-(1-(benzo[d][1,3]dioxol-5-yl)ethyl)piperazin-1-yl)-7H-pyrrolo[2,3-d]pyrimidine

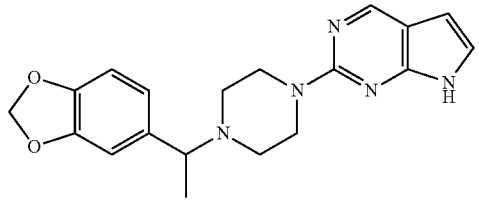 [SMILES: CC(c1ccc2c(c1)OCO2)N1CCN(c2ncc3cc[nH]c3n2)CC1]

To a stirred solution of Intermediate 2 (0.3 g, 11.15 mmol) in dry NMP (3 mL), DIPEA (0.8 mL, 44.6 mmol) and 2-chloro-7H-pyrrolo[2,3-d]pyrimidine (0.17 g, 11.15 mmol) were added at rt and the reaction mixture was stirred at 220° C. for 6 h in microwave. It was cooled to rt and concentrated. The resulting mixture was diluted with EtOAc (30 mL), washed with water (10 mL) and dried over anhydrous $Na_2SO_4$. After evaporation of the solvents, the crude product which was purified by MD Autoprep HPLC (Method B) to afford the title compound (off white solid). $^1H$ NMR (400 MHz, DMSO-$d_6$): δ 8.57 (s, 1H), 7.07 (t, J=2.8 Hz, 1H), 6.90 (s, 1H), 6.84 (d, J=7.6 Hz, 1H), 6.76 (d, J=8 Hz, 1H), 6.30 (m, 1H), 5.97 (dd, J=3.2 Hz, 2H), 3.67 (t, J=4.8 Hz, 4H), 3.37-3.35 (m, 1H), 2.45-2.44 (m, 2H), 2.38-2.36 (m, 2H), 1.28 (d, J=76.4 Hz, 3H). LCMS: (Method A) 352.2 (M+H), Rt 2.10 min, 99.36% (Max). HPLC: (Method A) Rt. 2.01 min, 99.36% (Max).

Example 114: N-(5-(4-(1-(benzo[d]thiazol-5-yl)ethyl)piperazin-1-yl)-1,3,4-thiadiazol-2-yl)acetamide

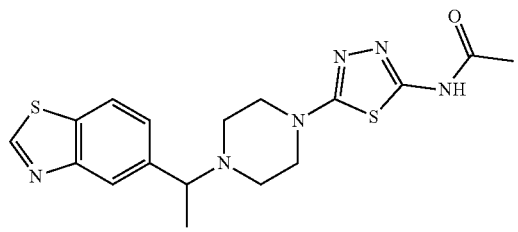 [SMILES: CC(=O)Nc1nnc(N2CCN(C(C)c3ccc4scnc4c3)CC2)s1]

To a stirred solution of Intermediate 7 (0.5 g, 1.9 mmol) in DMF (5 mL), DIPEA (0.99 mL, 5.6 mmol) and Intermediate 17 (0.374 g, 1.9 mmol) were added at 0-5° C. The reaction mixture was stirred at 100° C. overnight. The completion of the reaction was confirmed by TLC. The reaction mixture was evaporated at 50° C. under reduced pressure and diluted with ethyl acetate (30 mL). The organic layer washed with water (10 mL), brine solution (10 mL) and dried over $Na_2SO_4$. After evaporation of the solvents, the crude product was purified by flash chromatography (5-8% MeOH in DCM) to give the title compound (pale brown solid). $^1H$ NMR (400 MHz, DMSO-$d_6$): δ 12.01 (s, 1H), 9.38 (s, 1H), 8.11 (d, J=8.4 Hz, 1H), 8.01 (s, 1H), 7.48 (d, J=8.4 Hz, 1H), 3.69-3.65 (m, 1H), 3.36-3.32 (m, 4H), 2.58-2.50 (m, 2H), 2.50-2.43 (m, 2H), 2.08 (s, 3H), 1.39 (d, J=6.4 Hz, 3H). LCMS: (Method A) 389.0 (M+H), Rt. 2.17 min, 99.5% (Max). HPLC: (Method A) Rt 2.04 min, 99.2% (Max).

Example 115: N-(5-(4-(1-(quinolin-7-yl)ethyl)piperazin-1-yl)-1,3,4-thiadiazol-2-yl)acetamide

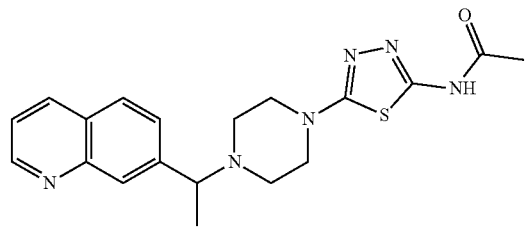 [SMILES: CC(=O)Nc1nnc(N2CCN(C(C)c3ccc4cccnc4c3)CC2)s1]

The title compound was synthesized according the protocol used for Example 114, using Intermediate 7 (0.39 g, 2.05 mmol) and Intermediate 9 (0.5 g, 2.6 mmol) as starting materials. The crude product was purified by MD Autoprep (Method B) to afford title compound as white solid. $^1H$ NMR (400 MHz, DMSO-$d_6$): δ 12.03 (s, 1H), 8.9 (dd, J=1.6, 4.4 Hz, 1H), 8.35 (t, J=1.2 Hz, 1H), 7.96 (d, J=8.8 Hz, 1H), 7.92 (s, 1H), 7.65 (dd, J=5.2, 6.8 Hz, 1H), 7.51 (dd, J=4.4, 8.4 Hz, 1H), 3.76-3.71 (m, 1H), 3.39-3.35 (m, 4H), 2.62-2.58 (m, 2H), 2.48-2.45 (m, 2H), 2.09 (s, 3H), 1.43 (d, J=6.8 Hz, 3H). LCMS: (Method B) 383.0 (M+H), Rt. 4.4 min, 96.3% (Max). HPLC: (Method B) Rt. 4.3 min, 95.4% (Max).

Example 116: N-(2-(4-(1-(benzo[d]thiazol-5-yl)ethyl)piperazin-1-yl)pyrimidin-5-yl)acetamide

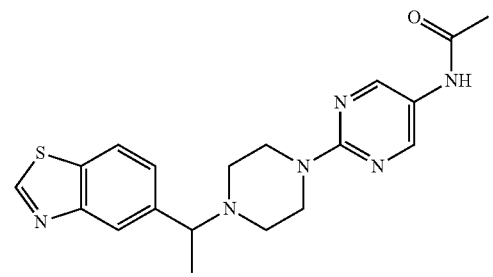 [SMILES: CC(=O)Nc1cnc(N2CCN(C(C)c3ccc4scnc4c3)CC2)nc1]

The title compound was synthesized according the protocol used for Example 114, using Intermediate 10 (0.5 g, 1.9 mmol) and Intermediate 17 (0.383 g, 1.9 mmol) as starting materials. The crude product was purified by flash chromatography (7% MeOH in DCM) followed by MD Autoprep HPLC (Method B) to afford title compound (off white solid). $^1H$ NMR (400 MHz, DMSO-$d_6$): δ 9.81 (s, 1H), 9.38 (s, 1H), 8.46 (s, 1H), 8.11 (d, J=8.4 Hz, 1H), 8.02 (s, 1H), 7.52-7.48 (m, 1H), 3.66-3.63 (m, 5H), 2.52-2.50 (m, 2H), 2.40-2.37 (m, 2H), 2.00 (s, 3H), 1.40 (d, J=6.8 Hz, 3H). LCMS: (Method A) 383.0 (M+H), Rt. 2.17 min, 93.53% (Max). HPLC: (Method A) Rt. 2.05 min, 94.64% (Max).

Example 117: N-(5-(4-(1-(benzo[d]thiazol-5-yl)ethyl)piperazin-1-yl)-1,3,4-thiadiazol-2-yl)acetamide

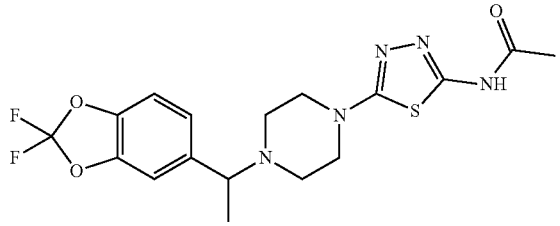 [SMILES: CC(=O)Nc1nnc(N2CCN(C(C)c3ccc4c(c3)OC(F)(F)O4)CC2)s1]

The title compound was synthesized according the protocol used for Example 114, using Intermediate 7 (0.5 g, 1.9 mmol) and Intermediate 18 (0.418 g, 1.9 mmol). The crude product was purified by flash chromatography (5-8% MeOH in DCM) to give the title compound (pale brown solid). $^1$H NMR (400 MHz, DMSO-$d_6$): δ 12.01 (s, 1H), 7.38-7.33 (m, 2H), 7.15 (d, J=8.4 Hz, 1H), 3.55-3.51 (m, 1H), 3.35-3.32 (m, 4H), 2.56-2.42 (m, 2H), 2.41-2.32 (m, 2H), 2.09 (s, 3H), 1.30 (d, J=8.0 Hz, 3H). LCMS: (Method A) 412.3 (M+H), Rt. 3.06 min, 99.3% (Max). HPLC: (Method A) Rt. 2.98 min, 98.6% (Max).

Example 118: N-(5-(4-(1-(benzo[d]thiazol-5-yl)ethyl)piperazin-1-yl)-1,3,4-thiadiazol-2-yl)acetamide

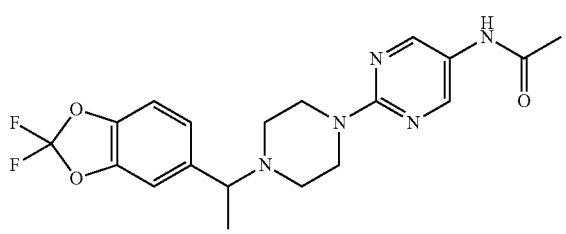 [SMILES: CC(=O)Nc1cnc(N2CCN(C(C)c3ccc4c(c3)OC(F)(F)O4)CC2)nc1]

The title compound was synthesized according the protocol used for Example 114, using Intermediate 10 (0.5 g, 1.9 mmol) and Intermediate 18 (0.418 g, 1.9 mmol) as starting material. The crude product was purified by flash chromatography (5-8% MeOH in DCM) to give the title compound (pale brown solid). $^1$H NMR (400 MHz, DMSO-$d_6$): δ 9.81 (s, 1H), 8.461 (s, 2H), 7.38-7.32 (m, 2H), 7.16 (d, J=6.8 Hz, 1H), 3.63 (t, J=9.6 Hz, 4.8 Hz, 4H), 3.50-3.47 (m, 1H), 2.50-2.43 (m, 2H), 2.36-2.32 (m, 2H), 1.99 (s, 3H), 1.30 (d, J=6.8 Hz, 3H). LCMS: (Method A) 406.2 (M+H), Rt. 3.05 min, 99.2% (Max). HPLC: (Method A) Rt. 2.98 min, 99.6% (Max).

Example 119: 2-(4-(1-(benzo[d][1,3]dioxol-5-yl)ethyl)piperazin-1-yl)quinazoline

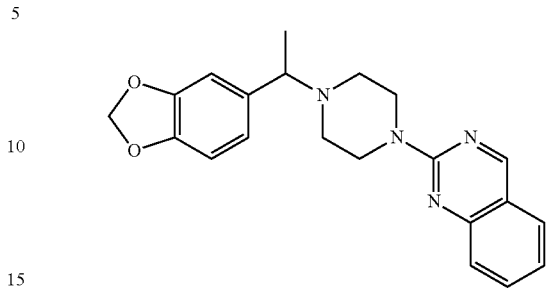

To a stirred solution of Intermediate 2 (0.3 g, 1.28 mmol) in dry DMF (10 mL), TEA (1.5 mL, 1.09 mmol) and 2-chloroquinazoline (0.5 g, 2.74 mmol) were added at rt and the resulting mixture was stirred at 80° C. for 12 h. It was cooled to rt, and concentrated. The crude residue was diluted with dichloromethane (50 mL), was washed with brine (10 mL), and dried over anhydrous $Na_2SO_4$. After evaporation of the solvents, the crude product was purified by MD Autoprep HPLC (Method B) (off white solid). $^1$H NMR (400 MHz, DMSO-$d_6$): 9.17 (s, 1H), 7.81 (d, J=7.6 Hz, 1H), 7.70 (t, J=8.0 Hz, 1H), 7.47 (d, J=8.4 Hz, 1H), 7.25 (t, J=7.6 Hz, 1H), 6.90 (s, 1H), 6.84 (d, J=8.0 Hz, 1H), 6.76 (d, J=8.0 Hz, 1H), 5.98 (d, J=2.4 Hz, 2H), 3.83 (t, J=5.6 Hz, 4H), 3.38 (t, J=6.0 Hz, 1H), 2.37-2.40 (m, 4H), 1.23 (d, J=2.4 Hz, 3H), LCMS: (Method A) 363.3 (M+H), Rt. 2.94 min, 99.0% (Max). HPLC: (Method A) Rt. 2.95 min, 98.5% (Max).

Example 120: N-(2-(4-(1-(quinolin-7-yl)ethyl)piperazin-1-yl)pyrimidin-5-yl)acetamide

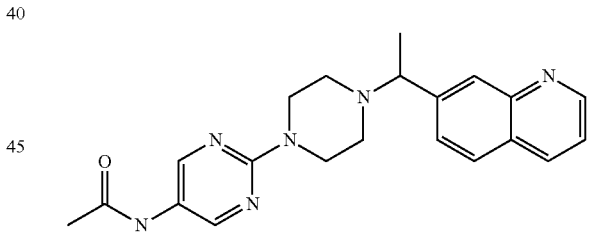

To a stirred solution of Intermediate 10 (0.72 g, 2.80 mmol) in dry ACN (10 mL), DIPEA (2 mL, 11.20 mmol) and Intermediate 9 (0.54 g, 2.80 mmol) were added at rt and the reaction mixture was stirred overnight at 80° C. It was cooled to rt and concentrated. The resulting mixture was diluted with EtOAc (50 mL), washed with water (15 mL) and dried over anhydrous $Na_2SO_4$. After evaporation of the solvents, the crude product was purified by flash column chromatography to afford the title compound (brown solid). $^1$H NMR (400 MHz, DMSO-$d_6$): δ 9.81 (s, 1H), 8.89-8.88 (m, 1H), 8.46 (s, 2H), 8.34 (d, J=8.0 Hz, 1H), 7.95 (d, J=8.4 Hz, 1H), 7.91 (s, 1H), 7.67-7.65 (m, 1H), 7.51-7.50 (m, 1H), 3.67-3.66 (m, 5H), 2.51-2.50 (m, 2H), 2.42-2.40 (m, 2H), 2.02 (s, 3H), 1.42 (d, J=6.8 Hz, 3H). LCMS: (Method A) 377.2 (M+H), Rt. 1.42 min, 99.10% (Max). HPLC: (Method A) Rt. 1.40 min, 96.61% (Max).

Example 121: N-(2-(4-(1-(benzorciri,2,51oxadiazol-5-yl)ethyl)piperazin-1-yl)pyrimidin-5-vOacetamide

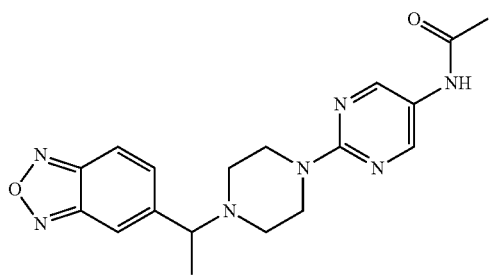 [SMILES: CC(=O)Nc1cnc(N2CCN(C(C)c3ccc4nonc4c3)CC2)nc1]

To a stirred solution of Intermediate 10 (0.59 g, 2.68 mmol) in dry DMF (10 mL), TEA (1.4 mL, 10.7 mmol) and Intermediate 13 (0.5 g, 2.68 mmol) were added at rt and the reaction mixture was stirred at 90° C. for 12 h. It was cooled to rt and concentrated. The crude product was diluted with dichloromethane (50 mL), washed with brine (10 mL) and dried over anhydrous $Na_2SO_4$. After evaporation of the solvents, the crude product was purified by MD Autoprep HPLC (Method B) (off white solid). $^1$H NMR (400 MHz, DMSO-d6): 9.83 (s, 2H), 8.48 (s, 2H), 7.90 (s, 1H), 7.71 (dd, J=1.2, 9.2 Hz, 1H), 3.63-3.68 (m, 5H), 2.39-2.50 (m, 4H), 2.01 (s, 3H), 1.37 (d, J=6.4 Hz, 3H), LCMS: (Method A) 368.0 (M+H), Rt. 2.08 min, 98.5% (Max). HPLC: (Method A) Rt. 2.05 min, 95.9% (Max).

Example 122: N-(2-(4-(1-(benzorcin,2,51thiadiazol-5-yl)ethyl)piperazin-1-yl)pyrimidin-5-vOacetamide

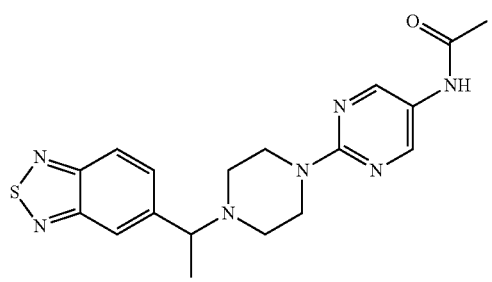 [SMILES: CC(=O)Nc1cnc(N2CCN(C(C)c3ccc4nsnc4c3)CC2)nc1]

The title compound was synthesized according the protocol used for Example 114, using Intermediate 10 (0.3 g, 1.16 mmol) and Intermediate 19 (0.323 g, 1.6 mmol) as starting material. The crude product was purified by flash chromatography (7% MeOH in DCM) and then again purified by MD Autoprep HPLC (Method C) to give the title compound (off white solid). $^1$H NMR (400 MHz, DMSO-$d_6$): δ 9.81 (s, 1H), 8.46 (s, 2H), 8.05 (d, J=8.8 Hz, 1H), 7.96 (s, 1H), 7.79 (d, J=8.8 Hz, 1H), 3.69-3.65 (m, 5H), 2.55-2.53 (m, 2H), 2.43-2.38 (m, 2H), 1.99 (s, 3H), 1.40 (d, J=6.4 Hz, 3H). LCMS: (Method A) 384.2 (M+H), Rt. 2.20 min, 97.23% (Max). HPLC: (Method A) Rt. 2.13 min, 98.37% (Max).

Example 123: N-(5-(4-(1-(benzorcin,2,51thiadiazol-5-yl)ethyl)piperazin-1-yl)-1,3,4-thiadiazol-2-vOacetamide

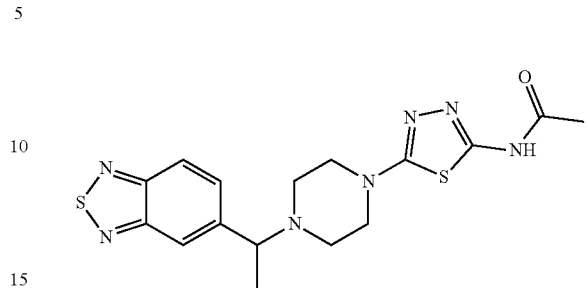

The title compound was synthesized according the protocol used for Example 114, using Intermediate 7 (0.5 g, 1.8 mmol) and Intermediate 19 (0.527 g, 2.65 mmol) as starting materials. The crude product was purified by flash chromatography (7% MeOH in DCM) to give the title compound (pale brown solid). $^1$H NMR (400 MHz, DMSO-$d_6$): δ 12.03 (s, 1H), 8.05 (d, J=9.2 Hz, 1H), 7.98 (s, 1H), 7.80 (dd, J=9.2, 1.2 Hz, 1H), 3.77-3.72 (m, 1H), 3.39-3.34 (m, 4H), 2.63-2.59 (m, 2H), 2.53-2.46 (m, 2H), 2.09 (s, 3H), 1.41 (d, J=6.4 Hz, 3H). LCMS: (Method A) 390.0 (M+H), Rt. 2.19 min, 99.17% (Max). HPLC: (Method A) Rt. 2.13 min, 98.91% (Max).

Example 124: N-(5-(4-(1-(benzorciri,2,51thiadiazol-5-yl)ethyl)piperazin-1-yl)-1,3,4-thiadiazol-2-vOacetamide

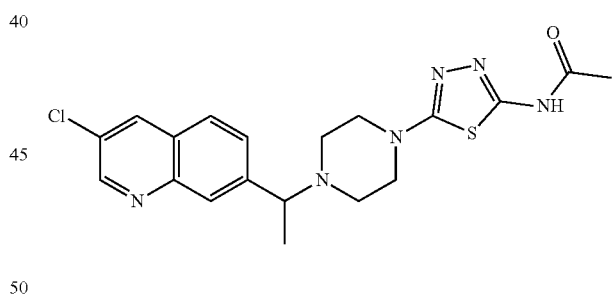

The title compound was synthesized according the protocol used for Example 114, using Intermediate 7 (0.250 g, 0.9 mmol) and Intermediate 20 (0.30 g, 1.3 mmol) as starting materials. The crude product was purified by flash chromatography (7% MeOH in DCM) to give the title compound (pale brown solid). $^1$H NMR (400 MHz, DMSO-$d_6$): δ 12.02 (s, 1H), 8.88-8.87 (m, 1H), 8.56-8.55 (m, 1H), 7.98-7.95 (m, 2H), 7.72 (d, J=8.4 Hz, 1H), 3.75 (q, J=6.8 Hz, 1H), 3.37 (t, J=4.4 Hz, 4H), 2.61-2.58 (m, 2H), 2.51-2.45 (m, 2H), 2.09 (s, 3H), 1.41 (d, J=6.8 Hz, 3H). LCMS: (Method A) 417.0 (M+H), Rt. 2.65 min, 98.42% (Max). HPLC: (Method A) Rt. 2.58 min, 98.73% (Max).

Example 125: N-(2-(4-(1-(3-chloroquinolin-7-yl)ethyl)piperazin-1-yl)pyrimidin-5-yl)acetamide

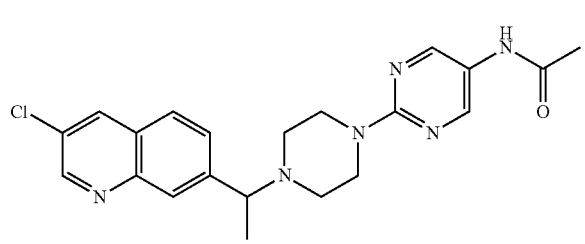 [SMILES: CC(=O)Nc1cnc(N2CCN(C(C)c3ccc4cc(Cl)cnc4c3)CC2)nc1]

The title compound was synthesized according the protocol used for Example 114, using Intermediate 10 (0.250 g, 0.9 mmol) and Intermediate 20 (0.307 g, 1.3 mmol) as starting materials. The crude product was purified by MD Autoprep HPLC (Method B) to give the title compound (pale brown solid). $^1$H NMR (400 MHz, DMSO-$d_6$): δ 9.81 (s, 1H), 8.87 (d, J=2.4 Hz, 1H), 8.55 (d, J=2.4 Hz, 1H), 8.46 (s, 2H), 7.97-7.95 (m, 2H), 7.73 (d, J=7.6 Hz, 1H), 3.70-3.65 (m, 5H), 2.50-2.41 (m, 2H), 2.42-2.37 (m, 2H), 2.00 (s, 3H), 1.41 (d, J=6.4 Hz, 3H). LCMS: (Method A) 411.2 (M+H), Rt. 2.60 min, 99.12% (Max). HPLC: (Method A) Rt. 2.59 min, 98.33% (Max).

Example 126: N-(2-(4-(1-(3,4-dihydro-2H-benzorbin,41dioxepin-7-yl)ethyl)piperazin-1-yl)pyrimidin-5-yl)acetamide

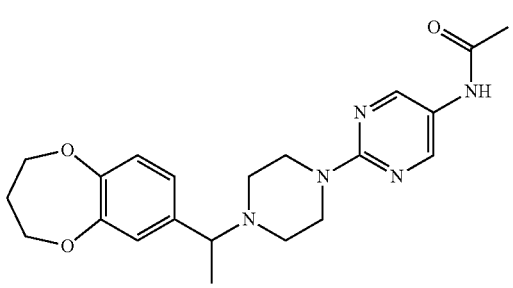 [SMILES: CC(=O)Nc1cnc(N2CCN(C(C)c3ccc4c(c3)OCCCO4)CC2)nc1]

The title compound was synthesized according the same protocol as described for the synthesis of Example 121, using Intermediate 14 and Intermediate 10 as starting materials. The crude product was purified by MD Autoprep HPLC (Method C) (off white solid). $^1$H NMR (400 MHz, DMSO-$d_6$): δ 9.80 (s, 1H), 8.45 (s, 2H), 6.88 (d, J=4.8 Hz, 3H), 4.10-4.08 (m, 3H), 337-3.38 (m, 2H), 3.32-3.29 (m, 4H), 2.49-2.48 (m, 2H), 2.46-2.44 (m, 2H), 2.07-2.01 (m, 2H), 1.99 (s, 3H), 1.24 (d, J=6.4 Hz, 3H). LCMS: (Method A) 397.3 (M+H), Rt. 2.43 min, 98.43% (Max). HPLC: (Method A) Rt. 2.41 min, 97.8% (Max).

Example 127: N-(2-(4-(1-(quinolin-8-yl)ethyl)piperazin-1-yl)pyrimidin-5-yl)acetamide

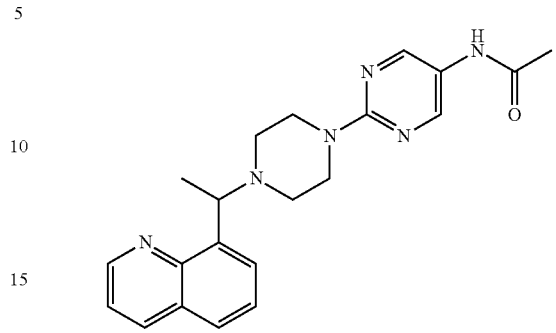

To a stirred solution of Intermediate 10 (0.4 g, 1.57 mmol) in dry DMF (10 mL), DIPEA (0.8 mL, 3.13 mmol) and Intermediate 15 (0.3 g, 1.57 mmol) were added at rt and the resulting reaction mixture was stirred at 80° C. for 12 h. It was cooled to rt and concentrated. The crude product was diluted with dichloromethane (50 mL), washed with brine (10 mL) and dried over anhydrous $Na_2SO_4$. After evaporation of the solvents, the crude product was purified by flash column chromatography to afford the title compound (off white solid). $^1$H NMR (400 MHz, DMSO-$d_6$): δ 9.81 (s, 1H), 8.91 (dd, J=4.0, 1.6 Hz, 1H), 8.46 (s, 2H), 8.37 (dd, J=8.0, 1.6 Hz, 1H), 7.92 (d, J=6.8 Hz 1H), 7.86 (d, J=8.0 Hz, 1H), 7.66-7.62 (m, 1H), 7.54 (dd, J=8.0, 4.0 Hz, 1H), 4.98 (q, J=6.4 Hz, 1H), 3.66-3.65 (m, 4H), 2.57-2.42 (m, 4H), 2.01 (s, 3H), 1.38 (d, J=6.4 Hz, 3H). LCMS: (Method A) 377.2 (M+H), Rt. 2.47 min, 98.0% (Max). HPLC: (Method A) Rt. 2.43 min, 97.5% (Max).

Example 128: N-(5-(4-(1-(2,3-dihydrobenzofuran-6-yl)ethyl)piperazin-1-yl)-1,3,4-thiadiazol-2-vPacetamide

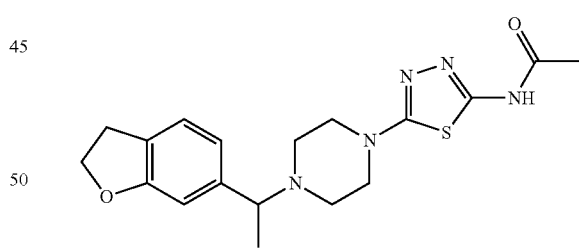

The title compound was synthesized according the protocol used for Example 114, using Intermediate 7 (0.3 g, 1.14 mmol) and Intermediate 21 (0.269 g, 1.48 mmol) as starting materials. The crude product was purified by flash chromatography (7% MeOH in DCM) followed by MD Autoprep HPLC (Method B) to give the title compound (off white solid). $^1$H NMR (400 MHz, DMSO-$d_6$): δ 12.02 (s, 1H), 7.12 (d, J=7.2 Hz, 1H), 6.76 (d, J=87.6 Hz, 1H), 6.71 (s, 1H), 4.51 (t, J=8.4 Hz, 2H), 3.39-3.28 (m, 5H), 3.14 (t, J=8.4 Hz, 2H), 2.42-2.39 (m, 4H), 2.09 (s, 3H), 1.28 (d, J=6.4 Hz, 3H). LCMS: (Method A) 374.2 (M+H), Rt. 2.34 min, 99.62% (Max). HPLC: (Method A) Rt. 2.32 min, 96.03% (Max).

Example 129: N-(2-(4-(1-(2,3-dihydrobenzofuran-6-yl)ethyl)piperazin-1-yl)pyrimidin-5-yl)acetamide

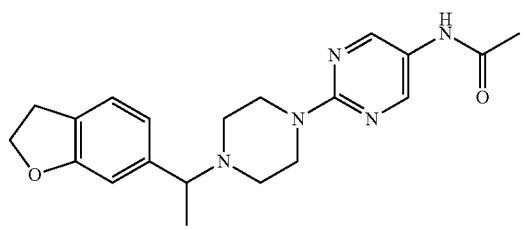 [SMILES: CC(=O)Nc1cnc(N2CCN(C(C)c3ccc4c(c3)OCC4)CC2)nc1]

The title compound was synthesized according the protocol used for Example 114, using Intermediate 10 (0.3 g, 1.16 mmol) and Intermediate 21 (0.274 g, 1.51 mmol) as starting materials. The crude product was purified by flash chromatography (10% MeOH in DCM) followed by MD Autoprep HPLC (Method B) to give the title compound (off white solid). $^1$H NMR (400 MHz, DMSO-d$_6$): δ 9.80 (s, 1H), 8.45 (s, 2H), 7.13 (d, J=7.6 Hz, 1H), 6.75-6.70 (m, 1H), 4.49 (t, J=8.4 Hz, 2H), 3.63-3.61 (m, 4H), 3.12 (t, J=8.4 Hz, 3H), 2.44-2.30 (m, 4H), 1.99 (s, 3H), 1.26 (d, J=6.4 Hz, 3H). LCMS: (Method A) 368.3 (M+H), Rt. 2.34 min, 99.74% (Max). HPLC: (Method A) Rt. 2.33 min, 99.52% (Max).

Example 130: 2-(4-(1-(benzo[d]1,3]dioxol-5-yl)ethyl)piperazin-1-yl)benzordithiazole

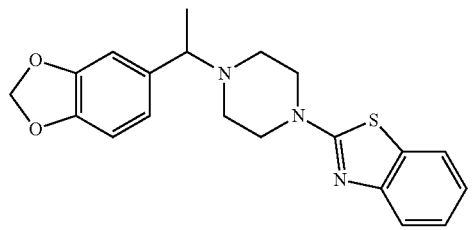 [SMILES: CC(c1ccc2c(c1)OCO2)N1CCN(c2nc3ccccc3s2)CC1]

To a stirred solution of Intermediate 2 (0.5 g, 2.13 mmol) in dry DMF (10 mL), DIPEA (0.8 mL, 6.3 mmol) and 2-bromo benzothiazole (0.5 g, 2.13 mmol) were added at rt and the reaction mixture was stirred at 90° C. for 12 h. It was cooled to rt and concentrated. The crude product was diluted with dichloromethane (50 mL), washed with brine (10 mL) and dried over anhydrous Na$_2$SO$_4$. After evaporation of the solvents, the crude product was purified by flash chromatography to give the title compound. $^1$H NMR (400 MHz, DMSO-d$_6$): δ 7.74 (d, J=0.8 Hz, 1H), 7.43 (d, J=7.6 Hz, 1H), 7.28-7.24 (m, 1H), 7.09-7.04 (m, 1H), 6.91 (d, J=1.6 Hz, 1H), 6.83 (d, J=8 Hz, 1H), 6.86-6.73 (m, 1H), 5.91 (d, J=1.6 Hz, 2H), 3.56-3.51 (m, 4H), 3.44-3.36 (m, 1H), 2.47-2.41 (m, 4H), 1.28 (d, J=6.8 Hz, 3H). LCMS: (Method A) 368.2 (M+H), Rt. 3.34 min, 95.18% (Max). HPLC: (Method A) Rt. 3.34 min, 97.15% (Max).

Example 131: N-(2-(4-(1-(quinolin-3-yl)ethyl)piperazin-1-yl)pyrimidin-5-yl)acetamide

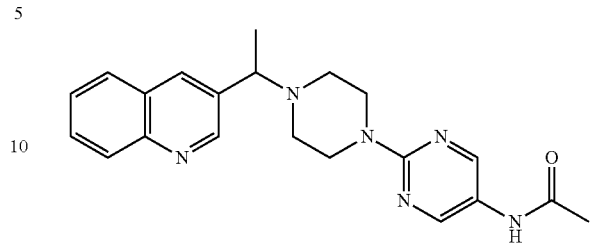

To a stirred solution of Intermediate 10 (0.5 g, 1.9 mmol) in DMF (5 mL), DIPEA (1.65 mL, 9.5 mmol) and Intermediate 23 (0.496 g, 2.59 mmol) were added at 0-5° C. The reaction mixture was stirred at 100° C. overnight. It was then concentrated under reduced pressure. The crude product was diluted with DCM (100 mL), washed with water (2×25 mL) and dried over Na$_2$SO$_4$. After evaporation of the solvents, the crude product was purified by flash chromatography (7% MeOH in DCM). It was triturated with ACN (5 mL) and diethyl ether (2×15 mL) to give the title compound as pale brown solid. $^1$H NMR (400 MHz, DMSO-d$_6$): δ 9.81 (s, 1H), 8.93-8.91 (m, 1H), 8.459 (s, 2H), 8.24-8.22 (m, 1H), 7.99 (t, J=8.0 Hz, 2H), 7.73-7.71 (m, 1H), 7.60-7.58 (m, 1H), 3.79-3.73 (m, 1H), 3.67-3.65 (m, 4H), 2.55-2.50 (m, 2H), 2.50-2.40 (m, 2H), 2.02 (s, 3H), 1.44 (d, J=6.4 Hz, 3H). LCMS: (Method A) 377.2 (M+H), Rt. 1.80 min, 94.43% (Max). HPLC: (Method A) Rt. 1.82 min, 94.95% (Max).

Example 132: (S)-5-(4-(1-(benzordiri,3]dioxol-5-yl)ethyl)piperazin-1-yl)-1,3,4-thiadiazol-2-amine

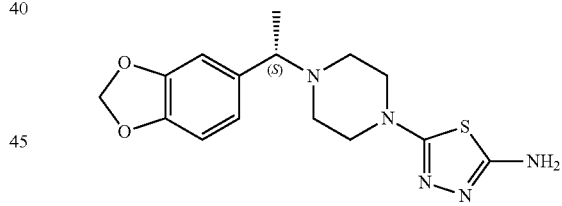

To a stirred solution of Intermediate 16 (3 g, 11.1 mmol) in ACN (30 mL), TEA (3.36 g, 33.3 mmol) and 5-bromo-1,3,4-thiadiazol-2-amine (2.19 g, 12.2 mmol) were added at rt and the mixture was heated at 85° C. overnight. The completion of the reaction was confirmed by TLC. The reaction mixture was evaporated under vacuum and the resulting crude solid was diluted with water (30 mL) and extracted with EtOAc (3×30 mL). The combined organic layer was washed with brine (30 mL), dried over Na$_2$SO$_4$ and evaporated at 45° C. under vacuum. The crude product was purified by flash chromatography (7% MeOH in DCM) to give the title compound (pale brown solid). $^1$H NMR (400 MHz, DMSO-d6): δ 6.88-6.83 (m, 2H), 6.76-6.74 (m, 1H), 6.46 (s, 2H), 5.91 (d, J=1.6 Hz, 2H), 3.39-3.37 (m, 1H), 3.20-3.17 (m, 4H), 2.46-2.30 (m, 4H), 1.25 (d, J=6.5 Hz, 3H). LCMS: (Method A) 334.0 (M+H), Rt. 1.85 min, 96.47% (Max). HPLC: (Method A) Rt. 1.79 min, 96.77% (Max). Chiral HPLC: (Method D) Rt. 20.96 min, 100.00%

Example 133: (S)—N-(5-(4-(1-(benzo[d]thiazol-5-yl)ethyl)piperazin-1-yl)-1,3,4-thiadiazol-2-yl)acetamide or ((R)—N-(5-(4-(1-(benzo[d]thiazol-5-yl)ethyl)piperazin-1-yl)-1,3,4-thiadiazol-2-yl)acetamide

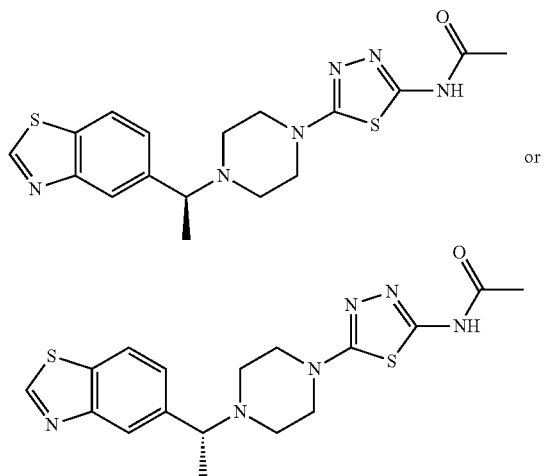

The two enantiomers of Example 114 were separated by chiral preparative HPLC (Method PF). Example 133 corresponds to the second eluting fraction (off white solid). $^1$H NMR (400 MHz, DMSO-d$_6$): δ 12.01 (s, 1H), 9.34 (s, 1H), 8.12 (d, J=8.0 Hz, 1H), 8.02 (s, 1H), 7.50 (d, J=8.4 Hz, 1H), 3.67 (d, J=6.0 Hz, 1H), 3.37-3.35 (m, 4H), 2.56-2.57 (m, 4H), 2.09 (s, 3H), 1.40 (d, J=6.8 Hz, 3H). LCMS: (Method A) 389.0 (M+H), Rt. 2.09 min, 96.5% (Max). HPLC: (Method A) Rt. 2.08 min, 97.4% (Max). Chiral HPLC: (Method D) Rt 15.28 min, 99.82%.

Example 134: (S) 2-(4-(1-(benzo[d][1,3]dioxol-5-yl)ethyl)piperazin-1-yl)-N-methylpyrimidine-5-carboxamide

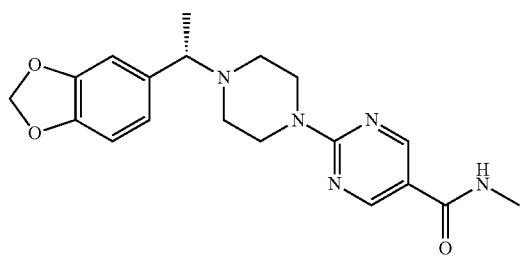 [SMILES: CNC(=O)c1cnc(N2CCN([C@@H](C)c3ccc4c(c3)OCO4)CC2)nc1]

Step 1: Ethyl (S)-2-(4-(1-(benzo[d][1,3]dioxol-5-yl)ethyl)piperazin-1-yl)pyrimidine-5-carboxylate To a stirred solution of Intermediate 16 (1.87 g, 6.94 mmol) in dry acetonitrile (10 mL), potassium carbonate (2.87 g, 20.8 mmol, Spectrochem) and ethyl 2-(methylsulfonyl) pyrimidine-5-carboxylate (1.6 g, 6.94 mmol, synthesis described in Example 98, steps, 1 and 2) were added. The resulting mixture was stirred at rt for 3 h. It was then filtered through celite and concentrated. The crude product was diluted with dichloromethane (25 mL), washed with water and dried over anhydrous Na$_2$SO$_4$. After evaporation of the solvent, the crude product was purified by flash column chromatography to afford the title compound (white solid). $^1$H NMR (400 MHz, DMSO-d$_6$): δ 8.74 (s, 1H), 6.78-6.72 (m, 2H), 5.97 (s, 1H), 4.38-4.36 (m, 1H), 3.81 (s, 2H), 2.37-2.47 (m, 9H), 1.26 (d, J=2.84 Hz, 3H), LCMS: (Method A) 385.2 (M+H), Rt. 3.22 min, 98.6% (Max).

Step 2: Lithium (S)-2-(4-(1-(benzo[d][1,3]dioxol-5-yl)ethyl)piperazin-1-yl)pyrimidine-5-carboxylate To a stirred solution of ethyl (S)-2-(4-(1-(benzo[d][1,3]dioxol-5-yl)ethyl)piperazin-1-yl)pyrimidine-5-carboxylate (1.6 g, 17.5 mmol) in a mixture of MeOH (2 mL), THF (7 mL) and water (1 mL), lithium hydroxide (0.431 g, 5.20 mmol, Spectrochem) was added at 0° C. and the resulting mixture was stirred at rt for 12 h. It was concentrated and the resulting product was taken for next step without any further purification. Yield: 96% (0.61 g, off white solid). $^1$H NMR (400 MHz, DMSO-d$_6$): δ 8.61 (s, 1H), 6.81-6.88 (m, 4H), 5.97 (d, J=1.8 Hz, 2H), 3.68 (d, J=6.2 Hz, 2H),3.22-3.21 (m, 1H), 2.28-2.35 (m, 6H), 1.26 (d, J=8.9 Hz, 3H), LCMS: (Method A) 357.0 (M+H), Rt. 2.41 min, 97.1% (Max)

Step 3: (S) 2-(4-(1-(benzo[d][1,3]dioxol-5-yl)ethyl)piperazin-1-yl)^-methylpyrimidine-5-carboxamide To a stirred solution of lithium (S)-2-(4-(1-(benzo[d][1,3]dioxol-5-yl)ethyl)piperazin-1-yl)pyrimidine-5-carboxylate (0.3 g, 0.82 mmol) in dry DCM (10 ml_), triethylamine (0.34 ml.) and methylamine in THF (2 M, 1.6 ml_, 3.32 mmol) were added at 0° C. The reaction mixture was stirred at rt for 1 h. The reaction progression was monitored by TLC. After completion of the reaction, the mixture was diluted with 10% sodium bicarbonate solution (10 ml.) and extracted with DCM (20 ml_). The organic layer was dried over Na$_2$SO$_4$ and evaporated to dryness. The crude product was purified by flash column chromatography. Yield: 56% (0.17 g, off white solid). $^1$H NMR (400 MHz, DMSO-d$_6$): δ 8.71 (s, 2H), 8.28 (d, J=4.8 Hz, 1H), 6.90-6.83 (m, 2H), 6.77-6.75 (m, 1H), 5.98 (d, J=2.0 Hz, 2H), 3.77 (t, J=4.8 Hz, 4H), 3.41-3.38 (m, 1H), 2.74 (d, J=4.4 Hz, 3H), 2.38-2.33 (m, 4H), 1.28 (d, J=6.8 Hz, 3H). LCMS: (Method A) 370.2 (M+H), Rt. 2.21 min, 98.9% (Max). HPLC: (Method A) Rt. 2.18 min, 99.3% (Max). Chiral HPLC: (Method G) Rt. 5.51 min, 100.00%

Example 135: 2-(4-(1-(quinoxalin-6-yl)ethyl)piperazin-1-yl)benzo[d]thiazole

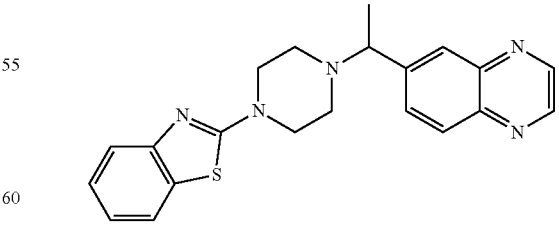

To a stirred solution of Intermediate 11 (0.26 g, 0.93 mmol) in dry DMF (3 mL), TEA (0.4 mL, 2.81 mmol) and 2-bromobenzothiazole (0.2 g, 0.93 mmol, combi blocks) were added at rt and the reaction mixture was stirred overnight at 95° C. It was cooled to rt and concentrated. To the resulting mixture, water (20 mL) was added and the product was extracted with EtOAc (2×40 mL). The combined organic layers were dried over anhydrous Na₂SO₄ and concentrated. The crude product was purified by flash column chromatography to afford the title compound (brown solid). H NMR (400 MHz, DMSO-d₆): δ 8.92 (d, J=4.0 Hz, 2H), 8.09 (d, J=8.8 Hz, 1H), 8.01 (s, 1H), 7.92 (d, J=8.0 Hz, 1H), 7.73 (d, J=8.0 Hz, 1H), 7.42 (d, J=8.0 Hz, 1H), 7.25 (t, J=7.6 Hz, 1H), 7.04 (t, J=7.6 Hz, 1H), 3.83-3.81 (m, 1H), 3.56 (t, J=4.8 Hz, 4H), 2.64-2.63 (m, 2H), 2.49 (m, 2H), 1.44 (d, J=6.8 Hz, 3H). LCMS: (Method A) 376.3 (M+H), Rt. 2.71 min, 99.382% (Max). HPLC: (Method A) Rt. 2.69 min, 98.44% (Max).

Example 136: (S)-2-(4-(1-(benzofdin,31dioxol-5-yl)ethyl)piperazin-1-vPbenzordlthiazole

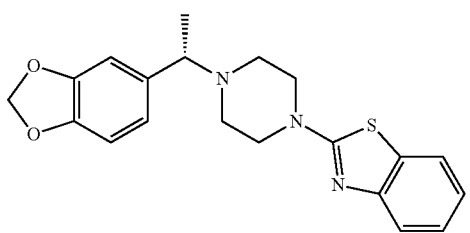 [SMILES: C[C@@H](c1ccc2c(c1)OCO2)N1CCN(c2nc3ccccc3s2)CC1]

To a stirred solution of Intermediate 16 (0.3 g, 1.27 mmol) in dry DMF (10 mL), TEA (0.67 mL, 3.82 mmol) and 2-bromo benzothiazole (0.27 g, 1.27 mmol) were added at rt and the reaction mixture was stirred at 90° C. for 12 h. It was cooled to rt, concentrated. The resulting mixture was diluted with dichloromethane (50 ml), washed with brine (10 ml) and dried over anhydrous Na₂SO₄. After evaporation of the solvents, the crude product was purified by flash chromatography to give the title compound (off white solid). ¹H NMR (400 MHz, DMSO-d₆): δ 7.74 (d, J=7.6 Hz, 1H), 7.43 (d, J=8.0 Hz, 1H), 7.27 (t, 1H), 7.05 (t, J=7.6 Hz, 1H), 6.90 (s, 1H), 6.83 (d, J=8.0 Hz, 1H), 6.77 (d, J=8.4 Hz, 1H), 5.91 (d, J=1.6 Hz, 2H), 3.53 (t, J=7.6 Hz, 4H), 3.44-3.38 (m, 1H), 2.47-2.44 (m, 4H), 1.28 (d, J=6.8 Hz, 3H). LCMS: (Method A) 368.0 (M+H), Rt. 3.28 min, 96.86% (Max). HPLC: (Method A) Rt. 3.33 min, 97.08% (Max). Chiral HPLC: (Method G) Rt. 8.00 min, 100.00%

Example 137: (S)-2-(4-(1-(benzofdin,31dioxol-5-vnethyl)piperazin-1-yl)-N,N-dimethylpyrimidine-5-carboxamide

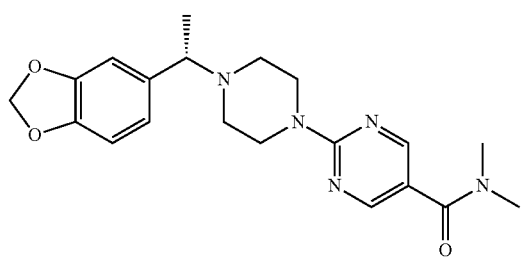 [SMILES: C[C@@H](c1ccc2c(c1)OCO2)N1CCN(c2ncc(C(=O)N(C)C)cn2)CC1]

The title compound was synthesized using the same procedure as described for Example 134, using lithium (S)-2-(4-(1-(benzo[d][1,3]dioxol-5-yl)ethyl)piperazin-1-yl) pyrimidine-5-carboxylate and N,N-dimethyl amine as solution in THF as starting materials. The crude product was purified by flash column chromatography (off white solid). ¹H NMR (400 MHz, DMSO-d₆): δ 8.45 (s, 2H), 6.90 (s, 1H), 6.84 (d, J=8.0 Hz, 1H), 6.74 (d, J=7.6 Hz, 1H), 5.98 (d, J=1.6 Hz, 2H), 3.76 (t, J=4.8 Hz, 4H), 3.39-3.37 (m, 1H), 2.97 (s, 6H), 2.44-2.43 (m, 2H), 2.37-2.35 (m, 2H), 1.28 (d, J=6.8 Hz, 3H). LCMS: (Method A) 384.2 (M+H), Rt. 2.44 min, 98.2% (Max). HPLC: (Method A) Rt. 2.44 min, 98.3% (Max). Chiral HPLC: (Method G) Rt. 6.98 min, 100.00%

Example 138: (S)-2-(4-(1-(benzofdlH,31dioxol-5-yl)ethyl)piperazin-1-yl)-1H-benzofdlimidazole

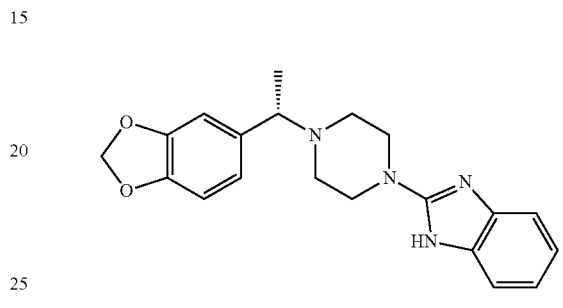

To a stirred solution of Intermediate 13 (0.25 g, 0.92 mmol) in dry DMF (3 mL), TEA (0.5 mL, 3.71 mmol) and 2-bromo-1H-benzoimidazole (0.18 g, 0.92 mmol, Arbor chemicals) were added at rt and the reaction mixture was stirred at 100° C. overnight. It was cooled to rt and concentrated. This crude product was purified by flash column chromatography to afford the title compound (brown solid). ¹H NMR (400 MHz, CDCl₃): 57.33 (m, 2H), 7.07-7.06 (m, 2H), 6.86 (d, J=1.2 Hz, 1H), 6.76-6.74 (m, 2H), 5.97-5.96 (m, 2H), 3.59-3.58 (m, 4H), 3.35-3.34 (m, 1H), 2.60-2.59 (m, 2H), 2.52-2.51 (m, 2H), 1.35 (d, J=8.0 Hz, 3H). LCMS: (Method A) 351.2 (M+H), Rt. 2.29 min, 95.81% (Max). HPLC: (Method A) Rt. 2.19 min, 96.33% (Max).

Example 139: (S)-2-(4-(1-(benzofdlH,31dioxol-5-yl)ethyl)piperazin-1-yl)thiazolor4,5-clpyridine

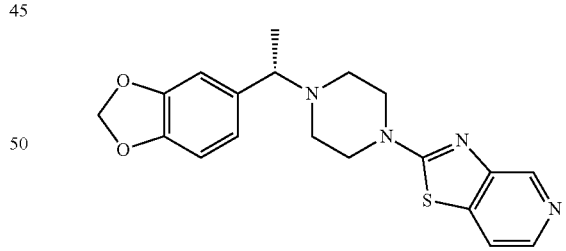

To a stirred solution of Intermediate 13 (0.189 g, 0.64 mmol) in dry DMF (5 mL), TEA (0.23 mL, 1.75 mmol) and 2-chlorothiazolo[4,5-C]pyridine (0.1 g, 0.58 mmol) were added at rt and the reaction mixture was stirred overnight at 100° C. It was cooled to rt and concentrated under vacuum. To this crude residue, water (5 mL) was added and extracted with EtOAc (2×25 mL). The combined organic layers were dried over anhydrous Na₂SO₄ and concentrated. The crude product was purified by flash column chromatography to afford the title compound (off white solid). ¹H NMR (400 MHz, DMSO-d₆): 1HNMR (400 MHz, DMSO-d6): δ 8.66 (s, 1H), 8.18 (d, J=5.2 Hz, 1H), 7.84 (d, J=5.2 Hz, 1H), 6.91

(d, J=1.2 Hz, 1H), 6.85 (d, J=8.0 Hz, 1H), 6.77 (d, J=8.0, 1.2 Hz, 1H), 5.60-5.99 (m, 2H), 3.59-3.57 (m, 2H), 3.45 (q, J=6.8 Hz, 1H), 2.51-2.46 (m, 4H), 1.29 (d, J=6.8 Hz, 3H). LCMS: (Method A) 369.0 (M+H), Rt. 1.90 min, 99.501% (Max). HPLC: (Method A) Rt. 1.82 min, 99.73% (Max). Chiral HPLC: (Method G) Rt. 8.31 min, 100.00%

Example 140: 2-(4-(1-(quinoxalin-6-yl)ethyl)piperazin-1-yl)thiazolo[4,5-c]pyridine

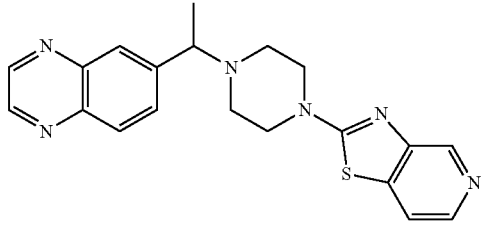 [SMILES: CC(c1ccc2nccnc2c1)N1CCN(c2nc3cnccc3s2)CC1]

To a stirred solution of Intermediate 11 (0.169 g, 0.58 mmol) in dry DMF (5 mL), TEA (0.23 mL, 1.75 mmol) and 2-chlorothiazolo[4,5-C]pyridine (0.18 g, 0.60 mmol) were added at rt and the reaction mixture was stirred overnight at 100° C. The reaction mixture was cooled to rt and concentrated under vacuum. To the crude residue, water (5 mL) was added and extracted with EtOAc (2×25 mL). The combined organic layers were dried over anhydrous Na₂SO₄ and concentrated. The crude product was purified by MD Autoprep HPLC (Method B) to afford the title compound (off white solid). ¹H NMR (400 MHz, DMSO-d₆): δ 8.94 (d, J=7.2 Hz, 1H), 8.92 (d, J=7.2 Hz, 1H), 8.65 (s, 1H), 7.16 (d, J=5.2 Hz, 1H), 8.09 (d, J=8.4 Hz, 1H), 7.91 (dd, J=8.3, 2.0 Hz, 1H), 7.83 (d, J=5.4 Hz, 1H), 3.84 (q, J=6.8 Hz, 1H), 3.62-3.60, 2.61-2.48 (m, 4H), 1.29 (d, J=6.8 Hz, 3H). LCMS: (Method A) 377.2 (M+H), Rt. 1.48 min, 99.79% (Max). HPLC: (Method A) Rt. 1.481 min, 99.10% (Max).

Example 141: (S)-5-(4-(1-(benzo[d]ri,31 dioxol-5-yl)ethyl)piperazin-1-yn-N-ethyl-1,3,4-thiadiazol-2-amine

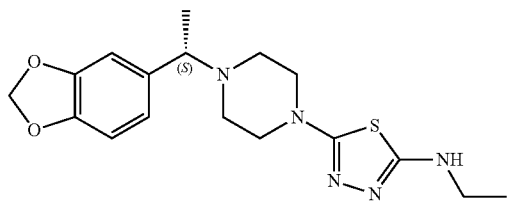

To a stirred solution of Example 132 (0.7 g, 2.1 mmol) in THF (14 mL), acetaldehyde (0.84 mL, 5M in THF) and titanium(IV)ethoxide (0.958 g, 4.2 mmol) were added and the resulting mixture was stirred at rt overnight. The completion of the reaction was confirmed by TLC. The reaction mixture was cooled to 0° C. and sodium borohydride (0.238 g, 6.3 mmol) was added. The reaction mixture was stirred 2 h at rt. It was quenched with water (10 mL) and filtered through celite. The celite bed washed with EtOAc (2×50 mL) and the filtrate was washed with water (10 mL), brine (10 mL), dried over Na₂SO₄. It was evaporated at 50° C. under vacuum. The crude product was purified by MD Autoprep HPLC (Method D) to give the title compound (off white solid). ¹H NMR (400 MHz, DMSO-d₆): δ 6.98 (t, J=5.2 Hz, 2H), 6.88 (d, J=1.2 Hz, 1H), 6.84 (d, J=8.0 Hz, 1H), 6.75 (dd, J=8.0, 1.2 Hz, 1H), 5.99-5.98 (m, 2H), 3.37 (q, J=6.8 Hz, 2H), 3.20-3.14 (m, 6H), 2.47-2.36 (m, 4H), 1.26 (d, J=6.8 Hz, 3H), 1.11 (t, J=7.2 Hz, 3H). LCMS: (Method A) 362.0 (M+H), Rt. 2.01 min, 99.75% (Max). HPLC: (Method A) Rt. 2.02 min, 97.69% (Max). Chiral HPLC: (Method B) Rt. 3.90 min, 100%

Example 142: (S)-5-(4-(1-(benzo[d][1,3]dioxol-5-yl)ethyl)piperazin-1-yl)-N-propyl-1,3,4-thiadiazol-2-amine

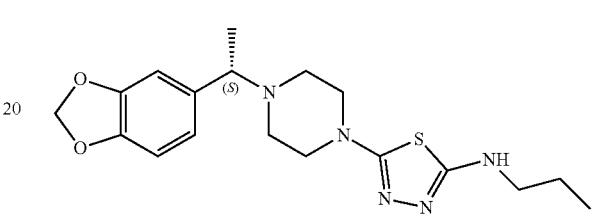

To a stirred solution of Example 132 (0.5 g, 1.5 mmol) in THF (10 mL), propionaldehyde (0.17 g, 3.0) and titanium (IV)ethoxide (0.684 g, 3.0 mmol) were added at rt and stirred overnight. The completion of the reaction was confirmed by TLC. The reaction mixture was cooled to 0° C. and sodium borohydride (0.17 g, 4.4 mmol) was added. The reaction mixture was stirred for 2 h at rt. It was quenched with water (10 mL) and filtered through celite. The celite bed washed with EtOAc (2×50 mL) and the filtrate was washed with water (10 mL), brine solution (10 mL) and dried over Na₂SO₄. It was evaporated at 50° C. under vacuum. The crude product was purified by MD Autoprep HPLC (Method D) to give the title compound (off white solid). ¹H NMR (400 MHz, DMSO-d₆): δ 7.02 (t, J=5.2 Hz, 2H), 6.88 (d, J=1.6 Hz, 1H), 6.84 (d, J=7.6 Hz, 1H), 6.75 (dd, J=7.6, 1.6 Hz, 1H), 5.99-5.98 (m, 2H), 3.41 (q, J=6.4 Hz, 2H), 3.20-3.17 (m, 4H), 3.11-3.06 (m, 2H), 2.45-2.32 (m, 4H), 1.56-1.47 (m, 2H), 1.26 (d, J=6.4 Hz, 3H), 0.86 (t, J=7.6 Hz, 3H). LCMS (Method A) 376.0.0 (M+H), Rt. 2.23 min, 99.08% (Max). HPLC: (Method A) Rt. 2.21 min, 97.11% (Max). Chiral HPLC: (Method B) Rt. 3.61. min, 100%.

Example 143: (R)-5-(4-(1-(benzo[d][1,3]dioxol-5-yl)ethyl)piperazin-1-yl)-1,3,4-thiadiazol-2-amine

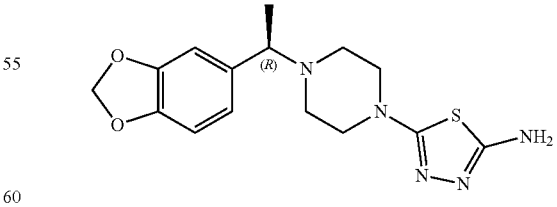

To a stirred solution of Intermediate 24 (1 g, 4.27 mmol) in ACN (10 mL), TEA (1.75 mL, 12.8 mmol) and 5-bromo-1,3,4-thiadiazol-2-amine (0.764 g, 4.27 mmol) were added at rt and the resulting mixture was heated at 85° C. overnight. Completion of the reaction was confirmed by TLC. Reaction mixture was evaporated under vacuum. To the resulting crude solid, water (50 mL) was added and stirred for 15 min. Then the reaction mixture was filtered and filtration cake was washed with water (20 mL) and pet ether (2×20 mL). The crude product was triturated with Et₂O (2×20 mL), filtered and dried under vacuum. The title compound was isolated as brown solid. ¹H NMR (400 MHz, DMSO-d₆): δ 6.88-6.83 (m, 2H), 6.76-6.74 (m, 1H), 6.46 (s, 2H), 5.99-5.97 (m, 2H), 3.36 (m, 1H), 3.20-3.17 (m, 4H), 2.50-2.33 (m, 4H), 1.26 (d, J=6.8 Hz, 3H). LCMS: (Method A) 334.0 (M+H), Rt. 1.82 min, 94.96% (Max). HPLC: (Method A) Rt. 1.81 min, 93.22% (Max). Chiral HPLC: (Method A) Rt. 18.36 min, 97.38%.

Example 144: 2-(4-(1-(Benzordiri,31dioxol-5-yl)ethyl)piperazin-1-yl)-4-methylthiazole

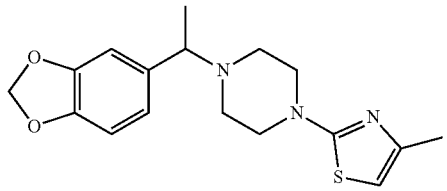 [SMILES: Cc1csc(N2CCN(C(C)c3ccc4c(c3)OCO4)CC2)n1]

Step 1: tert-Butyl 4-(4-methylthiazol-2-yl)piperazine-1-carboxylate

To a stirred solution of fert-butyl 4-carbamothioylpiperazine-1-carboxylate (synthesized according to Example 5, Step 1, 1.0 g, 4.08 mmol) in dioxane (10 mL), TEA (0.58 g, 5.3 mmol) and bromo acetone (0.67 mL, 5.3 mmol) were added at rt and the resulting mixture was stirred at 90° C. for 16 h. The completion of the reaction was monitored by TLC. The reaction mixture was diluted with water (10 mL) and extracted with EtOAc (2×25 mL). The organic layer was dried over anhydrous Na₂SO₄, concentrated under vacuum. The crude product was taken as such for next step. Yield: 77% (0.9 g, pale yellow solid). LCMS: (Method A) 284.0 (M+H), Rt. 2.74 min, 83.2% (Max).

Step 2: 4-Methyl-2-(piperazin-1-yl)thiazole hydrochloride

To a stirred solution of fert-butyl 4-(4-methylthiazol-2-yl)piperazine-1-carboxylate (1.0 g, 3.53 mmol) in dry dioxane (2 mL), HCl in dioxane (4 N, 10 mL) was added at rt and the resulting mixture was stirred for 3 h. It was concentrated under vacuum and the resulting crude product was triturated in Et₂O, filtrated and dried under vacuum to afford the title compound. Yield: 75% (500 mg, off white solid).

Step 3: 2-(4-(1-(Benzo[d][1,3]dioxol-5-yl)ethyl) piperazin-1-yl)-4-methylthiazole The title compound was synthesized by following general procedure D, using 4-methyl-2-(piperazin-1-yl)thiazole hydrochloride (1.01 g, 5.41 mmol) and Intermediate 1 (1.0 g, 5.41 mmol). The crude product was purified by flash chromatography (1.2-1.5% MeOH in DCM) to afford the title compound (colorless oil). ¹H NMR (400 MHz, DMSO-d₆): δ 6.88 (s, 1H), 6.83 (d, J=8.0 Hz, 1H), 6.75 (d, J=7.6 Hz, 1H), 6.34 (s, 1H), 5.97 (s, 2H), 3.39-3.37 (m, 1H), 3.32-3.29 (m, 4H), 2.46-2.43 (m, 2H), 2.41-2.37 (m, 2H), 2.10 (s, 1H), 1.26 (d, J=6.8 Hz, 3H). LCMS: (Method A) 332.0 (M+H), Rt. 2.04 min, 99.1% (Max). HPLC: (Method A) Rt. 2.02 min, 99.6% (Max).

Example 148: 2-(4-(1-(benzordiri,31 dioxol-5-yl)ethyl)piperazin-1-yl)-6,7-dihydrothiazolo[5,4-c1pyridin-4(5H)-one

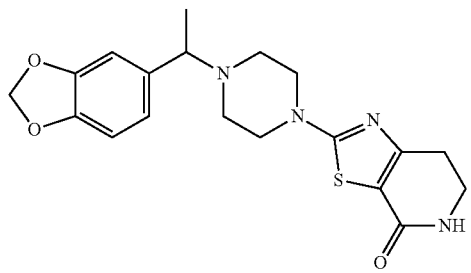 [SMILES: CC(c1ccc2c(c1)OCO2)N1CCN(c2nc3c(s2)C(=O)NCC3)CC1]

To a stirred solution of Intermediate 25 (0.75 g, 2.43 mmol) in dry DMF (7 mL), TEA (1.4 mL, 7.30 mmol) and Intermediate 1 (0.9 g, 4.87 mmol) were added at rt. The resulting mixture was stirred overnight at 120° C. It was cooled to rt and DMF was evaporated under reduced pressure. Resulting crude product was purified by flash column chromatography followed by MD Autoprep HPLC (Method B), affording the title product (off white solid). ¹H NMR (400 MHz, DMSO-d₆): δ 7.32 (s, 1H), 6.86-6.84 (m, 3H), 5.99-5.98 (m, 2H), 3.45-3.44 (m, 4H), 3.38-3.34 (m, 2H), 2.70-2.67 (m, 2H), 2.50-2.59 (m, 4H), 1.28-1.23 (m, 3H). LCMS: (Method A) 387.2 (M+H), Rt. 2.15 min, 96.71% (Max). HPLC: (Method A) Rt. 2.11 min, 94.32% (Max).

Example 165: 6-(1-(4-(5-(trifluoromethyl)pyridin-2-yl)piperazin-1-yl)ethyl)quinoxaline

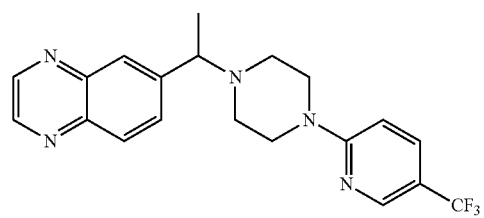 [SMILES: CC(c1ccc2nccnc2c1)N1CCN(c2ccc(C(F)(F)F)cn2)CC1]

To a stirred solution of Intermediate 11 (0.3 g, 1.23 mmol) in dry DMF (5 mL), TEA (0.5 mL, 3.71 mmol) and 2-chloro-5(trifluoromethyl) pyridine (0.22 g, 1.23 mmol) were added at rt. The resulting mixture was stirred at 90° C. overnight. It was cooled to rt and solvents were evaporated. Water (20 mL) was added and the desired product was extracted with EtOAc (2×30 mL). The resulting organic layer was dried over Na₂SO₄ and concentrated. The crude product was purified by flash column chromatography, affording the title compound (brown oil). ¹H NMR (400 MHz, DMSO-d₆): δ 8.94-8.93 (m, 2H), 8.38 (s, 1H), 8.09 (d, J=8.8 Hz, 1H), 8.01 (s, 1H), 7.93-7.91 (m, 1H), 7.77-7.75 (m, 1H), 6.91 (d, J=9.2 Hz, 1H), 3.78-3.77 (m, 1H), 3.62 (m, 4H), 2.58-2.57 (m, 2H), 2.46-2.44 (m, 2H), 1.44 (d, J=6.8 Hz, 3H). LCMS: (Method A) 388.0 (M+H), Rt. 3.17 min, 97.92% (Max). HPLC: (Method A) Rt 3.10 min, 96.45% (Max).

Example 166: (S)-1-(1-(benzordiri,31dioxol-5-yl) ethyl)-4-(5-(trifluoromethyl)pyridin-2-vDpiperazine

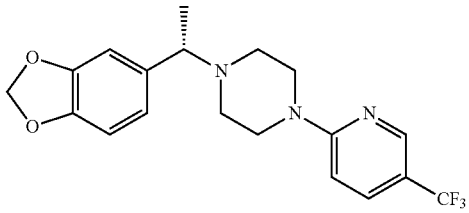 [SMILES: C[C@@H](c1ccc2c(c1)OCO2)N1CCN(c2ccc(C(F)(F)F)cn2)CC1]

To a stirred solution of Intermediate 16 (0.25 g, 0.93 mmol) in dry DMF (5 mL), TEA (0.4 mL, 2.7 mmol) and 2-chloro-5-fluoro methyl pyridine (0.16 g, 9.3 mmol) were added at rt. The resulting reaction mixture was stirred at 90° C. for 12 h. It was cooled to rt, concentrated and diluted with dichloromethane (30 mL). The resulting solution was washed with saturated NaCl solution (10 mL), dried over anhydrous $Na_2SO_4$ and concentrated. The resulting crude product was purified by flash chromatography affording the title compound (brown oil). $^1$H NMR (400 MHz, DMSO-$d_6$): δ 8.38 (s, 1H), 7.78 (dd, J=9.2, 2.4 Hz, 1H), 6.88 (d, J=8.0 Hz, 2H), 6.84 (d, J=8.0 Hz, 1H), 6.77-6.75 (m, 1H), 5.99-5.98 (m, 2H), 3.60 (t, J=4.8 Hz, 4H), 3.40-3.37 (m, 1H), 2.48-2.44 (m, 4H), 1.27 (d, J=6.4 Hz, 3H). LCMS: (Method A) 380.0 (M+H), Rt. 3.73 min, 98.89% (Max). HPLC: (Method A) Rt. 3.67 min, 99.06% (Max).

Example 167: (S)-1-(2-(4-(1-(benzo[d][1,31dioxol-5-yl)ethyl)piperazin-1-yl)pyrimidin-5-yl)ethan-1-one

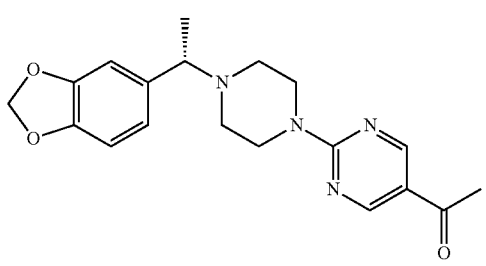 [SMILES: CC(=O)c1cnc(N2CCN([C@@H](C)c3ccc4c(c3)OCO4)CC2)nc1]

Step 1: 1-(2-chloropyrimidin-5-yl)ethan-1-one

5-Bromo 2-chloro pyrimidine (2 g, 10.33 mmol, Combi-Blocks) was degassed for 30 min. 1-Ethoxy vinyl tributyltin (4.1 mL, 11.3 mmol, Frontier Scientific) and bis(triphenylphosphine)palladium dichloride (0.36 g, 0.51 mmol) were added at rt. The resulting mixture was stirred overnight at 90° C. It was cooled to rt and filtered through celite. An aqueous HCl solution (6 N, 10 mL) was added and the mixture was stirred for 1 hour at rt. It was neutralized with sat.NaHCOs solution (15 mL), extracted with DCM (50 mL), dried over anhydrous $Na_2SO_4$ and concentrated. The crude product was purified by flash column chromatography to afford the title compound (pale yellow solid). $^1$H NMR (400 MHz, DMSO-$d_6$): δ 8.90 (s, 2H), 2.65 (s, 3H). LCMS: (Method B) 162.0 (M+H), Rt. 4.6 min, 98.01% (Max).

Step 2: (S)-1-(2-(4-(1-(benzo[d][1,3]dioxol-5-yl) ethyl)piperazin-1-yl)pyrimidin-5-yl)ethan-1-one To a stirred solution of Intermediate 16 (1.14 g, 4.24 mmol) in dry DMF (10 mL), TEA (1.1 mL, 16.5 mmol) and 1-(2-chloropyrimidin-5-yl)ethan-1-one obtained in the previous step (0.6 g, 3.85 mmol) were added at rt. The resulting mixture was heated to 90° C. for 12 h. It was cooled to rt and concentrated. Dichloromethane (50 mL) was added and was washed with a saturated NaCl solution (10 mL), dried over anhydrous $Na_2SO_4$ and concentrated. The crude product was purified by flash chromatography, affording the title compound (off white solid). $^1$H NMR (400 MHz, DMSO-$d_6$): δ 8.83 (s, 2H), 6.90 (s, 1H), 6.84 (d, J=7.6 Hz, 1H), 6.74 (dd, J=8.0, 1.2 Hz, 1H), 5.99-5.98 (m, 2H), 3.84 (t, J=4.8 Hz, 4H), 3.40-3.36 (m, 1H), 2.49-2.47 (m, 5H), 2.38-2.35 (m, 2H), 1.27 (d, J=6.8 Hz, 3H). LCMS: (Method A) 355.0 (M+H), Rt. 2.61 min, 99.78% (Max). HPLC: (Method A) Rt. 2.55 min, 99.51% (Max).

Example 168: 1-(2-(4-((S)-1-(benzo[dl]1,31dioxol-5-yl)ethyl)piperazin-1-yl)pyrimidin-5-yl)ethan-1-ol

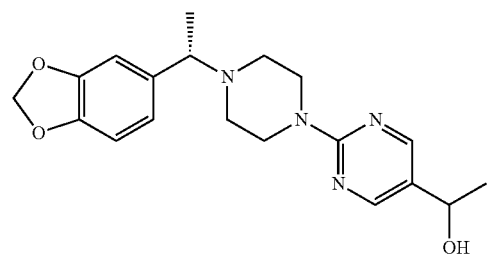 [SMILES: CC(O)c1cnc(N2CCN([C@@H](C)c3ccc4c(c3)OCO4)CC2)nc1]

To a stirred solution of Example 167 (0.2 g, 0.56 mmol) in dry MeOH (5 mL), sodium borohydride (0.48 g, 0.84 mmol, spectrochem) was added portion wise at 0° C. The resulting mixture was stirred at rt for 1 h. It was concentrated, diluted with DCM (20 mL) and washed with brine solution (5 mL) and dried over $Na_2SO_4$. After evaporation of the solvent, the crude product was purified by flash column chromatography to afford the titled compound. Yield: 77% (0.154 g, brown oil). $^1$H NMR (400 MHz, DMSO-$d_6$): δ 8.29 (s, 2H), 6.89 (s, 1H), 6.84 (d, J=8.0 Hz, 1H), 6.76 (dd, J=8.0, 1.6 Hz, 1H), 5.99-5.98 (m, 2H), 5.12 (d, J=4.4 Hz, 1H), 4.62-4.59 (m, 1H), 3.67 (t, J=5.2 Hz, 4H), 3.39-3.37 (m, 1H), 2.42-2.40 (m, 2H), 2.35-2.32 (m, 2H), 1.32-1.27 (m, 6H). LCMS: (Method A) 357.2 (M+H), Rt. 2.38 min, 99.04% (Max). HPLC: (Method A) Rt. 2.31 min, 98.15% (Max).

Example 169: N-(2-(4-(1-(2-methylbenzofd1thiazol-5-yl)ethyl)piperazin-1-yl)pyrimidin-5-yl)acetamide

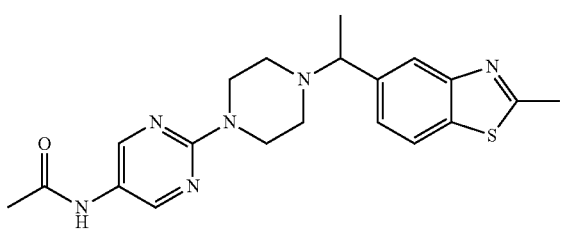 [SMILES: CC(=O)Nc1cnc(N2CCN(C(C)c3ccc4sc(C)nc4c3)CC2)nc1]

To a stirred solution of Intermediate 10 (0.17 g, 0.66 mmol) in dry DMF (3 mL), TEA (0.45 mL, 1.99 mmol) and Intermediate 26 (0.21 g, 0.99 mmol) were added at rt. The resulting reaction mixture was stirred at 120° C. overnight.

It was cooled to rt and concentrated under reduced pressure. The resulting crude product was purified by flash column chromatography, followed by MD Autoprep HPLC (Method B), affording the title product (brown oil). $^1$H NMR (400 MHz, DMSO-d$_6$): δ 9.80 (s, 1H), 8.45 (s, 2H), 7.95 (d, J=8.0 Hz, 1H), 7.83 (s, 1H), 7.38 (d, J=8.4 Hz, 1H), 3.58-3.57 (m, 5H), 2.78 (s, 3H), 3.36-2.35 (m, 4H), 1.99 (s, 3H), 1.37 (d, J=6.8 Hz, 3H). LCMS: (Method A) 397.2 (M+H), Rt. 2.38 min, 98.23% (Max). HPLC: (Method A) Rt. 2.31 min, 96.17% (Max).

Example 170: N-(5-(4-(1-(2-methylbenzorcnthiazol-5-yl)ethyl)piperazin-1-yl)-1,3,4-thiadiazol-2-yl)acetamide

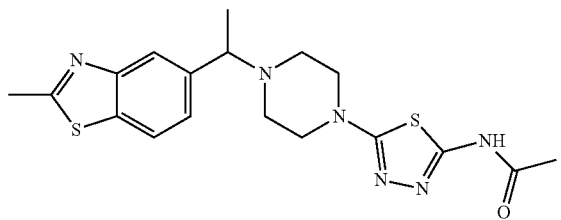 [SMILES: CC(=O)Nc1nnc(N2CCN(C(C)c3ccc4sc(C)nc4c3)CC2)s1]

To a stirred solution of Intermediate 7 (0.17 g, 0.64 mmol) in dry DMF (3 mL), TEA (0.3 mL, 1.93 mmol) and Intermediate 26 (0.21 g, 0.96 mmol) were added at rt and the reaction mixture was stirred at 120° C. overnight. The resulting reaction mixture was cooled to rt and the solvents were concentrated under reduced pressure. The resulting crude product was purified by flash chromatography followed by MD Autoprep HPLC (Method B) affording the title product (brown oil). $^1$H NMR (400 MHz, DMSO-d$_6$): δ 12.01 (s, 1H), 7.97 (d, J=8.0 Hz, 1H),7.84 (d, J=1.6 Hz, 1H), 7.39-7.37 (m, 1H), 3.64-3.62 (m, 1H), 3.36-3.33 (m, 4H), 2.79 (s, 3H), 2.53-2.52 (m, 2H), 2.49-2.47 (m, 2H), 2.07 (s, 3H), 1.38 (d, J=6.8 Hz, 3H). LCMS: (Method A) 403.0 (M+H), Rt. 2.45 min, 98.38% (Max). HPLC: (Method A) Rt. 2.32 min, 98.57% (Max).

Example 171: 2-(4-(1-(benzordiri.31 dioxol-5-vnethvnpiperazin-1-vn-6.7-dihydrothiazolo[5,4-c1pyridin-4(5H)-one

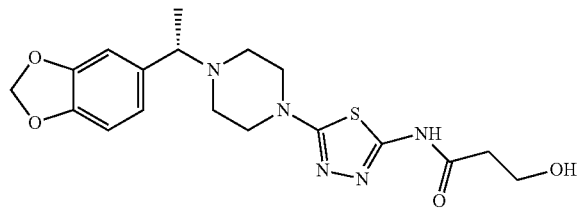 [SMILES: C[C@@H](c1ccc2c(c1)OCO2)N1CCN(c2nnc(NC(=O)CCO)s2)CC1]

To a stirred solution of 3-hydroxypropionaic acid (97 mg, 1.0 mmol) in dry NMP (5 mL), Example 132 (300 mg, 0.9 mmol), triethylamine (0.18 mg, 1.8 mmol) and HATU (513 mg, 1.3 mmol) were added at 0° C. The resulting mixture was stirred at rt for 1 h. It was was diluted with water (15 mL) and extracted with EtOAc (2×15 mL). Combined organic layers was dried over Na$_2$SO$_4$. After evaporation of the solvents, the crude product was further purified by MD Autoprep HPLC (Method B), affording the title compound (off white solid). $^1$H NMR (400 MHz, DMSO-d$_6$): δ11.98 (s, 1H), 6.88 (s, 1H), 6.84 (d, J=8.0 Hz, 1H), 6.75 (d, J=8.0 Hz, 1H), 5.98-5.97 (m, 2H), 4.71 (t, J=5.2 Hz, 1H), 3.69-3.64 (m, 2H), 3.40-3.32 (m, 5H), 2.54-2.32 (m, 6H), 1.25 (d, J=6.4 Hz, 3H). LCMS: (Method A) 406.0 (M+H), Rt. 2.15 min, 99.05% (Max). HPLC: (Method A) Rt. 2.11 min, 98.88% (Max).

Example 172: 6-(1-(4-(5-fluoropyrimidin-2-yl)piperazin-1-yl)ethyl)quinoxaline

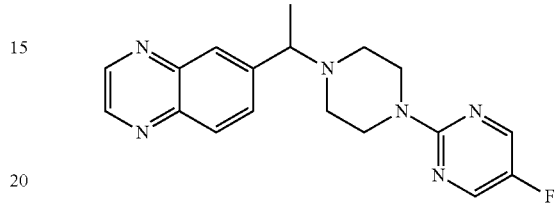

To the stirred solution of Intermediate 11 (0.25 g, 1.03 mmol) in dry DMF (3 mL), TEA (0.43 mL, 3.09 mmol) and 2-chloro-5-fluoropyrimidine (0.15 g, 1.13 mmol) were added at rt and the resulting mixture was stirred at 120° C. overnight. It was cooled to rt and solvent was evaporated under reduced pressure. The resulting crude product was purified by flash chromatography to afford the title product (brown oil). $^1$H NMR (400 MHz, DMSO-d$_6$): δ 8.93-8.91 (m, 2H), 8.41 (s, 2H), 8.07 (d, J=8.4 Hz, 1H), 7.99 (s, 1H), 7.91 (d, J=8.8 Hz, 1H), 3.75-3.74 (m, 1H), 3.68-3.65 (m, 4H), 2.56-2.53 (m, 2H), 2.42-2.41 (m, 2H), 1.42 (d, J=6.8 Hz, 3H). LCMS: (Method A) 339.0 (M+H), Rt. 2.32 min, 99.29% (Max). HPLC: (Method A) Rt. 2.23 min, 99.19% (Max).

Example 173: (S)-2-(4-(1-(benzofdin,31dioxol-5-yl)ethyl)piperazin-1-yl)-5-fluoropyrimidine

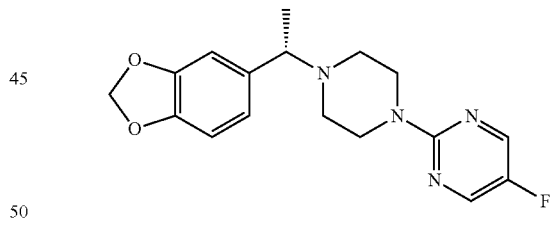

To a stirred solution of Intermediate 16 (0.4 g, 1.50 mmol) in dry DMF (10 mL), TEA (0.6 mL, 4.5 mmol) and 2-chloro-5-fluoro pyrimidine (0.2 g, 1.5 mmol) were added at rt and the reaction mixture was stirred at 90° C. for 12 h. It was cooled to rt and concentrated. Dichloromethane (50 mL) was added and the mixture was washed with sat NaCl solution (10 mL) dried over anhydrous Na$_2$SO$_4$. After evaporation of the solvents, the crude product was purified by flash chromatography to give the title compound (colourless oil). $^1$H NMR (400 MHz, DMSO-de): δ 8.42 (s, 2H), 7.43 (d, J=7.6 Hz, 1H), 6.89-6.85 (m, 1H), 6.75 (dd, J=7.6, 1.2 Hz, 1H), 5.99-5.98 (m, 2H), 3.65 (t, J=5.2 Hz, 4H), 3.37-3.35 (m, 1H), 2.43-2.41 (m, 2H), 2.37-2.35 (m, 2H), 1.28 (d, J=6.4 Hz, 3H). LCMS: (Method A) 331.0 (M+H), Rt. 2.88 min, 99.79% (Max). HPLC: (Method A) Rt. 2.82 min, 99.93% (Max).

Example 174: N-(2-(4-(1-(benzo[d]thiazol-6-yl)ethyl)piperazin-1-yl)pyrimidin-5-yl)acetamide

SGN020494-01-00045-078N01:

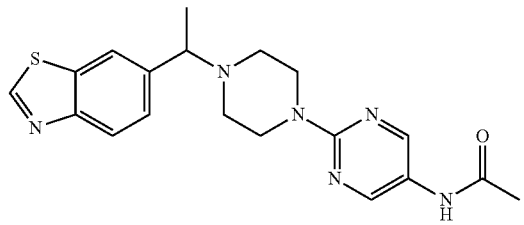 [SMILES: CC(=O)Nc1cnc(N2CCN(C(C)c3ccc4ncsc4c3)CC2)nc1]

To a stirred solution of Intermediate 10 (0.22 g, 0.85 mmol) in dry DMF (10 mL), DIPEA (0.6 mL, 3.43 mmol) and Intermediate 27 (0.25 g, 1.28 mmol) were added at rt and the reaction mixture was stirred overnight at 120° C. It was cooled to rt and the solvent was evaporated under reduced pressure. The resulting crude product was purified by flash column chromatography to afford the title product (off white solid). $^1$H NMR (400 MHz, DMSO-de): δ 9.81 (s, 1H), 9.35 (s, 1H), 8.46 (s, 2H), 8.11 (s, 1H), 8.04 (d, J=8.4 Hz, 1H), 7.55-7.53 (m, 1H), 3.65-3.62 (m, 5H), 2.52-2.51 (m, 2H), 2.34-2.33 (m, 2H), 2.00 (s, 3H), 1.39 (d, J=6.4 Hz, 3H). LCMS: (Method A) 383.3 (M+H), Rt. 2.03 min, 98.47% (Max). HPLC: (Method A) Rt. 1.98 min, 98.35% (Max).

Example 175: (S)-2-(4-(1-(benzo[d][1,3]dioxol-5-yl)ethyl)piperazin-1-yl)-5-bromopyrimidine

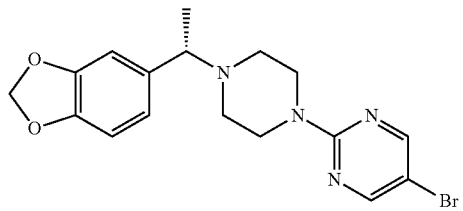 [SMILES: C[C@@H](c1ccc2c(c1)OCO2)N1CCN(c2ncc(Br)cn2)CC1]

To a stirred solution of Intermediate 16 (4.1 g, 15.5 mmol) in dry DMF (30 mL), TEA (6.4 mL, 46.5 mmol) and 5-bromo-2-chloro pyrimidine (3 g, 15.5 mmol) were added at rt and the reaction mixture was stirred at 90° C. for 12 h. It was cooled to rt and concentrated under reduced pressure. Dichloromethane (150 mL) was added. The solution was washed with brine (50 mL) and dried over anhydrous Na$_2$SO$_4$. After evaporation of the solvents, the crude product was purified by flash chromatography affording the title compound. Yield: 57% (3.5 g, white solid). $^1$H NMR (400 MHz, DMSO-d$_6$): δ 8.43 (s, 2H), 6.83-6.89 (m, 2H), 6.76 (d, J=7.8 Hz, 1H), 5.99-5.98 (m, 2H), 3.67 (t, J=4.8 Hz, 4H), 3.37-3.33 (m, 1H), 2.41-2.33 (m, 4H), 1.28 (d, J=6.6 Hz, 3H). LCMS: (Method A) 391.0 (M+H), Rt. 3.25 min, 99.9% (Max).

Example 176: (S)-2-(2-(4-(1-(benzo[d][1,3]dioxol-5-yl)ethyl)piperazin-1-yl)pyrimidin-5-yl)propan-2-ol

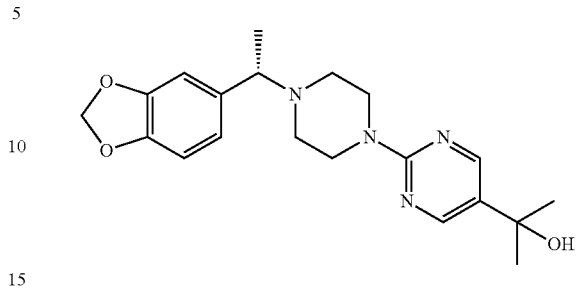

To a stirred solution of Example 175 (0.5 g, 1.28 mmol) in dry THF (10 mL) cooled at −78° C., n-BuLi (1.6 M, 1.2 mL, 19.2 mmol, Aldrich) was added. The mixture was stirred at −78° C. for 1 h. Dry acetone in THF (0.89 g, 1.53 mmol, Aldrich) was then added at the same temperature and the mixture was stirred for 10 minutes. The temperature was increased to rt over 1 h. The reaction mixture was quenched with saturated ammonium chloride solution (10 mL). The desired product was extracted with EtOAc (50 mL), washed with sat NaCl solution (20 mL) and dried over anhydrous Na$_2$SO$_4$. After evaporation of the solvents, the crude product was purified by MD Autoprep HPLC (Method D), affording the title product (off white solid). $^1$H NMR (400 MHz, DMSO-d$_6$): 8.33 (s, 2H), 6.89-6.83 (m, 2H), 6.77-6.74 (m, 1H), 5.99-5.98 (m, 2H), 5.05 (s, 1H), 3.66 (d, J=4.8 Hz, 4H), 3.38-3.35 (m, 1H), 2.45-2.43 (m, 2H), 2.35-2.32 (m, 2H), 1.59 (s, 6H), 1.28 (d, J=6.8 Hz, 3H). LCMS: (Method A) 371.2 (M+H), Rt. 2.5 min, 99.51% (Max). HPLC: (Method A) Rt. 2.46 min, 98.9% (Max).

Example 177: (S)—N-(2-(4-(1-(benzo[d][1,3]dioxol-5-yl)ethyl)piperazin-1-yl)pyrimidin-5-yl)-3-hydroxypropanamide

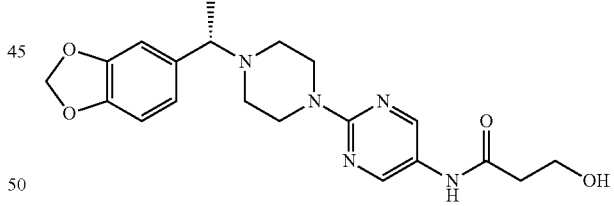

Step 1: (S)-2-(4-(1-(Benzo[d][1,3]dioxol-5-yl)ethyl)piperazin-1-yl)-4-nitropyrimidine To a stirred solution of Intermediate 16 (4.8 g, 18.7 mmol) in dry ACN (15 mL), Et$_3$N (10.5 mL, 75.0 mmol) and 2-chloro-5-nitropyrimidine (3.0 g, 18.7 mmol) were added at rt. The mixture was heated at 80° C. overnight. It was cooled to rt, diluted with DCM (20 mL), washed with water (15 mL) and brine (15 mL), and dried over anhydrous Na$_2$SO$_4$. After evaporation of the solvents, the crude product was triturated with MeOH, filtered and dried under vacuum, affording the title compound. Yield: 75% (3.8 g, pale yellow solid). LCMS: (Method A) 358.3 (M+H), Rt. 2.94 min, 98.07% (Max).

Step 2: (S)-2-(4-(1-(Benzo[d][1,3]dioxol-5-yl)ethyl) piperazin-1-yl)pyrimidin-5-amine To a stirred solution of (S)-2-(4-(1-(Benzo[d][1,3]dioxol-5-yl)ethyl)piperazin-1-yl)-4-nitropyrimidine obtained in the previous step (1.0 g, 62.9 mmol) in a mixture of methanol (100 mL) and THF (100 mL), 10% Pd/C (200 mg, 20% w/w) was added at rt. The reaction mixture was stirred under hydrogen atmosphere (1 kg/cm$^2$) at rt overnight. Completion of the reaction was confirmed by TLC. The reaction mixture was filtered through celite and washed with methanol. After evaporation of the solvents, the title compound was obtained and used in the next step without further purification. Yield: 96% (1.0 g, pale brown solid). LCMS: (Method A) 328.2 (M+H), Rt. 1.52 min, 90.58% (Max).

Step 3: (S)—N-(2-(4-(1-(benzo[d][1,3]dioxol-5-yl)ethyl)piperazin-1-yl)pyrimidin-5-yl)-3-hydroxypropanamide To a stirred solution of 3-hydroxypropionic acid (132 mg, 1.0 mmol) in dry DMF (2 mL), (S)-2-(4-(1-(benzo[d][1,3]dioxol-5-yl)ethyl)piperazin-1-yl)pyrimidin-5-amine obtained in the previous step (400 mg, 1.2 mmol), DIPA (236 mg, 1.83 mmol) and HATU (557 mg, 1.83 mmol) were added at 0° C. The reaction mixture was stirred at rt overnight. The completion of the reaction was monitored by TLC. The reaction mixture was diluted water (10 mL) and extracted with DCM (15 mL). The organic layer was dried over anhydrous Na$_2$SO$_4$ and evaporated. The crude product was purified by preparative HPLC (Method B), affording the title product (off white solid). $^1$H NMR (400 MHz, CDCl$_3$): δ 8.40 (s, 2H), 7.79 (br s, 1H), 6.88 (s, 1H), 6.75 (s, 2H), 5.96-5.95 (m, 2H), 3.97 (t, J=6.8 Hz, 2H), 3.77 (t, J=4.8 Hz, 4H), 3.35 (q, J=6.8 Hz, 1H), 2.56-2.62 (m, 2H), 2.48-2.55 (m, 2H), 2.42-2.51 (m, 2H), 1.37 (d, J=6.8 Hz, 3H). LCMS: (Method A) 400.2 (M+H), Rt. 2.11 min, 99.42% (Max). HPLC: (Method A) Rt. 2.06 min, 98.9% (Max).

Example 178: 2-(4-(1-(quinoxalin-6-yl)ethyl)piperazin-1-yl)-6,7-dihydrothiazolo[5,4-c]pyridin-4(5H)-one

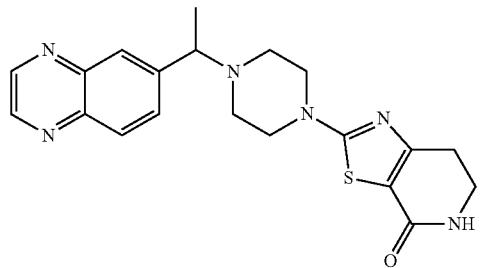 [SMILES: CC(c1ccc2nccnc2c1)N1CCN(c2nc3c(s2)C(=O)NCC3)CC1]

To a stirred solution of Intermediate 25 (0.7 g, 2.57 mmol) in dry DMF (10 mL), TEA (1.1 mL, 7.71 mmol) and Intermediate 6 (0.49 g, 2.57 mmol) were added at rt and the reaction mixture was stirred at 90° C. overnight. The reaction mixture was cooled to rt and concentrated. Water (50 mL) was added and the desired product was extracted with DCM (150 mL) and dried over anhydrous Na2SO$_4$. After evaporation of the solvents, the crude product was purified by MD Autoprep HPLC (Method B), affording the title compound (off white solid). $^1$H NMR (400 MHz, DMSO-d$_6$): δ 8.94 (d, J=6.0 Hz, 2H), 8.09 (d, J=8.4 Hz, 1H), 8.01 (s, 1H), 7.91 (d, J=8.4 Hz, 1H), 7.73 (s, 1H), 3.83-3.82 (m, 1H), 3.49-3.47 (m, 4H) 2.70-2.67 (m, 2H), 2.60-2.58 (m, 2H), 2.51-2.49 (m, 4H), 1.42 (d, J=6.8 Hz, 3H). LCMS: (Method A) 395.2 (M+H), Rt. 1.74 min, 99.66% (Max). HPLC: (Method A) Rt. 1.70 min, 99.19% (Max).

Example 179: N-(5-(4-(1-(benzo[d]thiazol-6-yl)ethyl)piperazin-1-yl)-1,3,4-thiadiazol-2-yl)acetamide

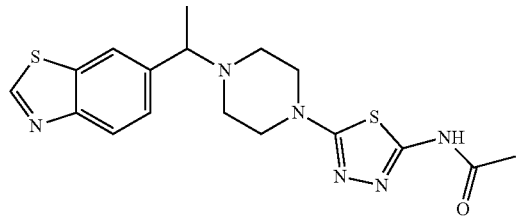 [SMILES: CC(=O)Nc1nnc(N2CCN(C(C)c3ccc4ncsc4c3)CC2)s1]

To a stirred solution of Intermediate 7 (0.22 g, 0.83 mmol) in dry DMF (3 mL), DIPEA (0.6 mL, 3.34 mmol) and Intermediate 27 (0.25 g, 1.25 mmol) were added at rt. The reaction mixture was stirred at 120° C. overnight. It was cooled to rt and DMF was evaporated under reduced pressure. The resulting crude product was purified by flash chromatography followed by MD Autoprep HPLC (Method B), affording the title product (off white solid). $^1$H NMR (400 MHz, DMSO-d$_6$): δ 9.34 (s, 1H), 8.10 (s, 1H), 8.03 (d, J=8.4 Hz, 1H), 7.52 (d, J=8.4 Hz, 1H), 3.63-3.61 (m, 1H), 3.29-3.28 (m, 4H), 2.56-2.53 (m, 2H), 2.43-2.42 (m, 2H), 1.93 (s, 3H), 1.37 (d, J=6.8 Hz, 3H). LCMS: (Method A) 389.0 (M+H), Rt. 2.04 min, 96.53% (Max). HPLC: (Method A) Rt. 1.93 min, 97.68% (Max).

Example 180: (S)-1-(2-(4-(1-(benzo[d][1,3]dioxol-5-yl)ethyl)piperazin-1-yl)pyrimidin-5-yl)cyclohexan-1-ol

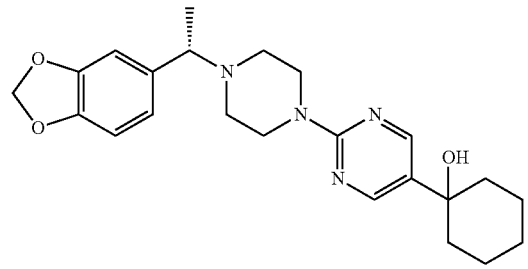 [SMILES: C[C@@H](c1ccc2c(c1)OCO2)N1CCN(c2ncc(C3(O)CCCCC3)cn2)CC1]

To a stirred solution of Example 175 (0.5 g, 1.28 mmol) in dry THF (10 mL) at −78° C., n-BuLi (1.6M, 0.9 mL, 15.3 mmol, Aldrich) was added and the reaction mixture was stirred at −78° C. for 1 h. Cyclohexanone (0.15 g, 1.53 mmol, Aldrich) in dry THF (1 mL) was added at −78° C. and the mixture was stirred for 10 minutes. The temperature was increased to rt over 1 h. The reaction completion was monitored by TLC. The reaction was quenched with saturated ammonium chloride solution (10 mL) and was extracted with EtOAc (50 mL). The organic layer was washed with sat NaCl solution (20 mL) dried over anhydrous Na$_2$SO$_4$ and the solvents were evaporated under reduced pressure. The crude product was purified by flash column chromatography to afford the title compound (off white solid). ¹H NMR (400 MHz, DMSO-de): δ 8.38 (s, 2H), 6.88 (s, 1H), 6.83 (d, J=7.6 Hz, 1H), 6.74 (d, J=7.6 Hz, 1H), 5.98-5.97 (m, 2H), 4.73 (s, 1H), 3.65-3.63 (m, 4H), 3.33-3.31 (m, 1H), 2.40-2.38 (m, 2H), 2.34-2.32 (m, 2H), 1.65-1.60 (m, 6H), 1.45-1.42 (m, 2H), 1.28-1.22 (m, 5H). LCMS: (Method A) 411.2 (M+H), Rt. 3.25 min, 96.51% (Max). HPLC: (Method A) Rt. 3.14 min, 97.88% (Max).

Example 181: (S)-1-(2-(4-(1-(benzofdlH,31dioxol-5-yl)ethyl)piperazin-1-yl)pyrimidin-5-yl)cyclopentan-1-ol

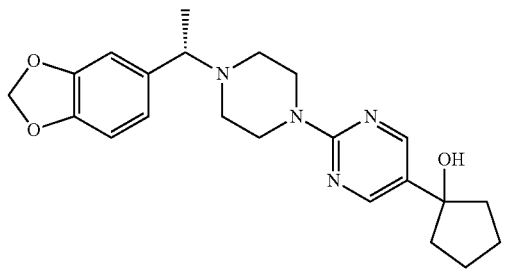 [SMILES: C[C@@H](c1ccc2c(c1)OCO2)N1CCN(c2ncc(C3(O)CCCC3)cn2)CC1]

The title compound was prepared according to the protocol described for the preparation of Example 180, replacing cyclohexanone with cyclopentanone (0.12 g, 1.53 mmol, Aldrich). The crude product was purified by flash column chromatography to afford the title compound (brown oil). ¹H NMR (400 MHz, DMSO-d₆): δ 8 8.38 (s, 2H), 6.88 (s, 1H), 6.83 (d, J=7.6 Hz, 1H), 6.74 (d, J=7.6 Hz, 1H), 5.98-5.97 (m, 2H), 4.80 (s, 1H), 3.65-3.63 (m, 4H), 3.32-3.30 (m, 1H), 2.49-2.45 (m, 2H), 2.34-2.32 (m, 2H), 1.82-1.7 (m, 8H), 1.28 (d, J=6.8 Hz, 3H). LCMS: (Method A) 397.2 (M+H), Rt. 2.90 min, 98.83% (Max). HPLC: (Method A) Rt. 2.87 min, 99.10% (Max).

Example 182: (S)-2-(4-(1-(benzofdlM,31dioxol-5-yl)ethyl)piperazin-1-yl)-4,5,6,7-tetrahydrothiazoloi5,4-clpyridine

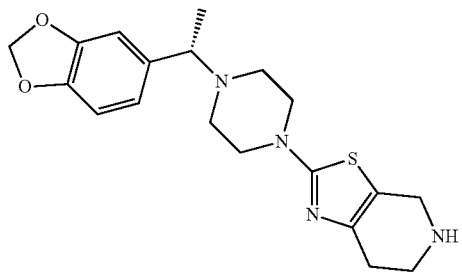 [SMILES: C[C@@H](c1ccc2c(c1)OCO2)N1CCN(c2nc3c(s2)CNCC3)CC1]

Step 1: tert-butyl-4-((trimethylsilyl)oxy)-3,6-dihydropyridine-1 (2H)-carboxylate To a stirred solution of N-boc piperidone (5 g, 25.09 mmol) in dry DMF (50 mL), TEA (6.95 mL, 50.18 mmol) and trimethylsilyl chloride (6.35 mL, 50.18 mmol) were added slowly at 0° C. and the mixture was stirred at 90° C. overnight. Solvents were evaporated under reduced pressure and EtOAc (70 mL) was added. This solution was washed with water (25 mL), 10% sodium bicarbonate solution (25 mL), (15 mL) and was dried over Na₂SO₄. Solvents were evaporated, affording the title product that was used in the next step without further purification. Yield: 99% (7.49 g, brown oil). ¹H NMR (400 MHz, DMSO-d₆): δ 4.80 (s, 1H), 3.62-3.59 (m, 2H), 3.44-3.41 (m, 2H), 2.02-2.00 (m, 2H), 1.40 (s, 9H), 0.17 (s, 9H).

Step 2: tert-butyl 3-bromo-4-oxopiperidine-1-carboxylate

To a stirred solution of te/t-butyl-4-((trimethylsilyl)oxy)-3,6-dihydropyridine-1(2H)-carboxylate, obtained in step 1, (7.48 g, 27.60 mmol) in dry CCl₄ (80 mL, 10 V), N-bromosuccinimide (5.42 g, 30.36 mmol) was added at 10° C. The reaction mixture was stirred at 10-15° C. for 2 h. It was evaporated under reduced pressure. Water (30 mL) was added and the desired product was extracted with EtOAc (2×60 mL). Organic layer was dried over Na₂SO₄ and the solvents were evaporated. The resulting crude product was purified by flash chromatography affording the title product (white solid). ¹H NMR (400 MHz, DMSO-de): δ 4.74 (s, 1H), 4.02-4.00 (m, 2H), 3.60-3.58 (m, 2H), 2.69-2.68 (m, 2H), 1.39 (s, 9H).

Step 3: (S)-4-(1-(benzo[d][1,3]dioxol-5-yl)ethyl)piperazine-1-carbothioamide

To stirred solution of Intermediate 16 (5 g, 18.51 mmol) in THF (50 mL), TEA (8.8 mL, 55.55 mmol) followed by N,N'-thiocarbonyldiimidazole (3.8 g, 22.22 mmol, Arbor chemicals) were added at rt and the mixture was stirred overnight at rt. Ammonia solution in methanol (7 N, 50 mL, 350 mmol) was added and the mixture was stirred overnight at 50° C. It was evaporated under reduced pressure, diluted with EtOAc (100 mL), washed with water (25 mL) and dried over Na₂SO₄. The title product was obtained after evaporation of the solvents and was used without further purification. Yield: 58% (3.6 g, brown liquid). ¹H NMR (400 MHz, DMSO-d₆): δ 7.61 (s, 2H), 6.99 (s, 1H), 6.70 (d, J=8.0 Hz, 2H), 5.97-5.96 (m, 2H), δ 3.67-3.65 (m, 1H), 3.40-3.37 (m, 2H), 2.77-2.75 (m, 2H), δ 2.33-2.25 (m, 4H), 1.24-1.22 (m, 3H). LCMS: (Method A) 294.00 (M+H), Rt. 2.03 min, 55.70% (Max).

Step 4: tei1-butyl(S)-2-(4-(1-(benzo[d][1,3]dioxol-5-yl)ethyl)piperazin-ˆ-yl)-6,7-dihydrothiazolo[5,4-c]pyridine-5(4H)-carboxylate To a stirred solution of (S)-4-(1-(benzo[d][1,3]dioxol-5-yl)ethyl)piperazine-1-carbothioamide (Example 182, Step 3, 3.6 g, 12.28 mmol) in isopropanol (35 mL), tert-butyl 3-bromo-4-oxopiperidine-1-carboxylate (Example 182, Step 2, 3.4 g, 12.28 mmol) was added at rt. The reaction mixture was stirred overnight at 90° C. After evaporation of the solvents, the crude product was purified by flash column chromatography to afford the title product (yellow liquid). ¹H NMR (400 MHz, DMSO-d₆): δ 6.88-6.87 (m, 2H), 6.85 (s, 1H), 5.99-5.98 (m, 2H), 4.35-4.34 (m, 1H), 4.06-4.04 (m, 2H), 3.57-3.56 (m, 2H), 3.42-3.41 (m, 2H), δ 3.32-3.29 (m, 2H), 2.49-2.46 (m, 2H), 2.41-2.40 (m, 4H), 1.42 (s, 9H), 1.24-1.22 (m, 3H). LCMS: (Method A) 473.0 (M+H), Rt. 3.54 min, 71.96% (Max).

Step 5: (S)-2-(4-(1-(benzo[d][1,3]dioxol-5-yl)ethyl)piperazin-ˆ-yl)-4,5,6,7-tetrahydrothiazolo[5,4-c]pyridine To a stirred solution of te/t-butyl(S)-2-(4-(1-(benzo[d][1,3]dioxol-5-yl)ethyl)piperazin-1-yl)-6,7-dihydrothiazolo[5, 4-c]pyridine-5(4H)-carboxylate obtained in previous step (1.7 g, 3.60 mmol) in 1,4-dioxane (17 mL), HCl in dioxane (4 N, 40 mmol, 10 mL, 6V) was added at 0° C. The reaction mixture was stirred for 2 h at rt. It was concentrated under reduced pressure. DCM was added (15 mL) and was evaporated. This process was repeated a second time. Saturated sodium bicarbonate solution (20 mL) was added and the mixture was stirred for 2 h. Resulting free amine was extracted with DCM (100 mL), washed with brine (15 mL) and dried over $Na_2SO_4$. After evaporation of the solvent, the resulting crude product was purified by flash column chromatography to afford the title compound (brown oil). $^1H$ NMR (400 MHz, DMSO-d$_6$): δ 6.88 (d, J=1.2 Hz, 1H), 6.85-6.83 (m, 1H), 6.76-6.74 (m, 1H), 5.99-5.98 (m, 2H), 3.68 (s, 2H), 3.42-3.40 (m, 1H), 3.30-3.27 (m, 4H), 2.91 (t, J=5.6 Hz, 4H), 2.40-2.38 (m, 4H), 1.27 (d, J=6.8 Hz, 3H). LCMS: (Method A) 373.3 (M+H), Rt. 1.82 min, 99.52% (Max). HPLC: (Method A) Rt. 1.80 min, 99.18% (Max).

Example 183: Ethyl (S)-6-(4-(1-(benzorcnri,31dioxol-5-yl)ethyl)piperazin-1-vDnicotinate

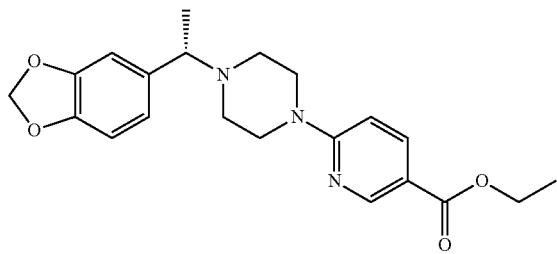 [SMILES: CCOC(=O)c1ccc(N2CCN([C@@H](C)c3ccc4c(c3)OCO4)CC2)nc1]

To a stirred solution of Intermediate 16 (1.0 g, 3.71 mmol) in dry DMF (10 mL), TEA (1.54 mL, 11.1 mmol) and ethyl-6-chloro nicotinate (0.69 g, 3.71 mmol) were added at rt and the reaction mixture was heated at 90° C. for 12 h. It was cooled to rt and concentrated. DCM (50 mL) was added and the resulting solution was washed with brine (30 mL) and dried over anhydrous $Na_2SO_4$. After evaporation of the solvents, the crude product was purified by flash chromatography to give the title compound (off white solid). $^1H$ NMR (400 MHz, DMSO-de): δ 8.61 (d, J=2.4 Hz, 1H), 7.92-7.90 (m, 1H), 6.89 (d, J=1.6 Hz, 1H), 6.85-6.81 (m, 2H), 6.77-6.75 (m, 1H), 5.99-5.98 (m, 2H), 4.27 (q, J=7.2 Hz, 2H) 3.61 (t, J=4.8 Hz, 4H), 3.39-3.37 (m, 1H), 2.45-2.33 (m, 5H), 1.29-1.26 (m, 3H). LCMS: (Method A) 384.2 (M+H), Rt. 3.14 min, 98.30% (Max). HPLC: (Method A) Rt. 3.11 min, 98.88% (Max).

Example 184: (S)-1-(2-(4-(1-(benzofdlfl,31dioxol-5-yl)ethyl)piperazin-1-yl)-6,7-dihydrothiazolo[5,4-c]pyridin-5(4H)-yl)ethan-1-one

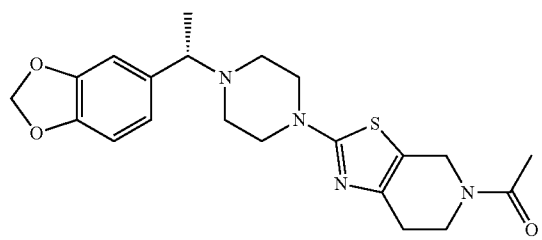 [SMILES: CC(=O)N1CCc2nc(N3CCN([C@@H](C)c4ccc5c(c4)OCO5)CC3)sc2C1]

To a stirred solution of Example 182 (0.18 g, 0.48 mmol) in dry DCM (2 mL), TEA (0.13 mL, 0.96 mmol) and acetic anhydride (0.07 mL, 0.72 mmol) were added at 0° C. and the reaction mixture was stirred at rt overnight. It was diluted with DCM (50 mL), washed with water (15 mL), brine (15 mL) and dried over anhydrous $Na_2SO_4$. After evaporation of the solvents, the crude product was purified by flash chromatography to give the title compound (brown oil). $^1H$ NMR (400 MHz, DMSO-d$_6$, performed at 80° C.): δ 6.87 (d, J=1.6 Hz, 1H), 6.84 (d, J=8.0 Hz, 1H), 6.75 (dd, J=1.6, 8.0 Hz, 1H), 5.99-5.98 (m, 2H), 4.48 (s, 2H), 3.71-3.65 (m, 2H), 3.47-3.43 (m, 1H), 3.35-3.30 (m, 4H), 2.60-2.54 (m, 2H), 2.47-2.40 (m, 4H), 2.06 (s, 3H), 1.29 (d, J=6.4 Hz, 3H). LCMS: (Method A) 415.3 (M+H), Rt. 2.20 min, 96.80% (Max). HPLC: (Method A) Rt 2.15 min, 97.88% (Max).

Example 185: (S)-(6-(4-(1-(benzofdlM,31dioxol-5-yl)ethyl)piperazin-1-yl)pyridin-3-vDmethanol

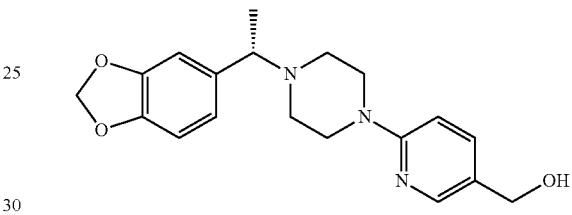

To a stirred solution of Example 183 (0.2 g, 0.56 mmol) in dry MeOH (5 mL) cooled at 0° C., was added lithium aluminium hydride (2.4 M, 0.24 mL, 1.17 mmol, spectrochem) dropwise and the mixture was stirred for 1 h at the same temperature. The reaction mixture was quenched with saturated ammonium chloride (5 mL) and extracted with ethyl acetate (20 mL). The organic phase was washed with brine solution (5 mL), dried over $Na_2SO_4$ and concentrated. The crude product was purified by flash column chromatography to afford the titled compound. Yield: 66% (88 mg, colorless oil). $^1H$ NMR (400 MHz, DMSO-d$_6$): δ 8.04 (d, J=2.0 Hz, 1H), 7.46 (dd, J=8.8, 2.4 Hz, 1H), 6.88-6.86 (m, 1H), 6.84-6.82 (m, 1H), 6.76-6.73 (m, 2H), 5.98-5.97 (m, 2H), 4.96 (t, J=5.6 Hz, 1H) 4.32 (d, J=5.6 Hz, 2H), 3.41 (t, J=9.6 Hz, 4H), 3.34-3.32 (m, 1H), 2.49-2.45 (m, 2H), 2.39-2.37 (m, 2H), 1.28 (d, J=6.8 Hz, 3H). LCMS: (Method A) 342.3 (M+H), Rt. 1.74 min, 99.28% (Max). HPLC: (Method A) Rt. 1.71 min, 98.49% (Max).

Example 186: (S)-6-(4-(1-(benzofdlM,31dioxol-5-yl)ethyl)piperazin-1-yl)-N-methylnicotinamide

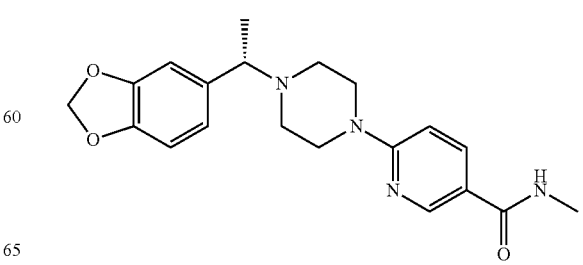

Step 1: Lithium (S)-6-(4-(1-(benzo[d][1,3]dioxol-5-yl)ethyl)piperazin-1-yl)nicotinate Example 183 (1 g, 2.62 mmol) was dissolved in a mixture of MeOH (2 mL), THF (7 mL) and water (1 mL). The resulting mixture was cooled to 0° C. and lithium hydroxide (0.32 g, 7.86 mmol, spectrochem) was added. The resulting mixture was heated at 90° C. for 2 h. It was then concentrated and used as such in next step. Yield: 85% (0.8 g, off white solid). $^1$H NMR (400 MHz, DMSO-$d_6$): δ 8.52 (d, J=2.3 Hz, 1H), 7.89-7.86 (m, 1H), 6.88-6.59 (m, 4H), 5.97-5.96 (m, 2H), 3.43-3.33 (m, 5H), 2.36-2.28 (m, 4H), 1.26 (d, J=8.7 Hz, 3H). LCMS: (Method A) 354.0 (M+H), Rt. 3.639 min, 93.32% (Max).

Step 2: (S)-6-(4-(1-(benzo[d][1,3]dioxol-5-yl)ethyl)piperazin-1-yl)-N-methylnicotinamide To a stirred solution of lithium (S)-6-(4-(1-(benzo[d][1,3]dioxol-5-yl)ethyl)piperazin-1-yl)nicotinate (0.3 g, 8.32 mmol) in dry DCM (10 mL) cooled to 0° C., were added triethylamine (0.5 mL, 3.72 mmol), methylamine in THF (2 M, 2 mL, 2.24 mmol) followed by T$_3$P (0.6 mL, 3.72 mmol). The resulting mixture was stirred at rt for 1 h. Reaction completion was monitored by TLC. The reaction mixture was washed with 10% sodium bicarbonate solution (10 mL). The organic layer was dried over Na$_2$SO$_4$ and evaporated to dryness. The crude product was purified by flash column chromatography (white solid). $^1$H NMR (400 MHz, DMSO-$d_6$): δ 8.54 (d, J=2.0 Hz, 1H), 8.18 (d, J=4.4 Hz, 1H), 7.89 (dd, J=2.4, 9.2 Hz, 1H), 6.89 (d, J=1.2 Hz, 1H), 6.85-6.77 (m, 1H), 6.77-6.74 (m, 2H), 5.99-5.98 (m, 2H), 3.54 (t, J=4.8 Hz, 4H), 3.37-3.35 (m, 1H), 2.73 (d, J=4.4 Hz, 3H), 2.45-2.43 (m, 2H), 2.39-2.32 (m, 2H), 1.28 (d, J=6.8 Hz, 3H). LCMS: (Method A) 369.2 (M+H), Rt. 2.05 min, 98.6% (Max). HPLC: (Method A) Rt. 2.00 min, 98.3% (Max).

Example 187: (S)-6-(4-(1-(benzofdlM,31dioxol-5-yl)ethyl)piperazin-1-yl)-N,N-dimethylnicotinamide

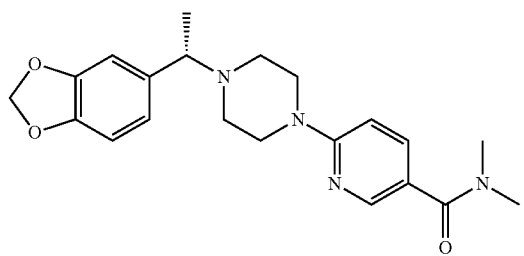 [SMILES: C[C@@H](c1ccc2c(c1)OCO2)N1CCN(c2ccc(C(=O)N(C)C)cn2)CC1]

To a stirred solution of lithium (S)-6-(4-(1-(benzo[d][1,3]dioxol-5-yl)ethyl)piperazin-1-yl)nicotinate (Example 186, Step 1, 0.5 g, 1.38 mmol) in dry DCM (10 mL) at 0° C., were added triethylamine (2.6 mL, 4.14 mmol), dimethylamine in THF (2 M, 2 mL, 2.24 mmol) followed by T$_3$P (2.6 mL, 4.14 mmol). The resulting mixture was stirred at rt for 1 h. Reaction completion was monitored by TLC. The reaction mixture was washed with 10% sodium bicarbonate solution (10 mL). The organic layer was dried over Na$_2$SO$_4$, and evaporated to dryness. The crude product was purified by flash column chromatography. Yield: 52% (279 mg, off white solid). $^1$H NMR (400 MHz, DMSO-$d_6$): δ 8.19 (d, J=2.4 Hz, 1H), 7.59 (dd, J=2.4, 8.8 Hz, 1H), 6.90 (s, 1H), 6.85 (d, J=8.0 Hz, 1H), 6.78 (t, J=7.2 Hz, 2H), 5.99-5.98 (m, 2H), 3.54-3.51 (m, 4H), 3.38-3.33 (m, 1H), 2.96 (s, 6H), 2.47-2.46 (m, 2H), 2.41-2.34 (m, 2H), 1.29 (d, J=6.8 Hz, 3H). LCMS: (Method A) 383.3 (M+H), Rt. 2.19 min, 99.8% (Max). HPLC: (Method A) Rt. 2.14 min, 99.6% (Max).

Example 188: (S)-4-(2-(4-(1-(benzo[dl]1,31dioxol-5-yl)ethyl)piperazin-1-yl)pyrimidin-5-yl)tetrahydro-2H-pyran-4-ol

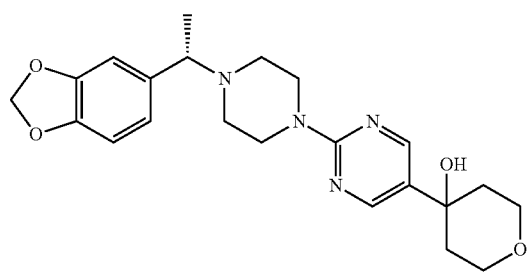 [SMILES: C[C@@H](c1ccc2c(c1)OCO2)N1CCN(c2ncc(C3(O)CCOCC3)cn2)CC1]

To a stirred solution of Example 175 (0.5 g, 1.28 mmol) in dry THF (10 mL) at −78° C. was added n-BuLi (1.6 M, 1.2 mL, 1.92 mmol, Aldrich) and the resulting mixture was stirred to −78° C. for 1 h. Tetrahydrofuran-4H-pyran-4-one (0.15 g, 1.53 mmol, Aldrich) in THF (5 mL) was added at −78° C. for 10 minutes. The temperature was increased to rt over 1 h. The reaction completion was monitored by TLC. The reaction mixture was quenched with saturated ammonium chloride solution (10 mL). It was extracted with EtOAc (50 mL). The organic phase was washed with saturated NaCl solution (20 mL) and dried over anhydrous Na$_2$SO$_4$. The crude product was purified by flash column chromatography to afford the title compound (off white solid). $^1$H NMR (400 MHz, DMSO-$d_6$): δ 8.42 (s, 2H), 6.90 (s, 1H), 6.84 (d, J=8.0 Hz, 1H), 6.76 (d, J=8.0 Hz, 1H), 5.99-5.98 (m, 2H), 5.07 (s, 1H), 3.77-3.66 (m, 8H), 3.39-3.37 (m, 1H), 2.44-2.40 (m, 2H), 2.37-2.33 (m, 2H), 1.95-1.87 (m, 2H), 1.57-1.54 (m, 2H), 1.28 (d, J=6.8 Hz, 3H). LCMS: (Method A) 413.3 (M+H), Rt. 2.32 min, 99.65% (Max). HPLC: (Method A) Rt. 2.27 min, 99.23% (Max).

Example 189: 3-(2-(4-((S)-1-(benzofdlH,31dioxol-5-yl)ethyl)piperazin-1-yl)pyrimidin-5-yl)tetrahydrofuran-3-ol

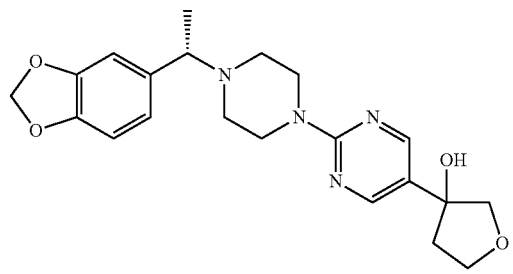 [SMILES: C[C@@H](c1ccc2c(c1)OCO2)N1CCN(c2ncc(C3(O)CCOC3)cn2)CC1]

Example 189 was prepared according the same procedure as Example 188, replacing tetrahydrofuran-4H-pyran-4-one with dihydrofuran(2H)-one (0.13 g, 1.53 mmol, Aldrich). The crude product was purified by flash column chromatography to afford the title compound (off white solid). $^1$H NMR (400 MHz, DMSO-$d_6$): δ 8.41 (s, 2H), 6.90 (d, J=1.2

Hz, 1H), 6.84 (d, J=7.6 Hz, 1H), 6.76 (d, J=7.6 Hz, 1H), 5.99-5.98 (m, 2H), 3.97-3.93 (m, 2H), 3.78-3.76 (m, 1H), 3.68-3.65 (m, 6H), 2.50-2.42 (m, 1H), 2.35-2.32 (m, 4H), 2.33-2.32 (m, 1H), 2.11-2.06 (m, 1H), 1.28 (d, J=6.4 Hz, 3H). LCMS: (Method A) 399.0 (M+H), Rt. 2.32 min, 97.39% (Max). HPLC: (Method A) Rt. 2.22 min, 97.15% (Max).

Example 190: (S)-2-(6-(4-(1-(benzorcnri,31dioxol-5-yl)ethyl)piperazin-1-yl)pyridin-3-yl)propan-2-ol

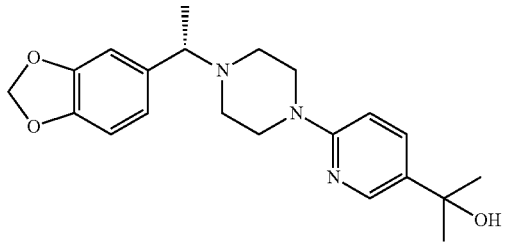 [SMILES: C[C@@H](c1ccc2c(c1)OCO2)N1CCN(c2ccc(C(C)(C)O)cn2)CC1]

To a stirred solution of Example 183 (0.3 g, 0.78 mmol) in dry THF (10 mil at 0° C. was added methyl magnesium bromide solution in THF (1.4 M, 0.8 ml_, 1.17 mmol, Aldrich). The resulting mixture was stirred at 0° C. for 1 h. The temperature was increased to rt and the mixture was stirred 12 h at that temperature. The reaction completion was monitored by TLC. The reaction mixture was quenched with saturated ammonium chloride solution (10 ml_) and extracted with EtOAc (50 ml_). The organic layer was washed with sat NaCl solution (20 ml_) and dried over anhydrous $Na_2SO_4$. The crude product was purified by flash column chromatography, yielding the title compound. Yield: 61% (0.178 g, colorless oil). $^1$H NMR (400 MHz, DMSO-$d_6$): δ 8.17 (d, J=2.0 Hz, 1H), 7.59-7.57 (m, 1H), 6.89-6.83 (m, 2H), 6.78-6.70 (m, 2H), 5.99-5.98 (m, 2H), 4.92 (s, 1H), 3.39 (t, J=4.8 Hz, 5H), 2.40-2.36 (m, 4H), 1.39 (s, 6H), 1.29 (d, J=6.8 Hz, 3H). LCMS: (Method A) 370.2 (M+H), Rt. 1.94 min, 99.3% (Max). HPLC: (Method A) Rt. 1.92 min, 99.60% (Max).

Example 191: (S)-1-(1-(benzordiri,31dioxol-5-yl)ethyl)-4-(5-bromopyridin-2-vDpiperazine

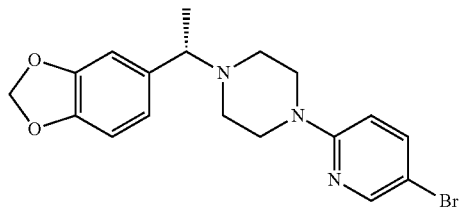

To a stirred solution of Intermediate 16 (5.5 g, 20.68 mmol) in dry DMF (50 mL), TEA (7.1 mL, 51.45 mmol) and 5-bromo-2-fluoropyridine (3 g, 17.24 mmol) were added at rt and the reaction mixture was stirred at 90° C. overnight. The reaction mixture was cooled to rt and concentrated under reduced pressure. Water (30 mL) was added and the compound was extracted with EtOAc (100 mL). The organic layer was dried over anhydrous $Na_2SO_4$ and concentrated. The resulting crude product was purified by flash chromatography to afford the title compound (white solid). $^1$H NMR (400 MHz, DMSO-$d_6$): δ 8.14 (d, J=2.4 Hz, 1H), 7.66-7.65 (m, 1H), 6.87 (d, J=1.2 Hz, 1H), 6.84 (d, J=7.6 Hz, 1H), 6.77-6.55 (m, 2H), 5.99-5.98 (m, 2H), 3.43 (t, J=4.8 Hz, 4H), 3.36-3.34 (m, 1H), 2.47-2.45 (m, 2H), 2.38-2.35 (m, 2H), 1.28 (d, J=6.8 Hz, 3H). LCMS: (Method A) 392.0 (M+H), Rt. 3.32 min, 99.88% (Max). HPLC: (Method A) Rt. 3.26 min, 99.96% (Max).

Example 192: (S)-1-(1-(benzorcnri,31dioxol-5-yl)ethyl)-4-(5-(methylthio)pyridin-2-vDpiperazine

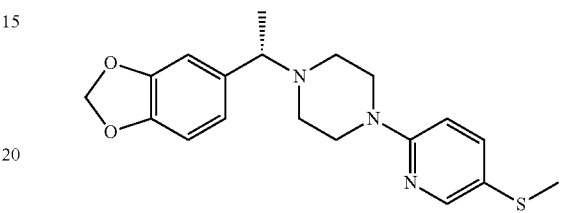

To a stirred solution of Example 191 (3.0 g, 7.71 mmol) in dry THF (30 mL), n-BuLi (6.0 mL, 9.2 mmol) was added at −78° C. and and stirred for 1 h. Dimethyl disulphide (45 mL) was added at same temperature and stirred for 1 h at rt. The reaction mixture was quenched with saturated N $H_4Cl$ and extracted with EtOAc. The organic layer was washed with water and dried over anhydrous $Na_2SO_4$ and concentrated. The resulting crude was purified by flash column chromatography to afford the title compound. Yield: 90% (2.58 g, yellow solid). $^1$H NMR (400 MHz, CDCl$_3$): δ 8.21 (d, J=2.4 Hz, 1H), 7.52-7.51 (m, 1H), 6.89 (s, 1H), 6.76 (s, 2H), 6.56 (d, J=8.8 Hz, 1H), 5.96-5.94 (m, 2H), 3.52 (m, 4H), 3.34 (d, J=6.0 Hz, 1H), 2.57-2.50 (m, 4H), 2.38 (s, 3H), 1.36 (d, J=6.4 Hz, 3H). LCMS: (Method A) 358.3.0 (M+H), Rt. 2.61 min, 97.99% (Max). HPLC: (Method A) Rt. 2.56 min, 97.57% (Max).

Example 193: (S)-2-(4-(1-(benzofdin,31dioxol-5-yl)ethyl)piperazin-1-yl)-5-(methylsulfonyl)-4,5,6,7-tetrahydrothiazolor5,4-c1pyridine

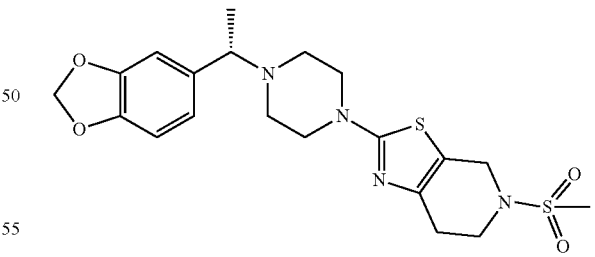

To a stirred solution of Example 182 (0.1 g, 0.26 mmol) in dry DCM (5 mL), TEA (0.07 mL, 0.54 mmol) and methane sulfonyl chloride (0.22 mL, 0.29 mmol) were added at 0° C. and the reaction mixture was stirred at rt for 1 h. The resulting reaction mixture was diluted with DCM (50 mL) and washed with 10% sodium bicarbonate solution (15 mL), water (15 mL) and brine (15 mL). The organic layer was dried over anhydrous $Na_2SO_4$ and concentrated. The resulting crude product was purified by flash column chromatography to afford the title compound (off white solid). ¹H NMR (400 MHz, DMSO-d₆): δ 6.87 (d, J=8.0 Hz, 1H), 6.85 (d, J=8.0 Hz, 1H), 6.76 (d, J=8.0 Hz, 1H), 5.99-5.98 (m, 2H), 4.26 (s, 2H), 3.46-3.44 (m, 2H), 3.41-3.39 (m, 1H), 2.98-2.93 (m, 3H), 2.67-2.65 (m, 4H), 2.54-2.52 (m, 2H), 2.39-2.38 (s, 4H), 1.27 (d, J=6.8 Hz, 3H). LCMS: (Method A) 451.2 (M+H), Rt. 2.46 min, 98.64% (Max). HPLC: (Method A) Rt. 2.56 min, 97.91% (Max).

Example 194: (S)-2-(4-(1-(benzordiri,31dioxol-5-yl)ethyl)piperazin-1-yl)-5-methyl-4,5,6,7-tetrahydrothiazoloi5,4-c1pyridine

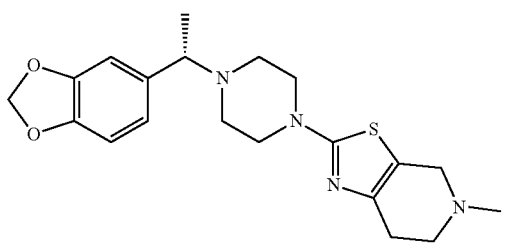 [SMILES: C[C@@H](c1ccc2c(c1)OCO2)N1CCN(c2nc3c(s2)CN(C)CC3)CC1]

To a stirred solution of Example 182 (0.1 g, 2.61 mmol) in dry THF (2 mL), sodium triacetoxy borohydride (0.17 g, 8.06 mmol) and formaldehyde (0.05 mL, 5.37 mmol, 40% solution in water) were added at rt and the reaction mixture was stirred at this temperature overnight. The reaction mixture was diluted with EtOAc (30 mL) and was washed with water (5 mL), brine (5 mL), dried over anhydrous Na₂SO₄ and concentrated under reduced pressure. The resulting crude product was purified by flash column chromatography to afford the title compound (brown oil). ¹H NMR (400 MHz, DMSO-d₆): δ 6.88 (s, 1H), 6.84 (d, J=8.0 Hz, 1H), 6.75 (d, J=8.0 Hz, 1H), 5.97 (m, 2H), 3.38-3.36 (m, 5H), 3.30-3.27 (m, 4H), 2.62-2.60 (m, 2H), 2.46-2.44 (m, 2H), 2.40-2.38 (m, 2H), 2.32 (s, 3H), 1.27 (d, J=6.8 Hz, 3H). LCMS: (Method A) 387.2 (M+H), Rt. 1.84 min, 99.86% (Max). HPLC: (Method A) Rt. 1.85 min, 99.51% (Max).

Example 195: (S)-2-(4-(1-(benzofdin,31dioxol-5-yl)ethyl)piperazin-1-yl)-5-methoxypyrimidine

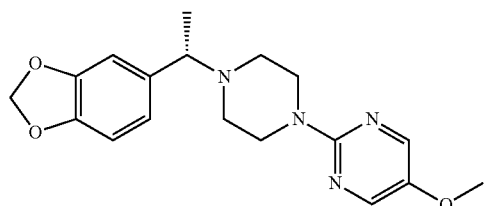

To a stirred solution of Intermediate 16 (0.55 g, 2.07 mmol) in dry DMF (5 mL), triethylamine (0.9 mL, 6.21 mmol, spectrochem) and 2-chloro-5-methoxy pyrimidine (0.3 g, 2.07 mmol, Combi-Blocks) were added and the resulting mixture was heated to 90° C. for 12 h. The reaction mixture was cooled down to rt and concentrated. Dichloromethane (25 mL) was added and the resulting solution was washed with water (20 mL), brind (20 mL) and dried over Na2SO₄. After evaporation of the solvents, the crude product was purified by flash column chromatography to afford the title compound (brown solid). ¹H NMR (400 MHz, DMSO-de): δ 8.18 (s, 2H), 6.87 (m, 2H), 6.76 (d, J=8.0 Hz, 1H), 5.99-5.98 (m, 2H), 3.76 (s, 3H), 3.58 (t, J=4.8 Hz, 4H), 3.38-3.36 (m, 1H), 2.45-2.42 (m, 2H), 2.36-2.33 (m, 2H), 1.28 (d, J=6.8 Hz, 3H). LCMS: (Method A) 343.2 (M+H), Rt. 2.73 min, 99.83% (Max). HPLC: (Method A) Rt. 2.71 min, 99.41% (Max).

Example 196: (S)-2-(4-(1-(benzofdin,31dioxol-5-yl)ethyl)piperazin-1-yl)-5-methoxypyrimidine

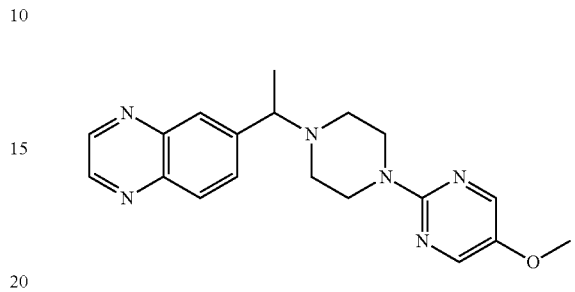

To a stirred solution of Intermediate 11 (0.2 g, 0.8 mmol) in dry DMF (2 mL), triethylamine (0.57 mL, 4.0 mmol, spectrochem) and 2-chloro-5-methoxy pyrimidine (0.14 g, 0.9 mmol, Combi-Blocks) were added and the resulting mixture was heated at 90° C. overnight. The reaction mixture was cooled down to rt and concentrated. Dichloromethane (25 mL) was added and the resulting mixture was washed with water (20 mL), brine (20 mL) and dried over Na₂SO₄. After evaporation of the solvents, the crude product was purified by flash chromatography to afford the title compound (gray solid). ¹H NMR (400 MHz, DMSO-d₆): δ 8.93-8.91 (m, 2H), 8.17 (s, 2H), 8.07 (d, J=8.8 Hz, 1H), 7.99 (s, 1H), 7.90 (d, J=8.8 Hz, 1H), 3.75-3.74 (m, 1H), 3.74 (s, 3H), 3.62-3.60 (m, 4H), 2.52-2.49 (m, 4H), 1.42 (d, J=6.8 Hz, 3H). LCMS: (Method A) 351.0 (M+H), Rt. 2.38 min, 99.86% (Max). HPLC: (Method A) Rt. 2.17 min, 98.71% (Max).

Example 197 and 198: (S)-1-(2-(4-((S)-1-(benzorcnri,31dioxol-5-yl)ethyl)piperazin-1-yl)pyrimidin-5-yl)ethan-1-ol and (S)-1-(2-(4-((R)-1-(benzordin,31dioxol-5-yl)ethyl)piperazin-1-yl)pyrimidin-5-yl)ethan-1-ol

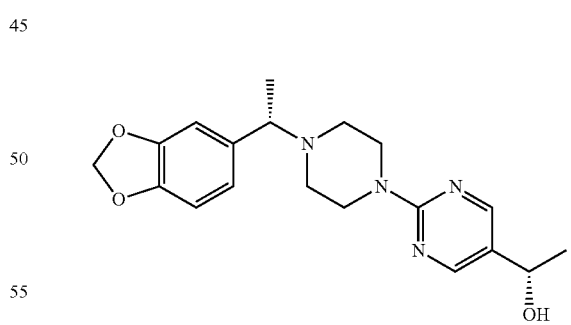

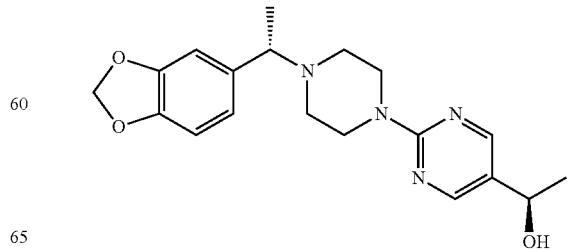

Example 168 was submitted to chiral preparative HPLC Method PK to separate both enantiomers. The first eluting compound was concentrated to give Example 198 (brown oil). $^{1}$H NMR (400 MHz, DMSO d$_{6}$): δ 8.29 (s, 2H), 6.89 (s, 1H), 6.84 (d, J=7.9 Hz, 1H), 6.75 (d, J=7.9 Hz, 1H), 5.99-5.98 (m, 2H), 5.12 (d, J=4.4 Hz, 1H), 4.62-4.61 (m, 1H), 3.67-3.65 (m, 4H), 3.38-3.36 (m, 1H), 2.51-2.33 (m, 4H), 1.31 (d, J=6.4 Hz, 3H), 1.28 (d, J=6.4 Hz, 3H). LCMS: (Method A) 357.2 (M+H), Rt. 2.30 min, 99.37% (Max). HPLC: (Method A) Rt. 2.30 min, 98.05% (Max). Chiral HPLC: (Method H) Rt. 7.06 min, 100%. The second eluting compound was concentrated to give Example 197 (brown oil). $^{1}$H NMR (400 MHz, DMSO d$_{6}$): δ 8.29 (s, 2H), 6.89 (s, 1H), 6.84 (d, J=8.0 Hz, 1H), 6.75 (d, J=8.0 Hz, 1H), 5.99-5.98 (m, 2H), 5.11 (d, J=4.4 Hz, 1H), 4.62-4.59 (m, 1H), 3.68-3.65 (m, 4H), 3.38-3.36 (m, 1H), 2.35-2.32 (m, 4H), 1.31 (d, J=6.4 Hz, 3H), 1.28 (d, J=6.8 Hz, 3H).

LCMS: (Method A) 357.2 (M+H), Rt. 2.29 min, 99.93% (Max). HPLC: (Method N) Rt. 2.26 min, 99.62% (Max). Chiral HPLC: (Method H) Rt 7.60 min, 100%.

Example 199: 1-(4-Bromo-3-methoxyphenyl)-4-(1-(2,3-dihydrobenzorbiri,41dioxin-6-vPethvPpiperazine

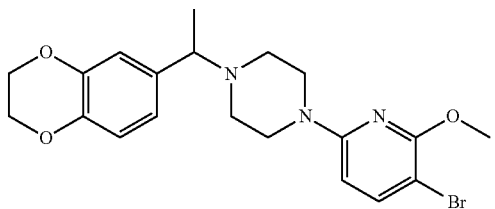 [SMILES: COc1nc(N2CCN(C(C)c3ccc4c(c3)OCCO4)CC2)ccc1Br]

To a stirred solution of Intermediate 4 (0.3 g, 1.056 mmol) in DMSO (6 mL), Cs$_{2}$CO$_{3}$ (1.38 g, 4.22 mmol) and 3-bromo-6-chloro-2-methoxypyridine (0.258 g, 1.16 mmol) were added at rt and the mixture was heated to 120° C. for 12 h. It was diluted with water (10 mL), extracted with EtOAc (25 mL) and dried over Na$_{2}$SO$_{4}$. After evaporation of the solvents, the crude product was purified by MD Autoprep (Method B) affording the title product (off white solid). $^{1}$H NMR (400 MHz, DMSO-d$_{6}$): δ 7.60 (d, J=8.4 Hz, 1H), 6.79-6.73 (m, 3H), 6.25 (d, J=8.4 Hz, 1H), 4.21 (s, 4H), 3.80 (s, 3H), 3.42-3.32 (m, 5H), 2.55-2.45 (m, 4H), 1.26 (d, J=6.8 Hz, 3H). LCMS: (Method B) 434.0 (M+1), Rt. 7.151 min, 96.67% (Max). HPLC: (Method B) Rt. 6.24 min, 95.29% (Max).

Example 200: 1-(1-(2,3-Dihydrobenzorbiri,41dioxin-6-yl)ethyl)-4-(3-methoxyphenyl)piperazine

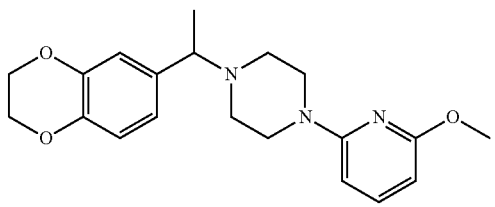 [SMILES: COc1cccc(N2CCN(C(C)c3ccc4c(c3)OCCO4)CC2)n1]

The title product was prepared according to the protocol described for Example 199, replacing 3-bromo-6-chloro-2-methoxypyridine with 2-chloro-6-methoxypyridine. The crude product was purified by MD Autoprep (Method B), affording the title product (brown solid). $^{1}$H NMR (400 MHz, DMSO-d$_{6}$): δ 7.40 (t, J=8.0 Hz, 1H), 6.78-6.73 (m, 3H), 6.24 (d, J=8.0 Hz, 1H), 5.99 (d, J=8.0 Hz, 1H), 4.21 (s, 4H), 3.73 (s, 3H), 3.42-3.37 (m, 5H), 2.37-2.32 (m, 4H), 1.26 (d, J=6.8 Hz, 3H). LCMS: (Method B) 356 (M+H), Rt. 6.622 min, 98.55% (Max). HPLC: (Method A) Rt. 3.23 min, 96.44% (Max).

Example 201: 3-Methyl-7-(1-(4-(pyrimidin-2-yl)piperazin-1-yl)ethyl)quinoline

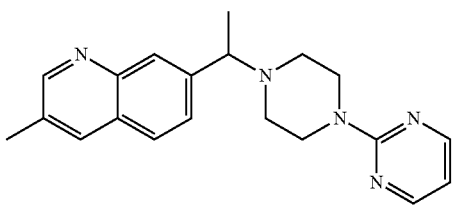 [SMILES: Cc1cnc2cc(C(C)N3CCN(c4ncccn4)CC3)ccc2c1]

To a stirred solution of 2-(piperazin-1-yl)pyrimidine (0.16 g, 0.97 mmol) in DMF (5 mL), TEA (0.4 mL, 2.9 mmol) and Intermediate 28 (0.3 g, 1.46 mmol) were added at room temperature. The reaction mixture was stirred at 100° C. for 16 h. The reaction completion was confirmed by TLC. The reaction mixture was cooled to room temperature and concentrated under reduced pressure. The resulting crude mixture was diluted with EtOAc (50 mL), washed with water (10 mL), brine solution (10 mL), dried over anhydrous Na$_{2}$SO$_{4}$ and concentrated. The crude product was purified by flash chromatography to afford the title compound (off white solid). $^{1}$HNMR (400 MHz, DMSO-d$_{6}$): δ 8.75 (d, J=2.0 Hz, 1H), 8.32 (d, J=4.8 Hz, 2H), 8.09 (s, 1H), 7.86 (d, J=8.0 Hz, 2H), 7.61 (d, J=10.0 Hz, 1H), 6.59 (t, J=4.8 Hz, 1H), 3.72-3.66 (m, 5H), 2.58-2.55 (m, 2H), 2.48 (s, 3H), 2.42-2.38 (m, 2H), 1.42 (d, J=6.8 Hz, 3H). LCMS: (Method A) 334.2 (M+H), Rt. 1.79 min, 99.76% (Max). HPLC: (Method A) Rt 1.73 min, 99.84% (Max).

Example 202: 3-Methyl-7-(1-(4-(3-(trifluoromethyl)pyridin-2-yl)piperazin-1-yl)ethyl)quinolone

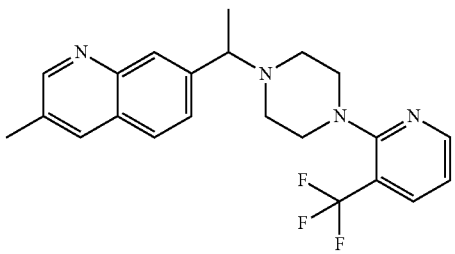 [SMILES: Cc1cnc2cc(C(C)N3CCN(c4ncccc4C(F)(F)F)CC3)ccc2c1]

To a stirred solution of Intermediate 29 (0.3 g, 1.29 mmol) in DMSO (5 mL), TEA (0.56 mL, 3.8 mmol) and Intermediate 28 (0.4 g, 1.94 mmol) were added at room temperature and the reaction mixture was stirred at 120° C. for 16 h. The reaction progression was followed by TLC. The reaction mixture was diluted with water (5 mL) and extracted with EtOAc (2×50 mL). The combined organic layer was dried over anhydrous Na$_{2}$SO$_{4}$ and concentrated under reduced pressure. The crude mass was purified by flash chromatography (gradient used: 1% MeOH in DCM), to afford the title compound (colorless gum). $^1$H NMR (400 MHz, DMSO-d$_6$): δ 8.75 (d, J=2.0 Hz, 1H), 8.50 (d, J=5.2 Hz, 1H), 8.10 (s, 1H), 8.03 (d, J=7.6 Hz, 1H), 7.86 (d, J=8.4 Hz, 2H), 7.61 (d, J=8.0 Hz, 1H), 7.16 (dd, J=2.8, 7.6 Hz, 1H), 3.68 (q, J=6.8 Hz, 1H), 3.21-3.18 (m, 4H), 2.63-2.60 (m, 2H), 2.50-2.48 (m, 5H), 1.42 (d, J=6.8 Hz, 3H). LCMS: (Method A) 401.2 (M+H), Rt. 2.63 min, 99.88% (Max). HPLC: (Method A) Rt 2.57 min, 99.84% (Max).

Example B01: Human O-GlcNAcase Enzyme Inhibition Assay

5 µl of the appropriate concentration of a solution of inhibitor in McIlvaine's Buffer (pH 6.5) in 2% DMSO (for a dose response curve calculation) is added into each well of a 384-well plate (Greiner, 781900). Then, 20 nM of His-Tagged hOGA and 10 µM of FL-GlcNAc (Fluorescein mono-beta-D-(2-deoxy-2-N-acetyl) glucopyranoside; Marker Gene Technologies Inc, M1485) were added to the 384-well plate for a final volume of 20 µl. After incubation for 60 min at room temperature, the reaction was terminated by the addition of 10 µL of stop buffer (200 mM glycine, pH 10.75). The level of fluorescence ($\lambda_{ex}$485 nm; ($\lambda_{em}$m520 nm) was read on a PHERAstar machine. The amount of fluorescence measured was plotted against the concentration of inhibitor to produce a sigmoidal dose response curve to calculate an IC$_{50}$. All individual data was corrected by subtraction of the background (Thiamet 3 uM=100% inhibition) whilst 0.5% DMSO was considered as the control value (no inhibition).

Example B02: Pharmacodynamic Model: Total Protein O-GlcNAcylation Immunoassay (RL2 mAb, Meso Scale Electrochemiluminescence (ECL) Assay)

The test compound was administered orally to C57BL/6J mice. At defined time intervals after compound administration, typically a time ranging between 2 and 48 hours, preferably between 4 and 24 hours, mice were sacrificed by decapitation for blood collection and forebrain dissection. Right brain hemispheres were placed in 2 ml Precellys tubes, snap frozen in dry ice and stored at −80° C. Left hemispheres were placed in 2 ml Eppendorf tubes, snap frozen in dry ice and stored at −80° C. until further processing. Blood samples were collected in Sarstedt tubes containing 35 IU of Heparin and kept at 4° C. After centrifugation for 10 min at 3800×g, 4° C., 50 µL of plasma from each sample was transferred to a 1.5 ml Eppendorf tube and stored at −80° C.

For the preparation of soluble brain protein for the immunoassay the hemispheres were homogenized in ice-cold Cytobuster reagent (71009—Merck Millipore) buffer with protease inhibitor cocktail. After centrifugation for 15 min at 17000×g at 4° C. the supernatants were transferred into polycarbonate tubes (1 ml). The supernatants were cleared by centrifugation for 1 h. at 100000×g, 4° C., and the protein concentrations were determined by using the BCA kit (23227—Pierce, Rockford, Ill.) according to the manufacturer's instructions.

Total Protein O-GlcNAcylation Immunoassay:

Samples were randomised and 120 µg/ml (25 µl/well) of soluble brain protein was directly coated on a Multi-array 96-well high bind plate (L15XB-3 High bind—Meso Scale Discovery) overnight at 4° C. After washing (3× with PBS-T buffer), the plate was blocked with MSD blocker A solution for 1 h. at room temperature (RT) under agitation. After washing (3× with PBS-T buffer), the plate was incubated with 0.1 µg/ml of a mouse monoclonal antibody directed against O-GlcNAc moieties (RL2; MA1-072—Thermo Scientific) for 1 h. at RT under agitation. For the ECL assay, after washing (3× with PBS-T buffer), 1 µg/ml of a SULFO-TAG™ labeled anti-mouse secondary antibody (Meso Scale Discovery) was added and the plate was incubated for 1 h. at RT under agitation and protected from light. After washing (3× with PBS-T buffer), 150 µl/well of 1× Read Buffer T was added to the plates before reading on a Sector Imager 6000 (Meso Scale Discovery).

Example B03: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of NaH$_2$PO$_4$.2H$_2$O, 28.48 g of Na$_2$HPO$_4$.12 H$_2$O and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such away that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:
1. A compound of formula (I)

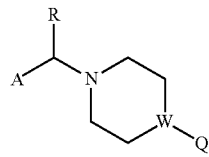

wherein
R is straight chain or branched alkyl having 1 to 6 carbon atoms, wherein 1 to 5 hydrogen atoms may be replaced by Hal or OH;
W is CH or N;
A is:

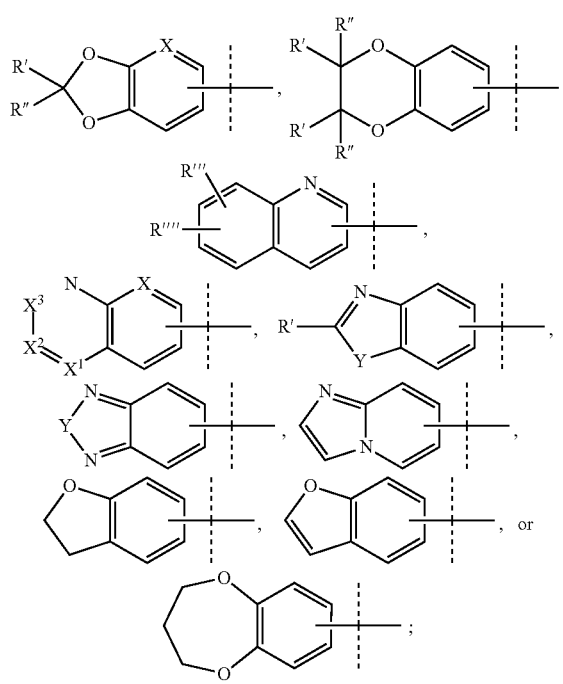

X is N or CR''';
$X^1$, $X^2$ is N or CR''';
$X^3$ is N or CR'''';
Y is O, S, SO, or $SO_2$;
R', R" are, independently, H, Hal, or straight chain or branched alkyl having 1 to 12 carbon atoms;
R''', R'''' are, independently, H, Hal, $NR^3R^4$, $CHR^3R^4$, $OR^3$, CN, or straight chain or branched alkyl having 1 to 12 carbon atoms, wherein 1 to 3 $CH_2$-groups may be replaced by a group selected from O, $NR^3$, S, SO, $SO_2$, CO, COO, OCO, $CONR^3$, and $NR^3CO$; and wherein 1 to 5 hydrogen atoms may be replaced by Hal, $NR^3R^4$, or $NO_2$;
R''''' is H, Hal, $NR^3R^4$, $CHR^3R^4$, CN, or straight chain or branched alkyl having 1 to 12 carbon atoms, wherein 1 to 3 $CH_2$-groups may be replaced by a group selected from $NR^3$, S, SO, $SO_2$, CO, COO, OCO, $CONR^3$, and $NR^3CO$; and wherein 1 to 5 hydrogen atoms may be replaced by Hal, $NR^3R^4$, or $NO_2$;
$R^3$, $R^4$ are, independently, H or a straight chain or branched alkyl group having 1 to 12 carbon atoms;
Q is:

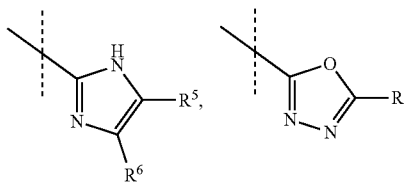

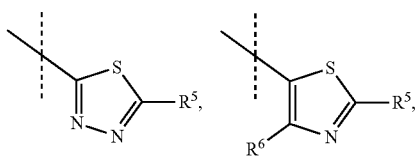

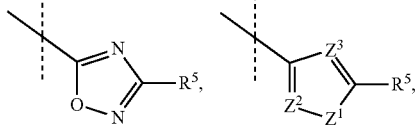

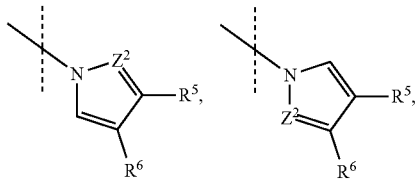

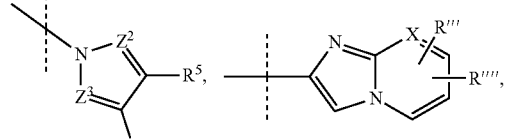

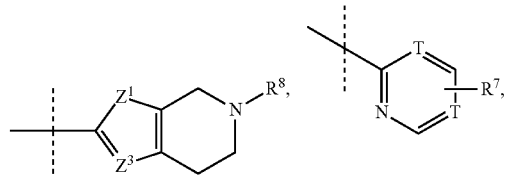

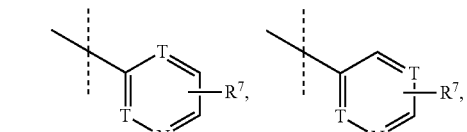

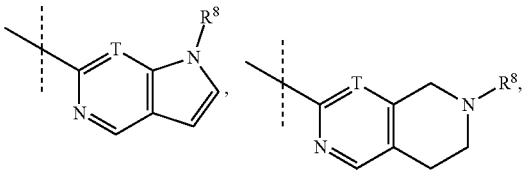

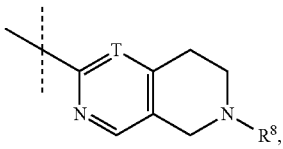

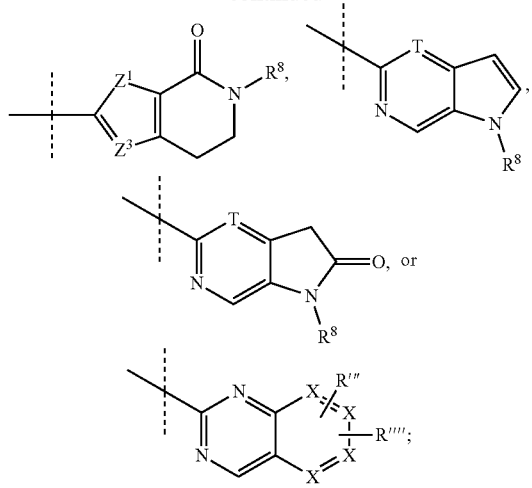

Z¹ is S, O, or NR³;
Z², Z³ are, independently, CR⁵, CR⁶, or N;
T is N, CH, or CR⁷;
R⁵, R⁶, R⁷ are, independently, H, Hal, NR³R⁴, NO₂, Ar, Het, Cyc, or straight chain or branched alkyl having 1 to 12 carbon atoms, wherein 1 to 3 CH₂-groups may be replaced by a group selected from O, NR³, S, SO, SO₂, CO, COO, OCO, CONR³, and NR³CO; and wherein 1 to 5 hydrogen atoms may be replaced by Hal, NR³R⁴, NO₂, OR³, Het, Ar, or Cyc;
R⁸ is H, methyl, or straight chain or branched alkyl having 2 to 12 carbon atoms, wherein 1 to 3 CH₂-groups may be replaced by a group selected from O, NR³, S, SO, SO₂, CO, COO, OCO, CONR³, and NR³CO; and wherein 1 to 5 hydrogen atoms may be replaced by Hal, NR³R⁴, or NO₂;
Hal is F, Cl, or I;
Het is a saturated, unsaturated, or aromatic ring, being monocyclic or bicyclic or fused-bicyclic and having 3- to 8-members and containing 1 to 4 heteroatoms selected from N, O and S, which may be substituted by 1 to 3 substituents selected from R⁵, Hal, and OR³;
Ar is a 6-membered carbocyclic aromatic ring or a fused or non-fused bicyclic ring system, which is optionally substituted by 1 to 3 substituents independently selected from R⁵, OR³, and Hal;
Cyc is a saturated carbocyclic ring having from 3 to 8 carbon atoms which is optionally substituted by 1 to 3 substituents independently selected from R⁵, Hal and OH;

or a solvate, salt, tautomer, enantiomer, racemate, stereoisomer, compound of formula (I) where one or more H atoms are replaced by deuterium, or any mixture thereof in any ratio.

2. A compound of formula Ia or Ib

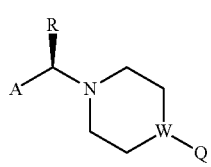
(Ia)

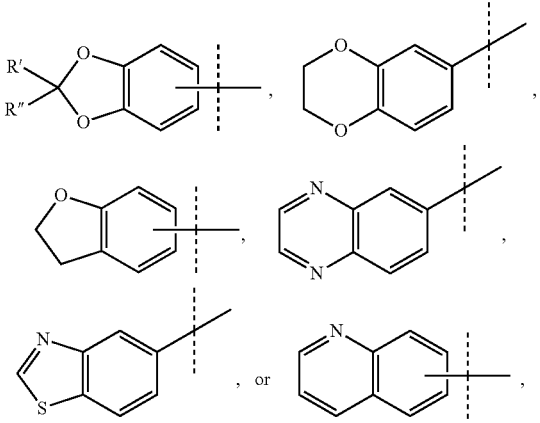

wherein A, R, W, and Q have the meanings given in claim 1.

3. A mixture comprising compounds (Ia) and (Ib) according to claim 2, in equal or unequal amounts, wherein:
the A groups in (Ia) and (Ib) are identical; the R groups in (Ia) and (Ib) are identical;
the W groups in (Ia) and (Ib) are identical; and the Q groups in (Ia) and (Ib) are identical.

4. The compound of claim 1, wherein R is methyl.

5. The compound of claim 1, wherein A is:

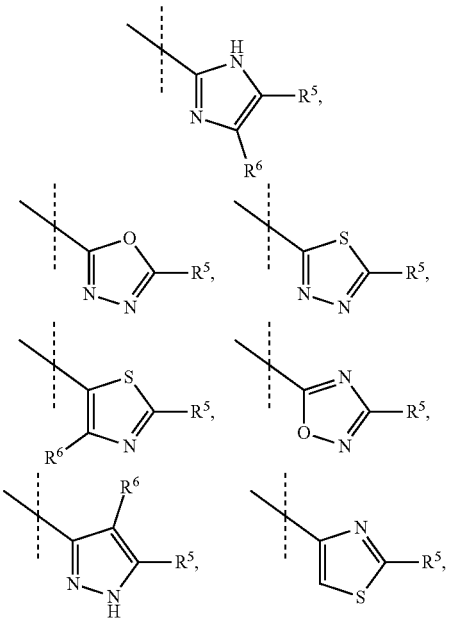

wherein R' and R" have the meaning given in claim 1.

6. The compound of claim 1, wherein Q is:

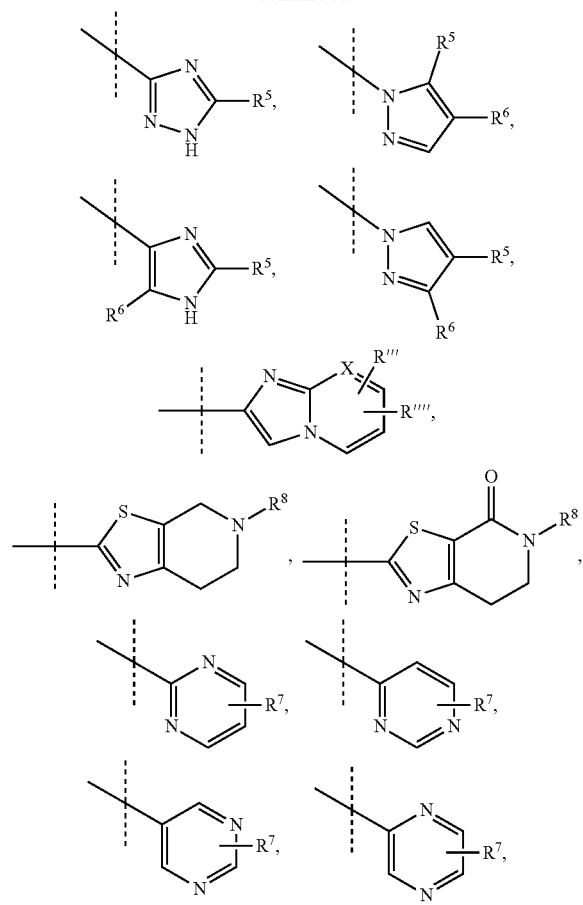
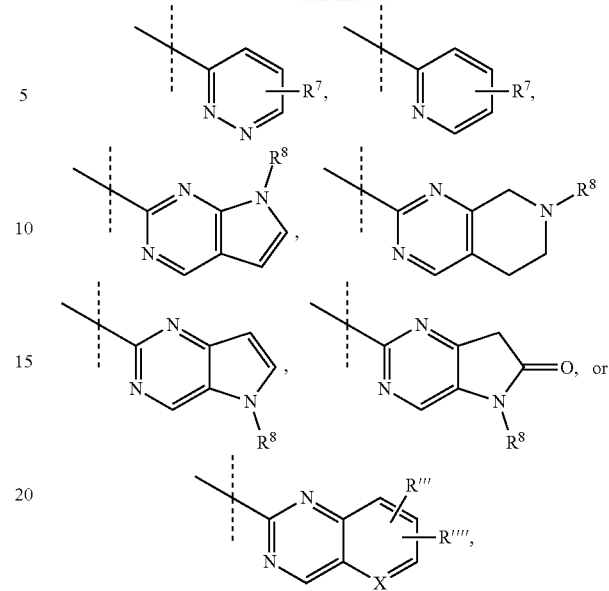

wherein X, R''', R'''', $R^5$, $R^6$, $R^7$ and $R^8$ have the meaning given in claim 1.

7. The compound of claim 1, wherein $R^5$, $R^6$, and $R^7$ are independently H, Hal, $NR_3R_4$, phenyl, 2-, 3- or 4-hydroxy or methoxyphenyl, alkyl, $CF_3$, alkoxy, hydroxyalkylene, alkoxyalkylene, COOH, COOalkyl, CONHalkyl, $CONH_2$, $CON(CH_3)_2$, NHCOalkyl, CO—N-morpholinyl, $CON(CH_3)CH_2CH_2N(CH_3)_2$, CO-1-piperidinyl, CO-4-hydroxy-1-piperidinyl, CO-1-piperazinyl, CO-4-methyl-1-piperazinyl, $CH_2$—N-morpholinyl, $CH_2N(H)COCH_3$, $CH_2N(CH_3)COCH_3$, substituted Cyc or Het, or unsubstituted Cyc or Het.

8. A compound selected from the group consisting of:

| No | Structure |
|---|---|
| 2 | 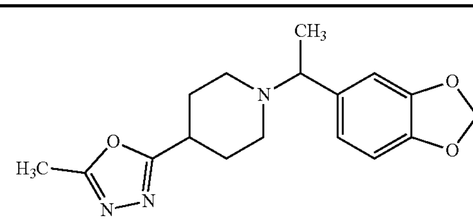 |
| 3 | 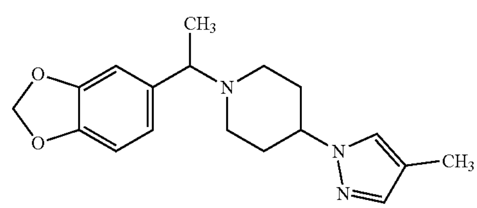 [SMILES: Cc1cnn(C2CCN(C(C)c3ccc4c(c3)OCO4)CC2)c1] |
| 4 | 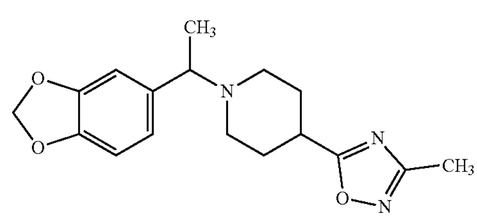 [SMILES: Cc1noc(C2CCN(C(C)c3ccc4c(c3)OCO4)CC2)n1] |

| No | Structure |
|---|---|
| 8 | 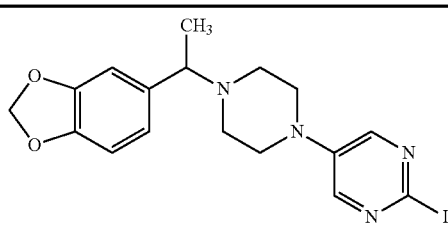 |
| 9 | 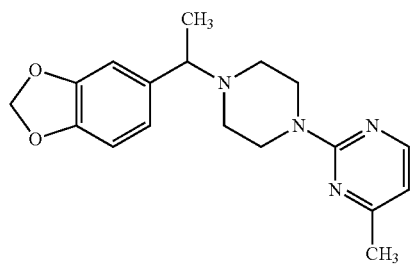 |
| 10 | 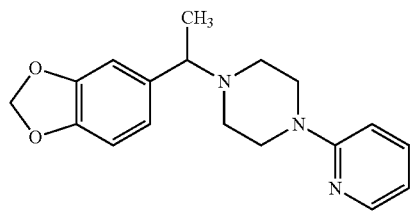 [SMILES: CC(c1ccc2c(c1)OCO2)N1CCN(c2ccccn2)CC1] |
| 11 | 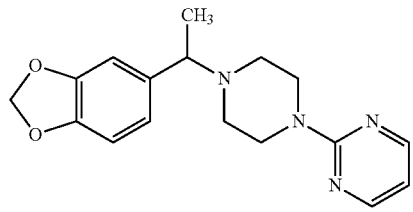 [SMILES: CC(c1ccc2c(c1)OCO2)N1CCN(c2ncccn2)CC1] |
| 14 | 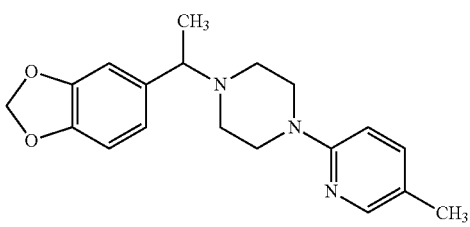 |
| 15 | 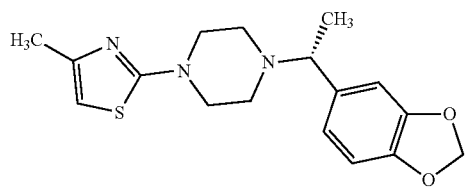 [SMILES: Cc1csc(N2CCN([C@H](C)c3ccc4c(c3)OCO4)CC2)n1] |
| 20 | 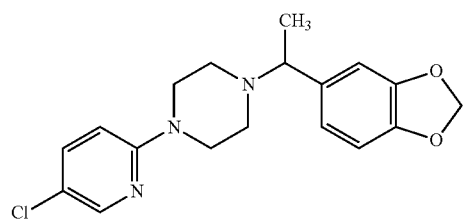 [SMILES: CC(c1ccc2c(c1)OCO2)N1CCN(c2ccc(Cl)cn2)CC1] |

-continued
| No | Structure |
|---|---|
| 21 | 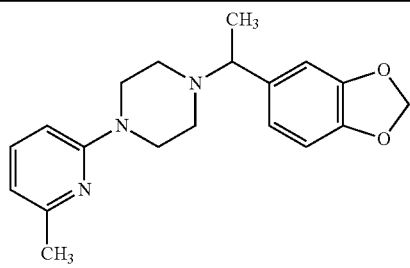 |
| 22 | 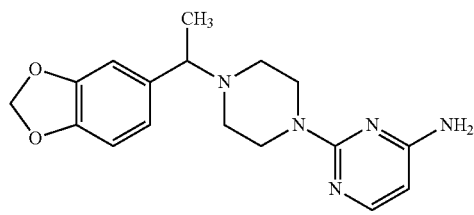 [SMILES: CC(c1ccc2c(c1)OCO2)N1CCN(c2nccc(N)n2)CC1] |
| 23 | 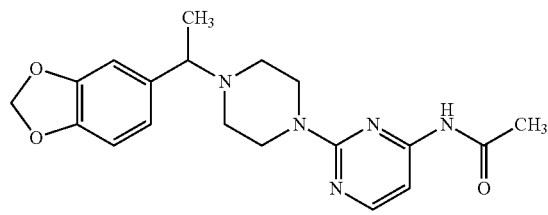 [SMILES: CC(=O)Nc1ccnc(N2CCN(C(C)c3ccc4c(c3)OCO4)CC2)n1] |
| 24 | 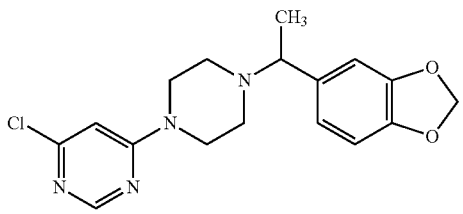 [SMILES: CC(c1ccc2c(c1)OCO2)N1CCN(c2cc(Cl)ncn2)CC1] |
| 25 | 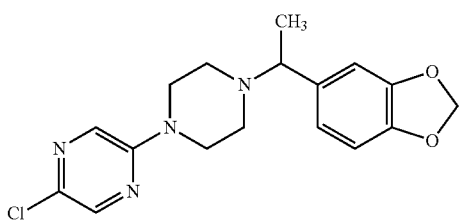 [SMILES: CC(c1ccc2c(c1)OCO2)N1CCN(c2cnc(Cl)cn2)CC1] |
| 26 | 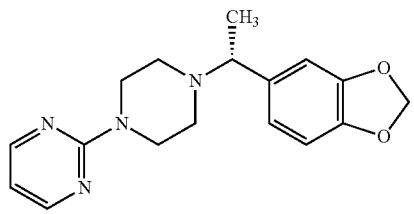 [SMILES: C[C@H](c1ccc2c(c1)OCO2)N1CCN(c2ncccn2)CC1] |
| 31 | 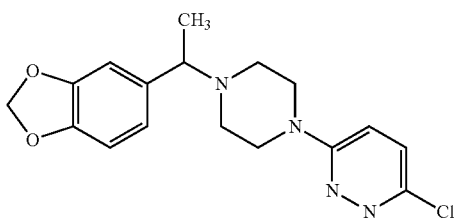 [SMILES: CC(c1ccc2c(c1)OCO2)N1CCN(C2=CC=C(Cl)NN2)CC1] |

| No | Structure |
|---|---|
| 34 | 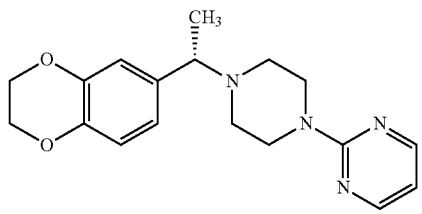 [SMILES: C[C@@H](c1ccc2c(c1)OCCO2)N1CCN(c2ncccn2)CC1] |
| 37 | 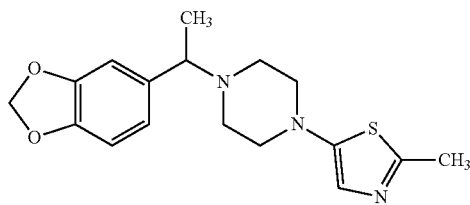 [SMILES: Cc1ncc(N2CCN(C(C)c3ccc4c(c3)OCO4)CC2)s1] |
| 38 | 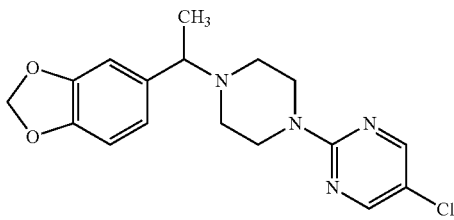 [SMILES: CC(c1ccc2c(c1)OCO2)N1CCN(c2ncc(Cl)cn2)CC1] |
| 39 | 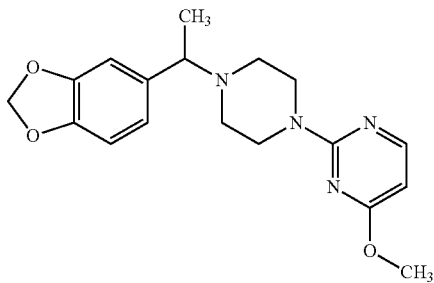 [SMILES: COc1ccnc(N2CCN(C(C)c3ccc4c(c3)OCO4)CC2)n1] |
| 40 | 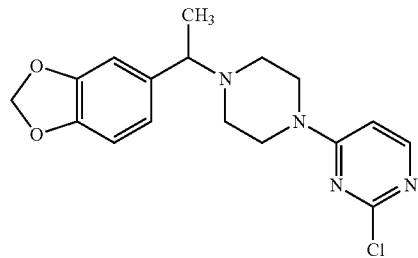 [SMILES: CC(c1ccc2c(c1)OCO2)N1CCN(c2ccnc(Cl)n2)CC1] |
| 41 | 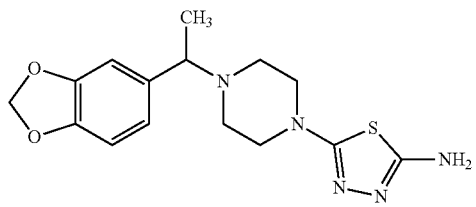 |

-continued
| No | Structure |
|---|---|
| 44 | 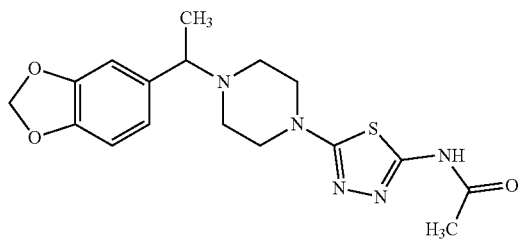 [SMILES: CC(=O)Nc1nnc(N2CCN(C(C)c3ccc4c(c3)OCO4)CC2)s1] |
| 45 | 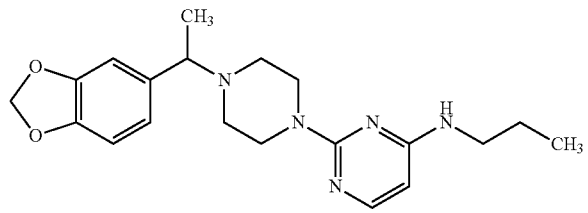 [SMILES: CCCNc1ccnc(N2CCN(C(C)c3ccc4c(c3)OCO4)CC2)n1] |
| 46 | 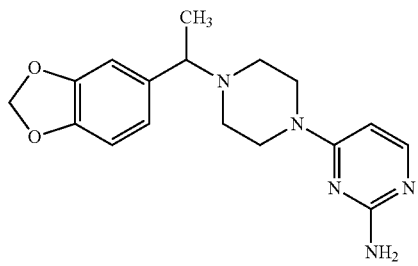 [SMILES: CC(c1ccc2c(c1)OCO2)N1CCN(c2ccnc(N)n2)CC1] |
| 51 | 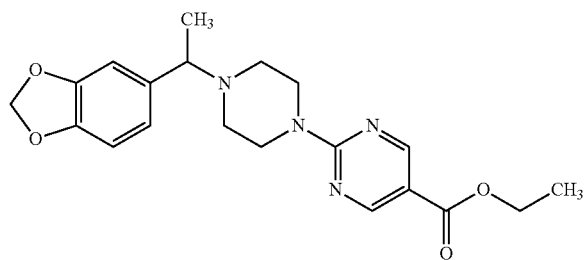 [SMILES: CCOC(=O)c1cnc(N2CCN(C(C)c3ccc4c(c3)OCO4)CC2)nc1] |
| 52 | 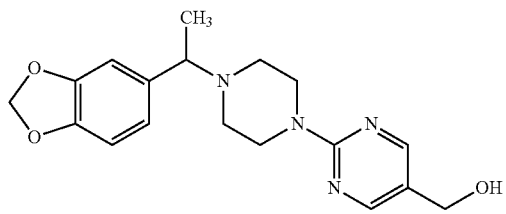 [SMILES: CC(c1ccc2c(c1)OCO2)N1CCN(c2ncc(CO)cn2)CC1] |
| 53 | 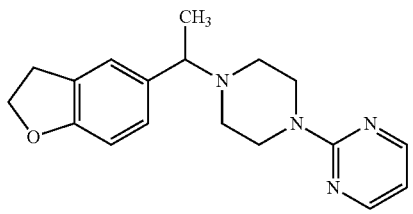 |

-continued
| No | Structure |
|---|---|
| 54 | 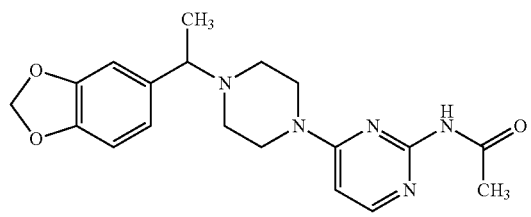 [SMILES: CC(=O)Nc1nccc(N2CCN(C(C)c3ccc4c(c3)OCO4)CC2)n1] |
| 55 | 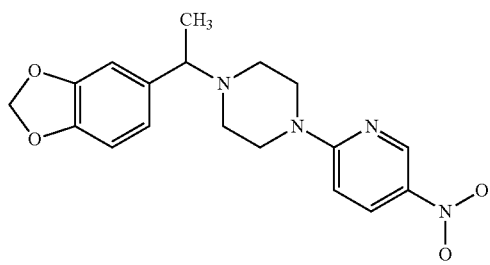 [SMILES: CC(c1ccc2c(c1)OCO2)N1CCN(c2ccc(N(O)O)cn2)CC1] |
| 58 | 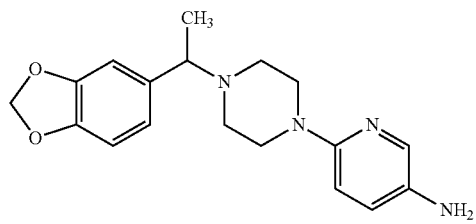 |
| 68 | 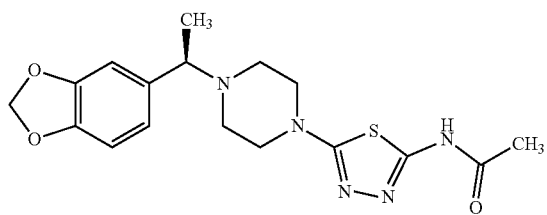 [SMILES: CC(=O)Nc1nnc(N2CCN([C@H](C)c3ccc4c(c3)OCO4)CC2)s1] |
| 69 | 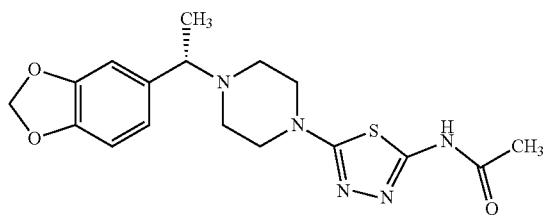 [SMILES: CC(=O)Nc1nnc(N2CCN([C@@H](C)c3ccc4c(c3)OCO4)CC2)s1] |
| 70 | 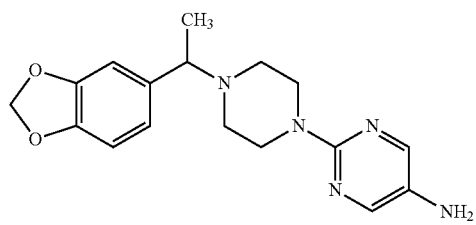 [SMILES: CC(c1ccc2c(c1)OCO2)N1CCN(c2ncc(N)cn2)CC1] |

-continued
| No | Structure |
|---|---|
| 72 | 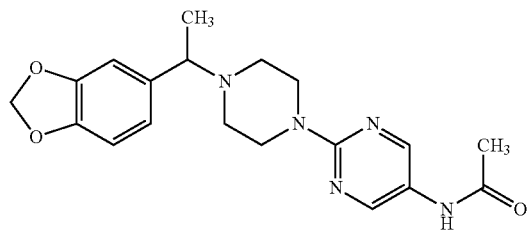 [SMILES: CC(=O)Nc1cnc(N2CCN(C(C)c3ccc4c(c3)OCO4)CC2)nc1] |
| 77 | 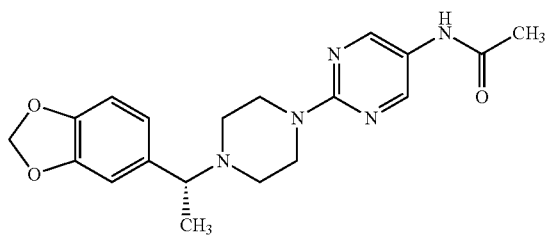 |
| 78 | 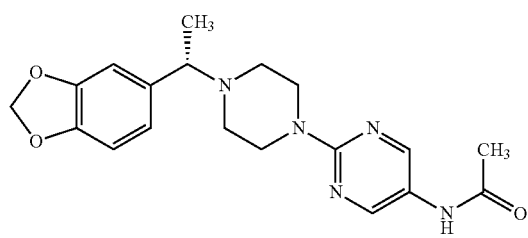 [SMILES: CC(=O)Nc1cnc(N2CCN([C@@H](C)c3ccc4c(c3)OCO4)CC2)nc1] |
| 82 | 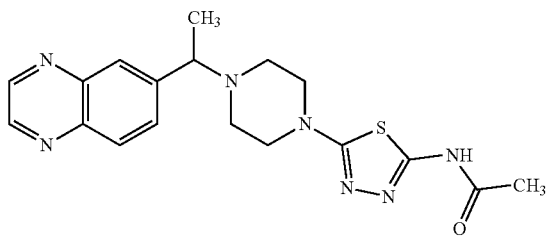 [SMILES: CC(=O)Nc1nnc(N2CCN(C(C)c3ccc4nccnc4c3)CC2)s1] |
| 83 | 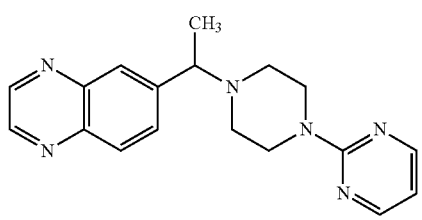 [SMILES: CC(c1ccc2nccnc2c1)N1CCN(c2ncccn2)CC1] |
| 86 | 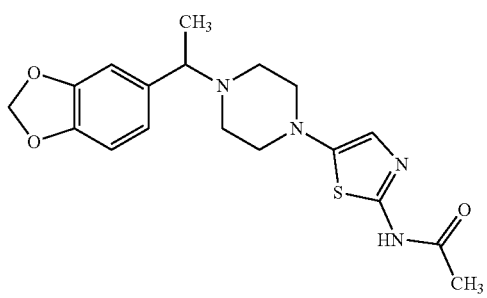 [SMILES: CC(=O)Nc1ncc(N2CCN(C(C)c3ccc4c(c3)OCO4)CC2)s1] |

-continued
| No | Structure |
|---|---|
| 89 | 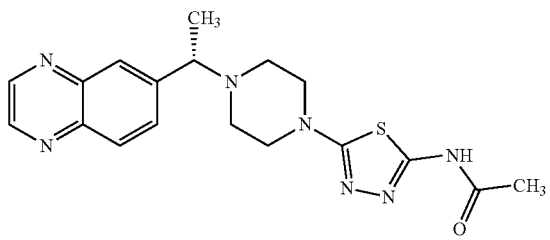 [SMILES: CC(=O)Nc1nnc(N2CCN([C@@H](C)c3ccc4nccnc4c3)CC2)s1] |
| 91 | 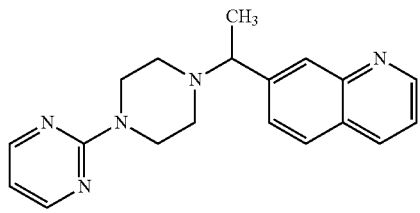 |
| 93 | 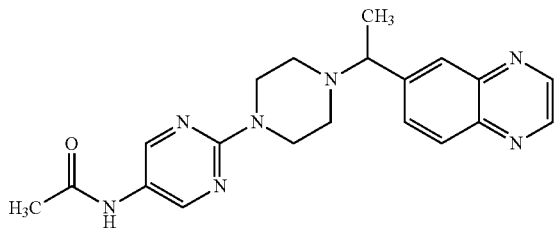 [SMILES: CC(=O)Nc1cnc(N2CCN(C(C)c3ccc4nccnc4c3)CC2)nc1] |
| 94 | 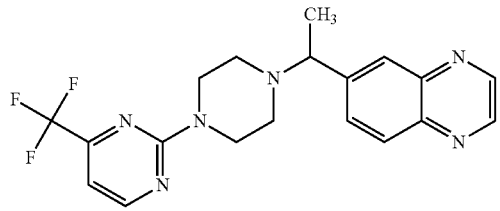 [SMILES: CC(c1ccc2nccnc2c1)N1CCN(c2nccc(C(F)(F)F)n2)CC1] |
| 95 | 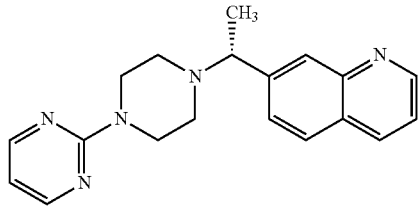 |
| 96 | 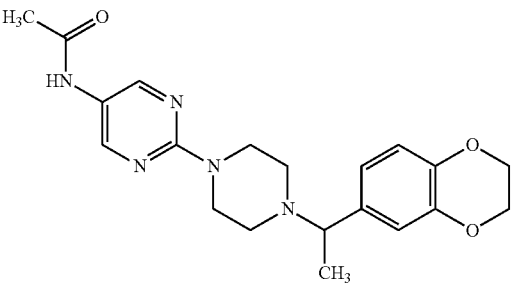 [SMILES: CC(=O)Nc1cnc(N2CCN(C(C)c3ccc4c(c3)OCCO4)CC2)nc1] |

-continued
| No | Structure |
|---|---|
| 97 | 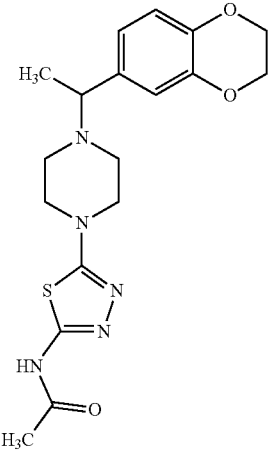 [SMILES: CC(=O)Nc1nnc(N2CCN(C(C)c3ccc4c(c3)OCCO4)CC2)s1] |
| 98 | 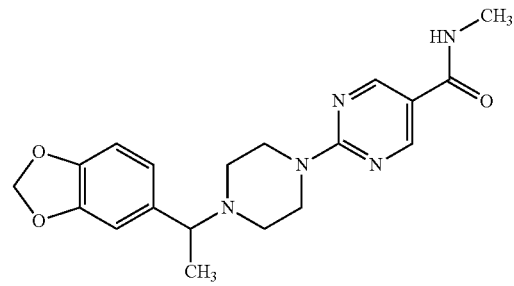 [SMILES: CNC(=O)c1cnc(N2CCN(C(C)c3ccc4c(c3)OCO4)CC2)nc1] |
| 99 | 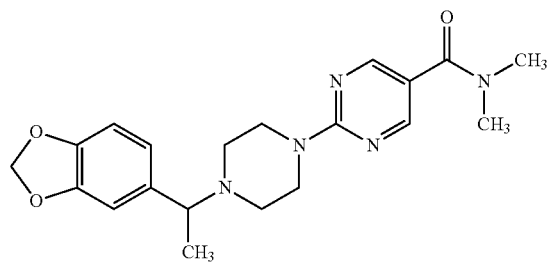 [SMILES: CC(c1ccc2c(c1)OCO2)N1CCN(c2ncc(C(=O)N(C)C)cn2)CC1] |
| 100 | 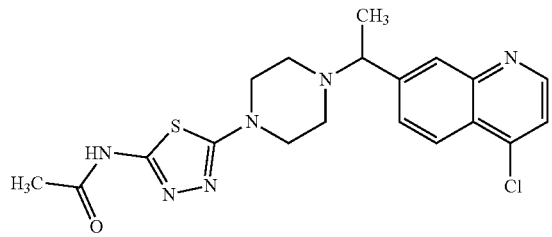 [SMILES: CC(=O)Nc1nnc(N2CCN(C(C)c3ccc4c(Cl)ccnc4c3)CC2)s1] |
| 101 | 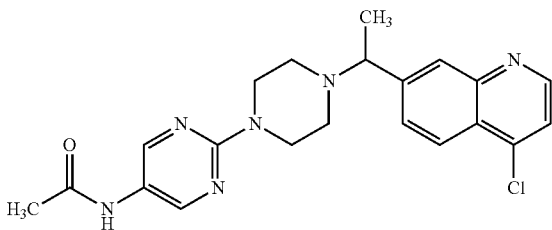 [SMILES: CC(=O)Nc1cnc(N2CCN(C(C)c3ccc4c(Cl)ccnc4c3)CC2)nc1] |

-continued
| No | Structure |
|---|---|
| 102 | 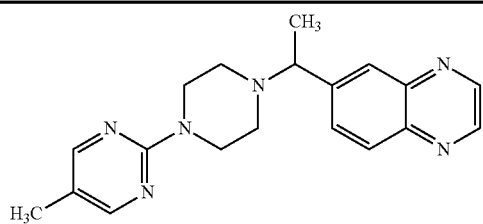 |
| 103 | 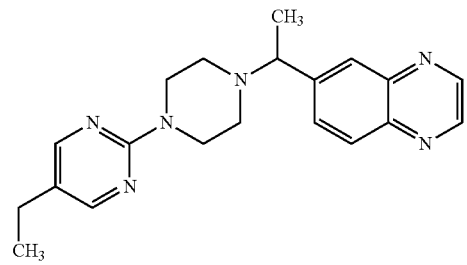 [SMILES: CCc1cnc(N2CCN(C(C)c3ccc4nccnc4c3)CC2)nc1] |
| 104 | 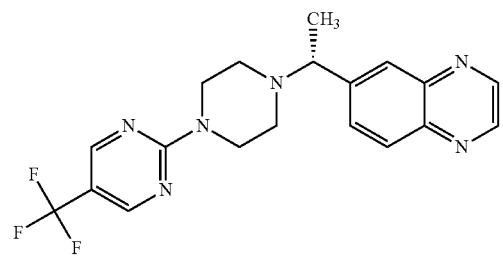 [SMILES: C[C@H](c1ccc2nccnc2c1)N1CCN(c2ncc(C(F)(F)F)cn2)CC1] |
| 105 | 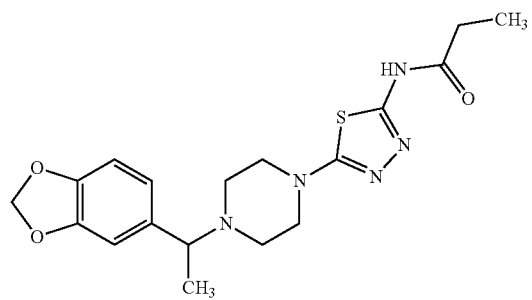 [SMILES: CCC(=O)Nc1nnc(N2CCN(C(C)c3ccc4c(c3)OCO4)CC2)s1] |
| 106 | 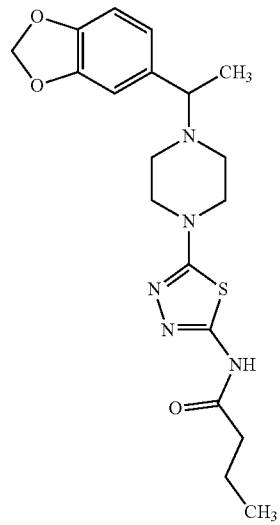 [SMILES: CCCC(=O)Nc1nnc(N2CCN(C(C)c3ccc4c(c3)OCO4)CC2)s1] |

-continued
| No | Structure |
|---|---|
| 107 | 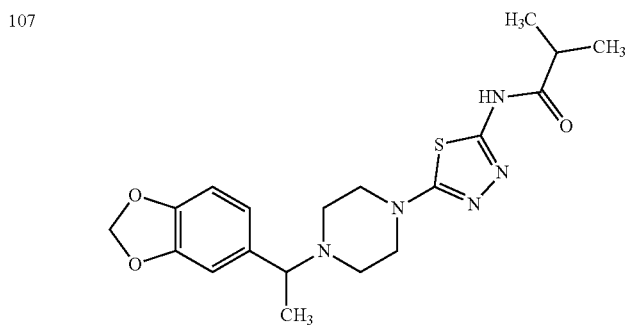 |
| 108 | 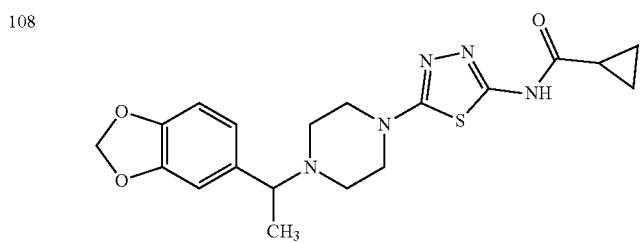 |
| 110 | 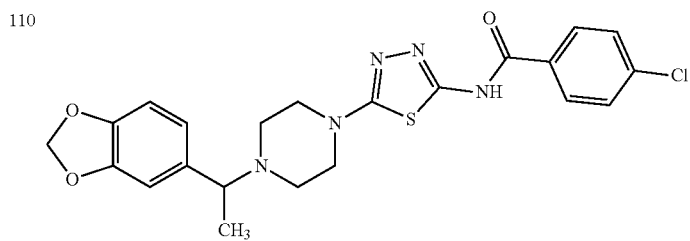 |
| 111 | 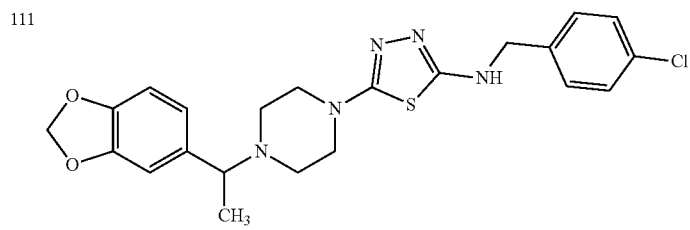 |
| 112 | 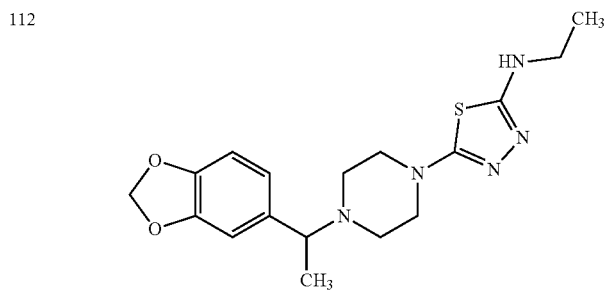 |

-continued
| No | Structure |
|---|---|
| 113 | 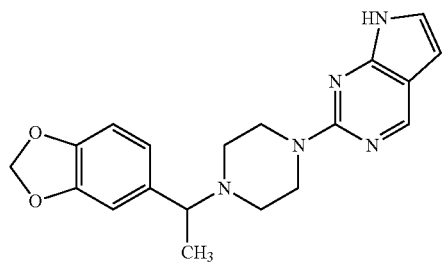 [SMILES: CC(c1ccc2c(c1)OCO2)N1CCN(c2ncc3cc[nH]c3n2)CC1] |
| 114 | 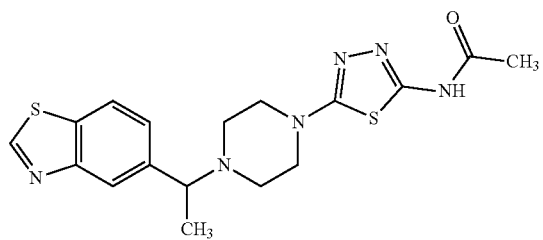 [SMILES: CC(=O)Nc1nnc(N2CCN(C(C)c3ccc4scnc4c3)CC2)s1] |
| 115 | 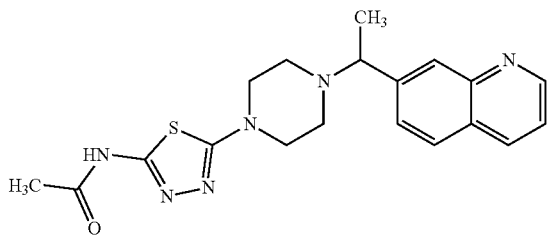 [SMILES: CC(=O)Nc1nnc(N2CCN(C(C)c3ccc4cccnc4c3)CC2)s1] |
| 116 | 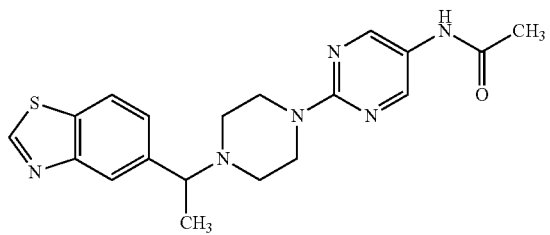 [SMILES: CC(=O)Nc1cnc(N2CCN(C(C)c3ccc4scnc4c3)CC2)nc1] |
| 117 | 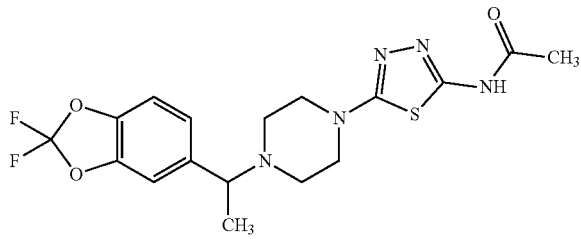 [SMILES: CC(=O)Nc1nnc(N2CCN(C(C)c3ccc4c(c3)OC(F)(F)O4)CC2)s1] |
| 118 | 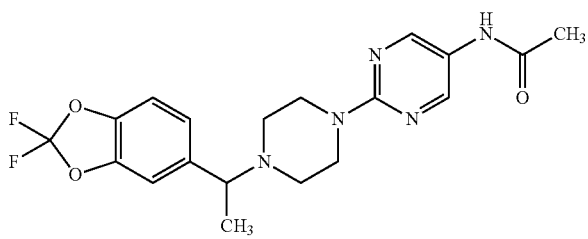 |

| No | Structure |
|---|---|
| 119 | 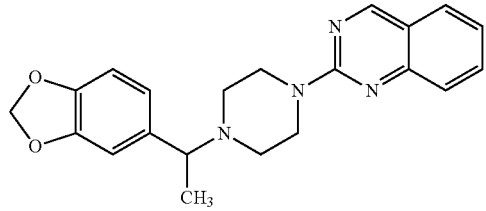 |
| 120 | 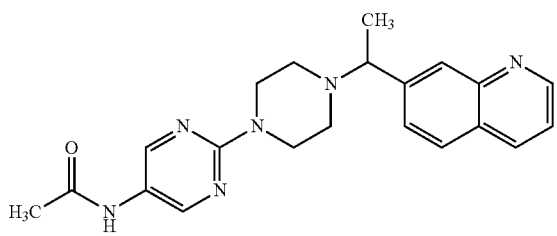 [SMILES: CC(=O)Nc1cnc(N2CCN(C(C)c3ccc4cccnc4c3)CC2)nc1] |
| 121 | 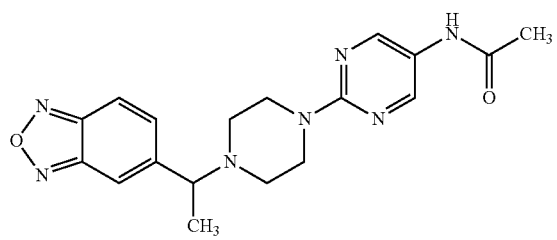 [SMILES: CC(=O)Nc1cnc(N2CCN(C(C)c3ccc4nonc4c3)CC2)nc1] |
| 122 | 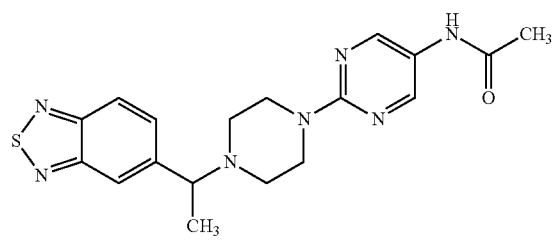 [SMILES: CC(=O)Nc1cnc(N2CCN(C(C)c3ccc4nsnc4c3)CC2)nc1] |
| 123 | 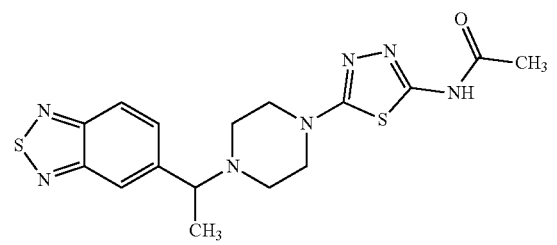 [SMILES: CC(=O)Nc1nnc(N2CCN(C(C)c3ccc4nsnc4c3)CC2)s1] |
| 124 | 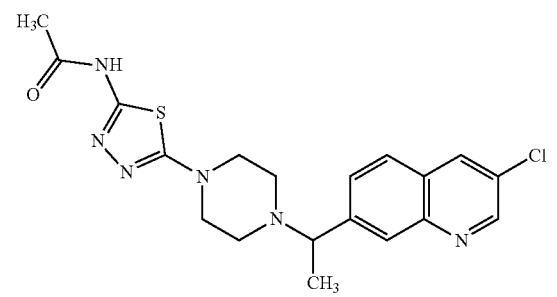 [SMILES: CC(=O)Nc1nnc(N2CCN(C(C)c3ccc4cc(Cl)cnc4c3)CC2)s1] |

-continued
| No | Structure |
|---|---|
| 125 | 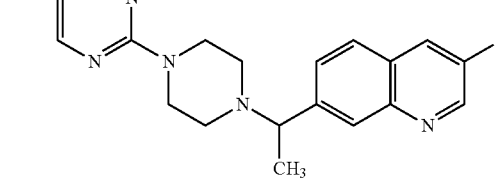 |
| 126 | 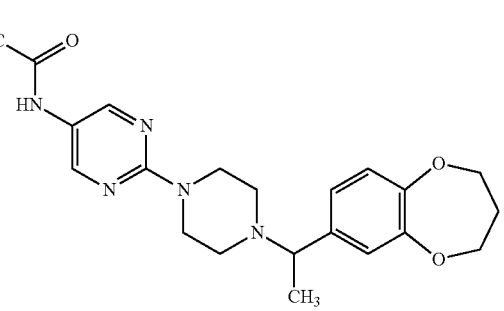 |
| 127 | 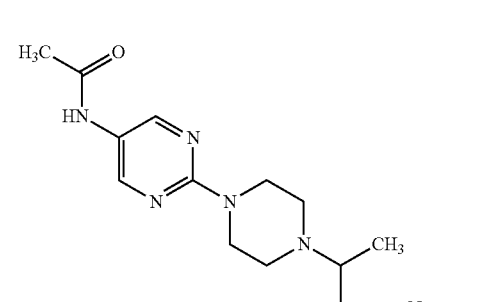 |
| 128 | 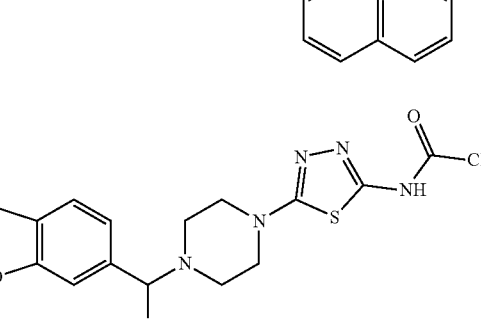 |
| 129 | 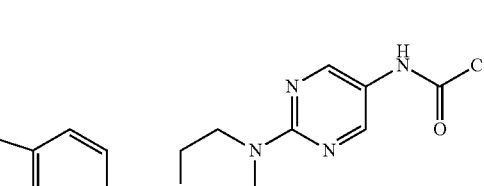 |

-continued
| No | Structure |
|---|---|
| 131 | 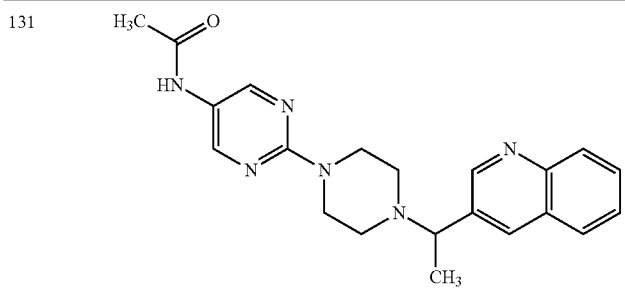 |
| 132 | 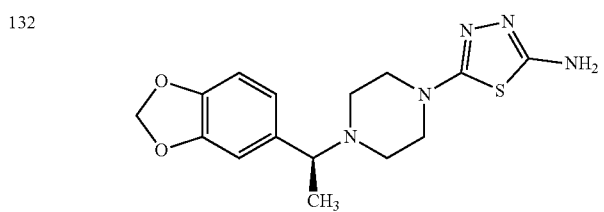 |
| 133 | 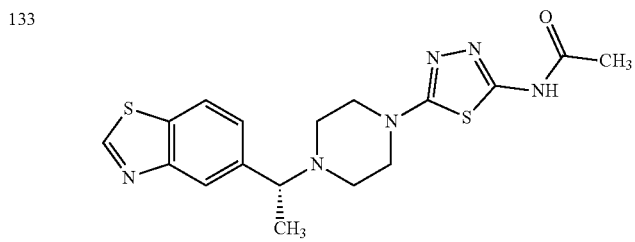 |
| 134 | 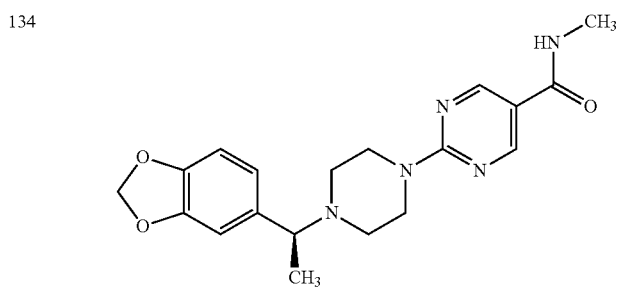 |
| 137 | 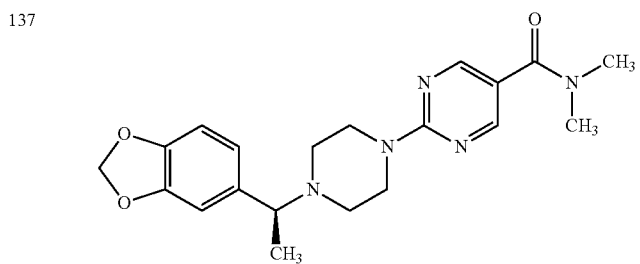 |
| 138 | 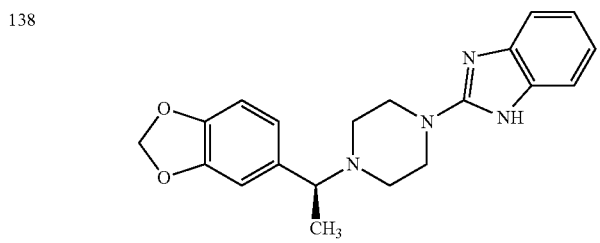 |

-continued
| No | Structure |
|---|---|
| 141 | 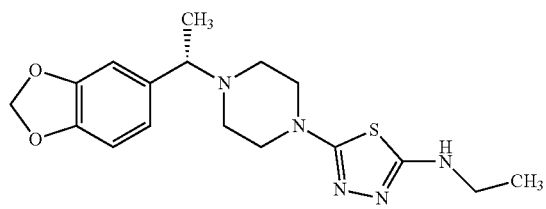 [SMILES: CCNc1nnc(N2CCN([C@@H](C)c3ccc4c(c3)OCO4)CC2)s1] |
| 142 | 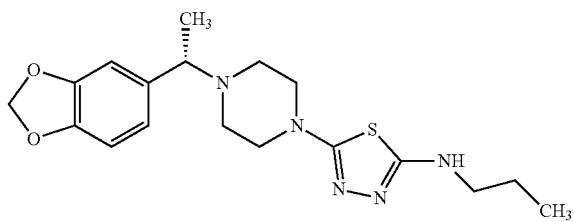 |
| 143 | 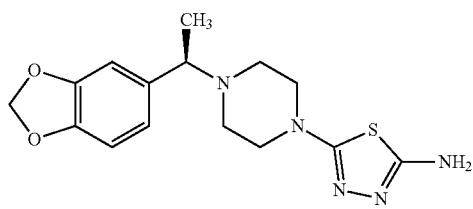 [SMILES: C[C@H](c1ccc2c(c1)OCO2)N1CCN(c2nnc(N)s2)CC1] |
| 145 | 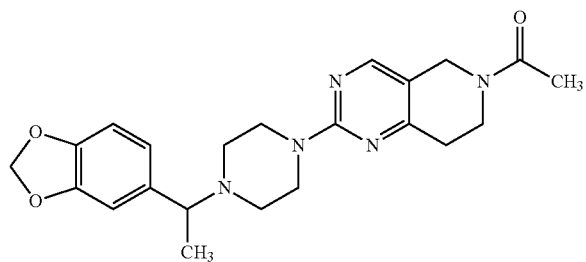 [SMILES: CC(=O)N1CCc2nc(N3CCN(C(C)c4ccc5c(c4)OCO5)CC3)ncc2C1] |
| 146 | 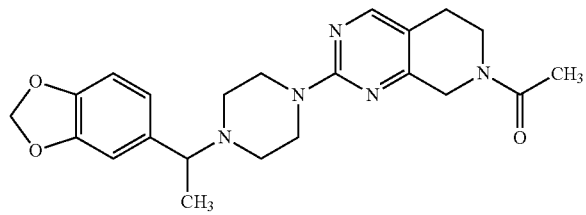 [SMILES: CC(=O)N1CCc2cnc(N3CCN(C(C)c4ccc5c(c4)OCO5)CC3)nc2C1] |
| 147 | 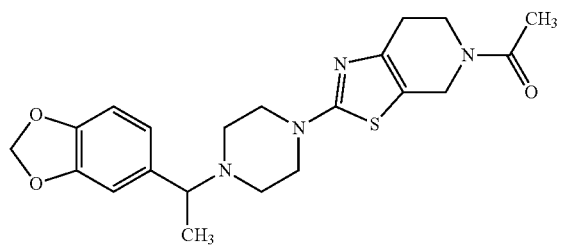 [SMILES: CC(=O)N1CCc2nc(N3CCN(C(C)c4ccc5c(c4)OCO5)CC3)sc2C1] |

-continued
| No | Structure |
|---|---|
| 148 | 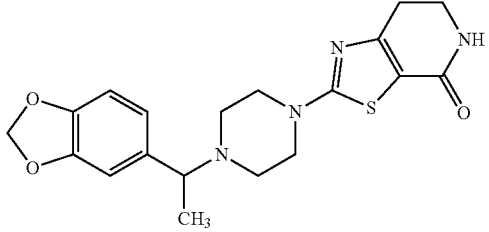 [SMILES: CC(c1ccc2c(c1)OCO2)N1CCN(c2nc3c(s2)C(=O)NCC3)CC1] |
| 150 | 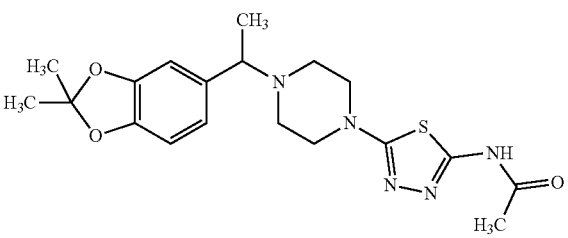 [SMILES: CC(=O)Nc1nnc(N2CCN(C(C)c3ccc4c(c3)OC(C)(C)O4)CC2)s1] |
| 151 | 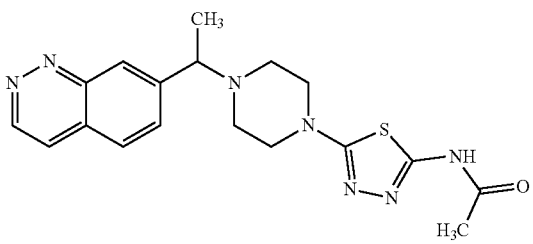 [SMILES: CC(=O)Nc1nnc(N2CCN(C(C)c3ccc4ccnnc4c3)CC2)s1] |
| 152 | 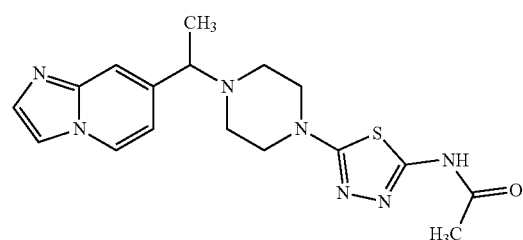 |
| 153 | 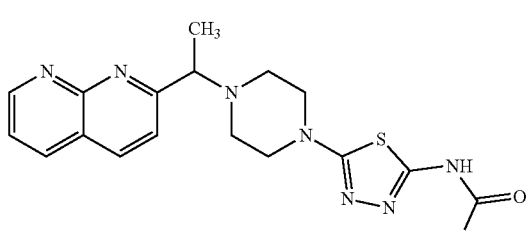 |
| 154 | 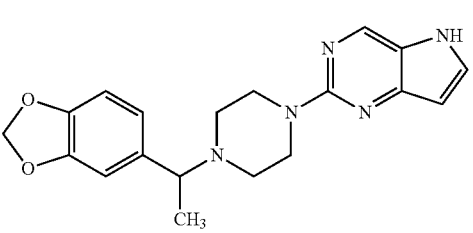 [SMILES: CC(c1ccc2c(c1)OCO2)N1CCN(c2ncc3[nH]ccc3n2)CC1] |

-continued

| No | Structure |
|---|---|
| 155 | 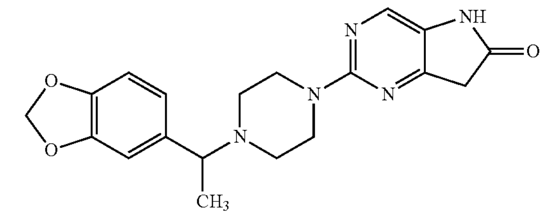 [SMILES: CC(c1ccc2c(c1)OCO2)N1CCN(c2ncc3c(n2)CC(=O)N3)CC1] |
| 156 | 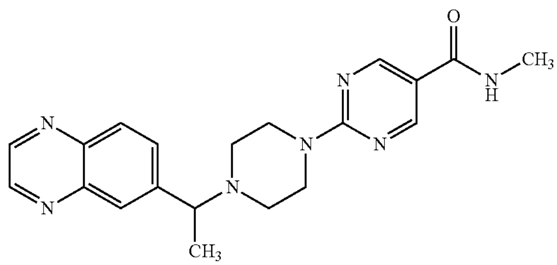 |
| 157 | 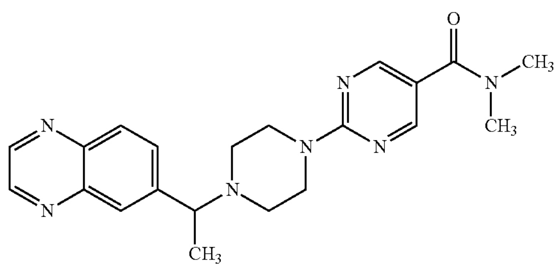 [SMILES: CC(c1ccc2nccnc2c1)N1CCN(c2ncc(C(=O)N(C)C)cn2)CC1] |
| 158 | 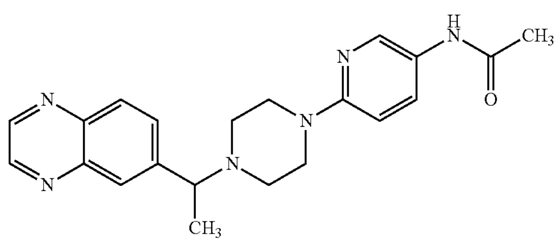 [SMILES: CC(=O)Nc1ccc(N2CCN(C(C)c3ccc4nccnc4c3)CC2)nc1] |
| 159 | 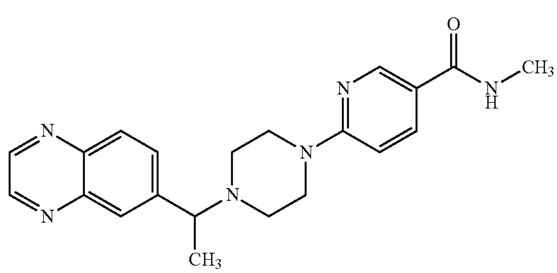 [SMILES: CNC(=O)c1ccc(N2CCN(C(C)c3ccc4nccnc4c3)CC2)nc1] |
| 160 | 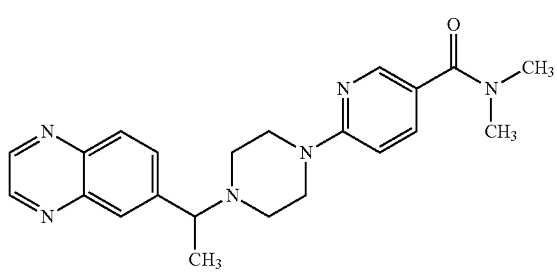 |

-continued
| No | Structure |
|---|---|
| 161 | 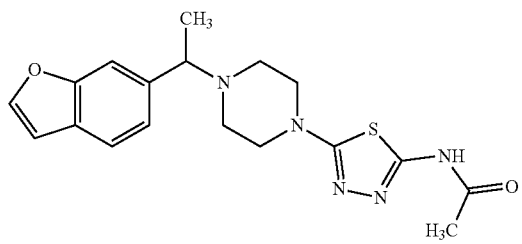 [SMILES: CC(=O)Nc1nnc(N2CCN(C(C)c3ccc4ccoc4c3)CC2)s1] |
| 162 | 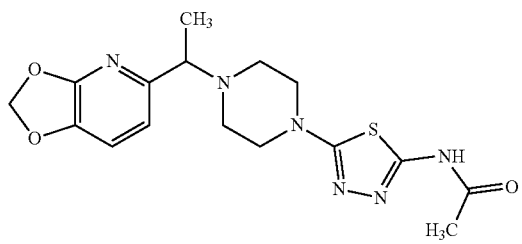 [SMILES: CC(=O)Nc1nnc(N2CCN(C(C)c3ccc4c(n3)OCO4)CC2)s1] |
| 163 | 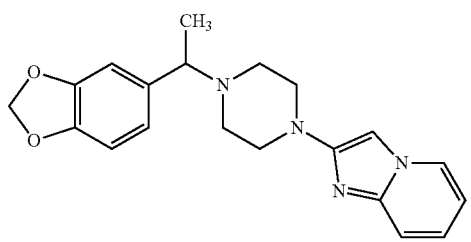 [SMILES: CC(c1ccc2c(c1)OCO2)N1CCN(c2cn3ccccc3n2)CC1] |
| 164 | 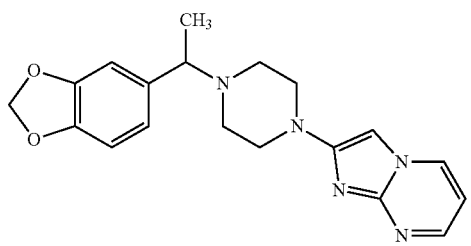 [SMILES: CC(c1ccc2c(c1)OCO2)N1CCN(c2cn3cccnc3n2)CC1] |
| 165 | 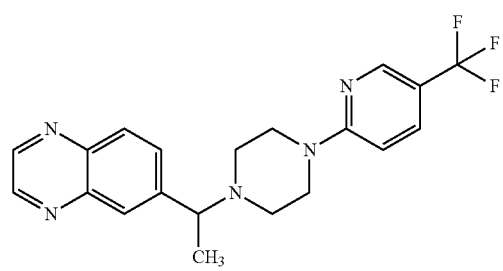 |
| 166 | 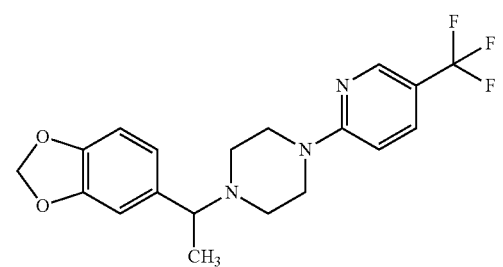 [SMILES: CC(c1ccc2c(c1)OCO2)N1CCN(c2ccc(C(F)(F)F)cn2)CC1] |

-continued
| No | Structure |
|---|---|
| 167 | 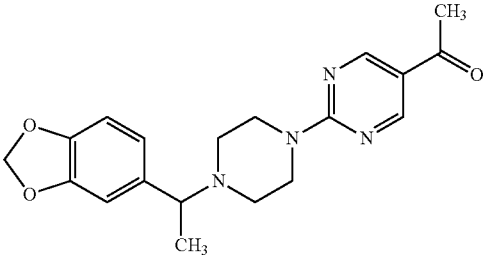 [SMILES: CC(=O)c1cnc(N2CCN(C(C)c3ccc4c(c3)OCO4)CC2)nc1] |
| 168 | 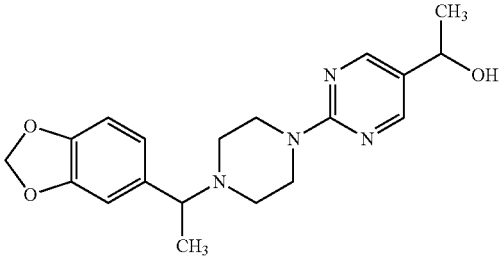 [SMILES: CC(O)c1cnc(N2CCN(C(C)c3ccc4c(c3)OCO4)CC2)nc1] |
| 169 | 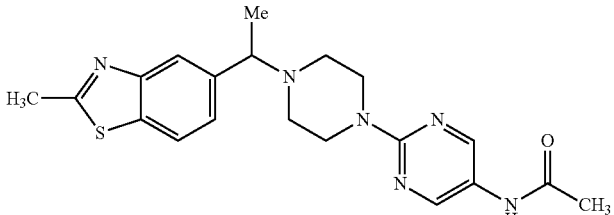 |
| 170 | 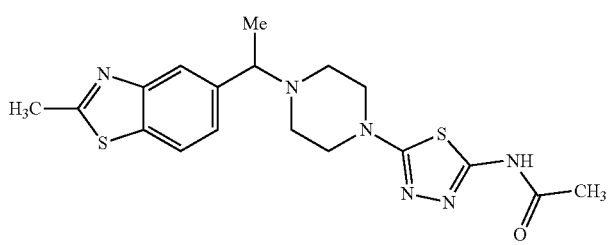 [SMILES: CC(=O)Nc1nnc(N2CCN(C(C)c3ccc4sc(C)nc4c3)CC2)s1] |
| 171 | 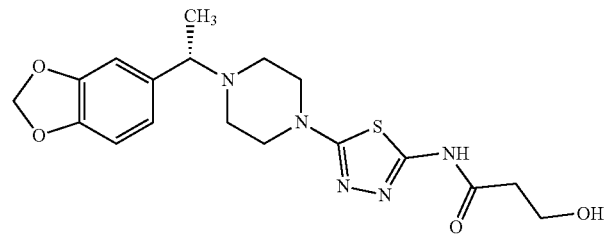 [SMILES: C[C@@H](c1ccc2c(c1)OCO2)N1CCN(c2nnc(NC(=O)CCO)s2)CC1] |
| 172 | 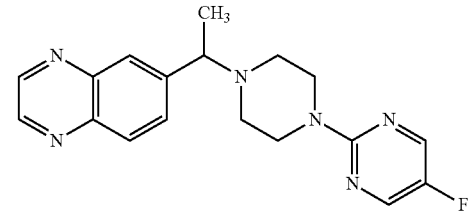 [SMILES: CC(c1ccc2nccnc2c1)N1CCN(c2ncc(F)cn2)CC1] |

-continued
| No | Structure |
|---|---|
| 173 | 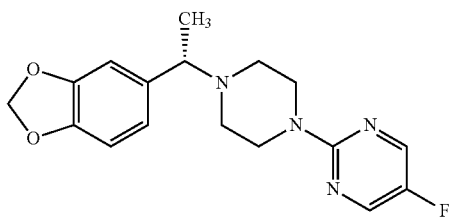 [SMILES: C[C@@H](c1ccc2c(c1)OCO2)N1CCN(c2ncc(F)cn2)CC1] |
| 174 | 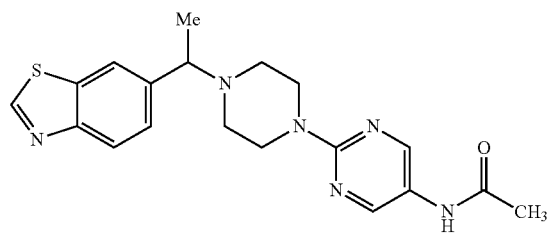 [SMILES: CC(=O)Nc1cnc(N2CCN(C(C)c3ccc4ncsc4c3)CC2)nc1] |
| 176 | 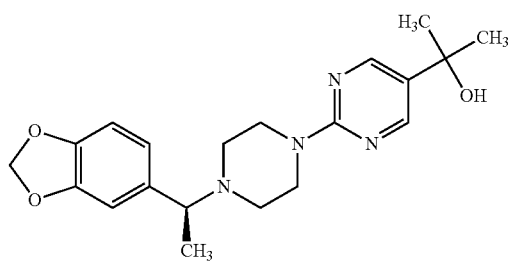 [SMILES: C[C@@H](c1ccc2c(c1)OCO2)N1CCN(c2ncc(C(C)(C)O)cn2)CC1] |
| 177 | 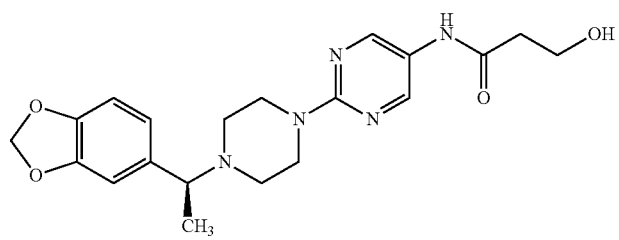 [SMILES: C[C@@H](c1ccc2c(c1)OCO2)N1CCN(c2ncc(NC(=O)CCO)cn2)CC1] |
| 178 | 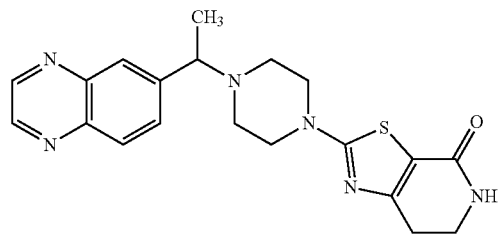 [SMILES: CC(c1ccc2nccnc2c1)N1CCN(c2nc3c(s2)C(=O)NCC3)CC1] |
| 179 | 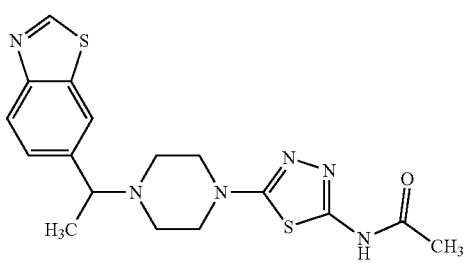 [SMILES: CC(=O)Nc1nnc(N2CCN(C(C)c3ccc4ncsc4c3)CC2)s1] |

-continued
| No | Structure |
|---|---|
| 180 | 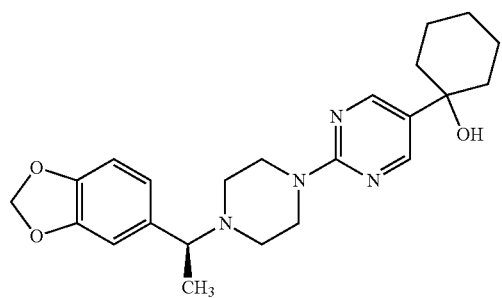 [SMILES: C[C@@H](c1ccc2c(c1)OCO2)N1CCN(c2ncc(C3(O)CCCCC3)cn2)CC1] |
| 181 | 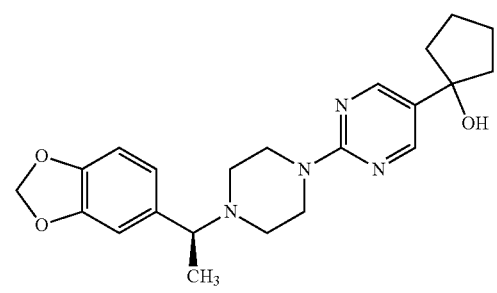 [SMILES: C[C@@H](c1ccc2c(c1)OCO2)N1CCN(c2ncc(C3(O)CCCC3)cn2)CC1] |
| 182 | 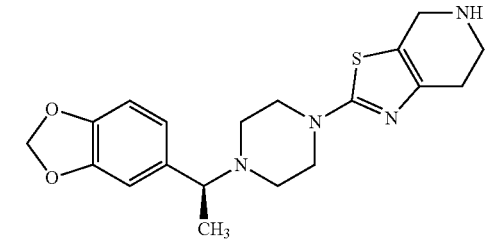 |
| 183 | 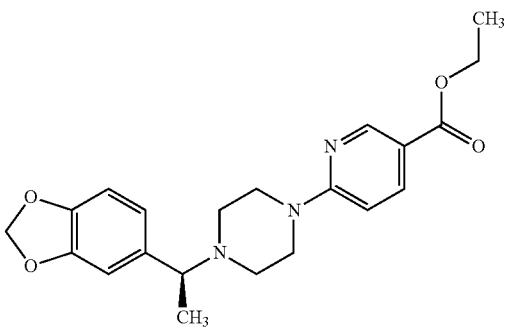 [SMILES: CCOC(=O)c1ccc(N2CCN([C@@H](C)c3ccc4c(c3)OCO4)CC2)nc1] |
| 184 | 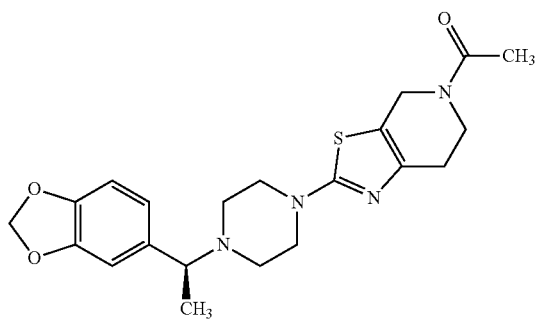 [SMILES: CC(=O)N1CCc2nc(N3CCN([C@@H](C)c4ccc5c(c4)OCO5)CC3)sc2C1] |

| No | Structure |
|---|---|
| 185 | 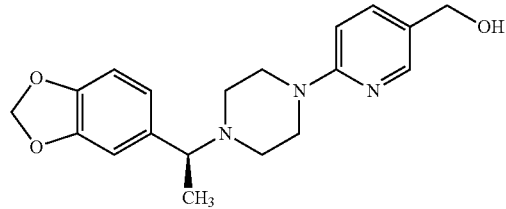 [SMILES: C[C@@H](c1ccc2c(c1)OCO2)N1CCN(c2ccc(CO)cn2)CC1] |
| 186 | 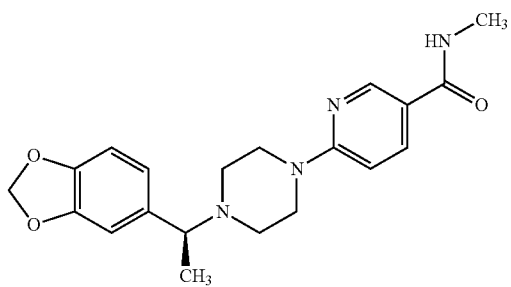 [SMILES: CNC(=O)c1ccc(N2CCN([C@@H](C)c3ccc4c(c3)OCO4)CC2)nc1] |
| 187 | 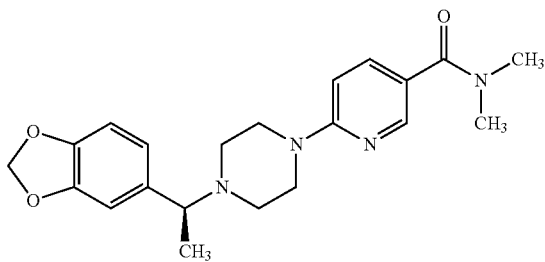 |
| 188 | 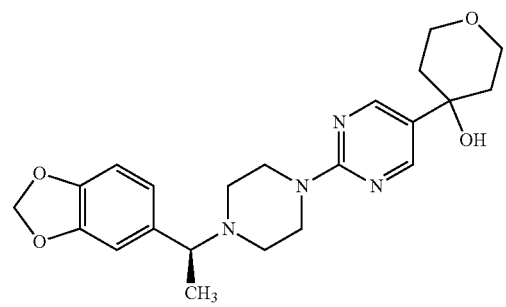 [SMILES: C[C@@H](c1ccc2c(c1)OCO2)N1CCN(c2ncc(C3(O)CCOCC3)cn2)CC1] |
| 189 | 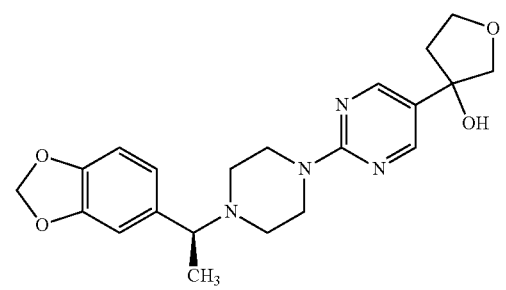 [SMILES: C[C@@H](c1ccc2c(c1)OCO2)N1CCN(c2ncc(C3(O)CCOC3)cn2)CC1] |

-continued
| No | Structure |
|---|---|
| 190 | 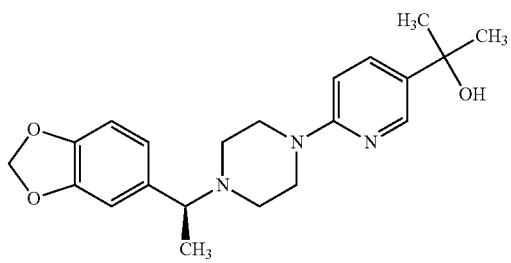 |
| 192 | 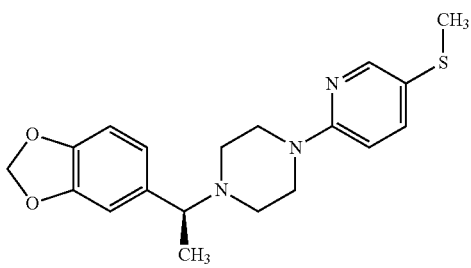 |
| 193 | 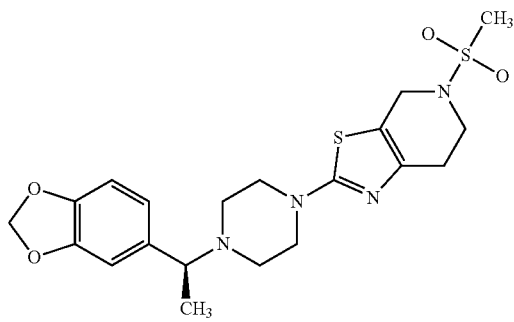 |
| 194 | 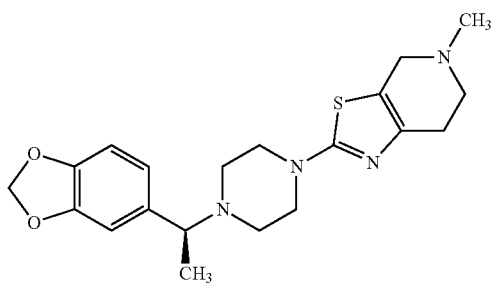 [SMILES: C[C@@H](c1ccc2c(c1)OCO2)N1CCN(c2nc3c(s2)CN(C)CC3)CC1] |
| 195 | 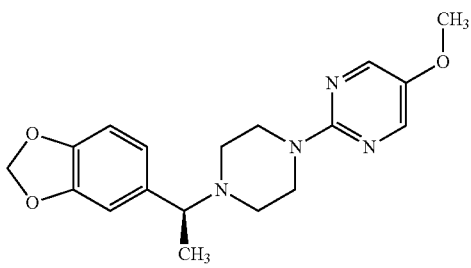 |

| No | Structure |
|---|---|
| 196 | (structure) |
| 197 | (structure) |
| 198 | (structure) |
| 200 | (structure) |
| 201 | (structure) |
| 202 | (structure) | or a solvate, salt, tautomer, enantiomer, racemate, stereoisomer, or any mixture thereof in any ratio.

9. A method of treating a disease that is mediated or propagated by O-GlcNAcase activity, comprising administering a therapeutically effective amount of a compound of claim 1 to a mammal in need of such treatment.

10. A method of treating a neurodegenerative disease, diabetes, cancer, or stress, comprising administering a therapeutically effective amount of a compound of claim 1 to a mammal in need of such treatment.

11. The method of claim 10, wherein the neurodegenerative disease is selected from the group consisting of one or more tauopathies, Alzheimer's disease, Dementia, Amyotrophic lateral sclerosis, Amyotrophic lateral sclerosis with cognitive impairment, Argyrophilic grain dementia, Bluit disease, Corticobasal degeneration, Dementia pugilistica, Diffuse neurofibrillary tangles with calcification, Down's syndrome, Familial British dementia, Familial Danish dementia, Frontotemporal dementia, Gerstmann-Straussler-Scheinker disease, Guadeloupean parkinsonism, Hallevorden-Spatz disease, Multiple system atrophy, Myotonic dystrophy, Niemann-Pick disease, Pallido-ponto-nigral degeneration, Parkinsonism-dementia complex of Guam, Pick's disease, Postencephalitic parkinsonism, and a Prion disease.

12. A method of treating a tauopathy, comprising administering a therapeutically effective amount of a compound of claim 1 to a mammal in need of such treatment.

13. A method of inhibiting a glycosidase, comprising contacting a system expressing the glycosidase with a compound of claim 1 under in-vitro conditions such that the glycosidase is inhibited.

14. A pharmaceutical composition comprising one or more compounds of claim 1, and one or more pharmaceutically tolerable adjuvants or excipients.

15. The compound of claim 1, wherein W is N.

16. The method of claim 11, wherein the Frontotemporal dementia is Frontotemporal dementia with parkinsonism linked to chromosome 17.

17. The method of claim 11, wherein the Niemann-Pick disease is Niemann-Pick disease type C.

18. The method of claim 11, wherein the Prion disease is Creutzfeldt-Jakob Disease, Variant Creutzfeldt-Jakob Disease, Fatal Familial Insomnia, Kuru, Progressive supercortical gliosis, Progressive supranuclear palsy, Steele-Richardson-Olszewski syndrome, Subacute sclerosing panencephalitis, Tangle-only dementia, Huntington's disease, or Parkinson's disease.

19. The method of claim 11, wherein the neurodegenerative disease is Alzheimer's disease.

20. The pharmaceutical composition of claim 14, further comprising one or more active ingredients.

* * * * *

UNITED STATES PATENT AND TRADEMARK OFFICE
CERTIFICATE OF CORRECTION

PATENT NO. : 11,046,712 B2
APPLICATION NO. : 16/412689
DATED : June 29, 2021
INVENTOR(S) : Anna Quattropani et al.

Page 1 of 1

It is certified that error appears in the above-identified patent and that said Letters Patent is hereby corrected as shown below:

In the Claims

Column 249, Claim 1, Line 43:
"selected from N, Q and S, which may be substituted by"
Should read:
--selected from N, O, and S, which may be substituted by--

Column 249, Claim 2, Line 57:
"A compound of fomula Ia or Ib"
Should read:
--A compound of formula Ia or Ib:--

Column 252, Claim 6, Line 25:
"wherein X, $R'''$, $R''''$, $R^5$, $R^6$, $R^7$ and $R^8$ have the meaning"
Should read:
--wherein X, $R'''$, $R''''$, $R^5$, $R^6$, $R^7$, and $R^8$ have the meaning--

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*